(12) United States Patent
Khvorova et al.

US010633653B2

(10) Patent No.: US 10,633,653 B2
(45) Date of Patent: Apr. 28, 2020

(54) BIOACTIVE CONJUGATES FOR OLIGONUCLEOTIDE DELIVERY

(71) Applicant: University of Massachusetts, Boston, MA (US)

(72) Inventors: Anastasia Khvorova, Westborough, MA (US); Mehran Nikan, Boston, MA (US); Matthew Hassler, Worcester, MA (US); Maire Osborn, Boston, MA (US); Reka Haraszti, Boston, MA (US); Andrew Coles, Boston, MA (US); Anton Turanov, Boston, MA (US); Neil Aronin, Newtonville, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 95 days.

(21) Appl. No.: 15/236,051

(22) Filed: Aug. 12, 2016

(65) Prior Publication Data

US 2017/0043024 A1    Feb. 16, 2017

Related U.S. Application Data

(60) Provisional application No. 62/317,118, filed on Apr. 1, 2016, provisional application No. 62/287,253, filed on Jan. 26, 2016, provisional application No. 62/286,406, filed on Jan. 24, 2016, provisional application No. 62/205,199, filed on Aug. 14, 2015.

(51) Int. Cl.
| | | |
|---|---|---|
| *C12N 15/11* | (2006.01) | |
| *C07H 21/00* | (2006.01) | |
| *A61K 47/54* | (2017.01) | |
| *C07H 21/02* | (2006.01) | |
| *A61K 47/61* | (2017.01) | |

(52) U.S. Cl.
CPC .......... *C12N 15/111* (2013.01); *A61K 47/542* (2017.08); *A61K 47/554* (2017.08); *A61K 47/61* (2017.08); *C07H 21/00* (2013.01); *C12N 2310/14* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,328,470 A | 7/1994 | Nabel et al. |
| 5,684,143 A | 11/1997 | Gryaznov et al. |
| 5,814,014 A | 9/1998 | Elsberry et al. |
| 5,858,988 A | 1/1999 | Wang |
| 6,093,180 A | 7/2000 | Elsberry |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,471,996 B1 | 10/2002 | Sokoll et al. |
| 6,472,375 B1 | 10/2002 | Hoon et al. |
| 6,489,464 B1 | 12/2002 | Agrawal et al. |
| 7,250,496 B2 | 7/2007 | Bentwich |
| 7,459,547 B2 | 12/2008 | Zamore et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,809,817 B2 | 11/2017 | Khvorova et al. |
| 9,862,952 B2 * | 1/2018 | Khvorova .......... C12N 15/1138 |
| 2003/0143732 A1 | 7/2003 | Fosnaugh et al. |
| 2004/0198640 A1 | 10/2004 | Leake et al. |
| 2005/0096284 A1 | 5/2005 | McSwiggen et al. |

(Continued)

FOREIGN PATENT DOCUMENTS

| | | |
|---|---|---|
| CN | 101199858 A | 6/2008 |
| EP | 2 853 597 A1 | 4/2015 |

(Continued)

OTHER PUBLICATIONS

Boutla et al (Current Biology 2001, 11:1776-1780) (Year: 2001).*
Nishina et al (Mol Ther. 16(4): 734-740, 2008) (Year: 2008).*
Raouane et al (Bioconjugate Chem. 2012, 23, 1091-1104) (Year: 2012).*
Yu et al. (Aug. 31, 2012) "Single-stranded RNAs use RNAi to potently and allele-selectively inhibit mutant huntingtin expression," Cell. 150(5):895-908.
Zeng et al. (2002) "Both natural and designed micro RNAs can inhibit the expression of cognate mRNAs when expressed in human cells," Mol. Cell. 9(6):1327-1333.

(Continued)

*Primary Examiner* — Richard A Schnizer
(74) *Attorney, Agent, or Firm* — Lathrop GPM LLP; James H. Velema, Esq.

(57) ABSTRACT

Provided herein are self-delivering oligonucleotides that are characterized by efficient RISC entry, minimum immune response and off-target effects, efficient cellular uptake without formulation, and efficient and specific tissue distribution.

18 Claims, 73 Drawing Sheets

Specification includes a Sequence Listing.

(56) References Cited

U.S. PATENT DOCUMENTS

| | | |
|---|---|---|
| 2005/0220766 A1 | 10/2005 | Amalfitano et al. |
| 2006/0009409 A1 | 1/2006 | Woolf |
| 2006/0078542 A1 | 4/2006 | Mah et al. |
| 2006/0094032 A1 | 5/2006 | Fougerolles et al. |
| 2007/0004664 A1 | 1/2007 | McSwiggen et al. |
| 2007/0099860 A1 | 5/2007 | Sah et al. |
| 2007/0135372 A1 | 6/2007 | MacLachlan et al. |
| 2007/0191273 A1 | 8/2007 | Ambati et al. |
| 2007/0259827 A1 | 11/2007 | Aronin et al. |
| 2008/0039415 A1 | 2/2008 | Stewart et al. |
| 2008/0119427 A1 | 5/2008 | Bhat et al. |
| 2008/0269149 A1 | 10/2008 | Bowles et al. |
| 2009/0143322 A1 | 6/2009 | Burkoth et al. |
| 2010/0186103 A1 | 7/2010 | Gao et al. |
| 2011/0039914 A1 | 2/2011 | Pavco et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0059046 A1 | 3/2012 | Woolf et al. |
| 2012/0065243 A1 | 3/2012 | Woolf et al. |
| 2013/0131141 A1 | 5/2013 | Khvorova et al. |
| 2013/0131142 A1 | 5/2013 | Libertine et al. |
| 2013/0197055 A1 | 8/2013 | Kamens et al. |
| 2014/0113950 A1 | 4/2014 | Khvorova et al. |
| 2014/0296486 A1 | 10/2014 | Gao et al. |
| 2014/0315974 A1 | 10/2014 | Khvorova et al. |
| 2014/0364482 A1 | 12/2014 | Khvorova et al. |
| 2015/0209441 A1 | 7/2015 | Carell et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0244765 A1 | 8/2016 | Khvorova et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0067056 A1 | 3/2017 | Khvorova et al. |
| 2017/0312367 A1 | 11/2017 | Khvorova et al. |

FOREIGN PATENT DOCUMENTS

| | | |
|---|---|---|
| WO | 2003/029459 A2 | 4/2003 |
| WO | 2004/008946 A2 | 1/2004 |
| WO | 2004/044136 A2 | 5/2004 |
| WO | 2006/019430 A2 | 2/2006 |
| WO | 2007/051045 A2 | 5/2007 |
| WO | 2007/094218 A1 | 8/2007 |
| WO | 2007/112414 A2 | 10/2007 |
| WO | 2008/154482 A2 | 12/2008 |
| WO | 2009/054551 A2 | 4/2009 |
| WO | 2009/099991 A2 | 8/2009 |
| WO | 2009/102427 A2 | 8/2009 |
| WO | 2010/008582 A2 | 1/2010 |
| WO | 2010/011346 A1 | 1/2010 |
| WO | 2010/033246 A1 | 3/2010 |
| WO | 2010/033247 A2 | 3/2010 |
| WO | 2010/033248 A2 | 3/2010 |
| WO | 2010/059226 A2 | 5/2010 |
| WO | 2010/078536 A1 | 7/2010 |
| WO | 2010/090762 A1 | 8/2010 |
| WO | 2011/109698 A1 | 9/2011 |
| WO | 2011/119852 A1 | 9/2011 |
| WO | 2011/119871 A1 | 9/2011 |
| WO | 2011/119887 A1 | 9/2011 |
| WO | 2012/005898 A2 | 1/2012 |
| WO | 2012/118911 A1 | 9/2012 |
| WO | 2013/165816 A2 | 11/2013 |
| WO | 2014/076195 A1 | 5/2014 |
| WO | 2015/161184 A1 | 10/2015 |
| WO | 2016/161374 A1 | 10/2016 |
| WO | 2017/015555 A1 | 1/2017 |

OTHER PUBLICATIONS

Zeng et al. (2003) "Sequence requirements for micro RNA processing and function in human cells," RNA. 9(1):112-123.

International Search Report with Written Opinion corresponding to International Patent Application No. PCT/US2016/025722, dated Aug. 12, 2016.

International Search Report with Written Opinion corresponding to International Patent Application No. PCT/US2016/025731, dated Sep. 9, 2016.

International Search Report with Written Opinion corresponding to International Patent Application No. PCT/US2016/025753, dated Sep. 14, 2016.

Felber et al. (Sep. 2012) "The interactions of amphiphilic antisense oligonucleotides with serum proteins and their effects on in vitro silencing activity," Biomaterials. 33(25):5955-5965.

International Search Report with Written Opinion corresponding to International Patent Application No. PCT/US2016/046810, dated Nov. 29, 2016.

Lai et al. (2003) "Computational identification of *Drosophila* microRNA genes," Genome Biol. 4(7):R42. pp. 1-20.

Lau et al. (2001) "An abundant class of tiny RNAs with probable regulatory roles in Caenorhabditis elegans," Science. 294(5543):858-862.

Lau et al. (2006) "Characterization of the piRNA complex from rat testes," Science. 313(5785):363-367.

Lee et al. (2001) "An extensive class of small RNAs in Caenorhabditis elegans," Science. 294(5543):862-864.

Lee et al. (2002) "Expression of small interfering RNAs targeted against HIV-1 rev transcripts in human cells," Nat. Biotechnol. 20:500-505.

Lim et al. (2003) "The microRNAs of Caenorhabditis elegans," Genes Dev. 17(8):991-1008.

Lim et al. (2003) "Vertebrate microRNA genes," Science. 299(5612):1540.

Lima et al. (Aug. 31, 2012) "Single-stranded siRNAs activate RNAi in animals," Cell. 150:883-894.

Lorenz et al. (2004) "Steroid and lipid conjugates of siRNAs to enhance cellular uptake and gene silencing in liver cells," Bioorg. Med. Chem. Lett. 14:4975-4977.

Luo et al. (Jun. 18, 2013) "Photoreceptor avascular privilege is shielded by soluble VEGF receptor-1," eLife. 6: e19456. pp. 1-22.

McCaffrey et al. (2002) "RNA interference in adult mice," Nature. 418(6893):38-39.

McManus et al. (2002) "Gene silencing using micro-RNA designed hairpins," RNA. 8:842-850.

Miyagishi et al. (2002) "U6 promoter-driven siRNAs with four uridine 3' overhangs efficiently suppress targeted gene expression in mammalian cells," Nat. Biotechnol. 20:497-500.

Molitoris et al. (2009) "siRNA Targeted to p53 Attenuates Ischemic and Cisplatin-Induced Acute Kidney Injury," Journal of the American Society of Nephrology. 20:1754-1764.

Myers et al. (1988) "Optimal alignments in linear space," Comput. Appl. Biosci. 4(1):11-17.

Nair et al. (Dec. 10, 2014) "Multivalent N-Acetylgalactosamine—Conjugated siRNA Localizes in Hepatocytes and Elicits Robust RNAi-Mediated Gene Silencing," J. Am. Chem. Soc. 136(49):16958-16961.

Nielsen et al. (2001) "Sequence-selective recognition of DNA by strand displacement with a thymine-substituted polyamide," Science. 254:1497-1500.

Nikan et al. (Aug. 9, 2016) "Docosahexaenoic Acid Conjugation Enhances Distribution and Safety of siRNA upon Local Administration in Mouse Brain," Mol Ther. Nucleic Acids. 5(8):e344. pp. 1-11.

Owen et al. (Mar. 15, 2012) "Morpholino-mediated increase in soluble Flt-1 expression results in decreased ocular and tumor neovascularization," PloS One. 7(3):e33576. pp. 1-9.

Paddison et al. (2002) "Short hairpin RNAs (shRNAs) induce sequence-specific silencing in mammalian cells," Gene Dev. 16:948-958.

Pasquinelli et al. (2000) "Conservation of the sequence and temporal expression of let-7 heterochronic regulatory RNA," Nature. 408(6808):86-89.

(56) References Cited

OTHER PUBLICATIONS

Paul et al. (2002) "Effective expression of small interfering RNA in human cells," Nature Biotechnol. 20:505-508.
Peel et al. (Feb. 12, 2015) "Conjugation and Evaluation of Small Hydrophobic Molecules to Triazole-Linked siRNAs," ACS Med. Chem. Lett. 6(2):117-122.
Petersen et al. (2003) "LNA: a versatile tool for therapeutics and genomics," Trends Biotechnol 21:74-81.
Putnam (1996) "Antisense strategies and therapeutic applications," Am. J. Health Syst. Pharm. 53(2):151-160.
Reinhart et al. (2002) "Small RNAs correspond to centromere heterochromatic repeats," Science. 297(5588):1831.
Rigo et al. (Apr. 20, 2014) "Pharmacology of a central nervous system delivered 2'-O-methoxyethyl-modified survival of motor neuron splicing oligonucleotide in mice and nonhuman primates," The Journal of Pharmacology and Experimental Therapeutics. 350:46-55.
Rodriguez-Lebron et al. (2005) "Intrastriatal rAAV-mediated delivery of anti-huntingtin shRNAs induces partial reversal of disease progression in R6/1 Huntington's disease transgenic mice," Mol. Ther. 12(4):618-633.
Rusckowski et al. (2000) "Biodistribution and metabolism of a mixed backbone oligonucleotide (GEM 231) following single and multiple dose administration in mice," Antisense Nucleic Acid Drug Dev. 10(5):333-345.
Schirle et al. (Oct. 31, 2014) "Gene Regulation. Structural basis for microRNA targeting," Science. 346:608-613.
Schwab et al. (1994) "An approach for new anticancer drugs: oncogene-targeted antisense DNA," Ann. Oncol. 5 (Suppl 4):55-58.
Schwarz et al. (2003) Asymmetry in the Assembly of the RNAi Enzyme Complex. Cell 115:199-208.
Song et al. (2003) "Sustained Small Interfering RNA-Mediated Human Immunodeficiency Virus Type 1 Inhibition in Primary Macrophages," Journal of Virology. 77:7174-7181.
Soutschek et al. (2004) "Therapeutic silencing of an endogenous gene by systemic administration of modified siRNAs," Nature. 432:173-178.
Stalder et al. (Mar. 19, 2013) "The rough endoplasmatic reticulum is a central nucleation site of siRNA-mediated RNA silencing," EMBO J. 32:1115-1127.
Stein (2001) "Inhibition of Vesivirus infections in mammalian tissue culture with antisense morpholino oligomers," Antisense Nucleic Acid Drug Dev. 11(5):317-25.
Stokman et al. (2010) "Application of siRNA in targeting protein expression in kidney disease," Advanced Drug Delivery Reviews. 62:1378-1389.
Sui et al. (2002) "A DNA vector-based RNAi technology to suppress gene expression in mammalian cells," Proc Natl Acad Sci USA. 99:5515-5520.
Tabernero et al. (Apr. 2013) "First-in-humans trial of an RNA interference therapeutic targeting VEGF and KSP in cancer patients with liver involvement," Cancer Discovery. 3:406-417.
Thomas et al. (2009) "A recently evolved novel trophoblast-enriched secreted form of fms-like tyrosine kinase-1 variant is up-regulated in hypoxia and preeclampsia," J. Clin. Endocrinel. Metabol. 94:2524-2530.
Tuschl (2002) "Expanding small RNA interference," Nat. Biotechnol. 20(5):446-448.
Tuschl et al. (May 6, 2004) "The siRNA User Guide," Accessible on the Internet at URL: http://diyhpl.us/~bryan/irc/protocol-online/protocol-cache/sirna.html. [Last Accessed Aug. 11, 2016].
Vaught et al. (2004) "T7 RNA Polymerase Transcription with 5-Position Modified UTP Derivatives," J. Am. Chem. Soc. 126:11231-11237.
Vorobjev et al. (2001) "Nuclease resistance and RNase H sensitivity of oligonucleotides bridged by oligomethylenediol and oligoethylene glycol linkers," Antisense Nucleic Acid Drug Dev. 11(2):77-85.
Watanabe et al. (2008) "Endogenous siRNAs from naturally formed dsRNAs regulate transcripts in mouse oocytes," Nature. 453(7194):539-543.
Wooddell et al. (Feb. 26, 2013) "Hepatocyte-targeted RNAi Therapeutics for the Treatment of Chronic Hepatitis B Virus Infection," Molecular Therapy. 21:973-985.
Xia et al. (2002) "siRNA-mediated gene silencing in vitro and in vivo," Nature Biotechnol. 20(10):1006-1010.
Young et al. (2010) "Pathogenesis of preeclampsia," Annual Review of Pathology. 5:173-192.
Younis et al. (2013) "Overview of the Nonclinical Development Strategies and Class-Effects of Oligonucleotide-Based Therapeutics," Ch. 26 In; A Comprehensive Guide to Toxicology in Preclinical Drug Development. Ed.: Faqi. Academic Press. pp. 647-664.
Yu et al. (2002) "RNA interference by expression of short-interfering RNAs and hairpin RNAs in mammalian cells," Proc Natl Acad Sci USA. 99:6047-6052.
Pubchem Database [Online] (2003) "AMINO-TEG-DIOL," PubChem Accession No. 22136768. National Institute for Biotechnology Information. Accessible on the Internet at URL: https://pubchem.ncbi.nlm.nih.gov/compound/2213676. [Last Accessed Aug. 31, 2017], 13 pgs.
Pubchem Database [Online] (2005) "SCHEMBL867745," PubChem Accession No. 12454428. National Institute for Biotechnology Information. Accessible on the Internet at URL: https://pubchem.ncbi.nlm.nih.gov/compound/12454428. [Last Accessed Aug. 31, 2017], 12 pgs.
International Search Report with Written Opinion corresponding to International Patent Application No. PCT/US2017/015633, dated May 11, 2017.
Alexopoulou et al. (2001) "Recognition of double-stranded RNA and activation of NF-κB by Toll-like receptor 3," Nature. 413:732-738.
Allerson et al. (2005) "Fully 2'-Modified Oligonucleotide Duplexes with Improved in Vitro Potency and Stability Compared to Unmodified Small Interfering RNA," J. Med. Chem. 48(4):901-904.
Alterman et al. (Dec. 12, 2015) "Hydrophobically Modified siRNAs Silence Huntingtin mRNA in Primary Neurons and Mouse Brain," Mol. Ther.: Nucleic Acids. 4(12):e266. pp. 1-12.
Altschul et al. (1997) "Gapped BLAST and PSI-BLAST: a new generation of protein database search programs," Nucleic Acids Res. 25(17):3389-3402.
Ameres et al. (2007) "Molecular basis for target RNA recognition and cleavage by human RISC," Cell. 130:101-112.
Anderson et al. (2008) "Experimental validation of the importance of seed complement frequency to siRNA specificity," RNA. 14:853-861.
Anderson et al. (2008) "Identifying siRNA-induced off-targets by microarray analysis," Ch.4 In; Methods in Molecular Biology. 442:45-63.
Bagella et al. (1998) "Cloning of murine CDK9/PITALRE and its tissue-specific expression in development," J. Cell. Physiol. 177:206-213.
Bartlett (2006) "Insights into the kinetics of siRNA-mediated gene silencing from live-cell and live-animal bioluminescent imaging," Nucleic Acids Research. 34:322-333.
Behlke et al. (2008) "Chemical modification of siRNAs for in vivo use," Oligonucleotides. 18:305-320.
Billy et al. (2001) "Specific interference with gene expression induced by long, double-stranded RNA in mouse embryonal teratocarcinoma cell lines," Proc Natl Acad Sci USA. 98(25):14428-14433.
Birmingham et al. (2006) "3' UTR seed matches, but not overall identity, are associated with RNAi off-targets," Nat. Methods. 3:199-204.
Birmingham et al. (2007) "A protocol for designing siRNAs with high functionality and specificity," Nature Protocols. 2:2068-2078.
Braasch et al. (2003) "RNA Interference in Mammalian Cells by Chemically-Modified RNA," Biochemistry 42:7967-7975.
Brennecke et al. (2003) "Towards a complete description of the microRNA complement of animal genomes," Genome Biol. 4(9):228.
Brummelkamp et al. (2002) "A system for stable expression of short interfering RNAs in mammalian cells," Science. 296:550-553.
Burchard et al. (2009) "MicroRNA-like off-target transcript regulation by siRNAs is species specific," RNA. 15:308-315.

(56) References Cited

OTHER PUBLICATIONS

Byrne et al. (Nov. 1, 2013) "Novel hydrophobically modified asymmetric RNAi compounds (sd-rxRNA) demonstrate robust efficacy in the eye," Journal of Ocular Pharmacology and Therapeutics. 29:855-864.
Calegari et al. (2002) "Tissue-specific RNA interference in postimplantation mouse embryos with endoribonuclease-prepared short interfering RNA," Proc. Natl. Acad. Sci. USA. 99(22):14236-14240.
Charrier et al. (May 3, 2012) "Inhibition of SRGAP2 function by its human-specific paralogs induces neoteny during spine maturation," Cell. 149(4):923-935.
Cho et al. (Feb. 13, 2012) "Vascular endothelial growth factor receptor 1 morpholino decreases angiogenesis in a murine corneal suture model," Invest. Opthamol. Visual Sci. 53(2):685-692.
Choe et al. (2005) "Crystal structure of human toll-like receptor 3 (TLR3) ectodomain," Science. 309:581-585.
Coelho et al. (Aug. 29, 2013) "Safety and efficacy of RNAi therapy for transthyretin amyloidosis," The New England Journal of Medicine. 369:819-829.
Deleavey et al. (Jan. 5, 2013) "The 5' binding MID domain of human Argonaute2 tolerates chemically modified nucleotide analogues" Nucleic Acid Therapeutics. 23:81-87.
Difiglia et al. (2007) "Therapeutic silencing of mutant huntingtin with siRNA attenuates striatal and cortical neuropathology and behavioral deficits," Proc. Natl. Acad. Sci. USA. 104(43):17204-17209.
Doench et al. (2003) "siRNAs can function as miRNAs," Genes Dev. 17(4):438-442.
Eckstein (2000) "Phosphorothioate Oligodeoxynucleotides: What is their Origin and what is Unique About Them?" Antisense Nucleic Acid Drug Dev. 10(2):117-121.
Elmen et al. (2005) "Locked nucleic acid (LNA) mediated improvements in siRNA stability and functionality," Nucleic Acids Res. 33(1):439-447.
Fan et al. (Oct. 20, 2014) "Endometrial VEGF induces placental sFLT1 and leads to pregnancy complications," J. Clin. Inves. 124(11):4941-4952.
Federov et al. (2006) "Off-target effects by siRNA can induce toxic phenotype," RNA. 12:1188-1196.
Frazier (Nov. 9, 2015) "Antisense Oligonucleotide Therapies: The Promise and the Challenges from a Toxicologic Pathologist's Perspective," Toxicologic Pathology. 43:78-89.
Gaglione et al. (2010) "Recent progress in chemically modified siRNAs," Mini Rev. Med. Chem. 10(7):578-595.
Godard et al. (1995) "Antisense Effects of Cholesterol-Oligodeoxynucleotide Conjugates Associated with Poly(alkylcyanoacrylate) Nanoparticles," Eur. J. Biochem. 232(2):404-410.
Grad et al. (2003) "Computational and experimental identification of C. elegans microRNAs," Mol. Cell. 11(5):1253-1263.
Griffiths-Jones (2004) "The microRNA Registry," Nuc. Acids Res. 32(Database Issue):D109-D111.
Grimm et al. (2006) "Fatality in mice due to oversaturation of cellular microRNA/short hairpin RNA pathways," Nature. 441:537-541.
Herdewijn (2000) "Heterocyclic modifications of oligonucleotides and antisense technology," Antisense Nucleic Acid Drug Dev. 10(4):297-310.
Heydarian et al. (2009) "Novel splice variants of sFlt1 are upregulated in preeclampsia," Placenta. 30:250-255.
Heyer et al. (Dec. 12, 2014) "An optimized kit-free method for making strand-specific deep sequencing libraries from RNA fragments," Nucleic Acids Res. 43(1):e2. pp. 1-14.
Hutvagner et al. (2002) "A microRNA in a multiple-turnover RNAi enzyme complex," Science. 297(5589):2056-2060.
Jackson et al. (2006) "Position-specific chemical modification of siRNAs reduces 'off-target' transcript silencing," RNA. 12:1197-1205.
Jackson et al. (2010) "Recognizing and avoiding siRNA off-target effects for target identification and therapeutic application," Nature Reviews in Drug Discovery. 9:57-67.
Jacque et al. (2002) "Modulation of HIV-1 replication by RNA interference," Nature. 418:435-438.
Judge et al. (2006) "Design of Noninflammatory Synthetic siRNA Mediating Potent Gene Silencing in Vivo," Molecular Therapy. 13:494-505.
Karlin et al. (1990) "Methods for assessing the statistical significance of molecular sequence features by using general scoring schemes," Proc. Natl. Acad. Sci. USA. 87:2264-2268.
Karlin et al. (1993) "Applications and statistics for multiple high-scoring segments in molecular sequences," Proc. Natl. Acad. Sci. USA 90:5873-5877.
Kenski et al. (2012) "siRNA-optimized Modifications for Enhanced In Vivo Activity," Mol. Ther. Nucleic Acids. 1:e5. pp. 1-8.
Khvorova et al. (2003) "Functional siRNAs and miRNAs Exhibit Strand Bias," Cell. 115:209-216.
Khvorova et al. (Mar. 15, 2016) "Abstract IA27: Advances in oligonucleotide chemistry for the treatment of neurodegenerative disorders and brain tumors," Cancer Res. 76(6) Abstract No. IA27.
Lagos-Quintana et al. (2001) "Identification of novel genes coding for small expressed RNAs," Science. 294(5543):853-858.
Raouane et al. (2012) "Lipid Conjugated Oligonucleotides: A Useful Strategy for Delivery," Bioconjugate Chemistry, 23:1091-1104.
Extended European Search Report for European Patent Application No. 16837593.9, dated Mar. 20, 2019.
Nikan et al. (2016) "Docosahexaenoic Acid 1-20 Conjugation Enhances Distribution and Safety of siRNA upon Local Administration in Mouse Brain—Supplementary Figures and Table S1," Molecular Therapy—Nucleic Acids, 5(1):e344.

* cited by examiner

5`-Cy3-(fC)#(mA)#(fG)(mU)(fA)(mA)(fA)(mG)(fA)(mG)(fA)(mU)(fU)#(mA)#(fA)-TegVitD-3`

Calculated: 1373.4
Observed: 1372.5

Fig. 1N
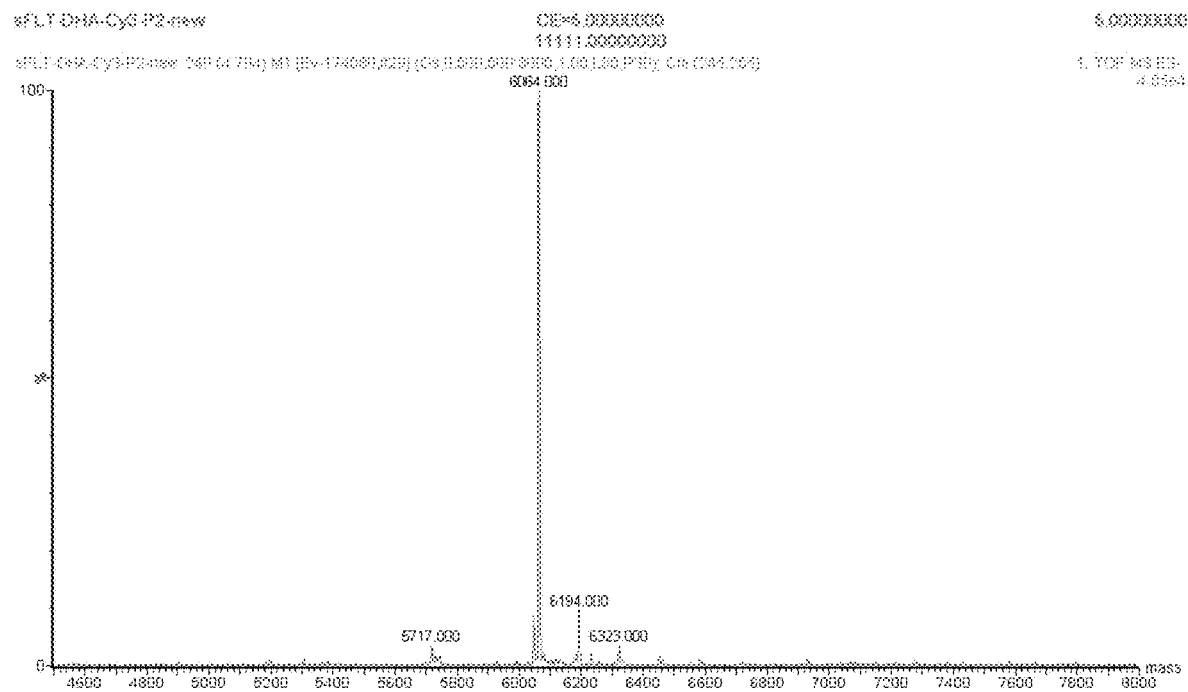
Calculated: 6063.97
Observed: 6064.00
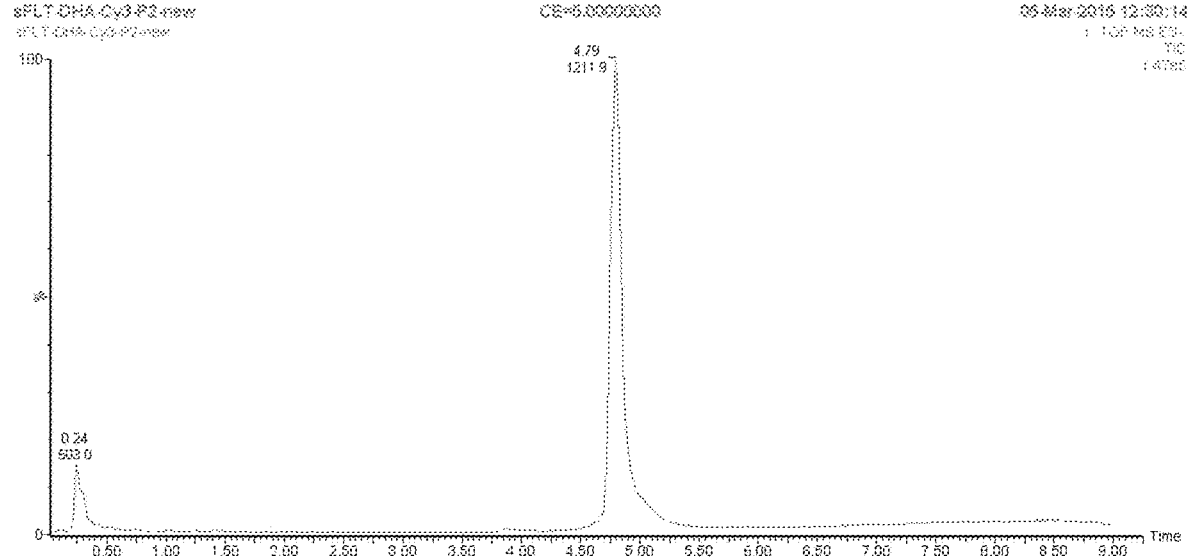

Calculated: 6063.97
Observed: 6064.00

Fig. 8

| # | | Pos | Targeting region (20 mer) | Targeting Region (30 mer) |
|---|---|---|---|---|
| 1 | | | | |
| 2 | sFLT1-i13 | 2247 | AAUCAGAGGUGAGCACUGCA | AUUACAAUCAGAGGUGAGCACUGCAACAAA |
| 3 | sFLT1-i13 | 2252 | GAGGUGAGCACUGCAACAAA | AAUCAGAGGUGAGCACUGCAACAAAAGGC |
| 4 | sFLT1-i13 | 2253 | AGGUGAGCACUGCAACAAAA | AUCAGAGGUGAGCACUGCAACAAAAGGCU |
| 5 | sFLT1-i13 | 2256 | UGAGCACUGCAACAAAAGG | AGAGGUGAGCACUGCAACAAAAGGCUGUU |
| 6 | sFLT1-i13 | 2279 | UUUUCUCUCGGAUCUCCAAA | GGCUGUUUUCUCUCGGAUCUCCAAAUUUAA |
| 7 | sFLT1-i13 | 2280 | UUUCUCUCGGAUCUCCAAAU | GCUGUUUUCUCUCGGAUCUCCAAAUUUAAA |
| 8 | sFLT1-i14 | 2283 | CUCUCGGAUCUCCAAAUUUA | GUUUUCUCUCGGAUCUCCAAAUUUAAAAGC |
| 9 | sFLT1-i13 | 2284 | UCUCGGAUCUCCAAAUUUAA | UUUUCUCUCGGAUCUCCAAAUUUAAAAGCA |
| 10 | sFLT1-i13 | 2286 | UCGGAUCUCCAAAUUUAAAA | UUCUCUCGGAUCUCCAAAUUUAAAAGCACA |
| 11 | sFLT1-i13 | 2293 | UCCAAAUUUAAAAGCACAAG | GGAUCUCCAAAUUUAAAAGCACAAGGAAUG |
| 12 | sFLT1-i13 | 2294 | CCAAAUUUAAAAGCACAAGG | GAUCUCCAAAUUUAAAAGCACAAGGAAUGA |
| 13 | sFLT1-i13 | 2295 | CAAAUUUAAAAGCACAAGGA | AUCUCCAAAUUUAAAAGCACAAGGAAUGAU |
| 14 | sFLT1-i13 | 2304 | AAGCACAAGGAAUGAUUGUA | UUUAAAAGCACAAGGAAUGAUUGUACCACA |
| 15 | sFLT1-i13 | 2313 | GAAUGAUUGUACCACACAAA | ACAAGGAAUGAUUGUACCACACAAAGUAAU |
| 16 | sFLT1-i13 | 2318 | AUUGUACCACACAAAGUAAU | GAAUGAUUGUACCACACAAAGUAAUGUAAA |
| 17 | sFLT1-i13 | 2321 | GUACCACACAAAGUAAUGUA | UGAUUGUACCACACAAAGUAAUGUAAAACA |
| 18 | sFLT1-i13 | 2322 | UACCACACAAAGUAAUGUAA | GAUUGUACCACACAAAGUAAUGUAAAACAU |
| 19 | sFLT1-i13 | 2324 | CCACACAAAGUAAUGUAAAA | UUGUACCACACAAAGUAAUGUAAAACAUUA |
| 20 | sFLT1-i13 | 2326 | ACACAAAGUAAUGUAAAACA | GUACCACACAAAGUAAUGUAAAACAUUAAA |
| 21 | sFLT1-i13 | 2332 | AGUAAUGUAAAACAUUAAAG | CACAAAGUAAUGUAAAACAUUAAAGGACUC |
| 22 | sFLT1-i13 | 2333 | GUAAUGUAAAACAUUAAAGG | ACAAAGUAAUGUAAAACAUUAAAGGACUCA |
| 23 | sFLT1-i13 | 2339 | UAAAACAUUAAAGGACUCAU | UAAUGUAAAACAUUAAAGGACUCAUUAAAA |
| 24 | sFLT1-i13 | 2343 | ACAUUAAAGGACUCAUUAAA | GUAAAACAUUAAAGGACUCAUUAAAAGUA |
| 25 | sFLT1-i13 | 2351 | GGACUCAUUAAAAGUAACA | UUAAAGGACUCAUUAAAAGUAACAGUUGU |
| 26 | sFLT1-i13 | 2353 | ACUCAUUAAAAGUAACAGU | AAAGGACUCAUUAAAAGUAACAGUUGUCU |
| 27 | sFLT1-i13 | 2362 | AAAGUAACAGUUGUCUCAUA | AUUAAAAGUAACAGUUGUCUCAUAUCAUC |
| 28 | | | | |
| 29 | sFLT1-i15a | 2471 | CAUCAUCAUCAUCAUAGCUA | GUCAUCAUCAUCAUCAUAGCUAUCAUC |
| 30 | sFLT1-i15a | 2474 | CAUCAUCAUAGCUAUCA | AUCAUCAUCAUCAUAGCUAUCAUCAUU |
| 31 | sFLT1-i15a | 2477 | CAUCAUCAUAGCUAUCAUCA | AUCAUCAUCAUCAUAGCUAUCAUCAUUAUC |
| 32 | sFLT1-i15a | 2508 | AUCAUCAUCAUCAUAGC | UCAUCAUCAUCAUCAUAGCUACCA |
| 33 | sFLT1-i15a | 2510 | CAUCAUCAUCAUAGCUA | AUCAUCAUCAUCAUCAUAGCUACCAUU |
| 34 | sFLT1-i15a | 2513 | CAUCAUCAUAGCUACCA | AUCAUCAUCAUCAUAGCUACCAUUUAU |
| 35 | sFLT1-i15a | 2518 | UCAUCAUAGCUACCAUUUAU | CAUCAUCAUCAUAGCUACCAUUUAUUGAAA |
| 36 | sFLT1-i15a | 2519 | CAUCAUAGCUACCAUUUAUU | AUCAUCAUCAUAGCUACCAUUUAUUGAAA |
| 37 | sFLT1-i15a | 2525 | AGCUACCAUUUAUUGAAAAC | AUCAUAGCUACCAUUUAUUGAAAACUAUUA |
| 38 | sFLT1-i15a | 2528 | UACCAUUUAUUGAAAACUAU | AUAGCUACCAUUUAUUGAAAACUAUUAUGU |
| 39 | sFLT1-i15a | 2556 | AACUUCAAAGAACUUAUCCU | GUGUCAACUUCAAAGAACUUAUCCUUUAGU |
| 40 | sFLT1-i15a | 2561 | CAAAGAACUUAUCCUUUAGU | AACUUCAAAGAACUUAUCCUUUAGUUGGAG |
| 41 | sFLT1-i15a | 2572 | UCCUUUAGUUGGAGAGCCAA | ACUUAUCCUUUAGUUGGAGAGCCAAGACAA |
| 42 | sFLT1-i15a | 2574 | CUUUAGUUGGAGAGCCAAGA | UUAUCCUUUAGUUGGAGAGCCAAGACAAUC |
| 43 | sFLT1-i15a | 2576 | UUAGUUGGAGAGCCAAGACA | AUCCUUUAGUUGGAGAGCCAAGACAAUCAU |
| 44 | sFLT1-i15a | 2577 | UAGUUGGAGAGCCAAGACAA | UCCUUUAGUUGGAGAGCCAAGACAAUCAUA |
| 45 | sFLT1-i15a | 2580 | UUGGAGAGCCAAGACAAUCA | UUUUAGUUGGAGAGCCAAGACAAUCAUAACA |
| 46 | sFLT1-i15a | 2582 | GGAGAGCCAAGACAAUCAUA | UAGUUGGAGAGCCAAGACAAUCAUAACAAU |
| 47 | sFLT1-i15a | 2585 | GAGCCAAGACAAUCAUAACA | UUGGAGAGCCAAGACAAUCAUAACAAUAAC |
| 48 | sFLT1-i15a | 2588 | CCAAGACAAUCAUAACAAUA | GAGAGCCAAGACAAUCAUAACAAUAACAAA |
| 49 | sFLT1-i15a | 2590 | AAGACAAUCAUAACAAUAAC | GAGCCAAGACAAUCAUAACAAUAACAAAUG |
| 50 | | | | |
| 51 | FLT1 | 331 | AGCUGUCUGCUUCUCACAGG | UGCUCAGCUGUCUGCUUCUCACAGGAUCUA |
| 52 | FLT1 | 376 | GAUCCUGAACUGAGUUUAAA | UAAAAGAUCCUGAACUGAGUUUAAAAGGCA |
| 53 | FLT1 | 377 | AUCCUGAACUGAGUUUAAAA | AAAAGAUCCUGAACUGAGUUUAAAAGGCAC |
| 54 | FLT1 | 381 | UGAACUGAGUUUAAAAGGCA | GAUCCUGAACUGAGUUUAAAAGGCACCCAG |
| 55 | FLT1 | 383 | GUUUAAAAGGCACCCAGCAC | ACUGAGUUUAAAAGGCACCCAGCACAUCAU |
| 56 | FLT1 | 867 | AUCAAAUGCAACGUACAAGA | AUCAUAUCAAAUGCAACGUACAAGAAAUAG |
| 57 | FLT1 | 868 | UCAAAUGCAACGUACAAAGA | UCAUAUCAAAUGCAACGUACAAAGAAAUAG |
| 58 | FLT1 | 1384 | GUUGUAUGGUUAAAAGAUGG | CGGAAGUUGUAUGGUUAAAAGAUGGGUUAC |
| 59 | FLT1 | 1528 | UUUUAAAAACCUCACUGCCAC | AUGUGUUUAAAAACCUCACUGCCACUCUAA |
| 60 | FLT1 | 1530 | UAAAAACCUCACUGCCACUC | GUGUUUAAAAACCUCACUGCCACUCUAAUU |
| 61 | FLT1 | 1532 | AAAACCUCACUGCCACUCUA | GUUUAAAAACCUCACUGCCACUCUAAUUGU |
| 62 | FLT1 | 1781 | GAAACAGAAUUGAGAGCAUC | CAUGGGAAACAGAAUUGAGAGCAUCACUCA |

Fig. 8 (continued)

| | | Pos | Targeting region (20 mer) | Sense Naked | Guide 20 mer |
|---|---|---|---|---|---|
| 1 | | | | | |
| 2 | sFLT1-i13 | 2247 | AAUCAGAGGUGAGCACUGCA | AAUCAGAGGUGAGCACUGCA | UGCAGUGCUCACCUCUGAUU |
| 3 | sFLT1-i13 | 2252 | GAGGUGAGCACUGCAACAAA | GAGGUGAGCACUGCAACAAA | UUUGUUGCAGUGCUCACCUC |
| 4 | sFLT1-i13 | 2253 | AGGUGAGCACUGCAACAAAA | AGGUGAGCACUGCAACAAAA | UUUUGUUGCAGUGCUCACCU |
| 5 | sFLT1-i13 | 2256 | UGAGCACUGCAACAAAAGG | UGAGCACUGCAACAAAAGG | CCUUUUGUUGCAGUGCUCA |
| 6 | sFLT1-i13 | 2279 | UUUCUCUCGGAUCUCCAAA | UUUCUCUCGGAUCUCCAAA | UUUGGAGAUCCGAGAGAAAA |
| 7 | sFLT1-i13 | 2280 | UUUCUCUCGGAUCUCCAAAU | UUUCUCUCGGAUCUCCAAAU | AUUUGGAGAUCCGAGAGAAA |
| 8 | sFLT1-i14 | 2283 | CUCUCGGAUCUCCAAAUUUA | CUCUCGGAUCUCCAAAUUUA | UAAAUUUGGAGAUCCGAGAG |
| 9 | sFLT1-i13 | 2284 | UCUCGGAUCUCCAAAUUUAA | UCUCGGAUCUCCAAAUUUAA | UUAAAUUUGGAGAUCCGAGA |
| 10 | sFLT1-i13 | 2286 | UCGGAUCUCCAAAUUUAAAA | UCGGAUCUCCAAAUUUAAAA | UUUUAAAUUUGGAGAUCCGA |
| 11 | sFLT1-i13 | 2293 | UCCAAAUUUAAAAGCACAAG | UCCAAAUUUAAAAGCACAAG | CUUGUGCUUUUAAAUUUGGA |
| 12 | sFLT1-i13 | 2294 | CCAAAUUUAAAAGCACAAGG | CCAAAUUUAAAAGCACAAGG | CCUUGUGCUUUUAAAUUUGG |
| 13 | sFLT1-i13 | 2295 | CAAAUUUAAAAGCACAAGGA | CAAAUUUAAAAGCACAAGGA | UCCUUGUGCUUUUAAAUUUG |
| 14 | sFLT1-i13 | 2304 | AAGCACAAGGAAUGAUUGUA | AAGCACAAGGAAUGAUUGUA | UACAAUCAUUCCUUGUGCUU |
| 15 | sFLT1-i13 | 2313 | GAAUGAUUGUACCACACAAA | GAAUGAUUGUACCACACAAA | UUUGUGUGGUACAAUCAUUC |
| 16 | sFLT1-i13 | 2318 | AUUGUACCACACAAAGUAAU | AUUGUACCACACAAAGUAAU | AUUACUUUGUGUGGUACAAU |
| 17 | sFLT1-i13 | 2321 | GUACCACACAAAGUAAUGUA | GUACCACACAAAGUAAUGUA | UACAUUACUUUGUGUGGUAC |
| 18 | sFLT1-i13 | 2322 | UACCACACAAAGUAAUGUAA | UACCACACAAAGUAAUGUAA | UUACAUUACUUUGUGUGGUA |
| 19 | sFLT1-i13 | 2324 | CCACACAAAGUAAUGUAAAA | CCACACAAAGUAAUGUAAAA | UUUUACAUUACUUUGUGUGG |
| 20 | sFLT1-i13 | 2326 | ACACAAAGUAAUGUAAACA | ACACAAAGUAAUGUAAACA | UGUUUACAUUACUUUGUGU |
| 21 | sFLT1-i13 | 2332 | AGUAAUGUAAACAUUAAAG | AGUAAUGUAAACAUUAAAG | CUUUAAUGUUUACAUUACU |
| 22 | sFLT1-i13 | 2333 | GUAAUGUAAACAUUAAAGG | GUAAUGUAAACAUUAAAGG | CCUUUAAUGUUUACAUUAC |
| 23 | sFLT1-i13 | 2338 | UAAAACAUUAAAGGACUCAU | UAAAACAUUAAAGGACUCAU | AUGAGUCCUUUAAUGUUUUA |
| 24 | sFLT1-i13 | 2343 | ACAUUAAAGGACUCAUUAAA | ACAUUAAAGGACUCAUUAAA | UUUAAUGAGUCCUUUAAUGU |
| 25 | sFLT1-i13 | 2351 | GGACUCAUUAAAAGUAACA | GGACUCAUUAAAAGUAACA | UGUUACUUUUAAUGAGUCC |
| 26 | sFLT1-i13 | 2353 | ACUCAUUAAAAGUAACAGU | ACUCAUUAAAAGUAACAGU | ACUGUUACUUUUAAUGAGU |
| 27 | sFLT1-i13 | 2362 | AAAGUAACAGUUGUCUCAUA | AAAGUAACAGUUGUCUCAUA | UAUGAGACAACUGUUACUUU |
| 28 | | | | | |
| 29 | sFLT1-i15a | 2471 | CAUCAUCAUCAUCAUAGCUA | CAUCAUCAUCAUCAUAGCUA | UAGCUAUGAUGAUGAUGAUG |
| 30 | sFLT1-i15a | 2474 | CAUCAUCAUCAUAGCUAUCA | CAUCAUCAUCAUAGCUAUCA | UGAUAGCUAUGAUGAUGAUG |
| 31 | sFLT1-i15a | 2477 | CAUCAUCAUAGCUAUCAUCA | CAUCAUCAUAGCUAUCAUCA | UGAUGAUAGCUAUGAUGAUG |
| 32 | sFLT1-i15a | 2508 | AUCAUCAUCAUCAUCAUAGC | AUCAUCAUCAUCAUCAUAGC | GCUAUGAUGAUGAUGAUGAU |
| 33 | sFLT1-i15a | 2510 | CAUCAUCAUCAUCAUAGCUA | CAUCAUCAUCAUCAUAGCUA | UAGCUAUGAUGAUGAUGAUG |
| 34 | sFLT1-i15a | 2513 | CAUCAUCAUCAUAGCUACCA | CAUCAUCAUCAUAGCUACCA | UGGUAGCUAUGAUGAUGAUG |
| 35 | sFLT1-i15a | 2518 | UCAUCAUAGCUACCAUUUAU | UCAUCAUAGCUACCAUUUAU | AUAAAUGGUAGCUAUGAUGA |
| 36 | sFLT1-i15a | 2519 | CAUCAUAGCUACCAUUUAUU | CAUCAUAGCUACCAUUUAUU | AAUAAAUGGUAGCUAUGAUG |
| 37 | sFLT1-i15a | 2525 | AGCUACCAUUUAUUGAAAAC | AGCUACCAUUUAUUGAAAAC | GUUUUCAAUAAAUGGUAGCU |
| 38 | sFLT1-i15a | 2528 | UACCAUUUAUUGAAAACUAU | UACCAUUUAUUGAAAACUAU | AUAGUUUUCAAUAAAUGGUA |
| 39 | sFLT1-i15a | 2556 | AACUUCAAAGAACUUAUCCU | AACUUCAAAGAACUUAUCCU | AGGAUAAGUUCUUUGAAGUU |
| 40 | sFLT1-i15a | 2561 | CAAAGAACUUAUCCUUUAGU | CAAAGAACUUAUCCUUUAGU | ACUAAAGGAUAAGUUCUUUG |
| 41 | sFLT1-i15a | 2572 | UCCUUUAGUUGGAGAGCCAA | UCCUUUAGUUGGAGAGCCAA | UUGGCUCUCCAACUAAAGGA |
| 42 | sFLT1-i15a | 2574 | CUUUAGUUGGAGAGCCAAGA | CUUUAGUUGGAGAGCCAAGA | UCUUGGCUCUCCAACUAAAG |
| 43 | sFLT1-i15a | 2576 | UUAGUUGGAGAGCCAAGACA | UUAGUUGGAGAGCCAAGACA | UGUCUUGGCUCUCCAACUAA |
| 44 | sFLT1-i15a | 2577 | UAGUUGGAGAGCCAAGACAA | UAGUUGGAGAGCCAAGACAA | UUGUCUUGGCUCUCCAACUA |
| 45 | sFLT1-i15a | 2580 | UUGGAGAGCCAAGACAAUCA | UUGGAGAGCCAAGACAAUCA | UGAUUGUCUUGGCUCUCCAA |
| 46 | sFLT1-i15a | 2582 | GGAGAGCCAAGACAAUCAUA | GGAGAGCCAAGACAAUCAUA | UAUGAUUGUCUUGGCUCUCC |
| 47 | sFLT1-i15a | 2585 | GAGCCAAGACAAUCAUAACA | GAGCCAAGACAAUCAUAACA | UGUUAUGAUUGUCUUGGCUC |
| 48 | sFLT1-i15a | 2588 | CCAAGACAAUCAUAACAAUA | CCAAGACAAUCAUAACAAUA | UAUUGUUAUGAUUGUCUUGG |
| 49 | sFLT1-i15a | 2590 | AAGACAAUCAUAACAAUAAC | AAGACAAUCAUAACAAUAAC | GUUAUUGUUAUGAUUGUCUU |
| 50 | | | | | |
| 51 | FLT1 | 331 | AGCUGUCUGCUUCUCACAGG | AGCUGUCUGCUUCUCACAGG | CCUGUGAGAAGCAGACAGCU |
| 52 | FLT1 | 376 | GAUCCUGAACUGAGUUUAAA | GAUCCUGAACUGAGUUUAAA | UUUAAACUCAGUUCAGGAUC |
| 53 | FLT1 | 377 | AUCCUGAACUGAGUUUAAAA | AUCCUGAACUGAGUUUAAAA | UUUUAAACUCAGUUCAGGAU |
| 54 | FLT1 | 381 | UGAACUGAGUUUAAAAGGCA | UGAACUGAGUUUAAAAGGCA | UGCCUUUUAAACUCAGUUCA |
| 55 | FLT1 | 389 | GUUUAAAAGGCACCCAGCAC | GUUUAAAAGGCACCCAGCAC | GUGCUGGGUGCCUUUUAAAC |
| 56 | FLT1 | 867 | AUCAAAUGCAACGUACAAAG | AUCAAAUGCAACGUACAAAG | CUUUGUACGUUGCAUUUGAU |
| 57 | FLT1 | 868 | UCAAAUGCAACGUACAAAGA | UCAAAUGCAACGUACAAAGA | UCUUUGUACGUUGCAUUUGA |
| 58 | FLT1 | 1384 | GUUGUAUGGUUAAAAGAUGG | GUUGUAUGGUUAAAAGAUGG | CCAUCUUUUAACCAUACAAC |
| 59 | FLT1 | 1528 | UUUAAAAACCUCACUGCCAC | UUUAAAAACCUCACUGCCAC | GUGGCAGUGAGGUUUUUAAA |
| 60 | FLT1 | 1530 | UAAAACCUCACUGCCACUC | UAAAACCUCACUGCCACUC | GAGUGGCAGUGAGGUUUUA |
| 61 | FLT1 | 1532 | AAAACCUCACUGCCACUCUA | AAAACCUCACUGCCACUCUA | UAGAGUGGCAGUGAGGUUUU |
| 62 | FLT1 | 1781 | GAAACAGAAUUGAGAGCAUC | GAAACAGAAUUGAGAGCAUC | GAUGCUCUCAAUUCUGUUUC |

Docosanoic acid (DCA)-hsiRNA

Docosahexaenoic acid (DHA)-hsiRNA

Phosphatidylcholine-DHA (g2DHA or DHAPCL)-hsiRNA

Fig. 14

| | siRNA ID | Gene | Targeting Position | Strand | Sequence and chemical modification pattern | Conjugate |
|---|---|---|---|---|---|---|
| 1 | Chol-hsiRNA*HTT* | HTT | 10150 | S | fC#mA#fG.mU.fA.mA.fA.mG.fA.mG.fA.mU.fU#mA#fA | 3'-Teg-Cholesterol |
| | | HTT | 10150 | AS | PmU#fU#mA.fA.mU.fC.mU.fC.mU.fU.mU.fA.mC#fU#mG#fA#mU#fA#mU#fA | |
| 2 | Cy3-Chol-hsiRNA*HTT* | HTT | 10150 | S | fC#mA#fG.mU.fA.mA.fA.mG.fA.mG.fA.mU.fU#mA#fA | 3'-Teg-Cholesterol, 5'-Cy3 |
| | | HTT | 10150 | AS | PmU#fU#mA.fA.mU.fC.mU.fC.mU.fU.mU.fA.mC#fU#mG#fA#mU#fA#mU#fA | |
| 3 | DHA-hsiRNA*HTT* | HTT | 10150 | S | fC#mA#fG.mU.fA.mA.fA.mG.fA.mG.fA.mU.fU#mA#fA | 3'-C7-DHA |
| | | HTT | 10150 | AS | PmU#fU#mA.fA.mU.fC.mU.fC.mU.fU.mU.fA.mC#fU#mG#fA#mU#fA#mU#fA | |
| 4 | C7-DHA-hsiRNA*HTT* | HTT | 10150 | S | fC#mA#fG.mU.fA.mA.fA.mG.fA.mG.fA.mU.fU#mA#fA | 3'-C7 |
| | | HTT | 10150 | AS | PmU#fU#mA.fA.mU.fC.mU.fC.mU.fU.mU.fA.mC#fU#mG#fA#mU#fA#mU#fA | |
| 5 | Cy3-DHA-hsiRNA*HTT* | HTT | 10150 | S | fC#mA#fG.mU.fA.mA.fA.mG.fA.mG.fA.mU.fU#mA#fA | 3'-C7-DHA, 5'-Cy3 |
| | | HTT | 10150 | AS | PmU#fU#mA.fA.mU.fC.mU.fC.mU.fU.mU.fA.mC#fU#mG#fA#mU#fA#mU#fA | |

Fig. 14 cont.

| | siRNA ID | Gene | Targeting Position | Strand | Sequence and chemical modification pattern | Conjugate |
|---|---|---|---|---|---|---|
| 6 | DHA-hsiRNA$^{PPIB}$ | PPIB | 437 | S | fC#mA#fA.mA.fU.mU.fC.mC.fA.mU.fC.mG.fU#mG#fA | 3'-C7-DHA |
| | | PPIB | 437 | AS | PmU#fC#mA.fC.mG.fA.mU.fG.mG.fA.mA.fU.mU#fU#mG#fC#mU#fG#mU#fU | |
| 7 | DHA-hsiRNA$^{PLK1}$ | PLK1 | 2140 | S | fG#mC#fA.mC.fA.mU.fU.mA.fA.mA.fC.mA.fG.mA.fA | 3'-C7-DHA |
| | | PLK1 | 2140 | AS | PmU#fU#mC.fU.mG.fU.mU.fU.mA.fA.mU.fG.mU#fG#mC#fA#mU#fA#mA#fA | |
| 8 | DHA-hsiRNA$^{NTC}$ | NTC | -- | S | fU#mG#fA.mC.fA.mA.fA.mU.fA.mC.fG.mA.fU#mU#fA | 3'-C7-DHA |
| | | | -- | AS | PmU#fA#mA.fU.mC.fG.mU.fA.mU.fU.mU.fG.mU#fC#mA#fA#mU#fC#mA#fU | |

Fig. 16
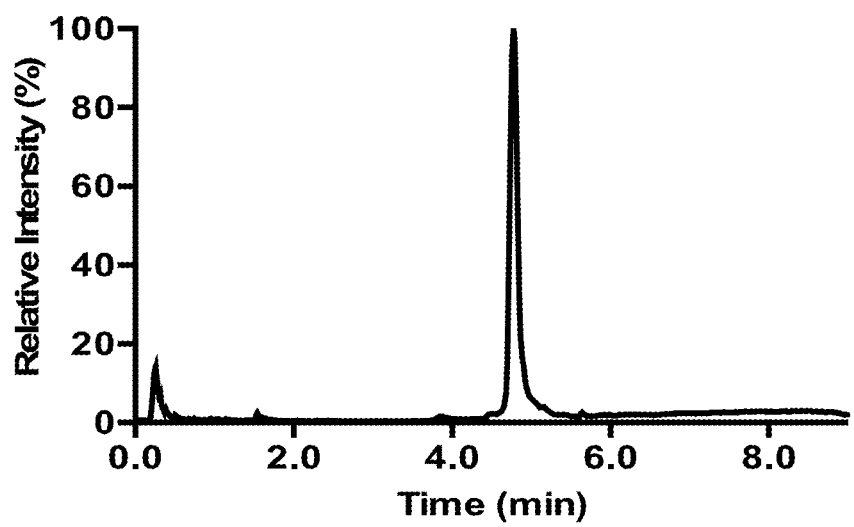
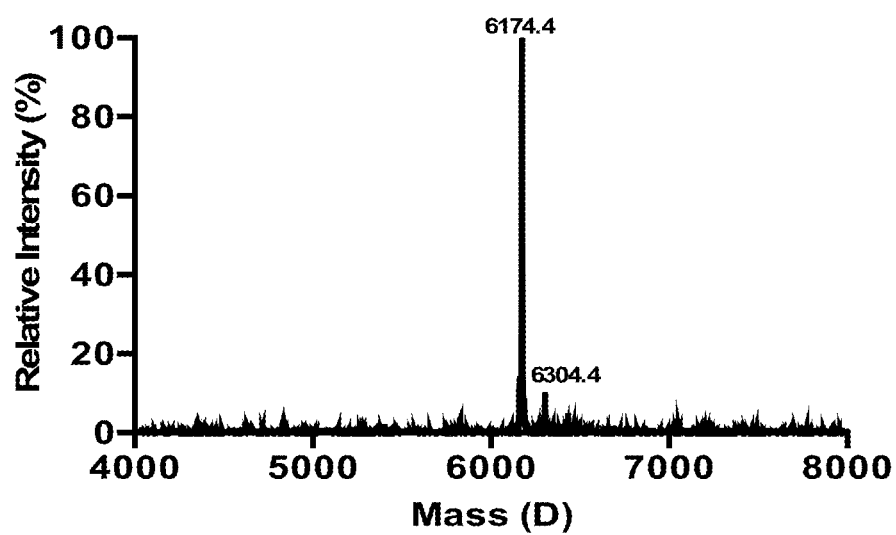

Fig. 23
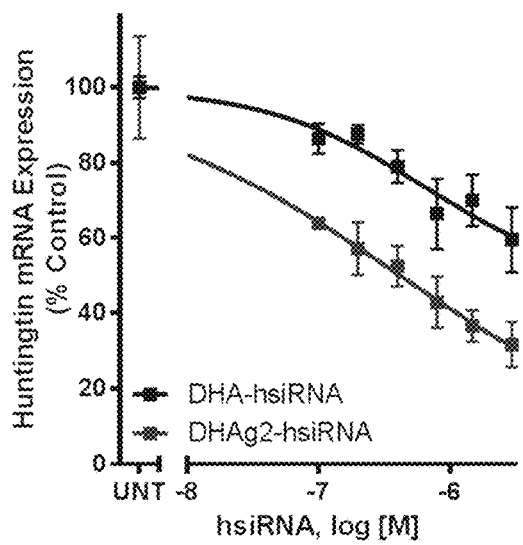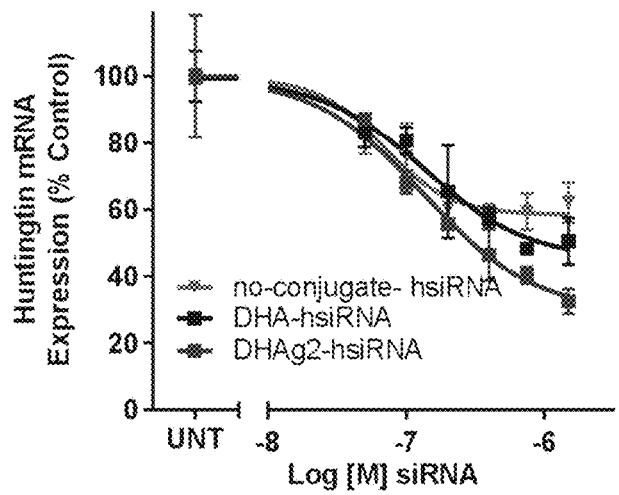
- Cortical Primary Neurons,
- 1 week
- QuantiGene®
- Normalized to PPIB

Fig. 44

| | VLDL | IDL | LDL | HDL |
|---|---|---|---|---|
| Enriched proteins | Apo B-100 | Apo B-100 | Apo B-100 | Apo A1, Apo A2 |
| Enriched lipids | Triglycerides | Triglycerides, Phospholipids, Cholesterol | Phospholipids, Cholesterol | Cholesterol |
| Primary Receptors | LDL (Apo B-100) receptor | LDL (Apo B-100) receptor | LDL (Apo B-100) receptor | Scavenger receptor B1 (SR-B1)<br>Megalin/Cubulin |
| Receptor expression patterns | Liver, Gut, Adrenal, Lung | Liver, Gut, Adrenal, Lung | Liver, Gut, Adrenal, Lung | SR-B1: Adrenals, Ovary, Testes, Liver<br>Megalin/Cubulin: Kidney, Placenta |

Fig. 47A
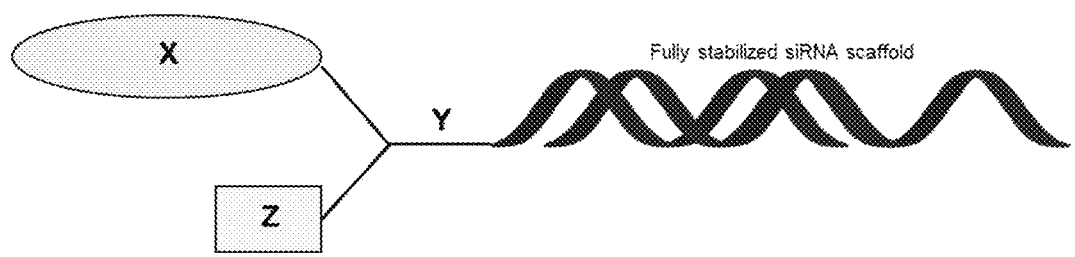
Fig. 47B
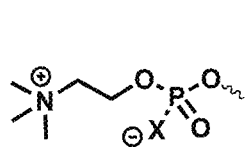  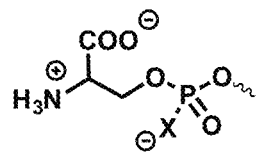
Phosphatidylcholine　　　　Phosphatidylserine
$X = O, S, BH_3$
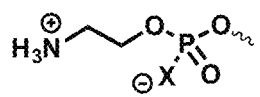　　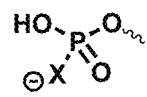
Phosphatidylamine　　　　Phosphoric acid

Fig. 48
Linkers and Spacers
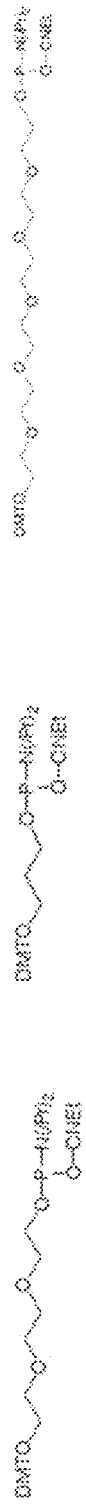
Polypeptides
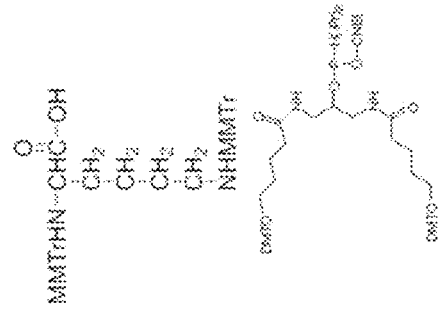
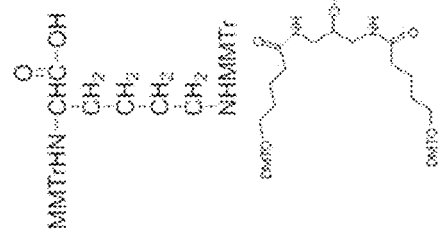
Branching Moieties
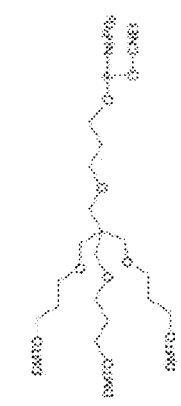
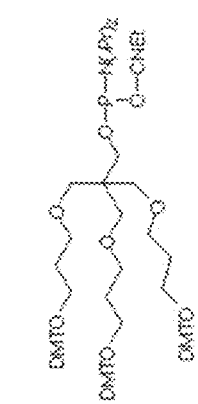
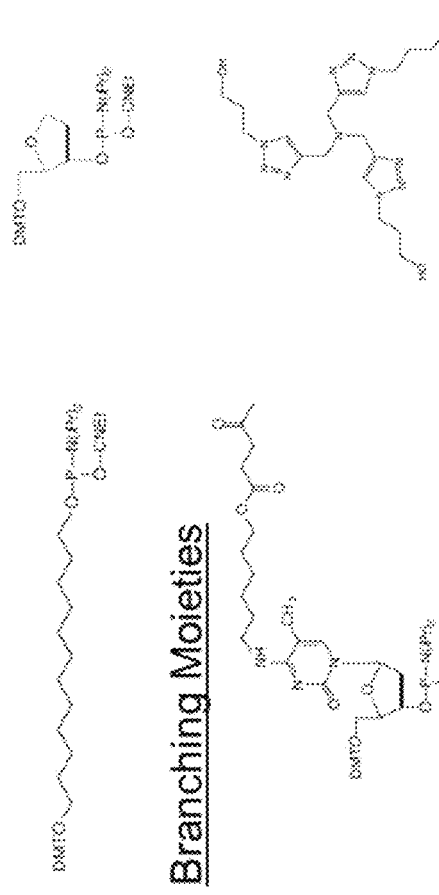

SEQUENCE LISTING

<160> NUMBER OF SEQ ID NOS: 186

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aaucagaggu gagcacugca                                               20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gaggugagca cugcaacaaa                                               20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aggugagcac ugcaacaaaa                                               20

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ugagcacugc aacaaaaagg                                               20

<210> SEQ ID NO 5

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uuuucucucg gaucuccaaa                                                   20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uuucucucgg aucccaaau                                                    20

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cucucggauc uccaaauuua                                                   20

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucucggaucu ccaaauuuaa                                                   20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ucggaucucc aaauuuaaaa                                                   20

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uccaaauuua aaagcacaag                                                   20

<210> SEQ ID NO 11
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ccaaauuuaa aagcacaagg                                                   20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
caaauuuaaa agcacaagga                                                   20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aagcacaagg aaugauugua                                                   20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gaaugauugu accacacaaa                                                   20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
auuguaccac acaaaguaau                                                   20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
guaccacaca aaguaaugua                                                   20

<210> SEQ ID NO 17
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 17
uaccacacaa aguaauguaa                                                     20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ccacacaaag uaauguaaaa                                                     20

<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
acacaaagua auguaaaaca                                                     20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aguaauguaa aacauuaaag                                                     20

<210> SEQ ID NO 21
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
guaauguaaa acauuaaagg                                                     20

<210> SEQ ID NO 22
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uaaaacauua aaggacucau                                                     20

<210> SEQ ID NO 23
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 23
acauuaaagg acucauuaaa                                                    20

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ggacucauua aaaguaaaca                                                    20

<210> SEQ ID NO 25
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
acucauuaaa aaguaacagu                                                    20

<210> SEQ ID NO 26
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aaaguaacag uugucucaua                                                    20

<210> SEQ ID NO 27
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
caucaucauc aucauagcua                                                    20

<210> SEQ ID NO 28
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
caucaucauc auagcuauca                                                    20

<210> SEQ ID NO 29
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 29
caucaucaua gcuaucauca                                              20

<210> SEQ ID NO 30
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
aucaucauca ucaucauagc                                              20

<210> SEQ ID NO 31
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
caucaucauc auagcuacca                                              20

<210> SEQ ID NO 32
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucaucauagc uaccauuuau                                              20

<210> SEQ ID NO 33
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
caucauagcu accauuuauu                                              20

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
agcuaccauu uauugaaaac                                              20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 35
uaccauuuau ugaaaacuau          20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
aacuucaaag aacuuauccu          20

<210> SEQ ID NO 37
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
caaagaacuu auccuuuagu          20

<210> SEQ ID NO 38
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uccuuuaguu ggagagccaa          20

<210> SEQ ID NO 39
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
cuuuaguugg agagccaaga          20

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uuaguuggag agccaagaca          20

<210> SEQ ID NO 41
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 41
uaguuggaga gccaagacaa                                              20

<210> SEQ ID NO 42
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uuggagagcc aagacaauca                                              20

<210> SEQ ID NO 43
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ggagagccaa gacaaucaua                                              20

<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gagccaagac aaucauaaca                                              20

<210> SEQ ID NO 45
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ccaagacaau cauaacaaua                                              20

<210> SEQ ID NO 46
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aagacaauca uaacaauaac                                              20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 47
agcugucugc uucucacagg                                               20

<210> SEQ ID NO 48
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gauccugaac ugaguuuaaa                                               20

<210> SEQ ID NO 49
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
auccugaacu gaguuuaaaa                                               20

<210> SEQ ID NO 50
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ugaacugagu uuaaaaggca                                               20

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
guuuaaaagg cacccagcac                                               20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
aucaaaugca acguacaaag                                               20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
```

-continued ucaaaugcaa cguacaaaga                                          20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
guuguauggu uaaaagaugg                                          20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uuuaaaaacc ucacugccac                                          20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uaaaaaccuc acugccacuc                                          20

<210> SEQ ID NO 57
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
aaaaccucac ugccacucua                                          20

<210> SEQ ID NO 58
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gaaacagaau ugagagcauc                                          20

<210> SEQ ID NO 59
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
auuacaauca gaggugagca cugcaacaaa                                              30

<210> SEQ ID NO 60
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
aaucagaggu gagcacugca acaaaaaggc                                              30

<210> SEQ ID NO 61
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
aucagaggug agcacugcaa caaaaaggcu                                              30

<210> SEQ ID NO 62
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
agaggugagc acugcaacaa aaaggcuguu                                              30

<210> SEQ ID NO 63
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ggcuguuuuc ucucggaucu ccaaauuuaa                                              30

<210> SEQ ID NO 64
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
gcuguuuucu cucggaucuc caaauuuaaa                                              30

<210> SEQ ID NO 65
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65 guuucucuc ggaucuccaa auuuaaaagc                                               30

<210> SEQ ID NO 66
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uuuucucucg gaucuccaaa uuuaaaagca                                      30

<210> SEQ ID NO 67
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uucucucgga ucuccaaauu uaaaagcaca                                      30

<210> SEQ ID NO 68
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ggaucuccaa auuuaaaagc acaaggaaug                                      30

<210> SEQ ID NO 69
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gaucuccaaa uuuaaaagca caaggaauga                                      30

<210> SEQ ID NO 70
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
aucuccaaau uuaaaagcac aaggaaugau                                      30

<210> SEQ ID NO 71
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uuuaaaagca caaggaauga uuguaccaca                                      30

<210> SEQ ID NO 72
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
acaaggaaug auuguaccac acaaaguaau                                    30

<210> SEQ ID NO 73
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
gaaugauugu accacacaaa guauguaaa                                     30

<210> SEQ ID NO 74
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ugauuguacc acacaaagua auguaaaaca                                    30

<210> SEQ ID NO 75
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gauuguacca cacaaaguaa uguaaaacau                                    30

<210> SEQ ID NO 76
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uuguaccaca caaaguaaug uaaaacauua                                    30

<210> SEQ ID NO 77
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
guaccacaca aaguaaugua aaacauuaaa                                    30

<210> SEQ ID NO 78
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 78
cacaaaguaa uguaaaacau uaaaggacuc                    30

<210> SEQ ID NO 79
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 79
acaaaguaau guaaaacauu aaaggacuca                    30

<210> SEQ ID NO 80
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 80
uaauguaaaa cauuaaagga cucauuaaaa                    30

<210> SEQ ID NO 81
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 81
guaaaacauu aaaggacuca uuaaaaagua                    30

<210> SEQ ID NO 82
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 82
uuaaaggacu cauuaaaaag uaacaguugu                    30

<210> SEQ ID NO 83
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 83
aaaggacuca uuaaaaagua acaguugucu                    30

<210> SEQ ID NO 84

<210> SEQ ID NO 84
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 84
auuaaaaagu aacaguuguc ucauaucauc                                         30

<210> SEQ ID NO 85
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 85
gucaucauca ucaucaucau agcuaucauc                                         30

<210> SEQ ID NO 86
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 86
aucaucauca ucaucauagc uaucaucauu                                         30

<210> SEQ ID NO 87
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 87
aucaucauca ucauagcuau caucauuauc                                         30

<210> SEQ ID NO 88
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 88
ucaucaucau caucaucauc auagcuacca                                         30

<210> SEQ ID NO 89
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 89
aucaucauca ucaucaucau agcuaccauu                                         30

<210> SEQ ID NO 90
<211> LENGTH: 30

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
aucaucauca ucaucauagc uaccauuuau                                       30

<210> SEQ ID NO 91
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
caucaucauc auagcuacca uuuauugaaa                                       30

<210> SEQ ID NO 92
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
aucaucauca uagcuaccau uuauugaaaa                                       30

<210> SEQ ID NO 93
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
aucauagcua ccauuuauug aaaacuauua                                       30

<210> SEQ ID NO 94
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
auagcuacca uuuauugaaa acuauuaugu                                       30

<210> SEQ ID NO 95
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gugucaacuu caaagaacuu auccuuuagu                                       30

<210> SEQ ID NO 96
<211> LENGTH: 30
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 96
aacuucaaag aacuuauccu uuaguuggag                                      30

<210> SEQ ID NO 97
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
acuuauccuu uaguuggaga gccaagacaa                                      30

<210> SEQ ID NO 98
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uuauccuuua guuggagagc caagacaauc                                      30

<210> SEQ ID NO 99
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
auccuuuagu uggagagcca agacaaucau                                      30

<210> SEQ ID NO 100
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uccuuuaguu ggagagccaa gacaaucaua                                      30

<210> SEQ ID NO 101
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uuuaguugga gagccaagac aaucauaaca                                      30

<210> SEQ ID NO 102
<211> LENGTH: 30
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 102
uaguuggaga gccaagacaa ucauaacaau                                          30

<210> SEQ ID NO 103
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uuggagagcc aagacaauca uaacaauaac                                          30

<210> SEQ ID NO 104
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
gagagccaag acaaucauaa caauaacaaa                                          30

<210> SEQ ID NO 105
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
gagccaagac aaucauaaca auaacaaaug                                          30

<210> SEQ ID NO 106
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
ugcucagcug ucugcuucuc acaggaucua                                          30

<210> SEQ ID NO 107
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uaaaagaucc ugaacugagu uuaaaaggca                                          30

<210> SEQ ID NO 108
<211> LENGTH: 30
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 108
aaaagauccu gaacugaguu uaaaaggcac                                           30

<210> SEQ ID NO 109
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gauccugaac ugaguuuaaa aggcacccag                                           30

<210> SEQ ID NO 110
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
acugaguuua aaaggcaccc agcacaucau                                           30

<210> SEQ ID NO 111
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
aucauaucaa augcaacgua caaagaaaua                                           30

<210> SEQ ID NO 112
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
ucauaucaaa ugcaacguac aaagaaauag                                           30

<210> SEQ ID NO 113
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
cggaaguugu augguuaaaa gaugggvuac                                           30

<210> SEQ ID NO 114
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 114
auguguuuaa aaaccucacu gccacucuaa                                30

<210> SEQ ID NO 115
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
guguuuaaaa accucacugc cacucuaauu                                30

<210> SEQ ID NO 116
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
guuuaaaaac cucacugcca cucuaauugu                                30

<210> SEQ ID NO 117
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
caugggaaac agaauugaga gcaucacuca                                30

<210> SEQ ID NO 118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ugcagugcuc accucugauu                                           20

<210> SEQ ID NO 119
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uuuguugcag ugcucaccuc                                           20

<210> SEQ ID NO 120
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 120
uuuuguugca gugcucaccu                                         20

<210> SEQ ID NO 121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
ccuuuuuguu gcagugcuca                                         20

<210> SEQ ID NO 122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
uuuggagauc cgagagaaaa                                         20

<210> SEQ ID NO 123
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
auuuggagau ccgagagaaa                                         20

<210> SEQ ID NO 124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uaaauuugga gauccgagag                                         20

<210> SEQ ID NO 125
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
uuaaauuugg agauccgaga                                         20

<210> SEQ ID NO 126
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 126
uuuuaaauuu ggagauccga                                               20

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
cuugugcuuu uaaauuugga                                               20

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ccuugugcuu uaaauuugg                                                20

<210> SEQ ID NO 129
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uccuugugcu uuuaaauuug                                               20

<210> SEQ ID NO 130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
uacaaucauu ccuugugcuu                                               20

<210> SEQ ID NO 131
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
uuuguguggu acaaucauuc                                               20

<210> SEQ ID NO 132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
```

```
auuacuuugu gugguacaau                                              20

<210> SEQ ID NO 133
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uacauuacuu ugugugguac                                              20

<210> SEQ ID NO 134
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
uuacauuacu uuguguggua                                              20

<210> SEQ ID NO 135
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
uuuuacauua cuuugugugg                                              20

<210> SEQ ID NO 136
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uguuuuacau uacuuugugu                                              20

<210> SEQ ID NO 137
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
cuuuaauguu uuacauuacu                                              20

<210> SEQ ID NO 138
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
```
ccuuuaaugu uuuacauuac                                           20

<210> SEQ ID NO 139
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
augaguccuu uaauguuuua                                           20

<210> SEQ ID NO 140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uuuaaugagu ccuuuaaugu                                           20

<210> SEQ ID NO 141
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uguuacuuuu uaaugagucc                                           20

<210> SEQ ID NO 142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
acuguuacuu uuuaaugagu                                           20

<210> SEQ ID NO 143
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uaugagacaa cuguuacuuu                                           20

<210> SEQ ID NO 144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
uagcuaugau gaugaugaug                                           20

<210> SEQ ID NO 145
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ugauagcuau gaugaugaug                                              20

<210> SEQ ID NO 146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
ugaugauagc uaugaugaug                                              20

<210> SEQ ID NO 147
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
gcuaugauga ugaugaugau                                              20

<210> SEQ ID NO 148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ugguagcuau gaugaugaug                                              20

<210> SEQ ID NO 149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
auaaauggua gcuaugauga                                              20

<210> SEQ ID NO 150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
aauaaauggu agcuaugaug                                              20

<210> SEQ ID NO 151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
guuuucaaua aaugguagcu                                               20

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
auaguuuuca auaaauggua                                               20

<210> SEQ ID NO 153
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
aggauaaguu cuuugaaguu                                               20

<210> SEQ ID NO 154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
acuaaaggau aaguucuuug                                               20

<210> SEQ ID NO 155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uuggcucucc aacuaaagga                                               20

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
ucuuggcucu ccaacuaaag                                               20

```
<210> SEQ ID NO 157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ugucuuggcu cuccaacuaa                                                     20

<210> SEQ ID NO 158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
uugucuuggc ucuccaacua                                                     20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ugauugucuu ggcucuccaa                                                     20

<210> SEQ ID NO 160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
uaugauuguc uuggcucucc                                                     20

<210> SEQ ID NO 161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uguuaugauu gucuuggcuc                                                     20

<210> SEQ ID NO 162
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uauuguuaug auugucuugg                                                     20

<210> SEQ ID NO 163
```

<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
guuauuguua ugauugucuu                                              20

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
ccugugagaa gcagacagcu                                              20

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uuuaaacuca guucaggauc                                              20

<210> SEQ ID NO 166
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
uuuuaaacuc aguucaggau                                              20

<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
ugccuuuuaa acucaguuca                                              20

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
gugcugggug ccuuuuaaac                                              20

<210> SEQ ID NO 169
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
cuuuguacgu ugcauuugau                                               20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ucuuuguacg uugcauuuga                                               20

<210> SEQ ID NO 171
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
ccaucuuuua accauacaac                                               20

<210> SEQ ID NO 172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
guggcaguga gguuuuuaaa                                               20

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
gaguggcagu gagguuuuua                                               20

<210> SEQ ID NO 174
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uagaguggca gugagguuuu                                               20

<210> SEQ ID NO 175
<211> LENGTH: 20
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 175
gaugcucuca auucuguuuc                                            20

<210> SEQ ID NO 176
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 176
caguaaagag auuaa                                                 15

<210> SEQ ID NO 177
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 177
uuaaucucuu uacugauaua                                            20

<210> SEQ ID NO 178
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 178
caaauuccau cguga                                                 15

<210> SEQ ID NO 179
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 179
ucacgaugga auuugcuguu                                            20

<210> SEQ ID NO 180
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 180
gcacauuaaa cagaa                                                 15

<210> SEQ ID NO 181
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 181
uucuguuuaa ugugcauaaa                                                    20

<210> SEQ ID NO 182
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ugacaaauac gauua                                                         15

<210> SEQ ID NO 183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
uaaucguauu ugucaaucau                                                    20

<210> SEQ ID NO 184
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
ggaucuccaa auuua                                                         15

<210> SEQ ID NO 185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
uauaaauggu agcuaugaug                                                    20

<210> SEQ ID NO 186
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uagcuaccau uuaua                                                         15
```

BIOACTIVE CONJUGATES FOR OLIGONUCLEOTIDE DELIVERY

CROSS REFERENCE TO RELATED APPLICATIONS

This application claims the benefit of U.S. Provisional Application No. 62/317,118, filed Apr. 1, 2016; U.S. Provisional Application No. 62/287,253, filed Jan. 26, 2016; U.S. Provisional Application No. 62/286,406, filed Jan. 24, 2016; and U.S. Provisional Application No. 62/205,199, filed Aug. 14, 2015, the contents of which are incorporated herein by reference in their entirety.

STATEMENT OF FEDERALLY SPONSORED RESEARCH

This invention was made with government support under Grant Nos. GM108803and TR000888awarded by the National Institutes of Health, and a grant from the CHDI Foundation. The Government has certain rights in the invention.

TECHNICAL FIELD

This disclosure relates to novel hydrophobically-conjugated oligonucleotides useful for RNA interference (RNAi). The oligonucleotide conjugates are designed to achieve unexpectedly high efficacy, uptake and tissue distribution.

BACKGROUND

RNA interference represents a simple and effective tool for inhibiting the function of genes. The promise of RNA interference as a general therapeutic strategy, however, depends on the ability to deliver small RNAs to a wide range of tissues. Currently, small therapeutic RNAs can only be delivered effectively to liver. There remains a need for self-delivering siRNA that are characterized by efficient RISC entry, minimal immune response and off-target effects, efficient cellular uptake without formulation, and efficient and specific tissue distribution.

SUMMARY

In one aspect, provided herein is a compound of formula (1):

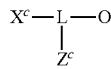

$$X^c - L - O \\ | \\ Z^c \qquad (1)$$

wherein:
O is a double-stranded nucleic acid comprising a first oligonucleotide and a second oligonucleotide, wherein:
  (1) the first oligonucleotide comprises at least 16 contiguous nucleotides, a 5' end, a 3' end and has complementarity to a target;
  (2) the second oligonucleotide comprises at least 15 contiguous nucleotides, a 5' end, a 3' end, and has homology with a target; and
  (3) a portion of the first oligonucleotide is complementary to a portion of the second oligonucleotide;
L is a divalent or trivalent linker;
$X^c$ is a hydrophobic moiety; and
$Z^c$ is a phosphodiester or phosphodiester derivative, or is absent.

In another aspect, provided herein is a method for selectively delivering a compound of formula (1), or a disclosed embodiment thereof, to a particular organ in a patient, comprising administering said compound to the patient, wherein the compound has a selective affinity for a serum lipoprotein.

BRIEF DESCRIPTION OF THE DRAWINGS

FIG. 1N shows a representative LC-MS profile following purification of a synthesized hsiRNA conjugate as in FIG. 1L; Cy3-labeled sFLT-DHA conjugate (pure product) shown.

FIG. 8 shows a series of targeting regions and corresponding sense- and guide-sequences (SEQ ID NOS 1-30, 27, 31-117, 1-30, 27, 31-58, 1-30, 27, 31-58, 118-147, 144, and 148-175, respectively, in order of columns).

FIG. 14 shows modified oligonucleotide sequences (SEQ ID NOS 176-177, 176-177, 176-177, 176-177, 176-177, 178-183, respectively, in order of appearance). Chemical modifications are abbreviated as follows, wherein "X" represents A, U, G, or C: fX (2'-fluoro), mX (2'-O-methyl), P (5'-phosphate), Chol (Cholesterol), '#' (phosphorothioate backbone modification), '.' (phosphodiester backbone).

FIG. 16 shows a representative LC-MS characterization of Cy3-DHA-hsiRNAHTT; Calculated: 6174.1 for [M−H]−, found: 6174.4. Conditions: Buffer A: 15 mM Dibutylamine/ 25 mM HFIP, Buffer B: 20% A in MeOH, Column: xbidge OST C18, 2.5 urn, Gradient: 0-10 min (1% B-80% B), 10-13 min (80% B-80% B), 13.1 min (80% B-1% B), 13.1-18 min (1% B-1% B).

FIG. 23 shows potency and delivery to primary neurons of DHA-hsiRNA and g2DHA-hsiRNA. hsiRNA-conjugate structures and modifications are shown in FIG. 9A-F and the HTT siRNA sequence is shown in FIG. 14.

FIG. 44 shows serum lipoprotein binding properties of lipid-conjugated siRNAs.

FIG. 47A-B shows chemical structures of novel hydrophobic siRNA constructs. Polyunsaturated fatty acids are typically circulated in the bloodstream in an esterified form, meaning they are linked to glycerol, long-chain aliphatic alcohols, amides, phosphatidylcholine, phosphatidylserine, phosphoric acid, and phosphatidylethanolamine, among others. Defining the path to synthesize metabolically stable analogs of these naturally existing circulating compounds is one way to improve polyunsaturated fatty acid-siRNA tissue distribution and cellular uptake. (A) A generic hydrophobic siRNA construct where X is a hydrophobic lipid bioconjugate (e.g. polyunsaturated fatty acid, cholesterol). Y is a chemically stable trifunctional spacer or linker, which could be cleavable or not. Z is a naturally occurring ester linkage (e.g. phosphatidycholine, phosphatidylserine, phosphoric acid, see FIG. 47B)

FIG. 48 shows examples of linkers, spacer, and branching moieties. The exact chemical composition of the linker is not essential for activity as long as the branching structure can be generated

DETAILED DESCRIPTION

Figure 1A:
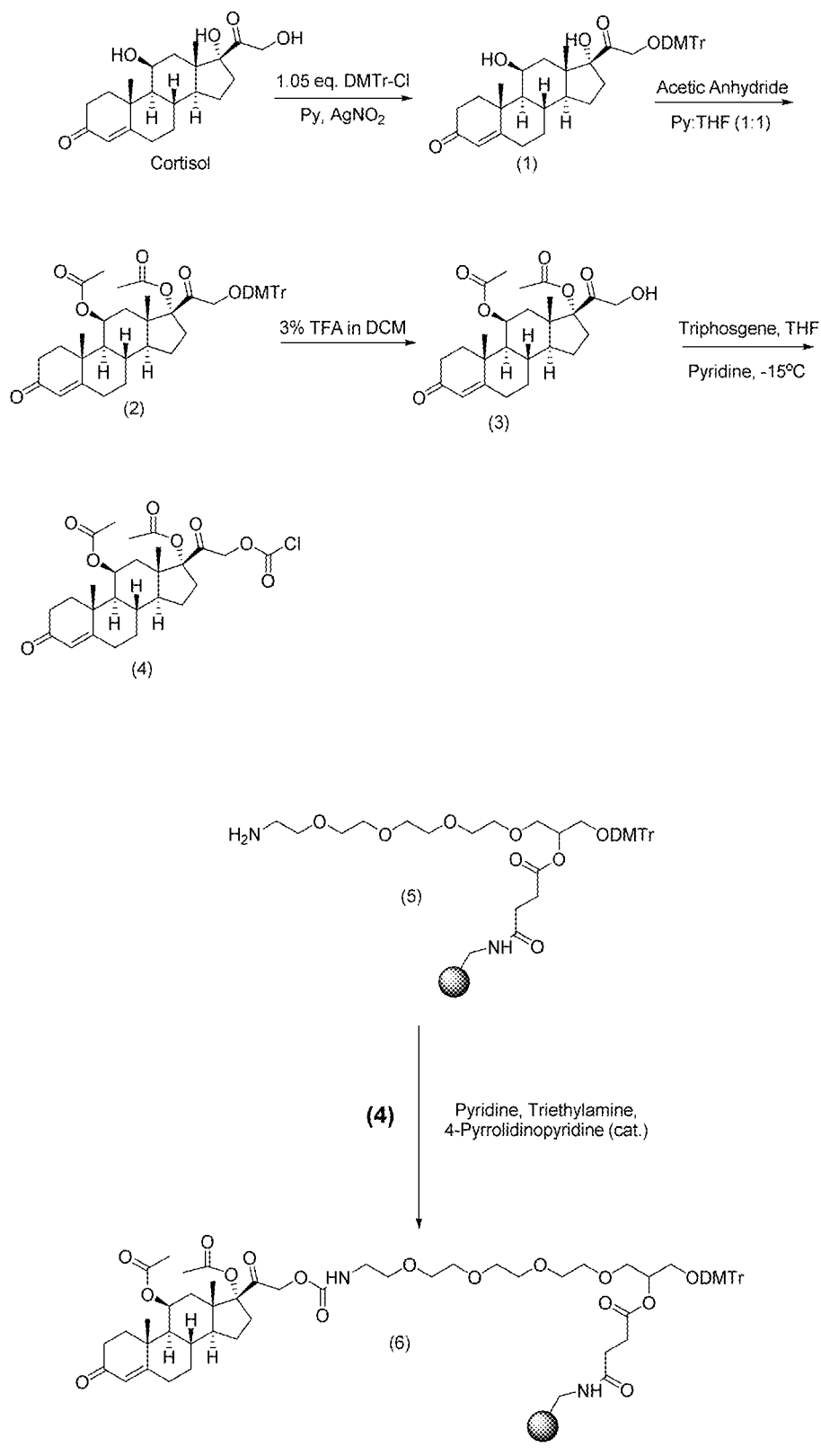
FIG. 1A shows a synthetic approach for cortisol-conjugated oligonucleotides.
Figure 1B:
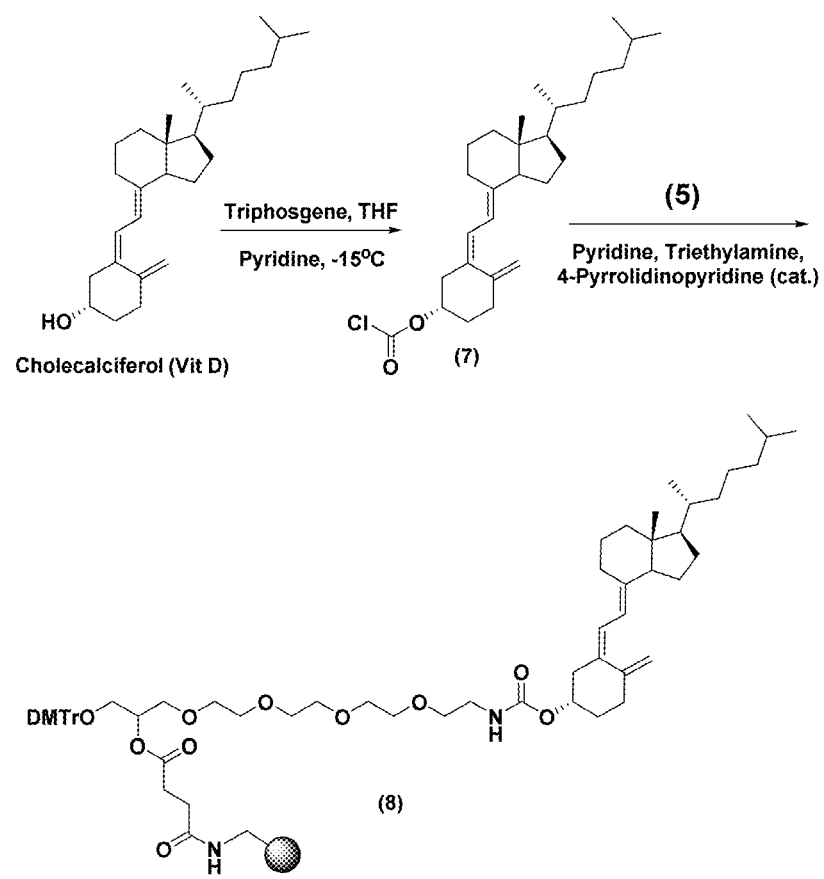
FIG. 1B shows a synthetic approach for calciferol-conjugated oligonucleotides.

The present disclosure relates to compositions comprising small RNAs that are completely stable and fully active. To identify chemical and biological properties that drive small RNA tissue distribution and cellular uptake, these small RNAs were conjugated to several naturally occurring bio-active steroids, endocannabinoid-like lipids, and nucleoside analogs. The resulting conjugates selectively delivered small RNAs to a range of tissues, including heart, kidneys, muscle, placenta, vasculature, and brain.

The compositions described herein promote simple, efficient, non-toxic delivery of metabolically stable siRNA, and promote potent silencing of therapeutic targets in a range of tissues in vivo. Provided herein is a chemistry platform for targeting other tissues matching the performance and clinical impact of GalNAc conjugates in the liver. Several bio-active steroids and endocannabinoid-like bioactive lipid conjugates were screened and identified. These compounds show unprecedented distribution, neuronal uptake, efficacy, and lack of toxicity in several tissues, including endothelia, kidneys, liver, spleen, heart, lung, mouse brain and spinal cord.

In certain aspects, the oligonucleotide conjugates of the invention were identified through a process involving: (1) providing a fully metabolically stable scaffolds (no RNA left); (2) selecting compounds which are biologically known to internalize inside the cells and identifying the ranges of hydrophobicities which allow efficient tissue distribution; (3) conjugating these hydrophobic compounds to the metabolically stable siRNAs; and (4) screening distribution, efficacy and toxicity in vivo. The discovery of the optimal range of hydrophobicity defines the chemical scaffold ranges expected to be efficacious. It was found that low hydrophobicity (cortisol like) was not sufficient to secure good tissue retention, whereas too much hydrophobicity (e.g., cholesterol) minimized distribution from the site of injection. The golden medium (e.g., DHA, DHAg2, calciferol) enabled good tissue retention and distribution.

In a first aspect, provided herein is a compound of formula (1):

wherein:

O is a double-stranded nucleic acid comprising a first oligonucleotide and a second oligonucleotide, wherein:
   (1) the first oligonucleotide comprises at least 16 contiguous nucleotides, a 5' end, a 3' end and has complementarity to a target;
   (2) the second oligonucleotide comprises at least 15 contiguous nucleotides, a 5' end, a 3' end, and has homology with a target; and
   (3) a portion of the first oligonucleotide is complementary to a portion of the second oligonucleotide;

L is a divalent or trivalent linker;

$X^c$ is a hydrophobic moiety; and $Z^c$ is a phosphodiester or phosphodiester derivative, or is absent.

Variable L

In one embodiment, L comprises an ethylene glycol chain, an alkyl chain, a peptide, RNA, DNA, a phosphodiester, a phosphorothioate, a phosphoramidate, an amide, a carbamate, or a combination thereof; and wherein L is attached to O via the second oligonucleotide. In one embodiment, L is a divalent linker. In another embodiment, L is a trivalent linker. In certain embodiments, L corresponds to a linker of FIG. 48.

In a particular embodiment, L is the trivalent linker L1, also referred to herein as C7:

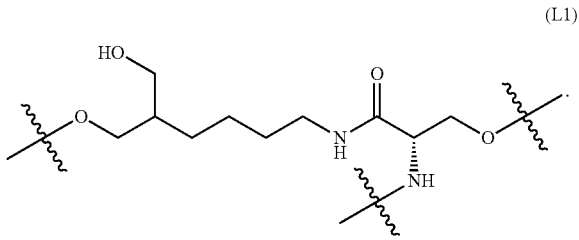 [SMILES: *N[C@@H](CO*)C(=O)NCCCCC(CO)CO*]

(L1)

In another particular embodiment, L is the divalent linker L2:

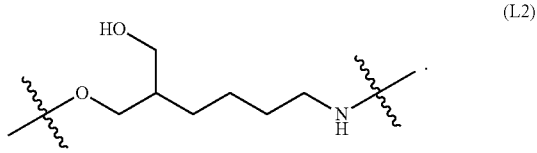 [SMILES: *NCCCCC(CO)CO*]

(L2)

Figure 1C:
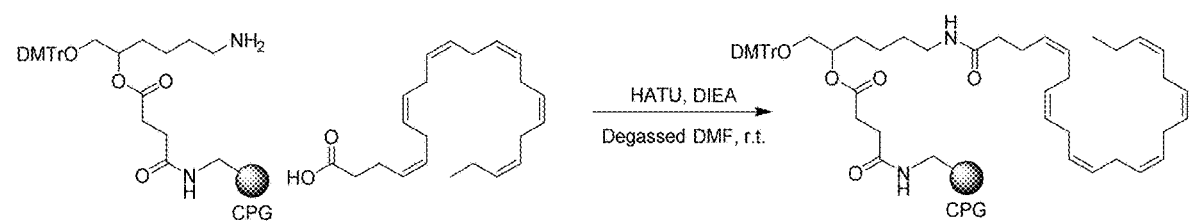
FIG. 1C shows a synthetic approach for DHA-conjugated oligonucleotides.
Figure 1D:
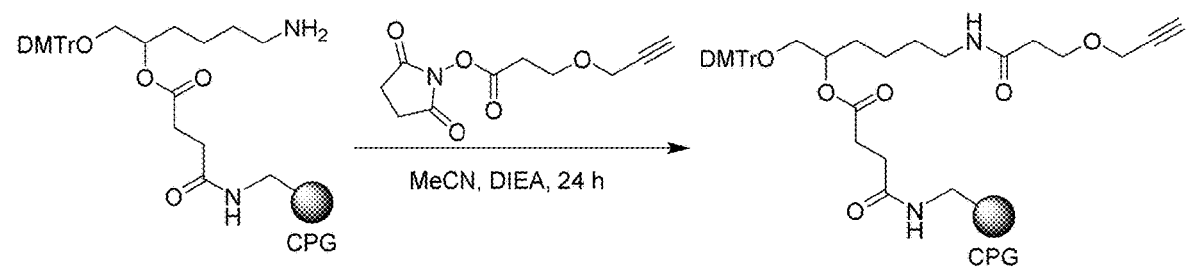
FIG. 1D shows a synthetic approach for preparation of an alkynylated-oligonucleotide for click conjugation.
Figure 1E:
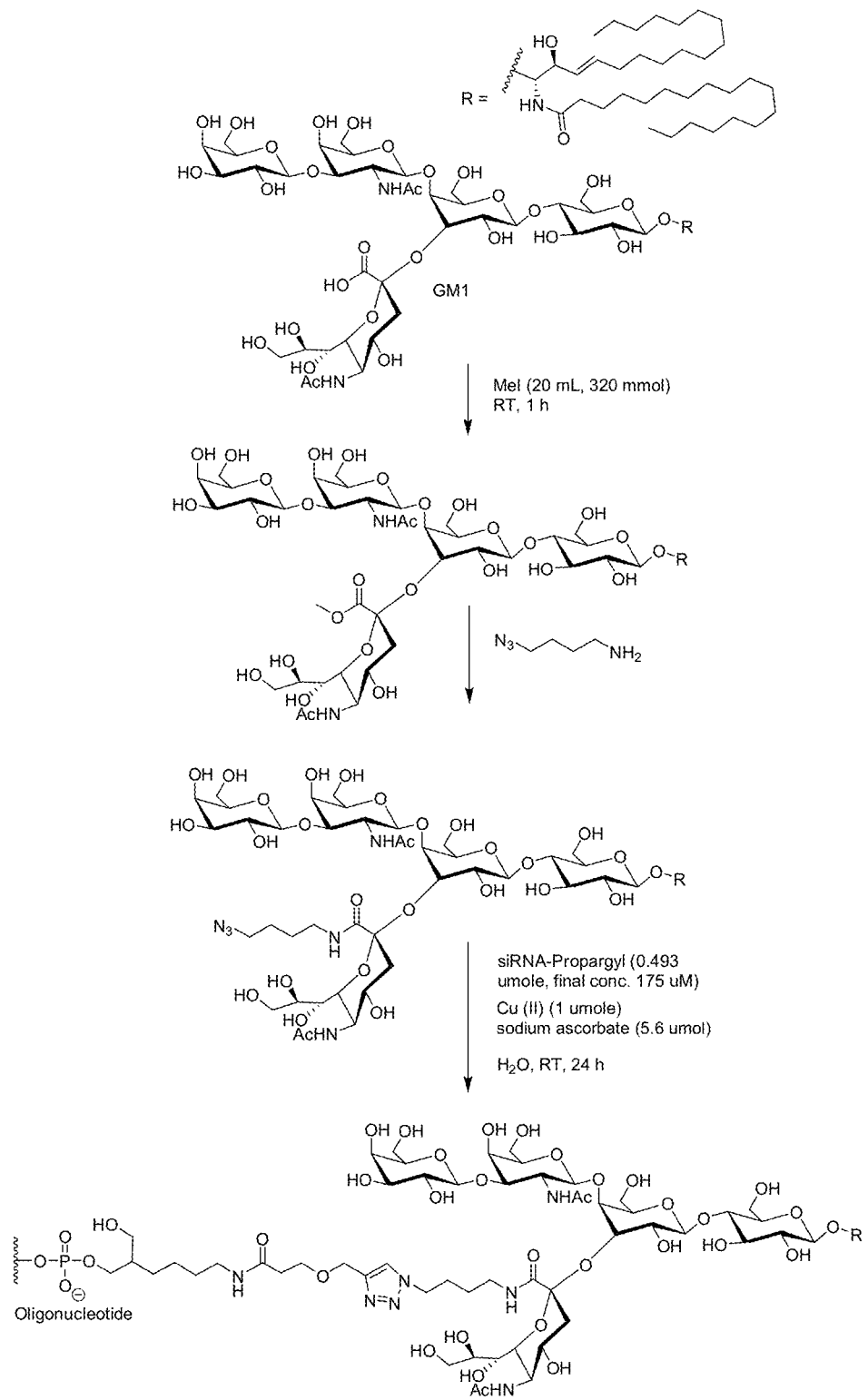
FIG. 1E shows a synthetic approach for GM1-conjugated oligonucleotides.
Figure 1F:
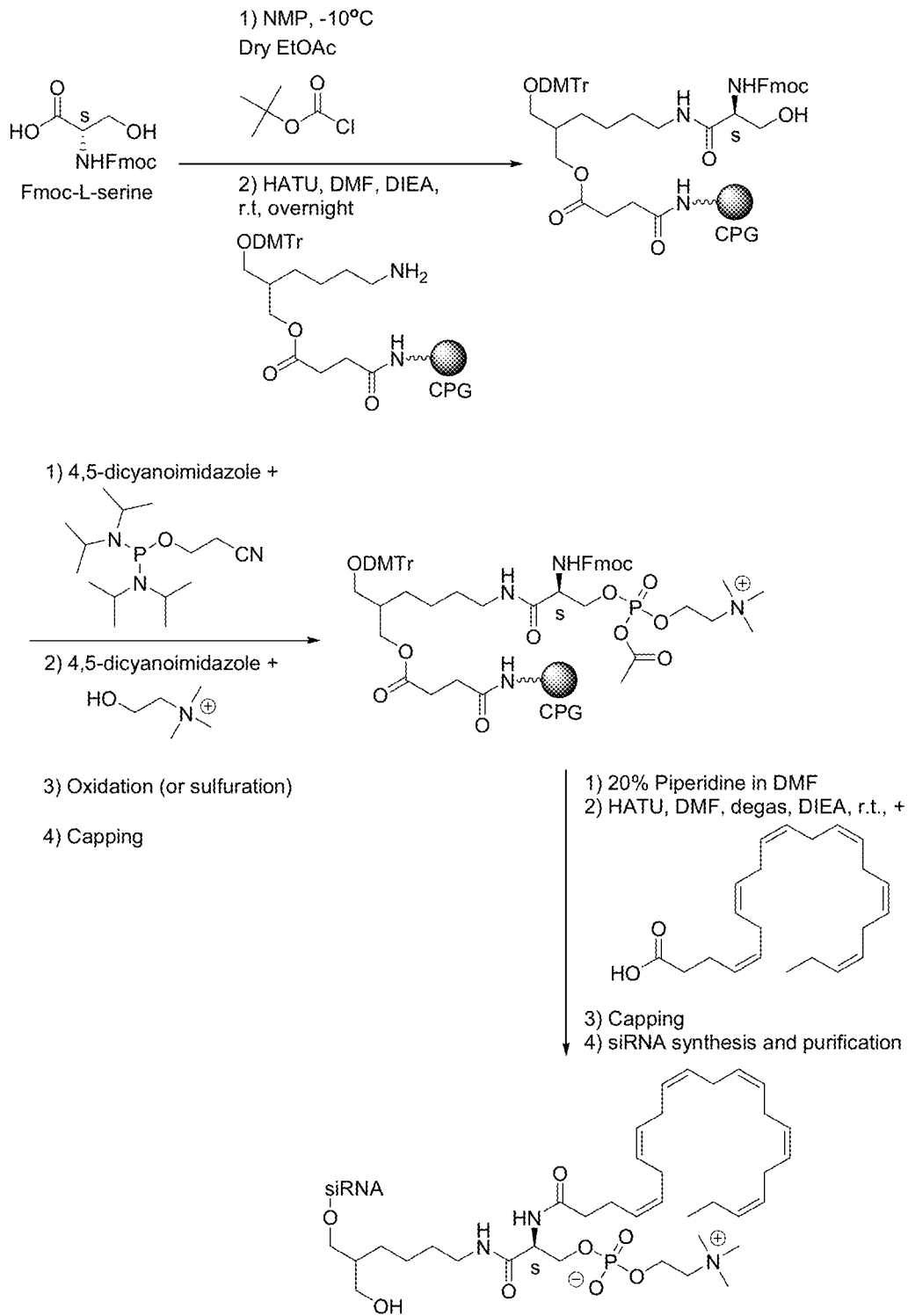
FIG. 1F shows a synthetic approach for lysophosphatidylcholine esterified DHA-hsiRNA conjugate (referred to as DHAPCL-hsiRNA, PC-DHA-hsiRNA, g2DHA-hsiRNA, or DHA-G2-hsiRNA).
Figure 1G:
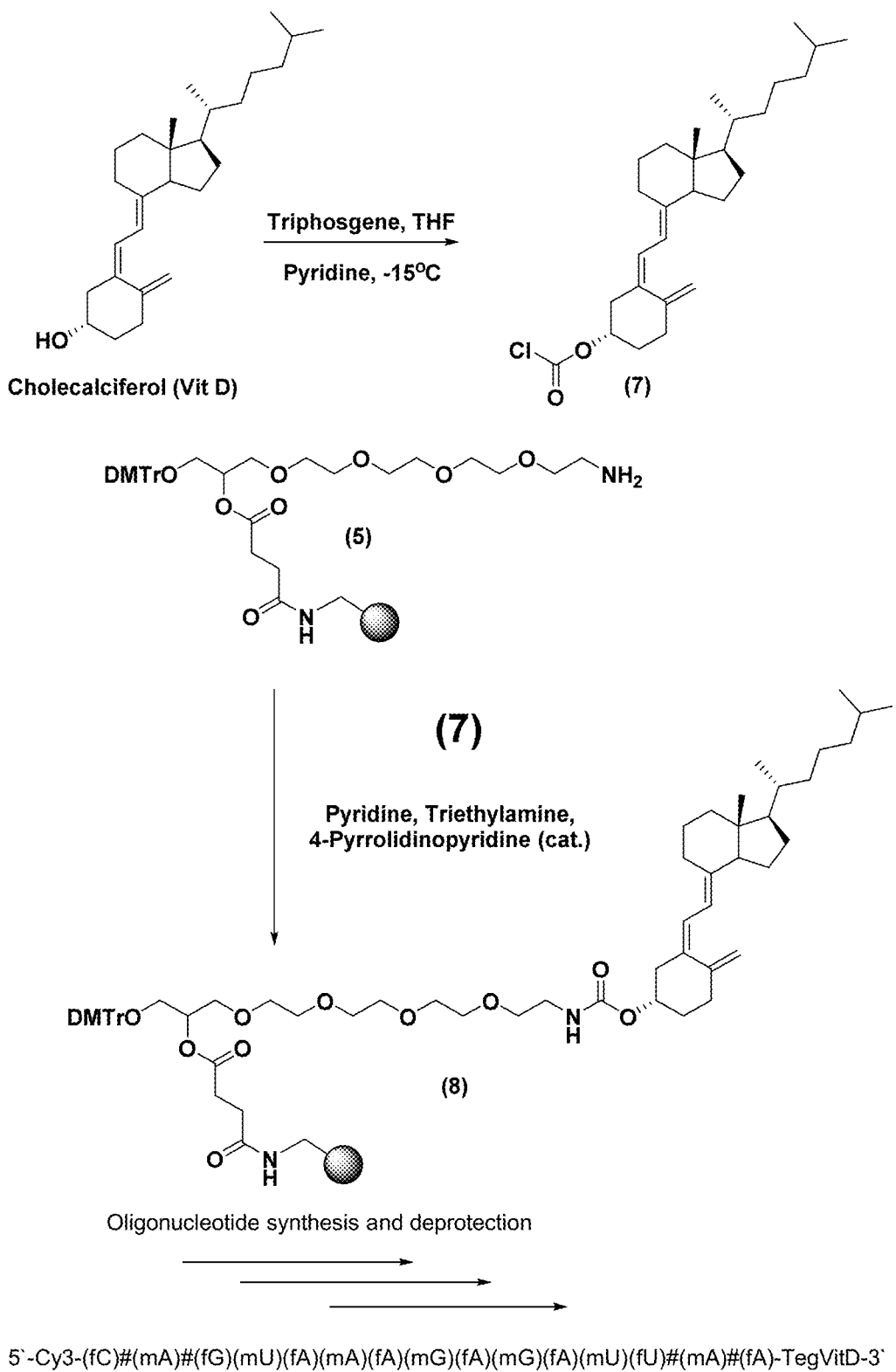
FIG. 1G shows a synthetic approach for an hsiRNA-Calciferol oligonucleotide (SEQ ID NO: 176).
Figure 1H:
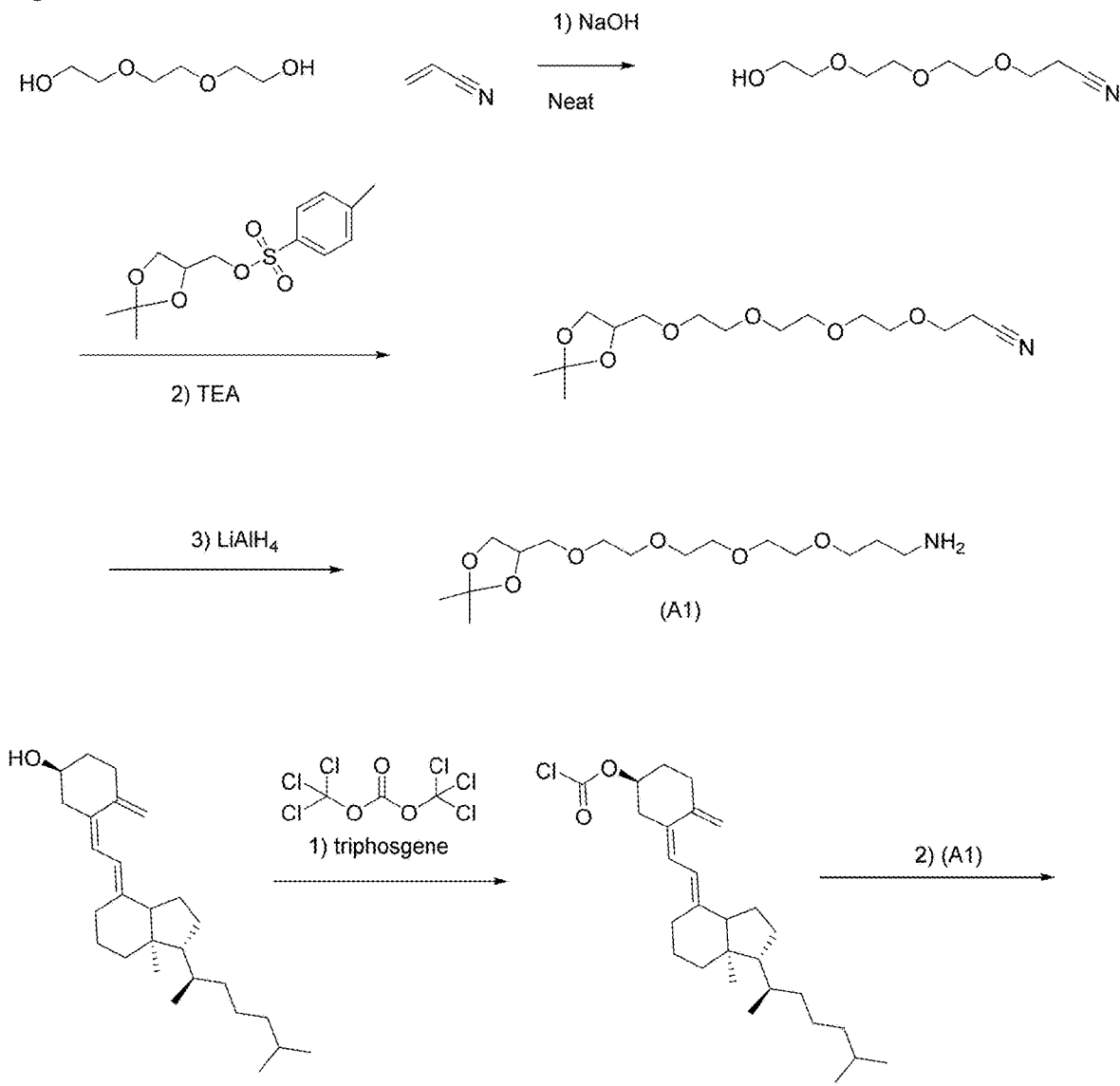
FIG. 1H shows an alternative synthetic approach for an hsiRNA-Calciferol oligonucleotide.
Figure 1H:
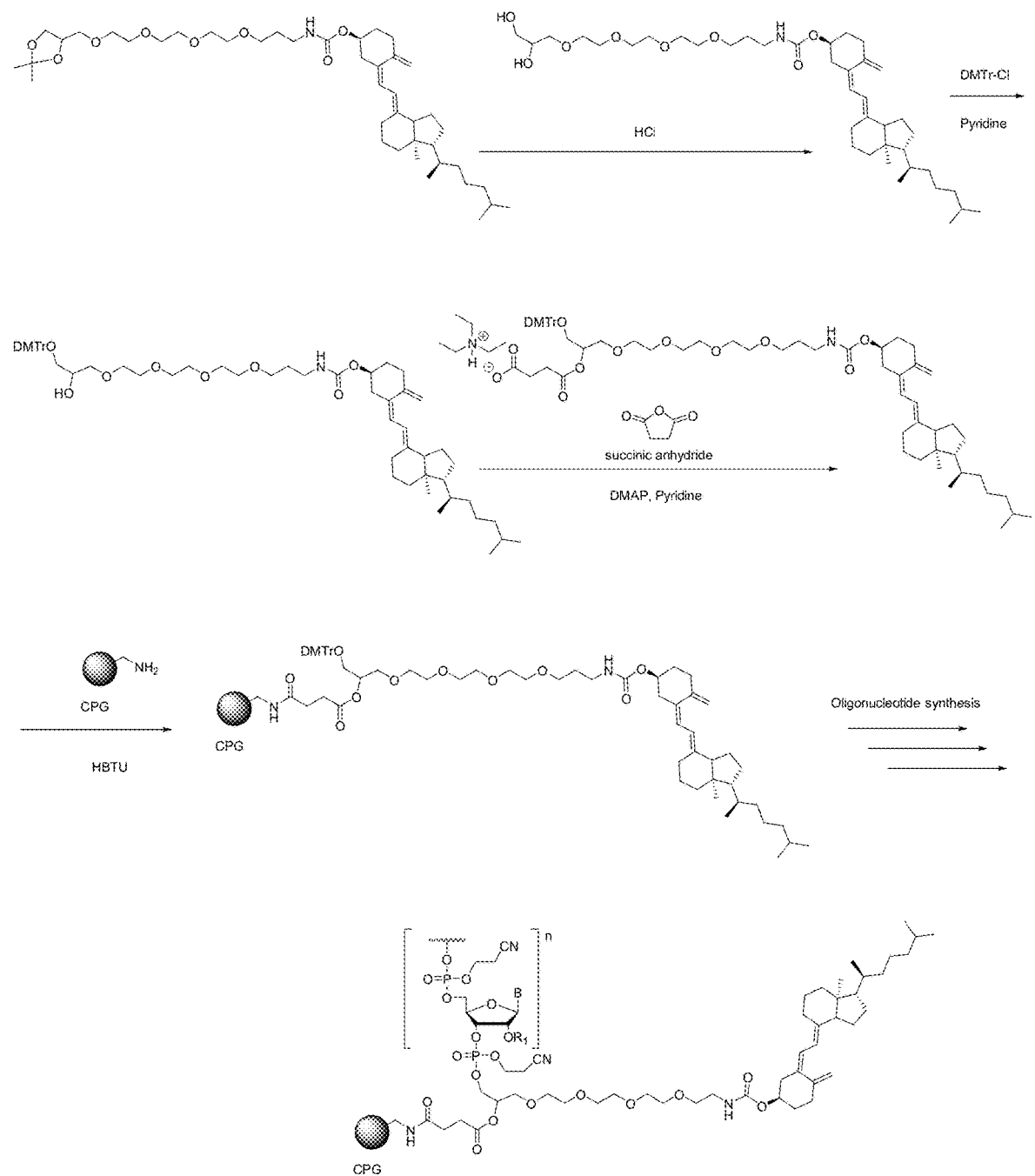
Figure 1I:
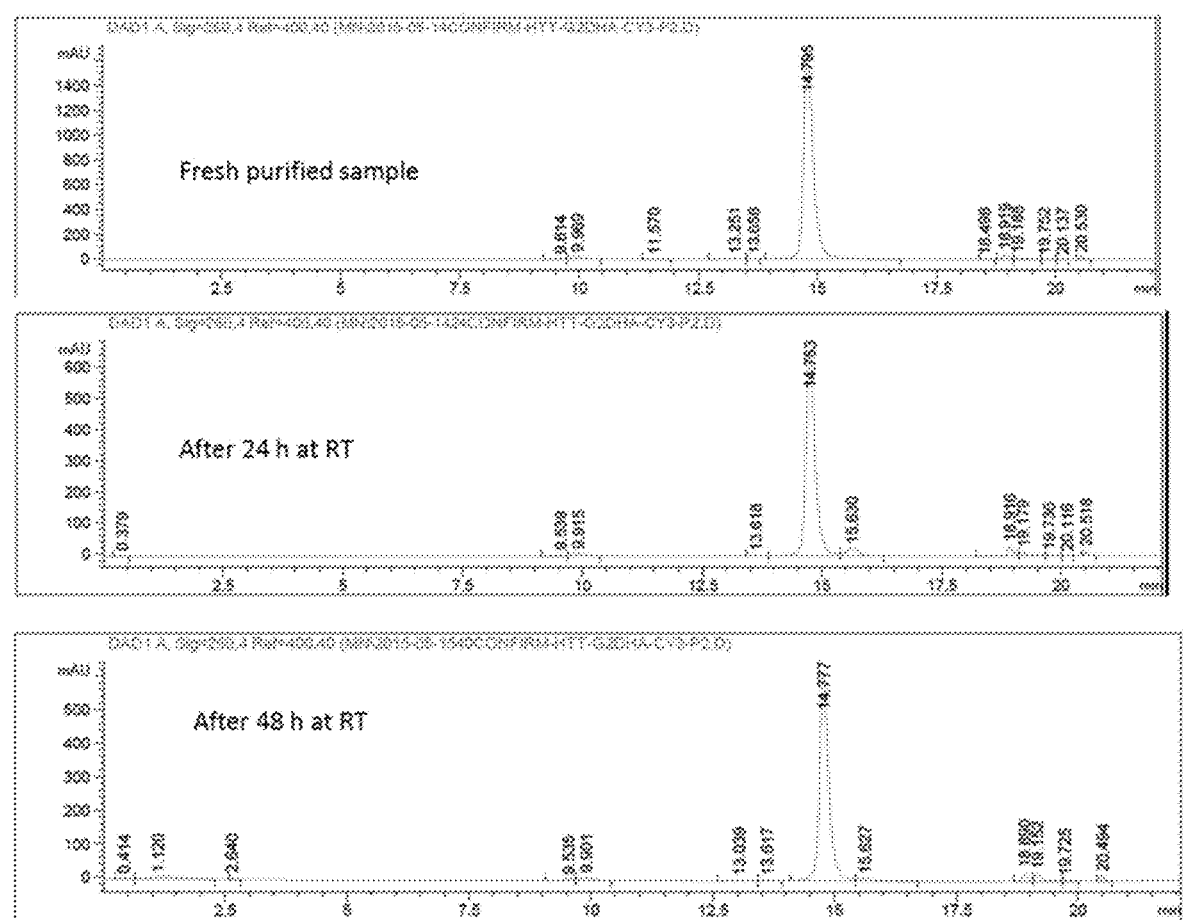
FIG. 1I shows a representative analytical HPLC trace of a synthesized hsiRNA conjugate, and its stability at room temperature immediately after purification, after 24 hours at room temperature, and after 48 hours at room temperature; sFLT-g2DHA-Cy3-P2 is shown.
Figure 1J:
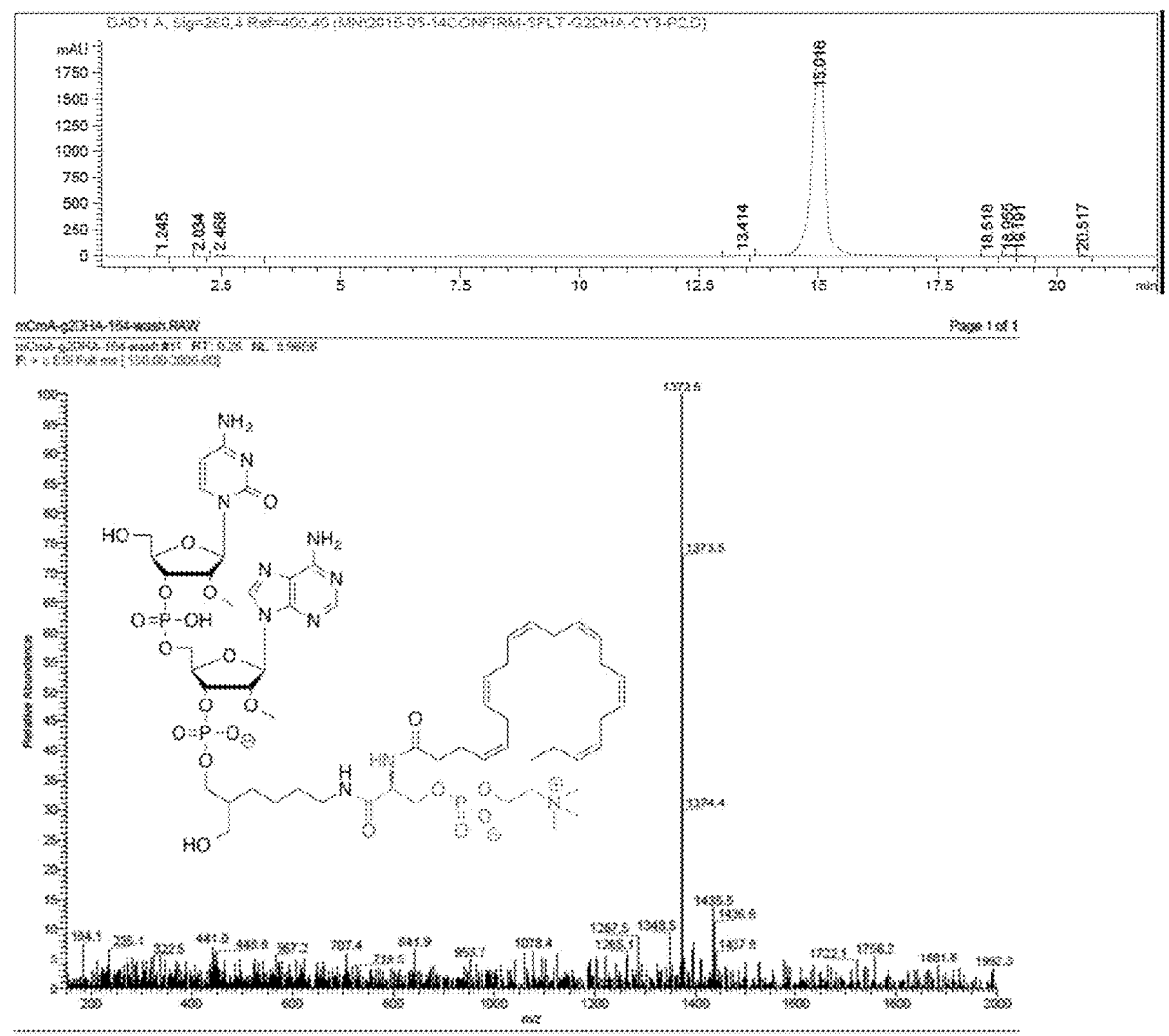
FIG. 1J shows a representative analytical HPLC trace and an ESI-MS spectra of a synthesized hsiRNA conjugate; lysophosphatidylcholine esterified DHA -hsiRNA conjugate is shown.
Figure 1K:
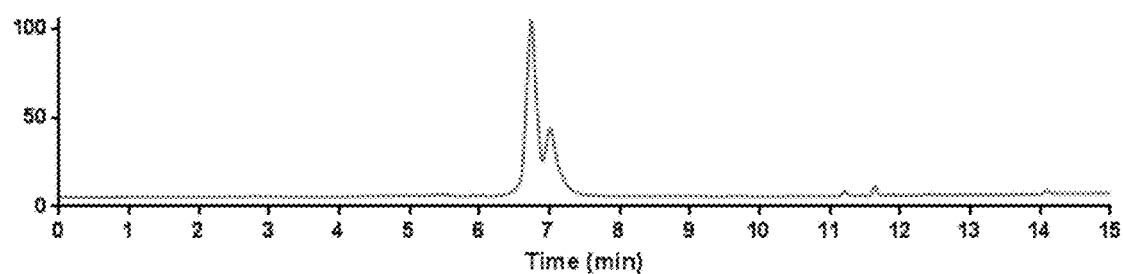
FIG. 1K shows a representative analytical HPLC trace of an hsiRNA conjugate prepared according to the synthetic approach of FIG. 1I; hsiRNA-Calciferol shown.

In one embodiment, an oxygen atom of L is bonded to the 3' position of the second oligonucleotide by a phosphodiester for example, as shown in FIG. 1j.

Variable $X^c$

In one embodiment, $X^c$ has an affinity for low density lipoprotein and/or intermediate density lipoprotein. In a related embodiment, $X^c$ is a saturated or unsaturated moiety having fewer than three double bonds.

In another embodiment, $X^c$ has an affinity for high density lipoprotein. In a related embodiment, $X^c$ is a polyunsaturated moiety having at three or more double bonds (e.g., having three, four, five, six, seven, eight, nine or ten double bonds). In a particular embodiment, $X^c$ is a polyunsaturated moiety having three double bonds. In a particular embodiment, $X^c$ is a polyunsaturated moiety having four double bonds. In a particular embodiment, $X^c$ is a polyunsaturated moiety having five double bonds. In a particular embodiment, $X^c$ is a polyunsaturated moiety having six double bonds.

In another embodiment, $X^c$ is selected from the group consisting of fatty acids, steroids, secosteroids, lipids, ganglio sides and nucleoside analogs, and endocannabinoids.

In another embodiment, $X^c$ is a neuromodulatory lipid, e.g., an endocannabinoid. Non-limiting examples of endocannabinoids include: Anandamide, Arachidonoylethanolamine, 2-Arachidonyl glyceryl ether (noladin ether), 2-Arachidonyl glyceryl ether (noladin ether), 2-Arachidonoylglycerol, and N-Arachidonoyl dopamine.

In another embodiment, $X^c$ is an omega-3 fatty acid. Non-limiting examples of omega-3 fatty acids include: Hexadecatrienoic acid (HTA), Alpha-linolenic acid (ALA), Stearidonic acid (SDA), Eicosatrienoic acid (ETE), Eicosatetraenoic acid (ETA), Eicosapentaenoic acid (EPA, Timnodonic acid), Heneicosapentaenoic acid (HPA), Docosapentaenoic acid (DPA, Clupanodonic acid), Docosahexaenoic acid (DHA, Cervonic acid), Tetracosapentaenoic acid, and Tetracosahexaenoic acid (Nisinic acid).

In another embodiment, $X^c$ is an omega-6 fatty acid. Non-limiting examples of omega-6 fatty acids include: Linoleic acid, Gamma-linolenic acid (GLA), Eicosadienoic acid, Dihomo-gamma-linolenic acid (DGLA), Arachidonic acid (AA), Docosadienoic acid, Adrenic acid, Docosapentaenoic acid (Osbond acid), Tetracosatetraenoic acid, and Tetracosapentaenoic acid.

In another embodiment, $X^c$ is an omega-9 fatty acid. Non-limiting examples of omega-9 fatty acids include: Oleic acid, Eicosenoic acid, Mead acid, Erucic acid, and Nervonic acid.

In another embodiment, $X^c$ is a conjugated linolenic acid. Non-limiting examples of conjugated linolenic acids include: α-Calendic acid, β-Calendic acid, Jacaric acid, α-Eleostearic acid, β-Eleostearic acid, Catalpic acid, and Punicic acid.

In another embodiment, $X^c$ is a saturated fatty acid. Non-limiting examples of saturated fatty acids include: Caprylic acid, Capric acid, Docosanoic acid, Lauric acid, Myristic acid, Palmitic acid, Stearic acid, Arachidic acid, Behenic acid, Lignoceric acid, and Cerotic acid.

In another embodiment, $X^c$ is an acid selected from the group consisting of: Rumelenic acid, α-Parinaric acid, β-Parinaric acid, Bosseopentaenoic acid, Pinolenic acid, and Podocarpic acid.

In another embodiment, $X^c$ is selected from the group consisting of: docosanoic acid (DCA), docosahexaenoic acid (DHA), and eicosapentaenoic acid (EPA). In a particular embodiment, $X^c$ is docosanoic acid (DCA). In another particular embodiment, $X^c$ is DHA. In another particular embodiment, $X^c$ is EPA.

In another embodiment, $X^c$ is a secosteroid. In a particular embodiment, $X^c$ is calciferol. In another embodiment, $X^c$ is a steroid other than cholesterol.

In a particular embodiment, $X^c$ is not cholesterol.

Figure 2A:
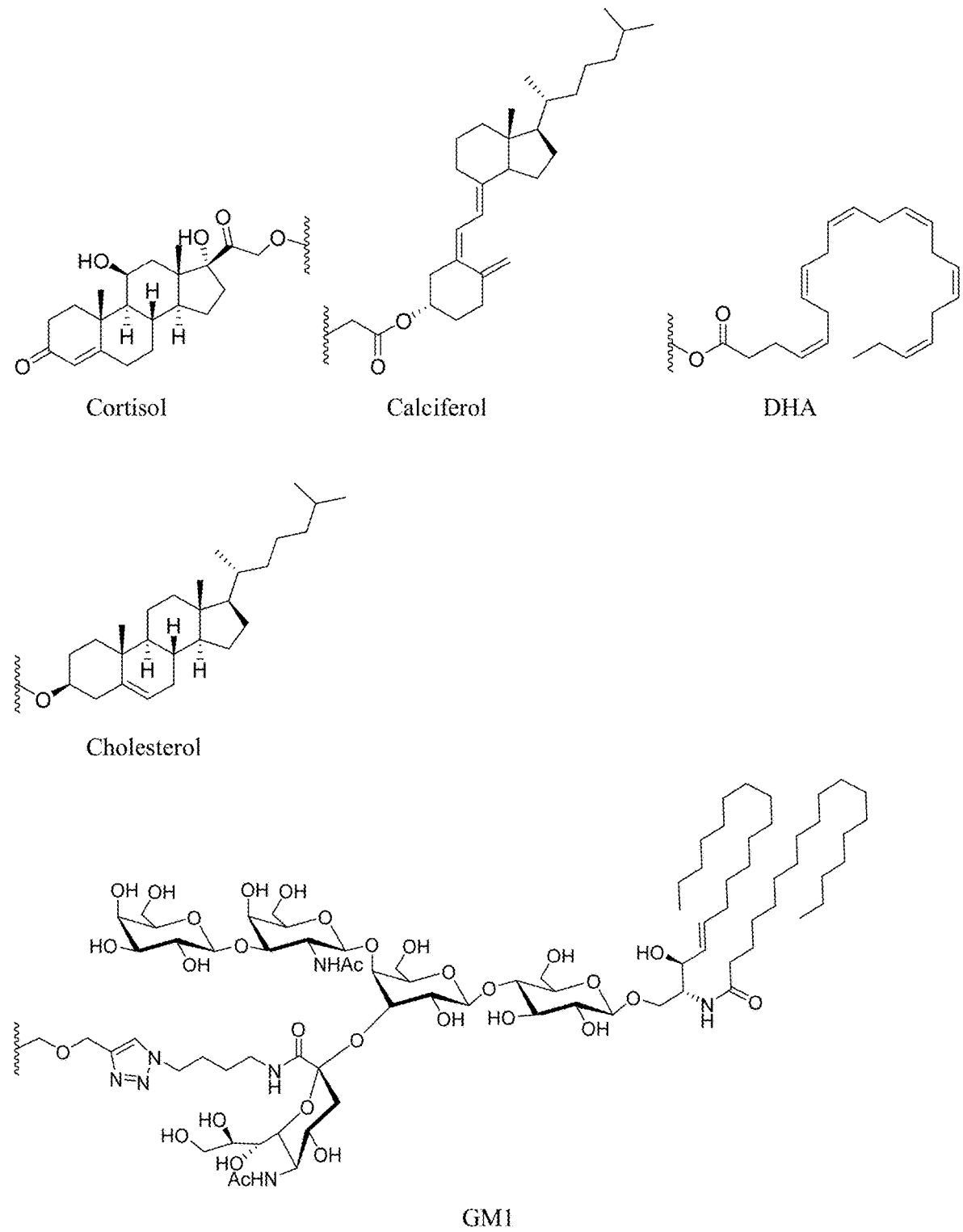
FIG. 2A depicts exemplary hydrophobic moieties.
Figure 29:
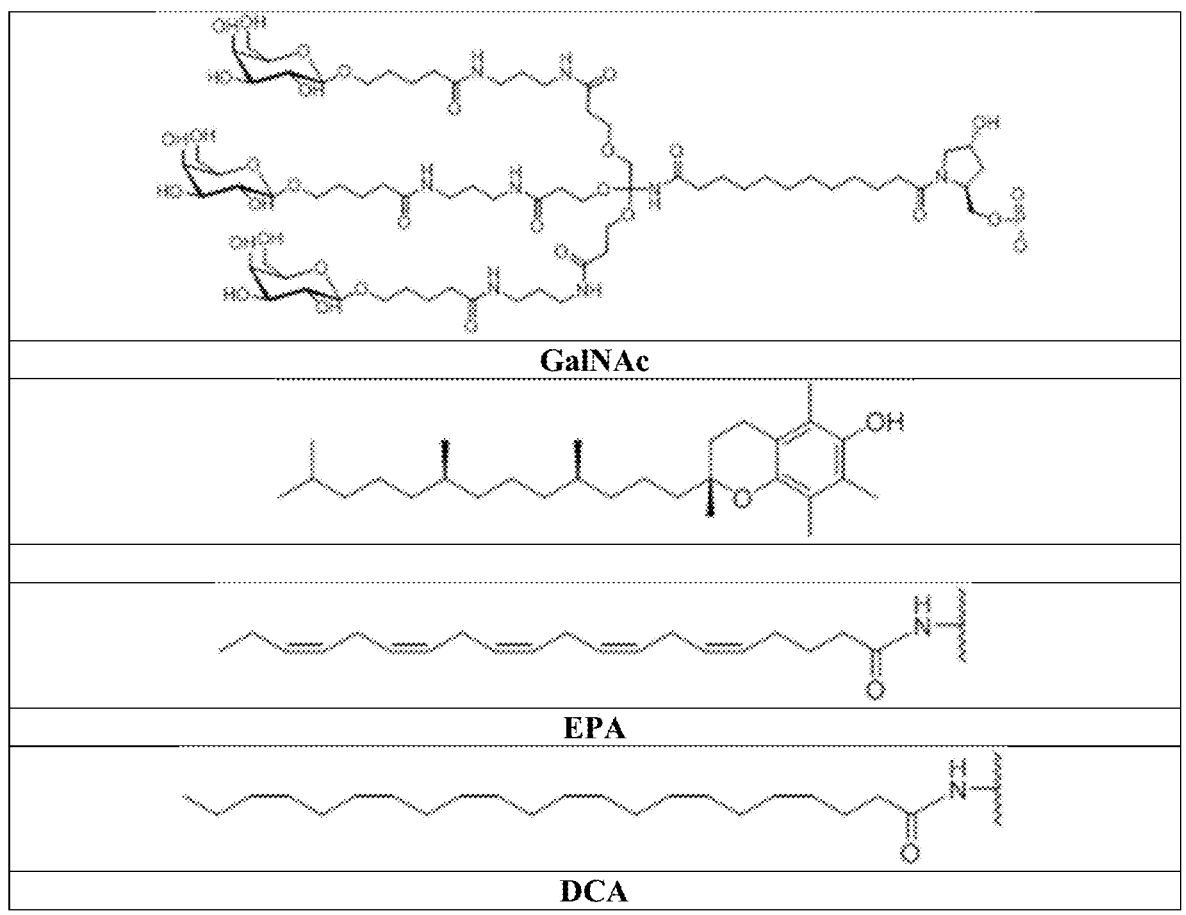
FIG. 29 depicts exemplary values of $X^c$.

In another embodiment, $X^c$ is an alkyl chain, a vitamin, a peptide, or a bioactive conjugate (including but not limited to: glycosphingolipids, polyunsaturated fatty acids, secosteroids, steroid hormones, sterol lipids. In other embodiments, the hydrophobic moiety comprises a moiety depicted in FIGS. 2a and 29.

In another embodiment of the oligonucleotide, $X^c$ is characterized by a clogP value in a range selected from: −10 to −9, −9 to −8, −8 to −7, −7 to −6, −6 to −5, −5 to −4, −4 to −3, −3 to −2, −2 to −1, −1 to 0, 0 to 1, 1 to 2, 2 to 3, 3 to 4, 4 to 5, 5 to 6, 6 to 7, 7 to 8, 8 to 9, and 9 to 10.

Variable $Z^c$

In one embodiment, $Z^c$ is selected from the group consisting of $Z^{c1}$, $Z^{c2}$, $Z^{c3}$ and $Z^{c4}$:

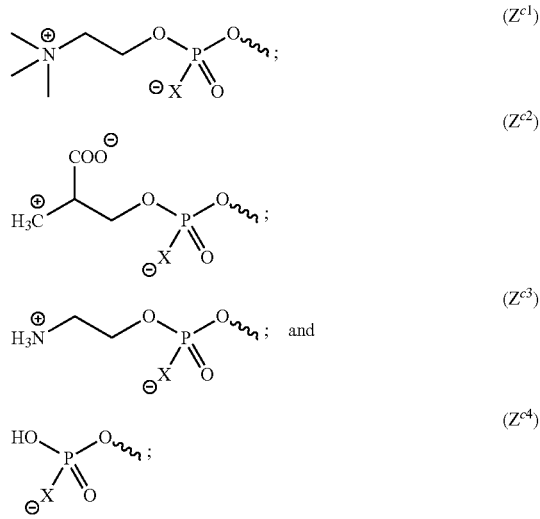

wherein X is O, S or $BH_3$.

In a particular embodiment, $Z^c$ is $Z^{c1}$, In another particular embodiment, $Z^c$ is not $Z^{c1}$, In another embodiment, $Z^c$ is selected from the group consisting of $Z^{c2}$, $Z^{c3}$ and $Z^{c4}$. In a particular embodiment, $Z^c$ is $Z^{c2}$, In a particular embodiment, $Z^c$ is $Z^{c3}$, In a particular embodiment, $Z^c$ is $Z^{c4}$, In a particular embodiment, X is O. In a particular embodiment, X is S. In a particular embodiment, X is $BH_3$.

Proviso

In a particular embodiment of compound (1), when $X^c$ is DHA, $Z^c$ is not $Z^{c1}$. In another particular embodiment, when $Z^c$ is $Z^{c1}$, $X^c$ is not DHA.

Variable O

In one embodiment, O comprises compound (I): an oligonucleotide of at least 16 contiguous nucleotides, said oligonucleotide having a 5' end, a 3' end and complementarity to a target. In one embodiment, the oligonucleotide has sufficient complementarity to the target to hybridize. In certain embodiments, the complementarity is >95%, >90%, >85%, >80%, >75%, >70%, >65%, >60%, >55% or >50%. In one embodiment, compound (Ia) has perfect complementarity to the target.

In another embodiment, O comprises compound (II): an oligonucleotide of at least 15 contiguous nucleotides, said oligonucleotide having a 5' end, a 3' end, and homology with a target, wherein the oligonucleotide is conjugated at the 3' end to $-L(X^c)(Z^c)$, described above.

In one embodiment, compound (II) comprises one or more chemically-modified nucleotides. In a particular embodiment, the oligonucleotide comprises alternating 2'-methoxy-nucleotides and 2'-fluoro-nucleotides. In another particular embodiment, the nucleotides at positions 1 and 2 from the 3' end of the oligonucleotide are connected to adjacent nucleotides via phosphorothioate linkages. In yet another particular embodiment, the nucleotides at positions 1 and 2 from the 3' end of the oligonucleotide and the nucleotides at positions 1 and 2 from the 5' end of the oligonucleotide are connected to adjacent nucleotides via phosphorothioate linkages.

In one embodiment, compound (II) has complete homology with the target. In a particular embodiment, the target is mammalian or viral mRNA. In another particular embodiment, the target is an intronic region of said mRNA.

In one embodiment, O is a double-stranded nucleic acid comprising a first oligonucleotide and a second oligonucleotide, wherein:

(1) the first oligonucleotide is compound (I), or any one of the previous embodiments thereof;

(2) the second oligonucleotide is compound (II), or any one of the previous embodiments thereof; and (3) a portion of the first oligonucleotide is complementary to a portion of the second oligonucleotide.

In one embodiment of 0, the first oligonucleotide comprises at least 16 contiguous nucleotides, a 5' end, a 3' end, and has complementarity to a target, wherein:

(1) the first oligonucleotide comprises alternating 2'-methoxy-nucleotides and 2'-fluoro-nucleotides;

(2) the nucleotides at positions 2 and 14 from the 5' end are not 2'-methoxy-nucleotides;

(3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In a particular embodiment of the nucleic acid, the first oligonucleotide has perfect complementarity to the target.

In one embodiment of the nucleic acid, the sequences of the first and second oligonucleotides are selected from the tables of FIG. 8 and FIG. 14

Advanced Stabilization Pattern

In one embodiment, compound (I) has the structure of Formula (Ia):

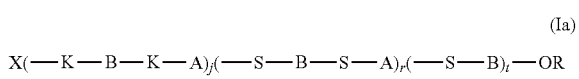

wherein:

X is selected from the group consisting of:

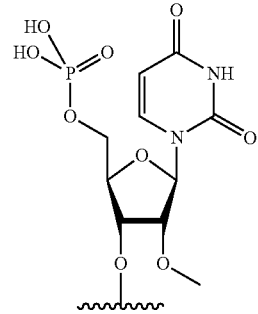

X1

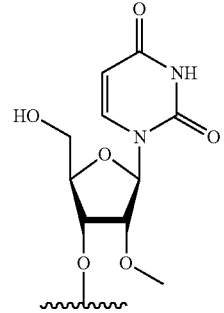

X2

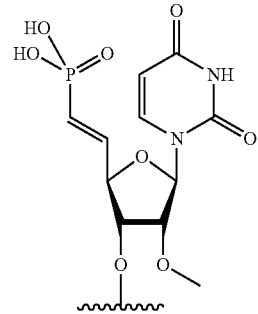

X3

X4
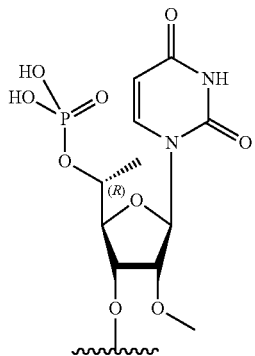

X5
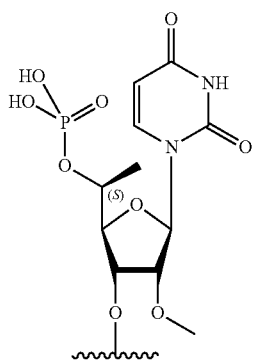

X6
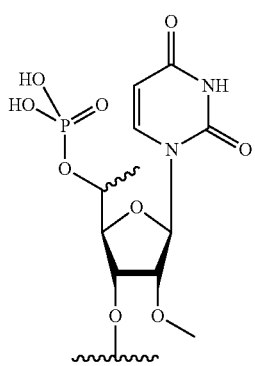

X7
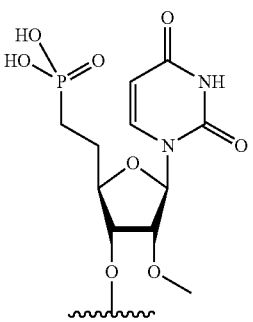

X8
[structure]

A, for each occurrence, independently is a 2'-methoxy-ribonucleotide;

B, for each occurrence, independently is a 2'-fluoro-ribonucleotide;

K, for each occurrence independently is a phosphodiester or phosphorothioate linker;

S is a phosphorothioate linker;

R is selected from hydrogen and a capping group (e.g., an acyl group such as acetyl);

j is 4, 5, 6 or 7;

r is 2 or 3; and t is 0 or 1.

In one embodiment, the oligonucleotide of Formula (Ia) has the structure of Formula (Ib):

$$X-A(-S-B-S-A)_m(-P-B-P-A)_n(-P-B-S-A)_q(-S-B-S-A)_r(-S-B)_t-OR \quad \text{(Ib)}$$

wherein:

X is as defined above;

A, for each occurrence, independently is a 2'-methoxy-ribonucleotide;

B, for each occurrence, independently is a 2'-fluoro-ribonucleotide;

S is a phosphorothioate linker;

P is a phosphodiester linker;

R is as defined above;

m is 0 or 1; n is 4, 5 or 6; q is 0 or 1; r is 2 or 3; and t is 0 or 1.

In a first particular embodiment of the oligonucleotide of Formula (Ib), m is 0; n is 6; q is 1; r is 2; and t is 1.

In a second particular embodiment of the oligonucleotide of Formula (Ib), m is 1; n is 5; q is 1; r is 2; and t is 1.

In a third particular embodiment of the oligonucleotide of Formula (Ib), m is 1; n is 5; q is 0; r is 3; and t is 1.

In a particular embodiment, R is hydrogen. In another particular embodiment, X is X1. In still another particular embodiment, X is X3.

In another embodiment, O is a double-stranded, chemically-modified nucleic acid comprising a first oligonucleotide and a second oligonucleotide, wherein:

(1) the first oligonucleotide is selected from the oligonucleotides of Formulas (I), (Ia), and (Ib);

(2) a portion of the first oligonucleotide is complementary to a portion of the second oligonucleotide; and (3) the second oligonucleotide is selected from the oligonucleotides of Formulas (II) and (IIa):

2'-fluoro-ribonucleotide; and the nucleotides at positions 2 and 14 from the 5' end of the second oligonucleotide are 2'-methoxy-ribonucleotides;

(3) the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages; and (4) the nucleotides of the second oligonucleotide are connected to adjacent nucleotides via phosphodiester or phosphorothioate linkages, wherein the nucleotides at positions 1 and 2 from the 3' end are connected to adjacent nucleotides via phosphorothioate linkages.

In one embodiment of O, the first oligonucleotide has 3-7 more ribonucleotides than the second oligonucleotide.

In one embodiment, O comprises 11-16 base pair duplexes, wherein the nucleotides of each base pair duplex have different chemical modifications (e.g., one nucleotide has a 2'-fluoro modification and the other nucleotide has a 2'-methoxy).

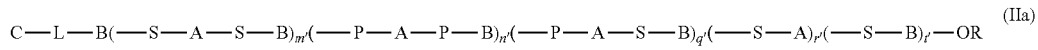

wherein:

C-L is:

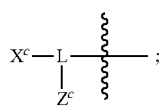

wherein

L; $X^c$; $Z^c$; A; B; S; P are defined above m' is 0 or 1; n' is 4, 5 or 6; q' is 0 or 1; r' is 0 or 1; and t' is 0 or 1.

In one embodiment of compound (1):

(1) the first oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the first oligonucleotide are not 2'-methoxy-ribonucleotides;

(2) the second oligonucleotide comprises alternating 2'-methoxy-ribonucleotides and 2'-fluoro-ribonucleotides, wherein each nucleotide is a 2'-methoxy-ribonucleotide or a In one embodiment of O, the first oligonucleotide has 3-7 more ribonucleotides than the second oligonucleotide. In another embodiment, each R is hydrogen.

In one embodiment of 0, the first oligonucleotide has structure: X(—S—B—S-A)(—P—B—P-A)$_5$(—P—B—S-A)(—S—B—S-A)$_2$(—S—B)—OR; and the second oligonucleotide has the structure: C-L-B(—S-A-S—B)(—P-A-P—B)$_5$(—S-A)(—S—B)—OR. In a particular embodiment, O has the structure of compound (IIIa):

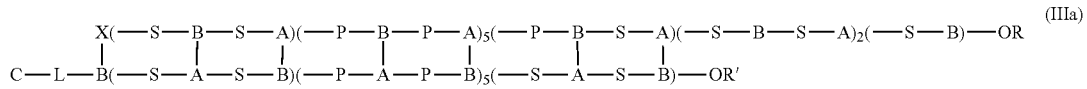

wherein each | represents a hydrogen bonding interaction (i.e., a base-pairing interaction).

In a particular embodiment of compound (IIIa), the first oligonucleotide comprises the sequence 5' UAAAUUUG-GAGAUCCGAGAG 3' (SEQ ID NO: 124); the second oligonucleotide comprises the sequence 3' AUUUAAAC-CUCUAGG 5' (SEQ ID NO: 184); X is X3; $X^c$ is DHA and $Z^c$ is $Z^{c1}$. In a further embodiment, R is hydrogen. In a further embodiment, R' is hydrogen. In a further embodiment, L is L1.

In another particular embodiment of compound (IIIa), the first oligonucleotide comprises the sequence 5' UAUAAAUGGUAGCUAUGAUG 3' (SEQ ID NO: 185);

the second oligonucleotide comprises the sequence 3' AUAUUUACCAUCGAU 5' (SEQ ID NO: 186); X is X3; $X^c$ is DHA and $Z^c$ is $Z^{c1}$. In a further embodiment, R is hydrogen. In a further embodiment, R' is hydrogen. In a further embodiment, L is L1.

In another particular embodiment of compound (IIIa), the first oligonucleotide comprises the sequence 5' UUAAU-CUCUUUACUGAUAUA 3' (SEQ ID NO: 177); the second oligonucleotide comprises the sequence 3' AAUUAGA-GAAAUGAC 5' (SEQ ID NO: 176); X is X3; $X^c$ is DHA and $Z^c$ is $Z^{c1}$. In a further embodiment, R is hydrogen. In a further embodiment, R' is hydrogen. In a further embodiment, L is L1.

In another particular embodiment of compound (IIIa), the first oligonucleotide comprises the sequence 5' UUAAU-CUCUUUACUGAUAUA 3' (SEQ ID NO: 177); the second oligonucleotide comprises the sequence 3' AAUUAGA-GAAAUGAC 5' (SEQ ID NO: 176); X is X3; $X^c$ is DHA and $Z^c$ is $Z^{c1}$. In a further embodiment, R is hydrogen. In a further embodiment, R' is hydrogen. In a further embodiment, L is L1.

In another particular embodiment of compound (IIIa), the first oligonucleotide comprises the sequence 5' UUAAU-CUCUUUACUGAUAUA 3' (SEQ ID NO: 177); the second oligonucleotide comprises the sequence 3' AAUUAGA-GAAAUGAC 5' (SEQ ID NO: 176); X is X3; $X^c$ is DHA and $Z^c$ is $Z^{c1}$. In a further embodiment, R is hydrogen. In a further embodiment, R' is hydrogen. In a further embodiment, L is L1.

In another particular embodiment of compound (IIIa), the first oligonucleotide comprises the sequence 5' UUAAU-CUCUUUACUGAUAUA 3' (SEQ ID NO: 177); the second oligonucleotide comprises the sequence 3' AAUUAGA-GAAAUGAC 5' (SEQ ID NO: 176); X is X3; $X^c$ is DHA and $Z^c$ is $Z^{c1}$. In a further embodiment, R is hydrogen. In a further embodiment, R' is hydrogen. In a further embodiment, L is L1.

In another particular embodiment of compound (IIIa), the first oligonucleotide comprises the sequence 5' UUAAU-CUCUUUACUGAUAUA 3' (SEQ ID NO: 177); the second oligonucleotide comprises the sequence 3' AAUUAGA-GAAAUGAC 5' (SEQ ID NO: 176); X is X3; and $X^c$ is cholesterol. In a further embodiment, R is hydrogen. In a further embodiment, R' is hydrogen. In a further embodiment, L comprises triethylene glycol.

In another particular embodiment of compound (IIIa), the first oligonucleotide comprises the sequence 5' UUAAU-CUCUUUACUGAUAUA 3' (SEQ ID NO: 177); the second oligonucleotide comprises the sequence 3' AAUUAGA-GAAAUGAC 5' (SEQ ID NO: 176); X is X3; and $X^c$ is GalNAc. In a further embodiment, R is hydrogen. In a further embodiment, R' is hydrogen. In a further embodiment, L comprises triethylene glycol.

In another embodiment of O, the first oligonucleotide has structure: X(—P—B—P-A)$_6$(—P—B—S-A)(—S—B—S-A)$_2$(—S—B)—OR; and the second oligonucleotide has the structure: C-L-B(—S-A-S—B)(—P-A-P—B)$_6$—OR. In a particular embodiment, O has the structure of compound (Mb):

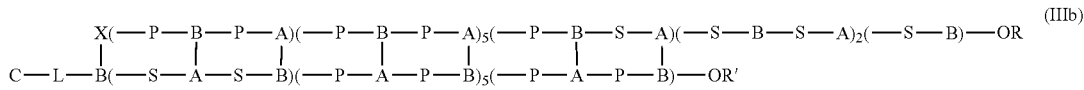

wherein each | represents a hydrogen bonding interaction (i.e., a base-pairing interaction).

In a particular embodiment of compound (Mb), the first oligonucleotide comprises the sequence 5' UAAAUUUG-GAGAUCCGAGAG 3' (SEQ ID NO: 124); the second oligonucleotide comprises the sequence 3' AUUUAAAC-CUCUAGG 5' (SEQ ID NO: 184); X is X3; $X^c$ is DHA and $Z^c$ is $Z^{c1}$. In a further embodiment, R is hydrogen. In a further embodiment, R' is hydrogen. In a further embodiment, L is L1.

In another particular embodiment of compound (Mb), the first oligonucleotide comprises the sequence 5' UAUAAAUGGUAGCUAUGAUG 3' (SEQ ID NO: 185); the second oligonucleotide comprises the sequence 3' AUAUUUACCAUCGAU 5' (SEQ ID NO: 186); X is X3; $X^c$ is DHA and $Z^c$ is $Z^{c1}$. In a further embodiment, R is hydrogen. In a further embodiment, R' is hydrogen. In a further embodiment, L is L1.

In another particular embodiment of compound (Mb), the first oligonucleotide comprises the sequence 5' UUAAU-CUCUUUACUGAUAUA 3' (SEQ ID NO: 177); the second oligonucleotide comprises the sequence 3' AAUUAGA-GAAAUGAC 5' (SEQ ID NO: 176); X is X3; $X^c$ is DHA and $Z^c$ is $Z^{c1}$. In a further embodiment, R is hydrogen. In a further embodiment, R' is hydrogen. In a further embodiment, L is L1.

In another embodiment of the double-stranded nucleic acid, the first oligonucleotide has structure: X(—S—B—S-A)(—P—B—P-A)$_5$(—S—B—S-A)$_3$(—S—B)—OR; the second oligonucleotide has structure: C-L-B(—S-A-S—B)(—P-A-P—B)$_5$(—S-A-S—B)—OR; and O has the structure of Formula (IIIc):

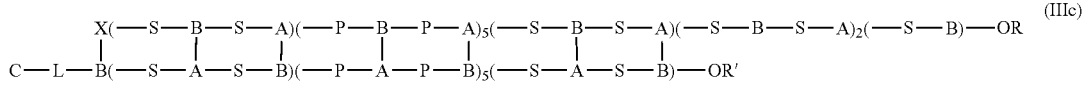

wherein each | represents a hydrogen bonding interaction (i.e., a base-pairing interaction).

In another particular embodiment of compound (IIIc), the first oligonucleotide comprises the sequence 5' UUAAU-CUCUUUACUGAUAUA 3' (SEQ ID NO: 177); the second oligonucleotide comprises the sequence 3' AAUUAGA-GAAAUGAC 5' (SEQ ID NO: 176); X is X3; $X^c$ is DHA and $Z^c$ is $Z^{c1}$. In a further embodiment, R is hydrogen. In a further embodiment, R' is hydrogen. In a further embodiment, R' is hydrogen. In a further embodiment, L is L1.

In one embodiment, the first oligonucleotide is the antisense strand and the second oligonucleotide is the sense strand. In certain embodiments, compounds (I), (Ia), (Ib), (II) and (IIa) comprise sequences of FIG. 8.

In another aspect, provided herein is a composition comprising a first nucleic acid of compound (IIIa), wherein the first oligonucleotide comprises the sequence 5' UAAAUUUGGAGAUCCGAGAG 3' (SEQ ID NO: 124); the second oligonucleotide comprises the sequence 3' AUUUAAACCUCUAGG 5' (SEQ ID NO: 184); X is X3; and C is cholesterol; and a second nucleic acid of compound (IIIa), wherein the first oligonucleotide comprises the sequence 5' UAUAAAUGGUAGCUAUGAUG 3' (SEQ ID NO: 185); the second oligonucleotide comprises the sequence 3' AUAUUUACCAUCGAU 5' (SEQ ID NO: 186); X is X3; and C is cholesterol. In one embodiment, R is hydrogen, phosphate, vinylphosphonate, or a capping group. In another embodiment, R' is hydrogen, phosphate, vinylphosphonate, or a capping group.

In another aspect, provided herein is a composition comprising a first nucleic acid of compound (IIIa), wherein the first oligonucleotide comprises the sequence 5' UAAAUUUGGAGAUCCGAGAG 3' (SEQ ID NO: 124); the second oligonucleotide comprises the sequence 3' AUUUAAACCUCUAGG 5' (SEQ ID NO: 184); X is X3; $X^c$ is DHA, $Z^c$ is Zc1 and L is L1; and a second nucleic acid of compound (IIIa), wherein the first oligonucleotide comprises the sequence 5' UAUAAAUGGUAGCUAUGAUG 3' (SEQ ID NO: 185); the second oligonucleotide comprises the sequence 3' AUAUUUACCAUCGAU 5' (SEQ ID NO: 186); X is X3; $X^c$ is DHA, $Z^c$ is Zc1 and L is L1. In one embodiment, R is hydrogen, phosphate, vinylphosphonate, or a capping group. In another embodiment, R' is hydrogen, phosphate, vinylphosphonate, or a capping group.

Pharmaceutical Compositions and Methods of Administration

In one aspect, provided herein is a pharmaceutical composition comprising a therapeutically effective amount of one or more compound, oligonucleotide, or nucleic acid as described herein, and a pharmaceutically acceptable carrier. In one embodiment, the pharmaceutical composition comprises one or more double-stranded, chemically-modified nucleic acid as described herein, and a pharmaceutically acceptable carrier. In a particular embodiment, the pharmaceutical composition comprises one double-stranded, chemically-modified nucleic acid as described herein, and a pharmaceutically acceptable carrier. In another particular embodiment, the pharmaceutical composition comprises two double-stranded, chemically-modified nucleic acids as described herein, and a pharmaceutically acceptable carrier.

In another particular embodiment, the pharmaceutical composition comprises a first nucleic acid of compound (IIIa), wherein the first oligonucleotide comprises the sequence 5' UAAAUUUGGAGAUCCGAGAG 3' (SEQ ID NO: 124); the second oligonucleotide comprises the sequence 3' AUUUAAACCUCUAGG 5' (SEQ ID NO: 184); X is X3; $X^c$ is DHA, $Z^c$ is Zc1 and L is L1; and a second nucleic acid of compound (IIIa), wherein the first oligonucleotide comprises the sequence 5' UAUAAAUGGUAGCUAUGAUG 3' (SEQ ID NO: 185); the second oligonucleotide comprises the sequence 3' AUAUUUACCAUCGAU 5' (SEQ ID NO: 186); X is X3; $X^c$ is DHA, $Z^c$ is Zc1 and L is L1. In one embodiment, R is hydrogen, phosphate, vinylphosphonate, or a capping group. In another embodiment, R' is hydrogen, phosphate, vinylphosphonate, or a capping group.

In another particular embodiment, the pharmaceutical composition comprises a first nucleic acid of compound (IIIa), wherein the first oligonucleotide comprises the sequence 5' UAAAUUUGGAGAUCCGAGAG 3' (SEQ ID NO: 124); the second oligonucleotide comprises the sequence 3' AUUUAAACCUCUAGG 5' (SEQ ID NO: 184); X is X3; and C is cholesterol; and a second nucleic acid of compound (IIIa), wherein the first oligonucleotide comprises the sequence 5' UAUAAAUGGUAGCUAUGAUG 3' (SEQ ID NO: 185); the second oligonucleotide comprises the sequence 3' AUAUUUACCAUCGAU 5' (SEQ ID NO: 186); X is X3; and C is cholesterol. In one embodiment, R is hydrogen, phosphate, vinylphosphonate, or a capping group. In another embodiment, R' is hydrogen, phosphate, vinylphosphonate, or a capping group.

The invention pertains to uses of the above-described agents for prophylactic and/or therapeutic treatments as described Infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Methods of Treatment

In one aspect, provided herein is a method for selectively delivering a compound of formula (1), or a disclosed embodiment thereof, to a particular organ in a patient, comprising administering said compound to the patient, wherein the compound has a selective affinity for a serum lipoprotein. In one embodiment, the organ is the kidneys and the compound has a selective affinity for high density lipoprotein versus low density lipoprotein and/or high density lipoprotein. In a particular embodiment, the organ is the kidneys and $X^c$ is a polyunsaturated moiety having at three or more double bonds (e.g., DHA).

In another embodiment, the organ is the liver and the compound has a selective affinity for low density lipoprotein and/or high density lipoprotein versus high density lipoprotein. In a particular embodiment, the organ is the liver and $X^c$ is a moiety that is saturated or has fewer than three double bonds.

In another embodiment, the organ is the brain and the compound has a selective affinity for high density lipoprotein versus low density lipoprotein and/or high density lipoprotein. In a particular embodiment, the organ is the brain and $X^c$ is a polyunsaturated moiety having three or more double bonds (e.g., DHA).

In another embodiment, the organ is the epidermis and the compound has a selective affinity for high density lipoprotein versus low density lipoprotein and/or high density lipoprotein. In a particular embodiment, the organ is the epidermis and $X^c$ is a polyunsaturated moiety having three or more double bonds (e.g., EPA).

In another aspect, provided herein is a method for selectively delivering a compound of formula (1), or a disclosed embodiment thereof, to the kidneys of a patient, comprising administering said compound to the patient intravenously, wherein $X^c$ is a polyunsaturated moiety having three or more double bonds (e.g., DHA).

In another aspect, provided herein is a method for treating a disease or disorder of the kidneys in a patient in need of such treatment, comprising administering to the patient a compound of formula (1), or a disclosed embodiment thereof, Non-limiting examples of such disease or disorders include: Abderhalden-Kaufmann-Lignac syndrome; Acute kidney injury; Acute proliferative glomerulonephritis; Adenine phosphoribosyltransferase deficiency; Alport syndrome; Analgesic nephropathy; Autosomal dominant polycystic kidney disease; Autosomal recessive polycystic kidney disease; Benign nephrosclerosis; Bright's disease; Cardiorenal syndrome; CFHRS nephropathy; Chronic kidney disease; Chronic kidney disease-mineral and bone disorder; Congenital nephrotic syndrome; Conorenal syndrome; Contrast-induced nephropathy; Cystic kidney disease; Danubian endemic familial nephropathy; Dent's disease; Diabetic nephropathy; Diffuse proliferative nephritis; Distal renal tubular acidosis; Diuresis; EAST syndrome; Epithelial-mesenchymal transition; Fanconi syndrome; Fechtner syndrome; Focal proliferative nephritis; Focal segmental glomerulosclerosis; Fraley syndrome; Galloway Mowat syndrome; Gitelman syndrome; Glomerulocystic kidney disease; Glomerulopathy; Glomerulosclerosis; Goldblatt kidney; Goodpasture syndrome; High anion gap metabolic acidosis; HIV-associated nephrapathy; Horseshoe kidney; Hydronephrosis; Hypertensive nephropathy; IgA nephropathy; Interstitial nephritis; Juvenile nephronophthisis; Kidney cancer; Lightwood-Albright syndrome; Lupus nephritis; Malarial nephropathy; Medullary cystic kidney disease; Medullary sponge kidney; Membranous glomerulonephritis; Mesoamerican nephropathy; Milk-alkali syndrome; Minimal mesangial glomerulonephritis; Multicystic dysplastic kidney; Nephritis; Nephrocalcinosis; Nephrogenic diabetes insipidus; Nephromegaly; Nephroptosis; Nephrosis; Nephrotic syndrome; Nutcracker syndrome; Papillorenal syndrome; Phosphate nephropathy; Polycystic kidney disease; Primary hyperoxaluria; Proximal renal tubular acidosis; Pyelonephritis; Pyonephrosis; Rapidly progressive glomerulonephritis; Renal agenesis; Renal angina; Renal artery stenosis; Renal cyst; Renal ischemia; Renal osteodystrophy; Renal papillary necrosis; Renal tubular acidosis; Renal vein thrombosis; Reninoma; Serpentine fibula-polycystic kidney syndrome; Shunt nephritis; Sickle cell nephropathy; Thin basement membrane disease; Transplant glomerulopathy; Tubulointerstitial nephritis and uveitis; Tubulopathy; Uremia and Wunderlich syndrome.

In another aspect, provided herein is a method for selectively delivering a compound disclosed herein to the liver of a patient, comprising administering said compound to the patient intravenously, wherein $X^c$ is a moiety that is saturated or has fewer than three double bonds.

In another aspect, provided herein is a method for treating a disease or disorder of the brain in a patient in need of such treatment, comprising administering to the patient a compound of formula (1), or a disclosed embodiment thereof, Non-limiting examples of such disease or disorders include: Acute Disseminated Encephalomyelitis, Agnosia, Alpers' Disease, Angelman Syndrome, Asperger Syndrome, Alzheimer's Disease, Amyotrophic Lateral Sclerosis, Aneurysm, Attention Deficit Hyperactivity Disorder, Autism, Bell's Palsy, Batten Disease, Brain Cancer, Canavan Disease, Concussion, Coma, Cerebral Hypoxia, Cerebral Palsy, Creutzfeldt-Jakob Disease, Dementia, Dravet Syndrome, Dyslexia, Epilepsy, Encephalitis, Farber's Disease, Febrile Seizures, Friedreich's Ataxia, Gaucher Disease, Huntinton's Disease, Hypersomnia, Migraine, Multiple Sclerosis, Narcolepsy, Parkinson's Disease, Stroke, and Traumatic Brain Injury, Tremor, and Wallenberg's Syndrome.

In another aspect, provided herein is a method for treating a disease or disorder of the epidermis in a patient in need of such treatment, comprising administering to the patient a compound of formula (1), or a disclosed embodiment thereof, Non-limiting examples of such disease or disorders include: Ichthyosis, Ectodermal Dysplasia, Psoriasis, Eczema, Darier's Disease, Infantile acropustulosis, Acrokeratoelastoidosis, Pityriasis rubra pilaris, Glucagonoma Syndrome, Acrodermatitis enteropathica, Porokeratosis, Acne, Vitiligo, Skin Cancer, Grover's Disease, Alopecia, Dermatitis, Leiner's Disease, Xeroderma pigmentosum, Toxic Epidermal Necrolysis, Seborrheic Keratoses, Uticaria, Erythema Multiforme, Pemphigus Vulgaris, Bullous Pemphigoid, Scleroderma, and Lupus Erythematosus.

In another aspect, provided herein is a method for treating a disease or disorder of the liver in a patient in need of such treatment, comprising administering to the patient a compound of formula (1), or a disclosed embodiment thereof, Non-limiting examples of such disease or disorders include: liver disease; acute fatty liver of pregnancy; acute liver failure; alcoholic liver disease; alpha-1 antitrypsin deficiency; alveolar hydatid disease; bacillary peliosis; Budd-Chiari syndrome; liver cancer; chronic liver disease; cirrhosis; congenital hepatic fibrosis; congestive hepatopathy; epithelial-mesenchymal transition; fatty liver; fibrolamellar hepatocellular carcinoma; focal fatty liver; gastric antral vascular extasia; hepatic encephalopathy; hepatolithiasis; hepatopulmonary syndrome; hapatorenal syndrome; hepatosplenomegaly; Laennec's cirrhosis; Liver abscess; Liver failure; Lyngstadaas syndrome; Non-alcoholic fatty liver disease; Non-cirrhotic portal fibrosis; Non-alcoholic fatty liver disease; Non-cirrhotic portal fibrosis; Non-alcoholic fatty liver disease; Pediatric end-stage liver disease; Peliosis hepatis; Polycystic liver disease; Primary biliary cirrhosis; Progressive familial intrahepatic cholestasis; steatohepatitis; viral hepatitis; Wilson's diease; Zahn infarct; and Zieve's syndrome.

In one aspect, the present disclosure provides for both prophylactic and therapeutic methods of treating a subject at risk of (or susceptible to) a disease or disorder caused, in whole or in part, by secreted Flt1 protein. In one embodiment, the disease or disorder is a liver disease or disorder. In another embodiment, the disease or disorder is a kidney disease or disorder. In one embodiment, the disease or disorder is a placental disease or disorder. In one embodiment, the disease or disorder is a pregnancy-related disease or disorder. In a preferred embodiment, the disease or disorder is a disorder associated with the expression of soluble FM protein and in which amplified expression of the soluble FM protein leads to clinical manifestations of PE (preeclampsia), postpartum PE, eclampsia and/or HELLP (i.e., HELLP syndrome).

In another aspect, the present invention provides for both prophylactic and therapeutic methods of treating a subject at risk of (or susceptible to) a disease or disorder caused, in whole or in part, by a gain of function mutant protein. In one embodiment, the disease or disorder is a trinucleotide repeat disease or disorder. In another embodiment, the disease or disorder is a polyglutamine disorder. In a preferred embodiment, the disease or disorder is a disorder associated with the expression of huntingtin and in which alteration of huntingtin, especially the amplification of CAG repeat copy number, leads to a defect in huntingtin gene (structure or function) or huntingtin protein (structure or function or expression), such that clinical manifestations include those seen in Huntington's disease patients.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for one or more target sequences within the gene, such that sequence specific interference with the gene is achieved. These methods can be performed in vitro (e.g., by culturing the cell with the agent) or, alternatively, in vivo (e.g., by administering the agent to a subject).

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the brain, spinal column, placenta, liver and/or kidneys) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. The dosage can be an amount effective to treat or prevent a neurological disease or disorder (e.g., Huntington's disease) or a liver-, kidney- or pregnancy-related disease or disorder (e.g., PE, postpartum PE, eclampsia and/or HELLP). In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

In one aspect, provided herein is a method of treating or managing preeclampsia, post-partum preeclampsia, eclampsia or HELLP syndrome comprising administering to a subject in need of such treatment or management a therapeutically effective amount of a compound, oligonucleotide, or nucleic acid as described herein, or a pharmaceutical composition comprising said compound, oligonucleotide, or nucleic acid.

In another aspect, provided herein is a method of treating or managing Huntington's disease comprising administering to a patient in need of such treatment or management a therapeutically effective amount of a compound, oligonucleotide, or nucleic acid as described herein, or a pharmaceutical composition comprising said compound, oligonucleotide, or nucleic acid.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base adenine (e.g., cytidine or a chemically-modified derivative thereof).

As used herein, the terms "DHAPCL-hsiRNA," "PC-DHA-hsiRNA," "g2DHA-hsiRNA," and "DHA-G2-hsiRNA" refer to an embodiment of compound (1) wherein $X^c$ is DHA, L is L1 and O is a fully chemically modified as described herein.

As used herein, the term "capping group" refers to a chemical moiety that replaces a hydrogen atom in a functional group such as an alcohol (ROH), a carboxylic acid ($RCO_2H$), or an amine ($RNH_2$). Non-limiting examples of capping groups include: alkyl (e.g., methyl, tertiary-butyl); alkenyl (e.g., vinyl, allyl); carboxyl (e.g., acetyl, benzoyl); carbamoyl; phosphate; and phosphonate (e.g., vinylphosphonate). Other suitable capping groups are known to those of skill in the art.

By "soluble FLT1 (sFLT1)" (also known as sVEGF-R1) is meant a soluble form of the FLT1 receptor that has sFLT1 biological activity (e.g., e.g., sFlt1-i13 short, sFlt1-i13 long and/or sFlt1-i15a). The biological activity of an sFLT1 polypeptide may be assayed using any standard method, for example, by assaying for one or more clinical symptoms of PE, eclampsia and/or HELLP, by assaying sFLT1 mRNA and/or protein levels, by assaying sFLT1 binding to VEGF and the like. sFLT1 proteins lack the transmembrane domain and the cytoplasmic tyrosine kinase domain of the FLT1 receptor. sFLT1 proteins can bind to VEGF and PlGF bind with high affinity, but cannot induce proliferation or angiogenesis and are therefore functionally different from the Flt-1 and KDR receptors. sFLT1 was initially purified from human umbilical endothelial cells and later shown to be produced by trophoblast cells in vivo. As used herein, sFlt-1 includes any sFlt-1 family member or isoform, e.g., sFLT1-i13 (e.g., FLT1-i13 short and/or sFLT1-i13 long (sFLT1_v1), sFlt1-i15a (sFLT1_v2), sFLT1-e15a, sFLT1_v3, sFLT1_v4 and the like.

By "trophoblast" is meant the mesectodermal cell layer covering the blastocyst that erodes the uterine mucosa and through which the embryo receives nourishment from the mother. Trophoblast cells contribute to the formation of the placenta.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; 0- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Linkers useful in conjugated compounds of the invention include glycol chains (e.g., polyethylene glycol), alkyl chains, peptides, RNA, DNA, and combinations thereof. As used herein, the abbreviation "TEG" refers to triethylene glycol.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 April 10(2):117-21, Rusckowski et al. Antisense Nucleic Acid Drug Dev. 2000 Oct. 10(5):333-45, Stein, Antisense Nucleic Acid Drug Dev. 2001 October 11(5): 317-25, Vorobjev et al. Antisense Nucleic Acid Drug Dev. 2001 April 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

Figure 30:
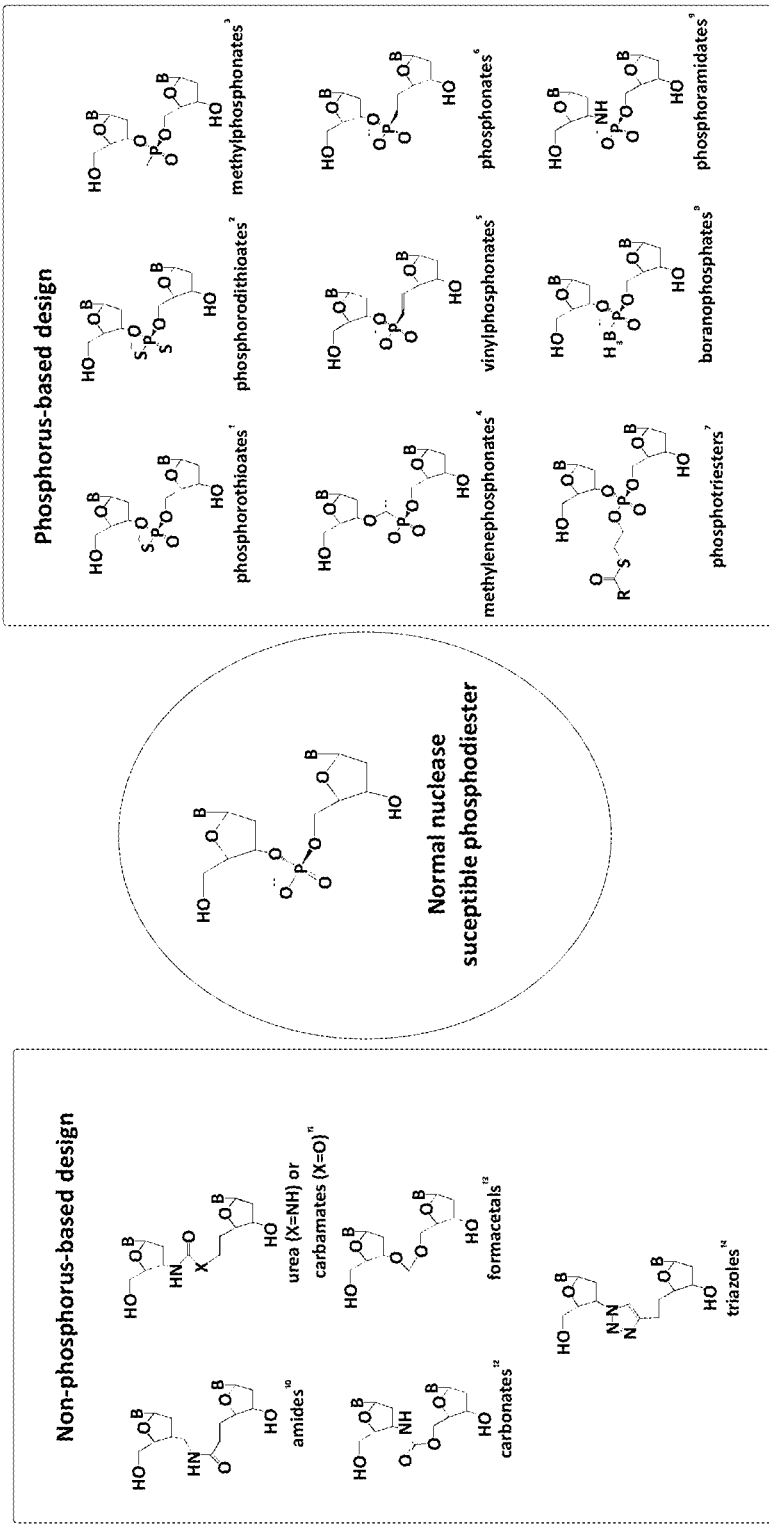
FIG. 30 depicts exemplary internucleotide linkages.

In some embodiments, the compounds, oligonucleotides and nucleic acids described herein may be modified to comprise the internucleotide linkages provided in FIG. 30. In particular embodiments, the compounds, oligonucleotides and nucleic acids described herein comprise internuclotide linkages selected from phosphodiester and phosphorothioate.

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

Figure 31:
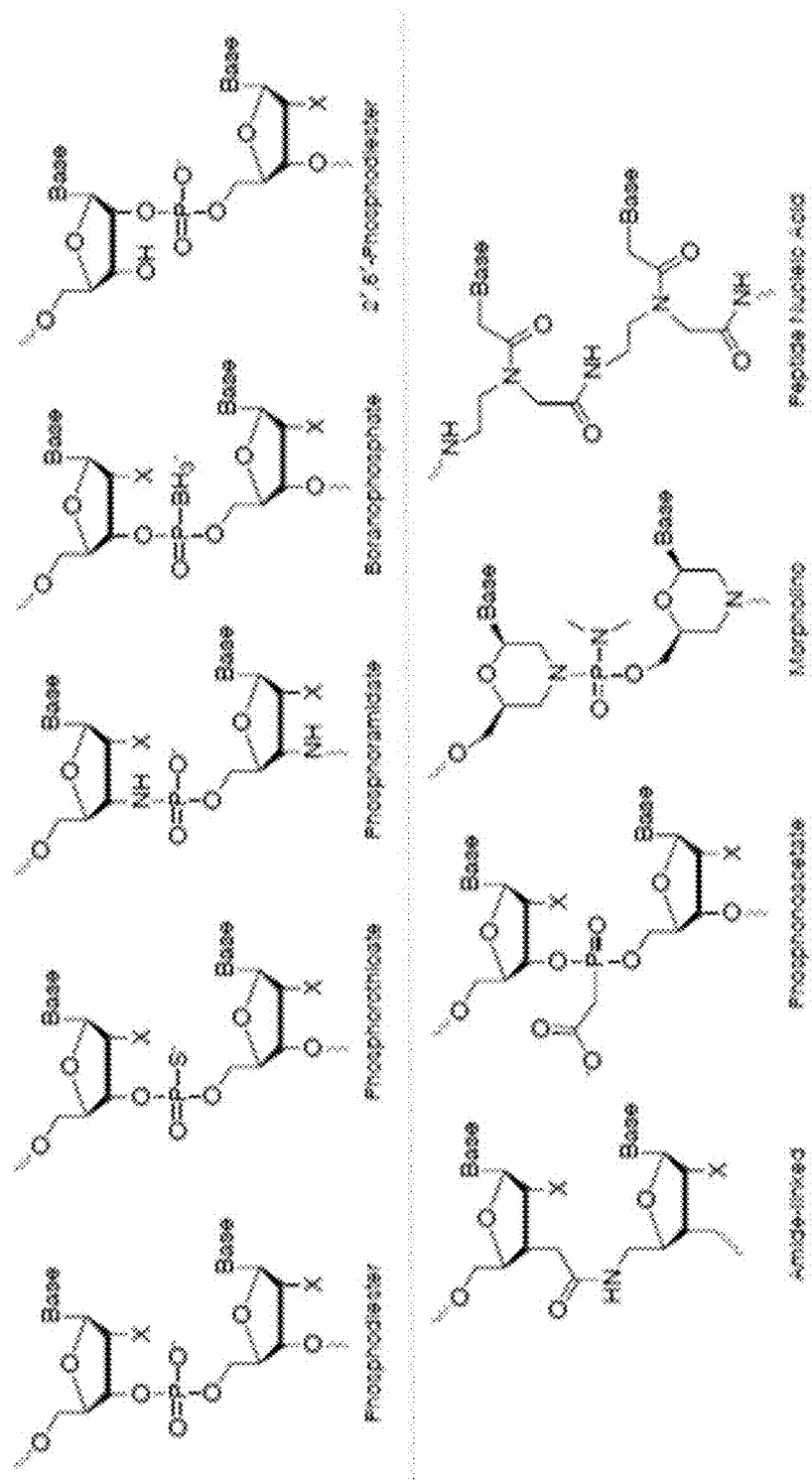
FIG. 31 depicts exemplary internucleotide backbone linkages.

Oligonucleotide backbones may comprise phosphates, phosphorothioates (a racemic mixture or stereospecific), diphosphorothioates, phosphoramidates, peptide nucleic acid, boranophosphate, 2'-5'phosphodiester, amides, phosphonoacetate, morpholino moieties, or a combination thereof. In some embodiments, the compounds, oligonucleotides and nucleic acids described herein may be modified to comprise the internucleotide backbone linkages provided in FIG. 31.

In certain embodiments, provided herein are compounds comprising a phosphate moiety (e.g., X1, X4, X5 and X6), a phosphonate moiety (e.g., X3, X7 and X8). These moieties will be partially or completely ionized as a function of the moiety's pKa and the pH of the environment. It is understood that negatively charged ions will be balanced by a cationic moiety, e.g., an alkali metal such as sodium or potassium, an alkali earth metal such as calcium or magnesium, or an ammonium or guanidinium ion.

Figure 32:
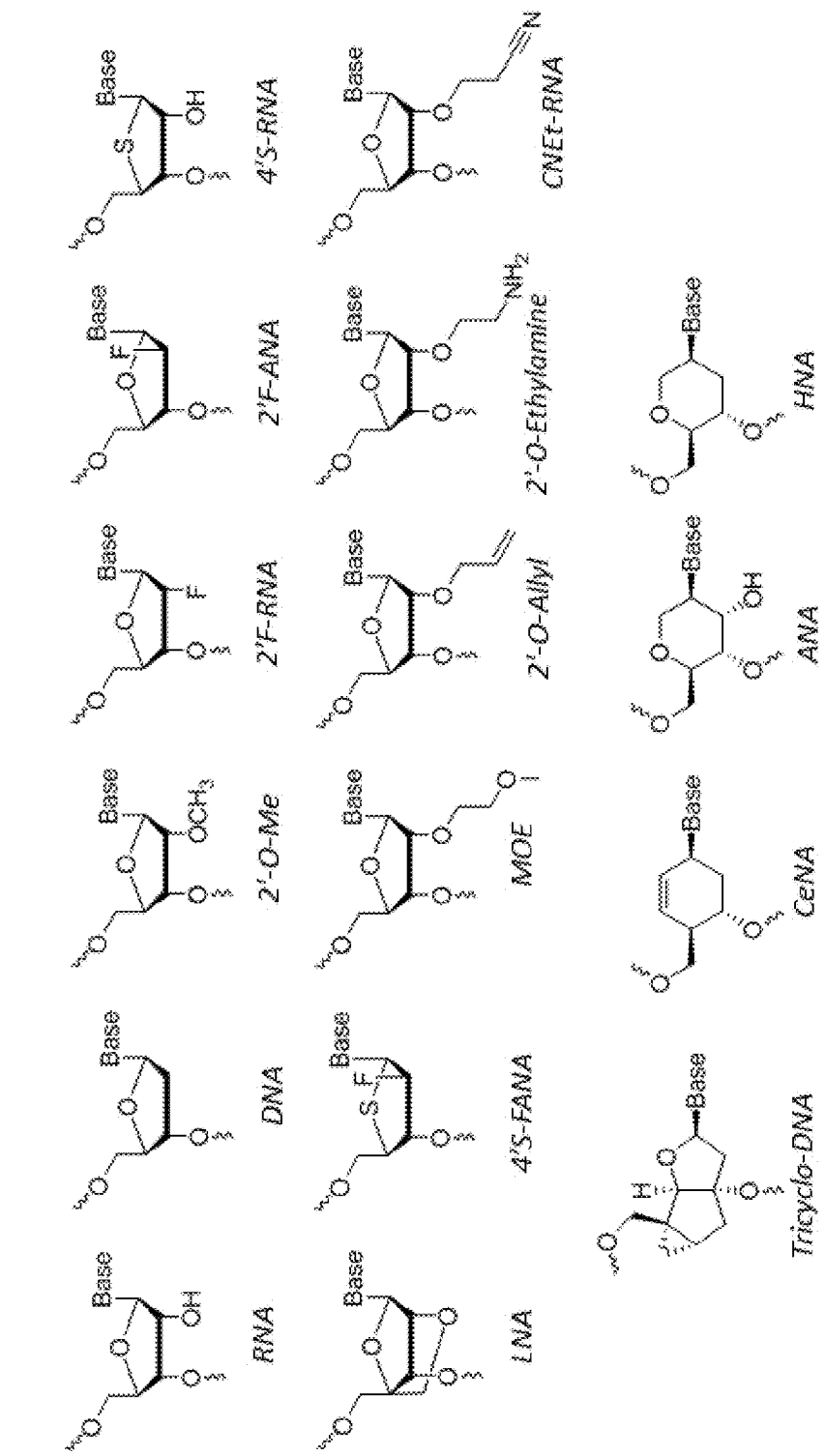
FIG. 32 depicts exemplary sugar modifications.
Figure 33A:
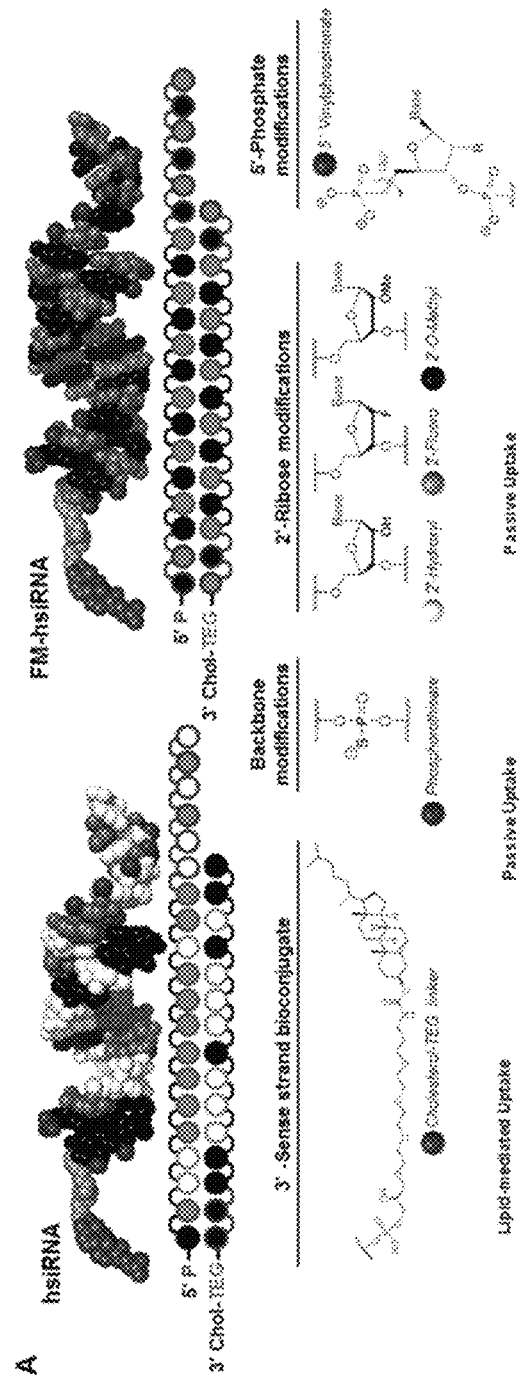
FIG. 33A-E depicts fully metabolically stabilized hsiRNAs (FM-hsiRNAs). (A) Schematics of partially and fully modified hsiRNAs. (B) hsiRNA and FM-hsiRNA have equal ability to enter RISC (HeLa, 72 hours, QuantiGene®). hsiRNA-conjugate structures, sequences, and modifications are found in FIG. 9A-F and FIG. 14. (C) FM-hsiRNA, but not naked siRNA, supports passive delivery. (D) Metabolically stable 5'-E-VP (Vinylphosphonate) is as active as 5'-P (Phosphate). The antisense strand of the hsiRNAs are capped at the 5' as follows: FM-hsiRNA-no P is capped with a 5'-OH; FM-hsiRNA is capped with a 5' phosphate; FM-hsiRNA-EVP is capped with a 5' vinyl phosphonate. (E) 5'-E-VP enables sustained delivery to distant tissues (7 days post injection, PNA assay). The antisense strand of the hsiRNAs are capped at the 5' as follows: 5'P-hsiRNA is capped with a 5' phosphate; 5VP'-hsiRNA is capped with a 5' vinyl phosphonate. The hsiRNA sequence for FIG. 33 D-E is PPIB, found in FIG. 14.
Figure 33B:
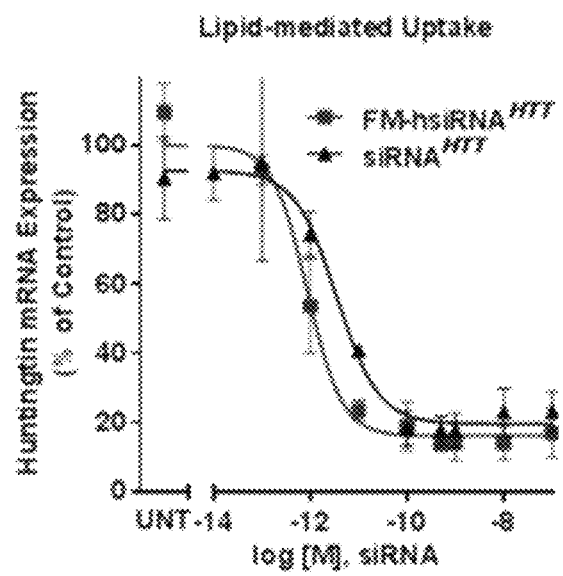
Figure 33C:
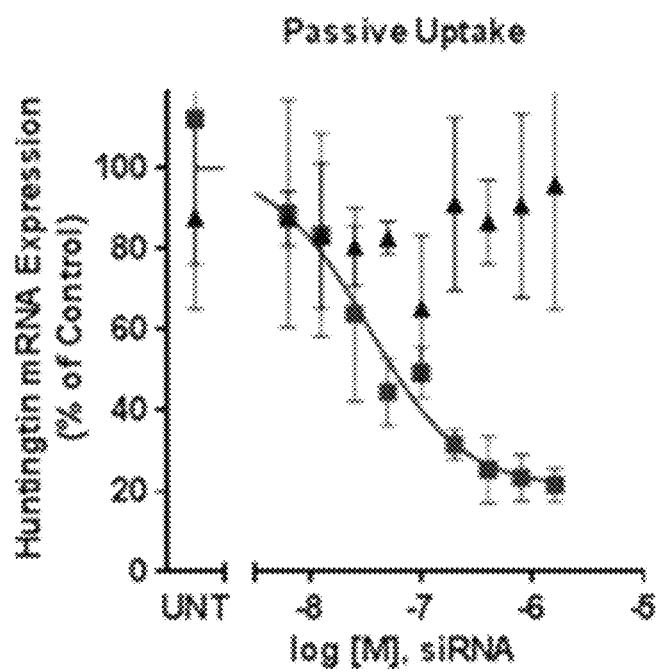
Figure 33D:
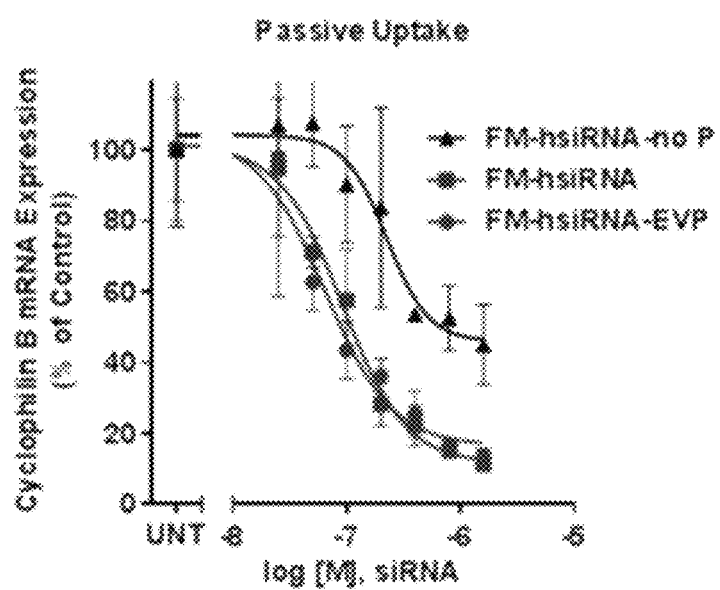
Figure 33E:
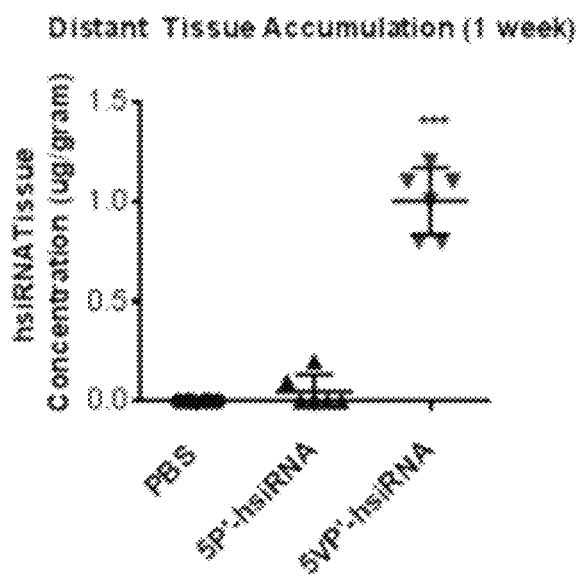

In some embodiments, the compounds, oligonucleotides and nucleic acids described herein may be modified to comprise the sugar modifications provided in FIG. 32.

Methods of Delivering Nucleic Acid

In another aspect, provided herein is a method for selectively delivering a nucleic acid as described herein to a particular organ in a patient, comprising administering said nucleic acid to the patient, wherein the nucleic acid comprises a bioactive molecule having an affinity for a receptor. In one embodiment, the organ is the liver. In another embodiment, the organ is the kidneys. In another embodiment, the organ is the spleen. In another embodiment, the organ is the heart. In another embodiment, the organ is the brain.

The nature of the conjugated hydrophobic moiety (e.g., DHA and EPA) dramatically alters tissue distribution profiles. In certain embodiments, cholesterol and saturated fatty acid (e.g., DCA)-conjugated hsiRNA distributes preferentially to the liver and spleen. In other embodiments, polyunsaturated fatty acid (e.g., DHA and EPA)-conjugated hsiRNA distributes preferentially to the kidneys and heart in addition to the liver and spleen. In a particular embodiment, DHA-conjugated hsiRNA distributes preferentially to the kidneys. In another particular embodiment, the delivery of DHA-conjugated hsiRNA to the kidneys is specific to proximal tubule cells, preferentially involved in a range of kidney diseases including diabetic nephropathy, renal cancer, and lupus. DHA-conjugated hsiRNA shows robust gene modulation in the liver and kidney after a single IV injection of 15 mg/kg.

Figure 36:
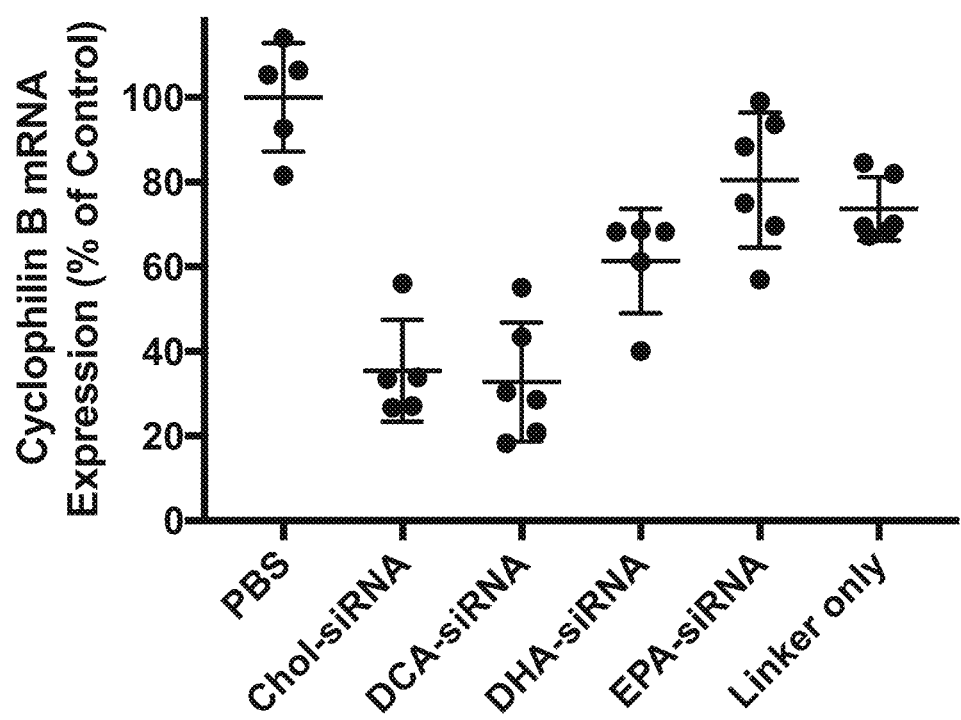
FIG. 36 shows that intravenous injection of lipid-siRNA conjugates induces differential levels of gene silencing in the liver, which is directly proportional to the degree of accumulation. Intravenous injection (20 mg/kg) of each siRNA conjugate. Animals sacrificed 7 days post-injection. Tissue punches taken from the liver tissue. mRNA was quantified using Affymetrix Quantigene 2.0 as per Coles et al. 2015. hsiRNA-conjugate structures and modifications are shown in FIG. 9A-F and the PPIB hsiRNA sequence is shown in FIG. 14.

As shown in FIG. 36, highly hydrophobic siRNA conjugates (e.g. cholesterol, docosanoic acid) distribute primarily to the liver after systemic (intravenous or subcutaneous) delivery, with residual accumulation in the spleen. Less hydrophobic siRNA conjugates (e.g. polyunsaturated fatty acids such as docosahexaenoic acid and eicosapentaenoic acid) distribute to the kidney, liver, and heart after systemic delivery. This distribution pattern correlates with the observed efficacy of this panel of conjugates in the liver, where Chol- and DCA-siRNA are highly accumulated and show higher silencing (~70%), while DHA- and EPA-siRNA conjugate accumulation is less pronounced and therefore shows lower levels of silencing (40% and 25%, respectively). An siRNA containing the tetraethylene glycol linker only (Linker only) shows residual levels of liver silencing as well.

Figure 37A:
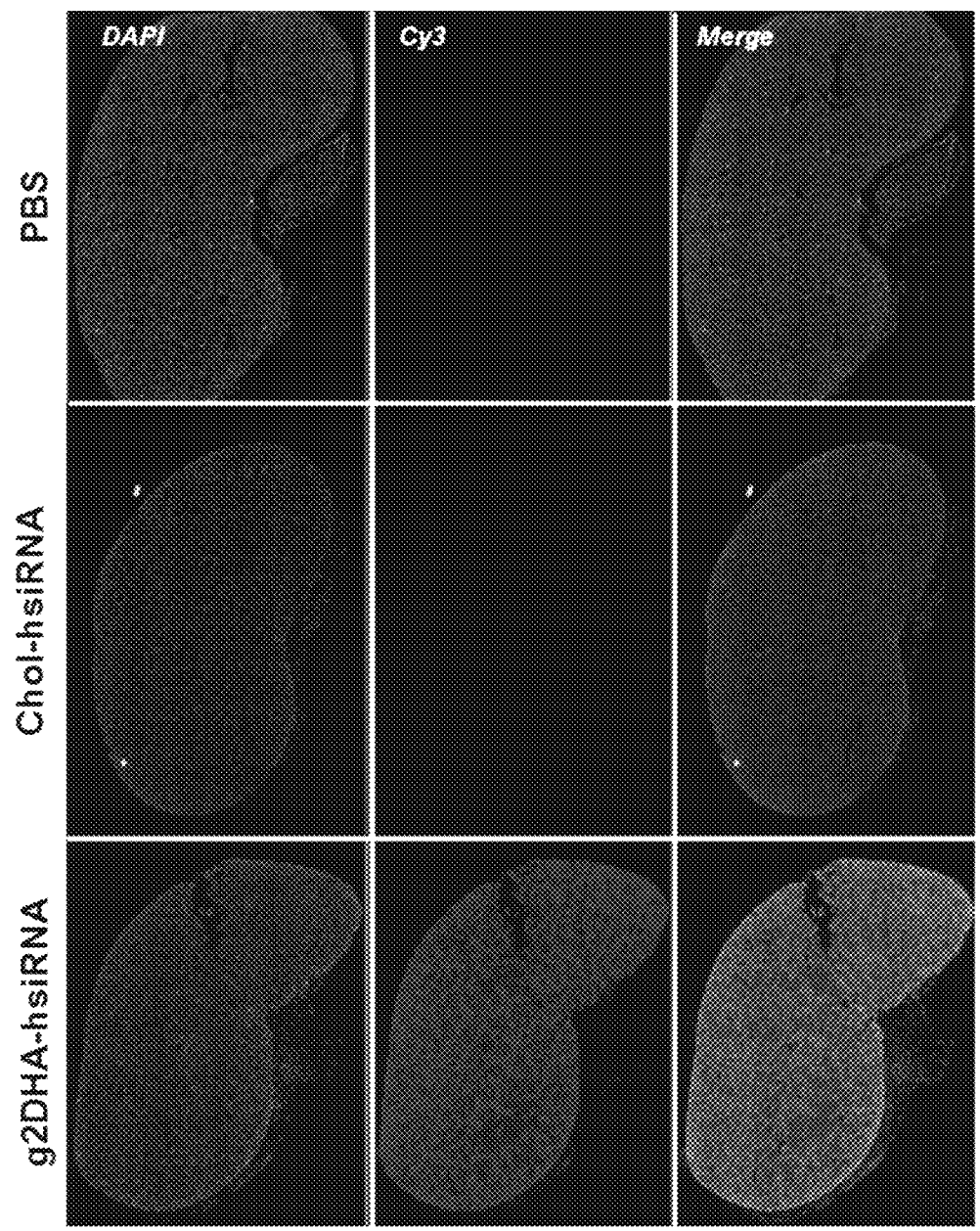
FIG. 37A-B depicts targeted kidney delivery with polyunsaturated fatty acid chemical scaffolds. (A) Intravenous injection of PBS, Chol-siRNA, or g2DHA-siRNA (20 mg/kg twice daily for two days). Animals sacrificed 7 days post-injection. 63× image of kidney sections showing Cy3-fluorescence of oligonucleotides. hsiRNA-conjugate structures and modifications are shown in FIG. 9A-F and the sFLT1 sequence is on FIG. 8. (B) siRNA antisense strands present in liver and kidney were quantified using Cy3-labeled complimentary PNA to hybridize to the strand and HPLC to quantify ng of oligo per mg of tissue. hsiRNA-conjugate structures and modifications are shown in FIG. 9A-F and the PPIB sequence is on FIG. 14.
Figure 37B:
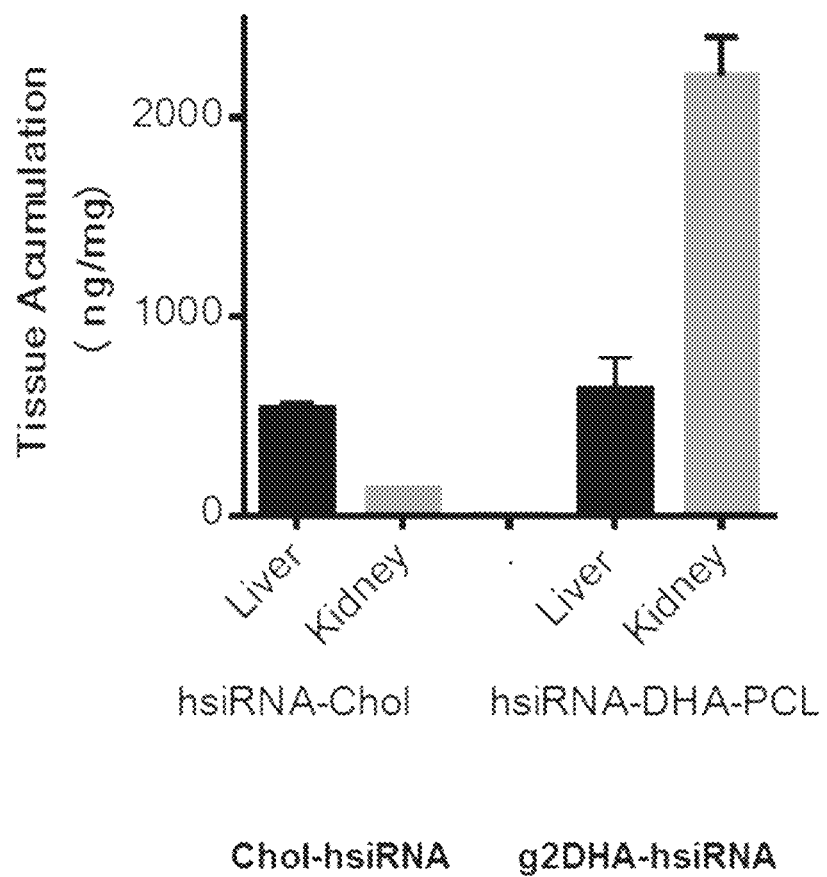
Figure 38:
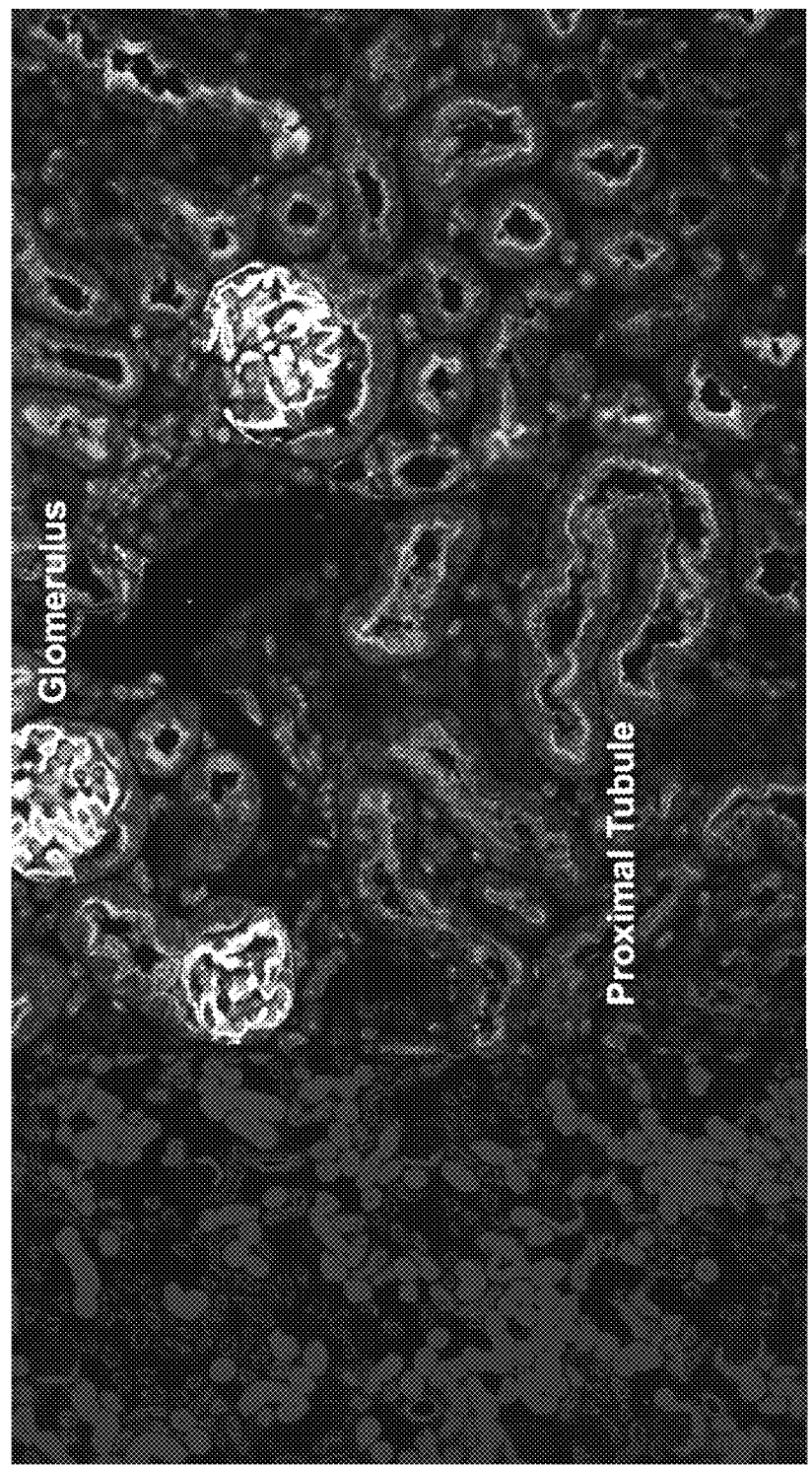
FIG. 38 shows that g2DHA-hsiRNA preferentially distributes to proximal convoluted tubule cells throughout the kidney following systemic administration (two IV injections of 20 mg/kg, 48 hours). This sharply contrasts with the predominant liver localization exhibited by most siRNA therapeutics in the clinic and opens the window to expand the clinical utility of siRNA beyond liver indications.
Figure 39:
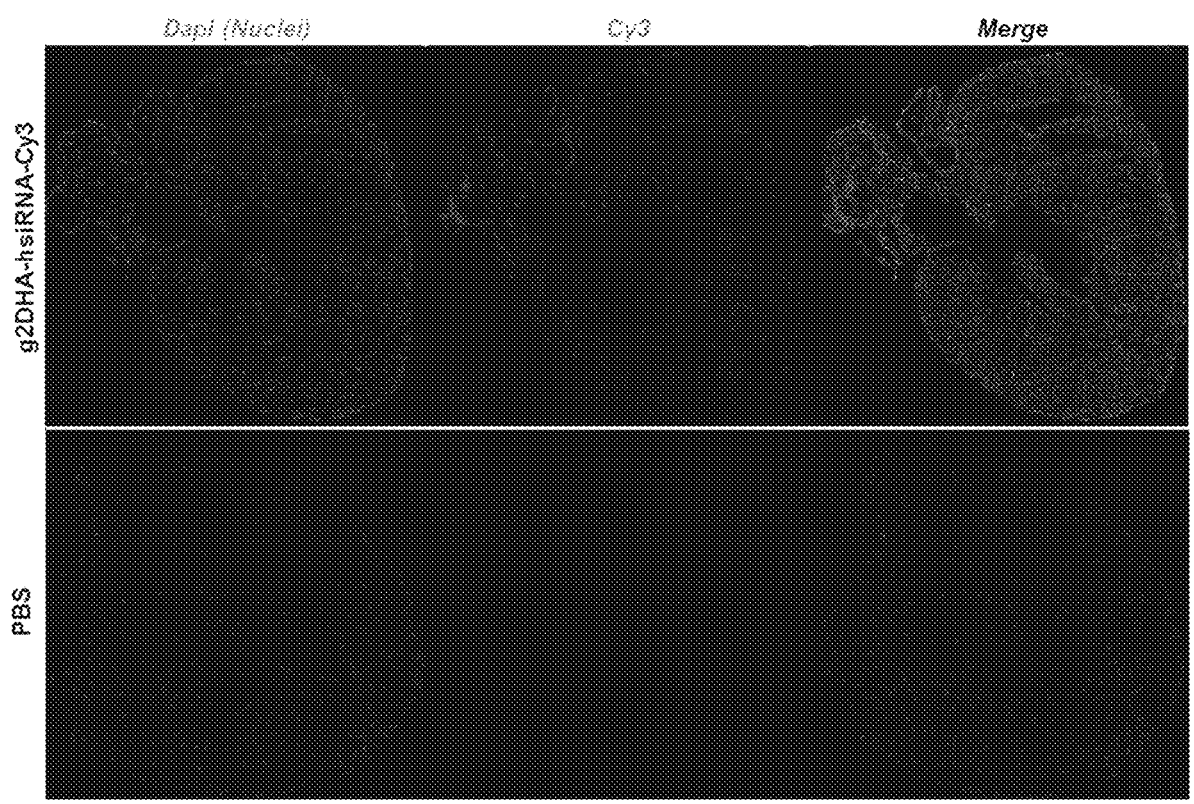
FIG. 39 shows g2DHA-hsiRNA distributed to heart tissue following systemic administration (one intravenous injection,10 mg/kg). These tissues are not typically accessed by therapeutic siRNAs following intravenous administration.
Figure 40:
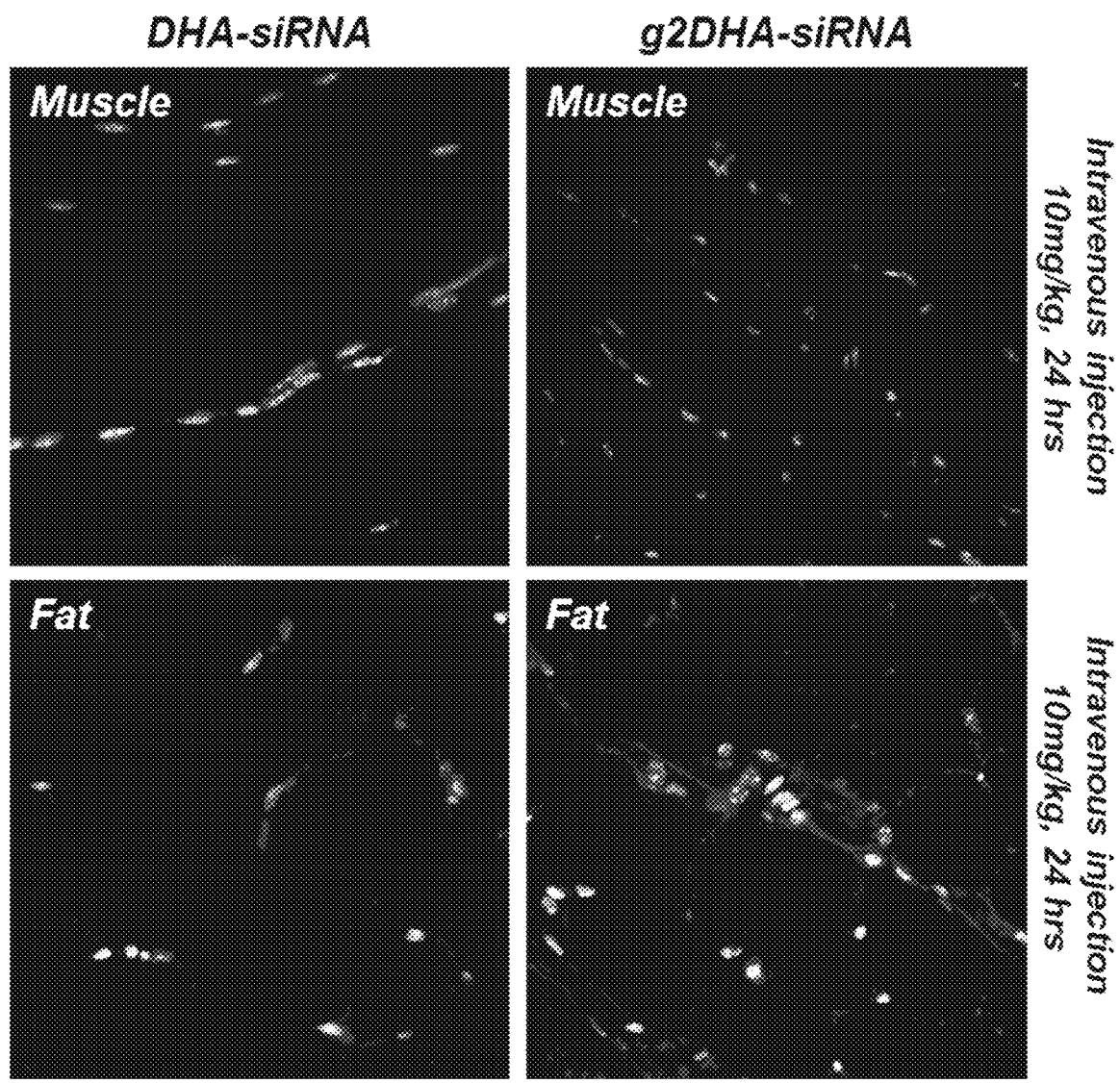
FIG. 40 shows g2DHA-hsiRNA distributed to muscle and fat tissue following systemic administration (one intravenous injection,10 mg/kg). These tissues are not typically accessed by therapeutic siRNAs following intravenous administration. hsiRNA-conjugate structures and modifications are shown in FIG. 9A-F and the sFLT1 sequence is on FIG. 8.
Figure 41:
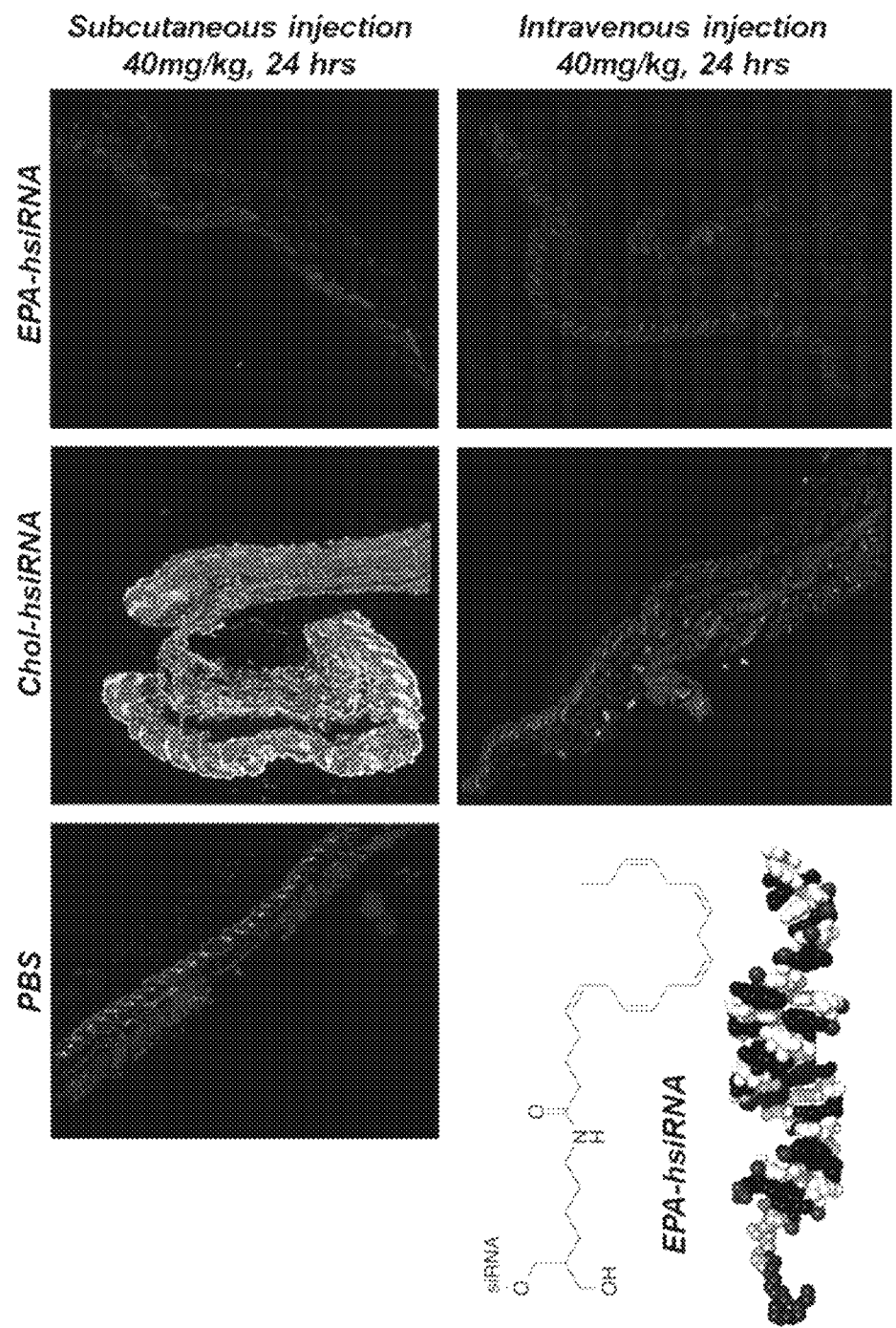
FIG. 41 shows Eicosapentanoic acid (EPA)-hsiRNA accumulation in the skin following subcutaneous injection. This can be directly compared to cholesterol-conjugated hsiRNA, which accumulates to a greater degree around the site of injection. This higher degree of accumulation may cause local toxicity and adverse effects, which is well documented for intrastriatal (CNS) administration. hsiRNA-conjugate structures and modifications are found in FIG. 9A-F and the sFLT1 sequence is shown in FIG. 8.
Figure 42:
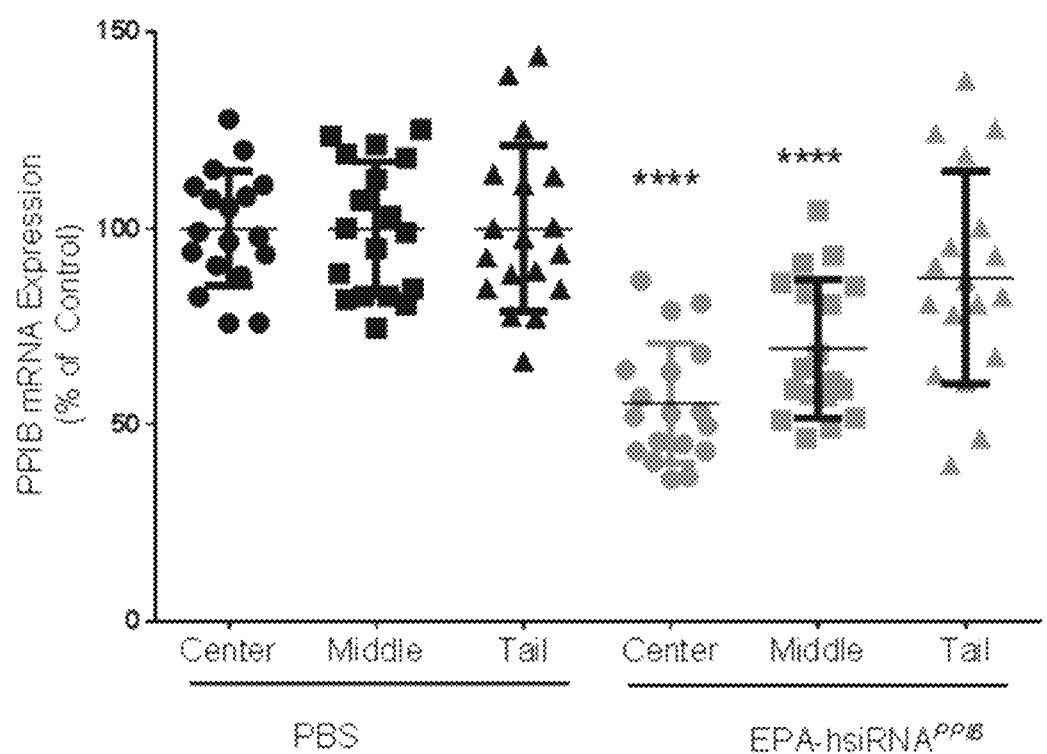
FIG. 42 shows that subcutaneous injection of EPA-hsiRNA induces gene silencing in the skin. Subcutaneous injection (40 mg/kg) EPA-siRNA. Animals sacrificed 7 days post-injection. Tissue punches taken from the center (skin from head to the center of the back), middle (skin around the midpoint of the animal), and tail skin. mRNA was quantified using Affymetrix Quantigene 2.0 as per Coles et al. 2015. hsiRNA sequence PPIB is found in FIG. 14.
Figure 43A:
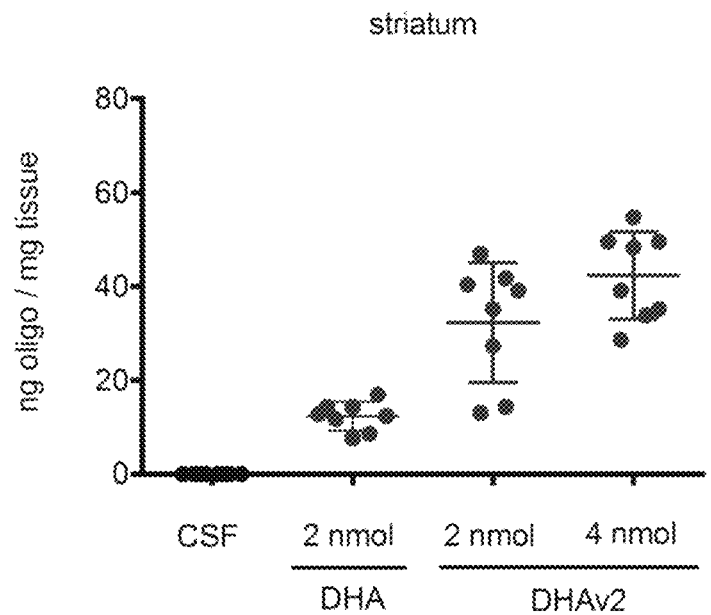
FIG. 43A-B shows that a single injection of DHA- or g2DHA-siRNA is detected in both the straitum (A) and cortex (B) on the injected side. Alternative methods of injection including intracerebralventricular may also facilitate bilateral distribution with only one injection. Intrastriatal injection 2-4 nmols DHA- or g2DHA-siRNA. Animals sacrificed 7 days post-injection. Tissue punches taken from the 300 um brain slices from the striatum and cortex. siRNA antisense strands present in different brain regions were quantified using Cy3-labeled complimentary PNA to hybridize to the strand and HPLC to quantify ng of oligo per mg of tissue. aCSF—Artificial CSF. hsiRNA-conjugate structures and modifications are found in FIG. 9A-F and the PPIB sequence is shown in FIG. 14.
Figure 43B:
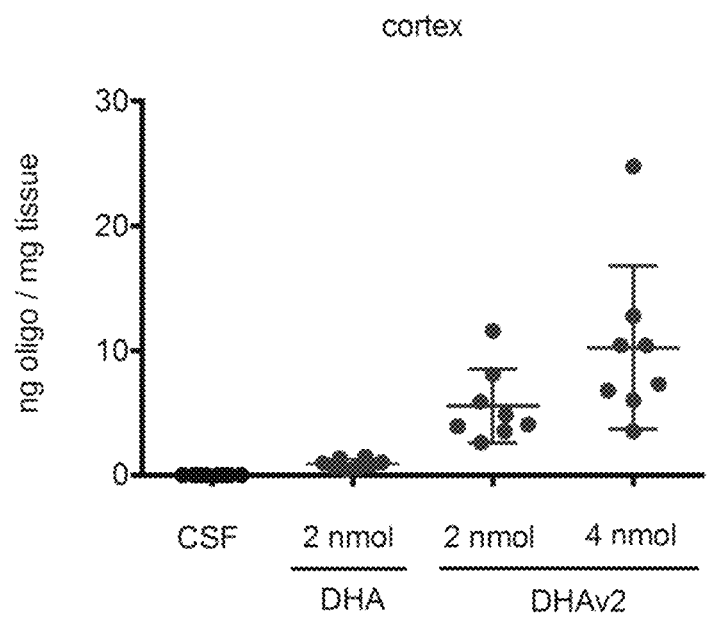

As shown in FIG. 37, g2DHA-siRNA shows preferential localization in the kidney following a single, intravenous injection, which directly contrasts the typical liver distribution observed for highly hydrophobic lipid-siRNA conjugates (e.g. cholesterol, DCA). The differences in the degree of accumulation was measured using a quantitative peptide nucleic acid hybridization assay. We observe a statistically significant increase in kidney accumulation and decrease in liver accumulation with g2DHA-siRNA compared to Chol-siRNA.

Serum lipoprotein complexes are responsible for trafficking endogenous fatty acids and lipids throughout the bloodstream. Lipid-conjugated siRNAs may avail themselves of this mechanism to achieve distribution to different tissues following intravenous administration. FIG. 44 describes the different lipid-binding and systemic distribution characteristics of each individual serum lipoprotein. Very low density lipoprotein (VLDL); Intermediate density lipoprotein (IDL); Low density lipoprotein (LDL); High density lipoprotein (HDL).

Figure 45:
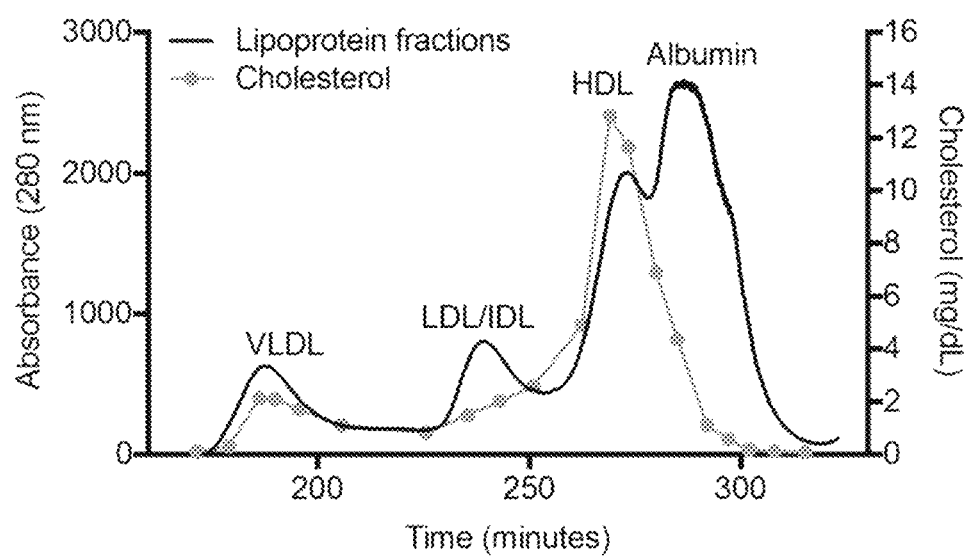
FIG. 45 shows the lipoprotein profile of FVB/NJ mice. Whole mouse blood (~500 µL) was collected in a sterile EDTA-coated tube following cardiac puncture. Samples were spun at 10,000 RPM for 10 minutes. 50 µL of serum was directly injected on Superose 360 size exclusion column. Fractions were collected over 300 minutes and analyzed for cholesterol content by the HDL/LDL Cholesterol Assay Kit (Abcam).

The different tissue distribution patterns observed in vivo for each distinct siRNA conjugate are determined by their lipoprotein binding profiles. These profiles can be determined empirically using size exclusion chromatography and monitoring the absorbance at 280 nm (protein). As shown in FIG. 45, protein peak fractions were collected and a cholesterol quantification assay was used to determine the identity of each peak in the trace. In wild-type FVB/NJ mice, cholesterol is primarily associated with HDL. From this, the albumin, HDL, LDL/IDL, and VLDL peaks were assigned.

Figure 46A:
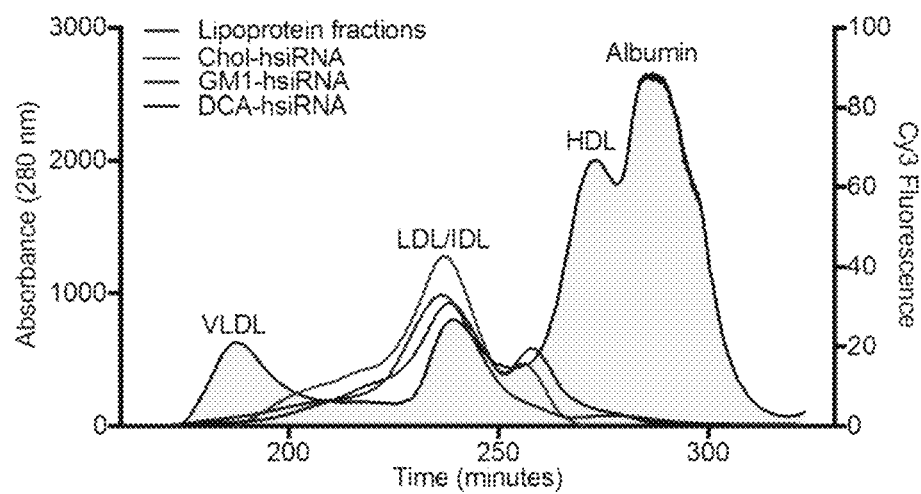
FIG. 46A-B depicts serum lipoprotein profile analysis of siRNA in mouse blood. (A) cholesterol, DCA, and GM1 conjugates preferentially associate with IDL and LDL. hsiRNA-conjugate structures and modifications are found in FIG. 9A-F. (B) EPA, DHA, and DHAg2 conjugates preferentially associate with HDL. The structure of the EPA conjugate can be found in FIG. 41. hsiRNA conjugates (15 µM) were incubated in 50 µL of serum at room temperature for 30 minutes. 50 µL of serum was directly injected on Superose 360 size exclusion column. Fractions were collected over 300 minutes and analyzed for cholesterol content by the HDL/LDL Cholesterol Assay Kit (Abcam). The HTT sequence is shown in FIG. 14.
Figure 46B:
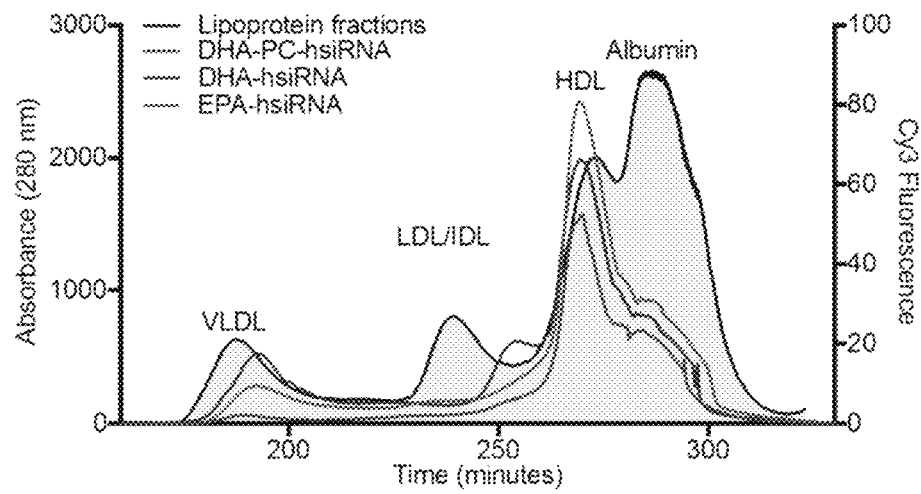
Figure 49:
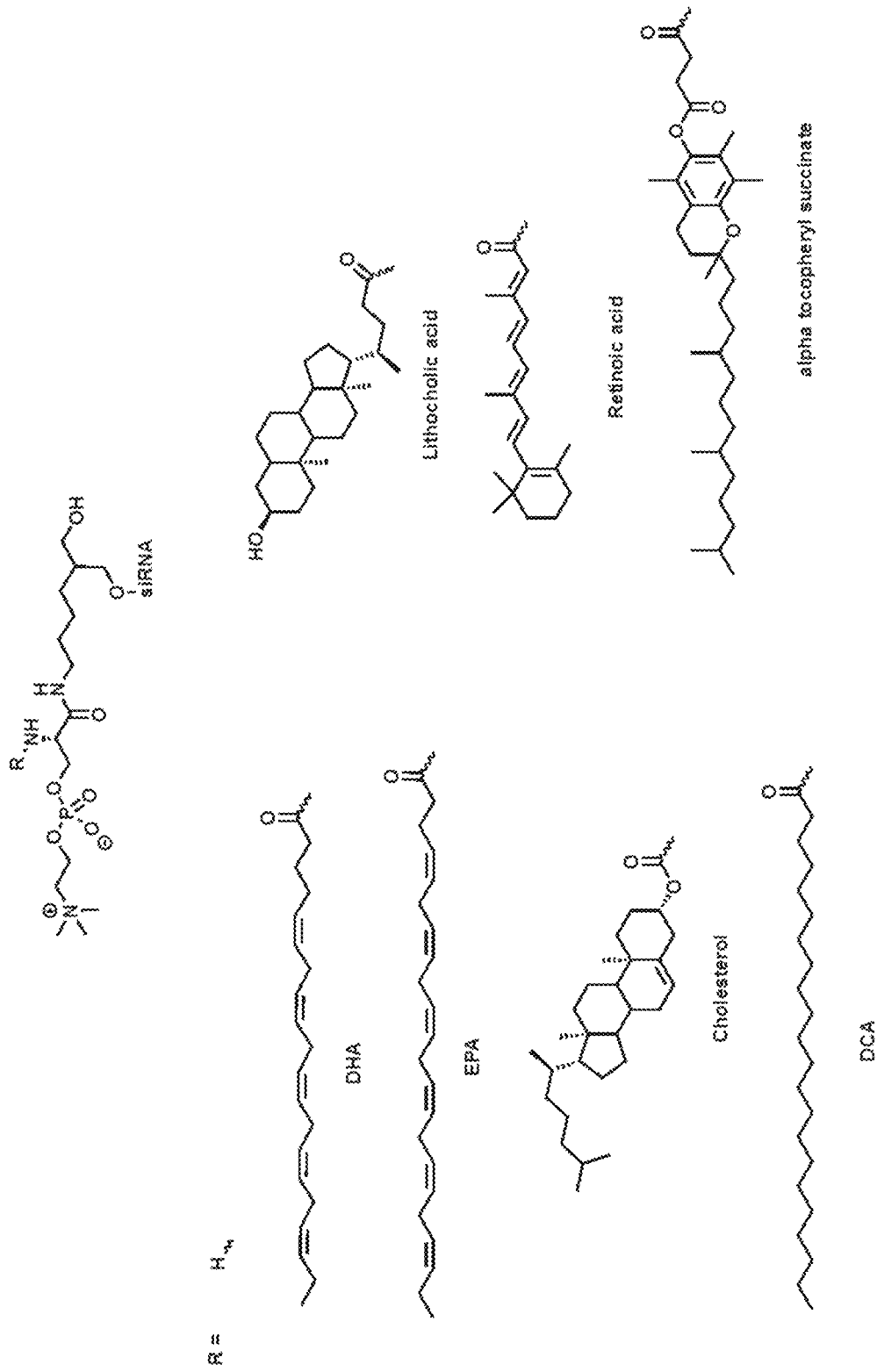
FIG. 49 shows hydrophobic siRNA conjugates with esterified phosphatidylcholine modifiers.

The serum lipoprotein progile of siRNA in mouse blood was analyzed. As shown in FIG. 46, Cy3-labeled siRNA conjugates were incubated ex vivo with serum isolated from wild type mice and analyzed as described previously by size exclusion chromatography. This lipoprotein binding correlates with observed PK/PD and distribution to the liver, kidney, and spleen (primarily VLDL, LDL, and IDL binding) or kidney, liver, and heart (HDL binding). Below, we demonstrate that cholesterol, DCA, and GM1 conjugates preferentially associate with IDL and LDL, while EPA, DHA, and DHAg2 conjugates preferentially associate with HDL. For polyunsaturated fatty acid-siRNA conjugates, the minimum number of double bonds necessary to achieve HDL binding and distribution to the kidney is >=3 (e.g. DHA, EPA, anandamide, alpha-linolenic acid, gamma-linolenic acid, arachidonic acid, etc.).

In another aspect, provided herein is a method for selectively delivering a nucleic acid as described herein to the kidneys of a patient, comprising administering said nucleic acid to the patient intravenously, wherein the hydrophobic moiety is characterized by a clogP value in a range selected from: −10 to −9, −9 to −8, −8 to −7, −7 to −6, −6 to −5, −5 to −4, −4 to −3, −3 to −2, −2 to −1, −1 to 0, 0 to 1, 1 to 2, 2 to 3, 3 to 4, 4 to 5, 5 to 6, 6 to 7, 7 to 8, 8 to 9, and 9 to 10.

Figure 20:
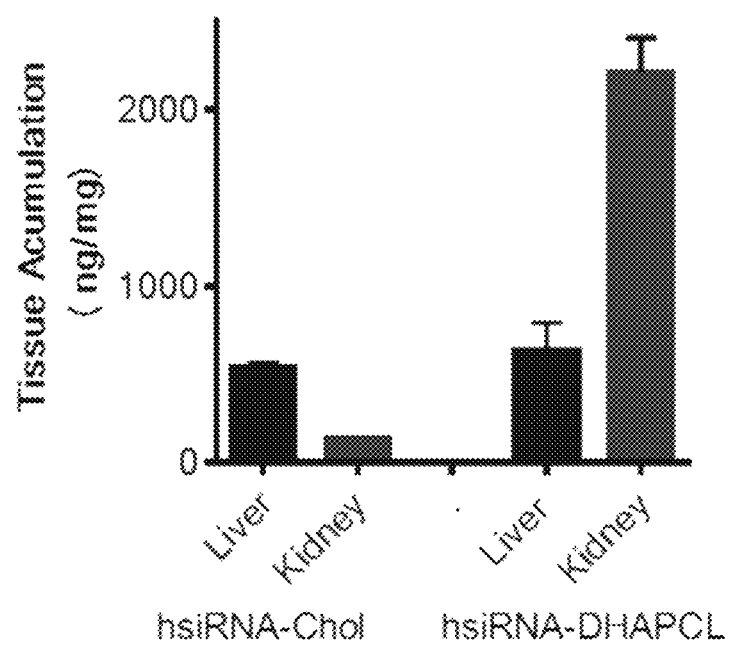
FIG. 20 shows targeted kidney delivery with DHA-PCL conjugated hsiRNA. hsiRNA-conjugate structures and modifications are shown in FIG. 9A-F and the HTT siRNA sequence is on FIG. 14.
Figure 21A:
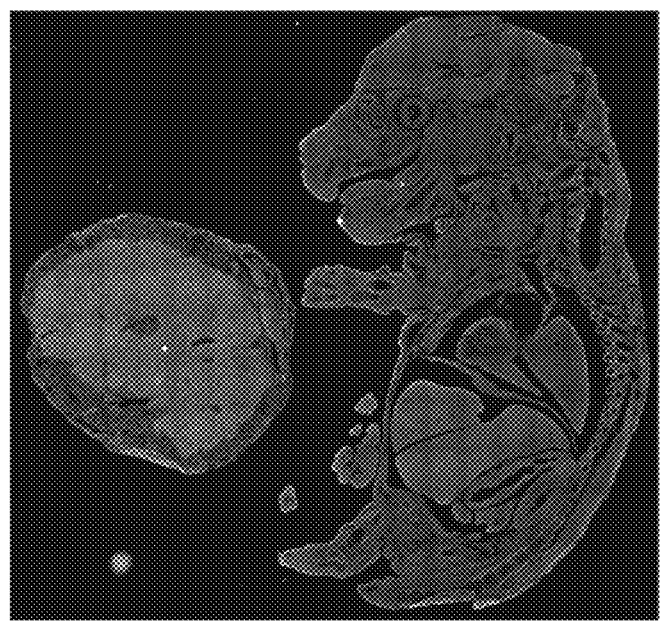
FIG. 21A-B shows targeted placental delivery with polyunsaturated fatty acid chemical scaffolds. DHA-conjugated oligonucleotides can be delivered intravenously to the mother and show targeted delivery to maternal kidney, liver, and placenta with no observed oligonucleotide transfer or toxicity in embryos. (A) Intravenous injection of DHA-siRNA (15 mg/kg). Animals sacrificed 7 days post-injection. 63× image of embryo and placenta showing Cy3-fluorescence of oligonucleotides. (B) Tissue punches taken from liver, kidney, and placenta. mRNA was quantified using Affymetrix Quantigene 2.0 as per Coles et al. 2015. hsiRNA-conjugate structures and modifications are shown in FIG. 9A-F and the sFLT1 sequence is shown in FIG. 8.
Figure 21B:
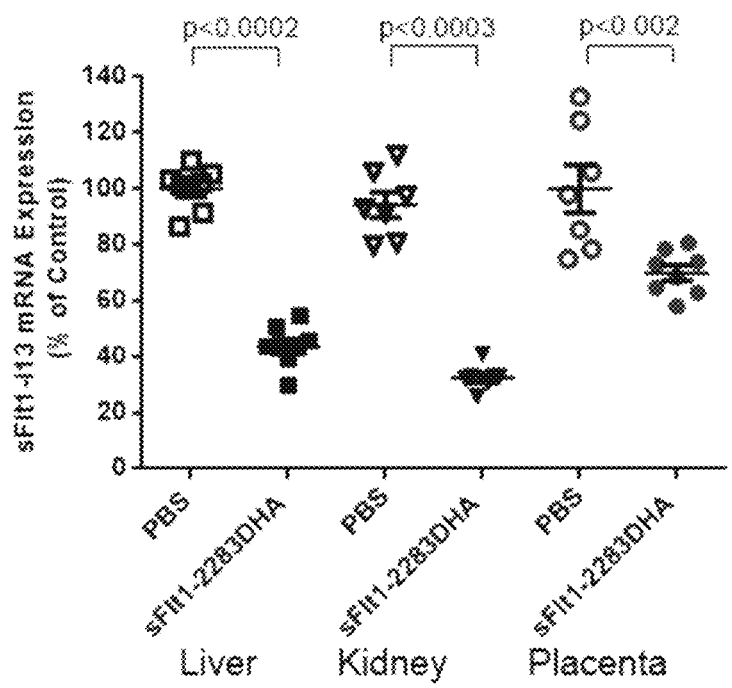
Figure 22:
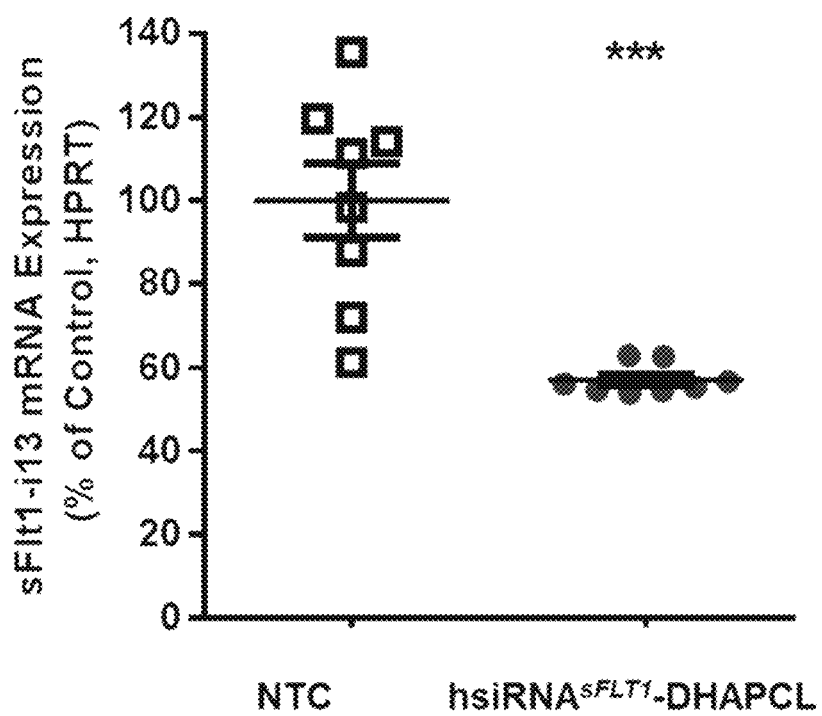
FIG. 22 shows efficient silencing in heart with a single DHA-PCL-hsiRNA injection (15 mg/kg). The sFLT1 sequence is shown in FIG. 8.
Figure 24:
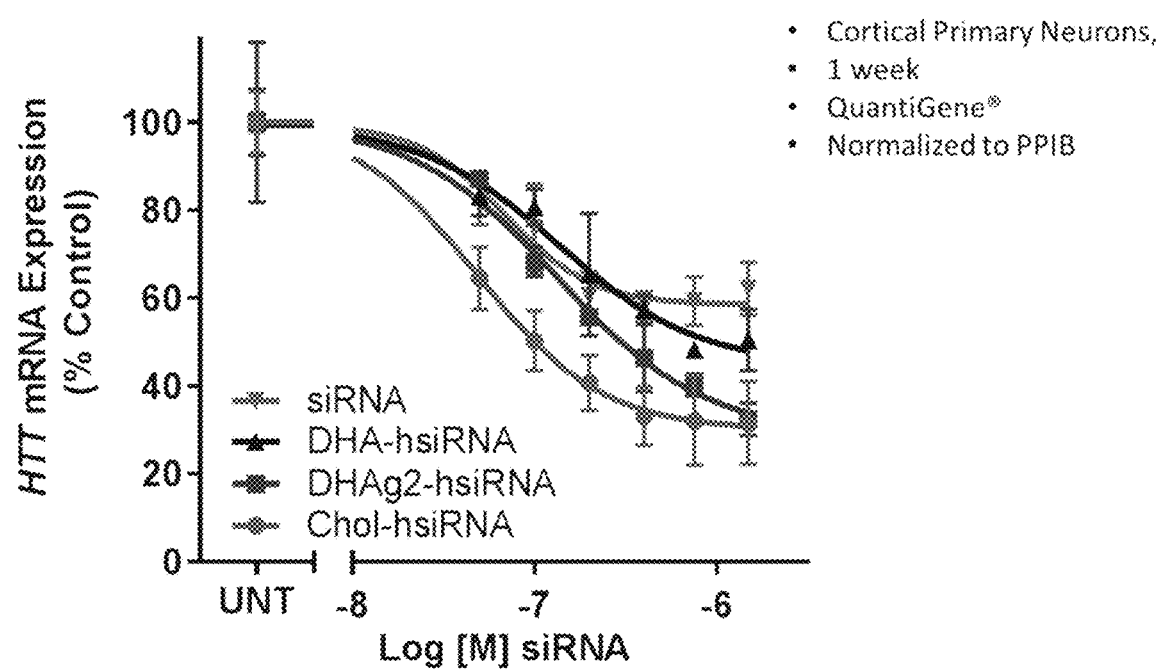
FIG. 24 shows data comparing the effect modified and unmodified hsiRNA on gene modulation in primary neurons. hsiRNA-conjugate structures and modifications are shown in FIG. 9A-F and the HTT siRNA sequence is on FIG. 14.
Figure 25:
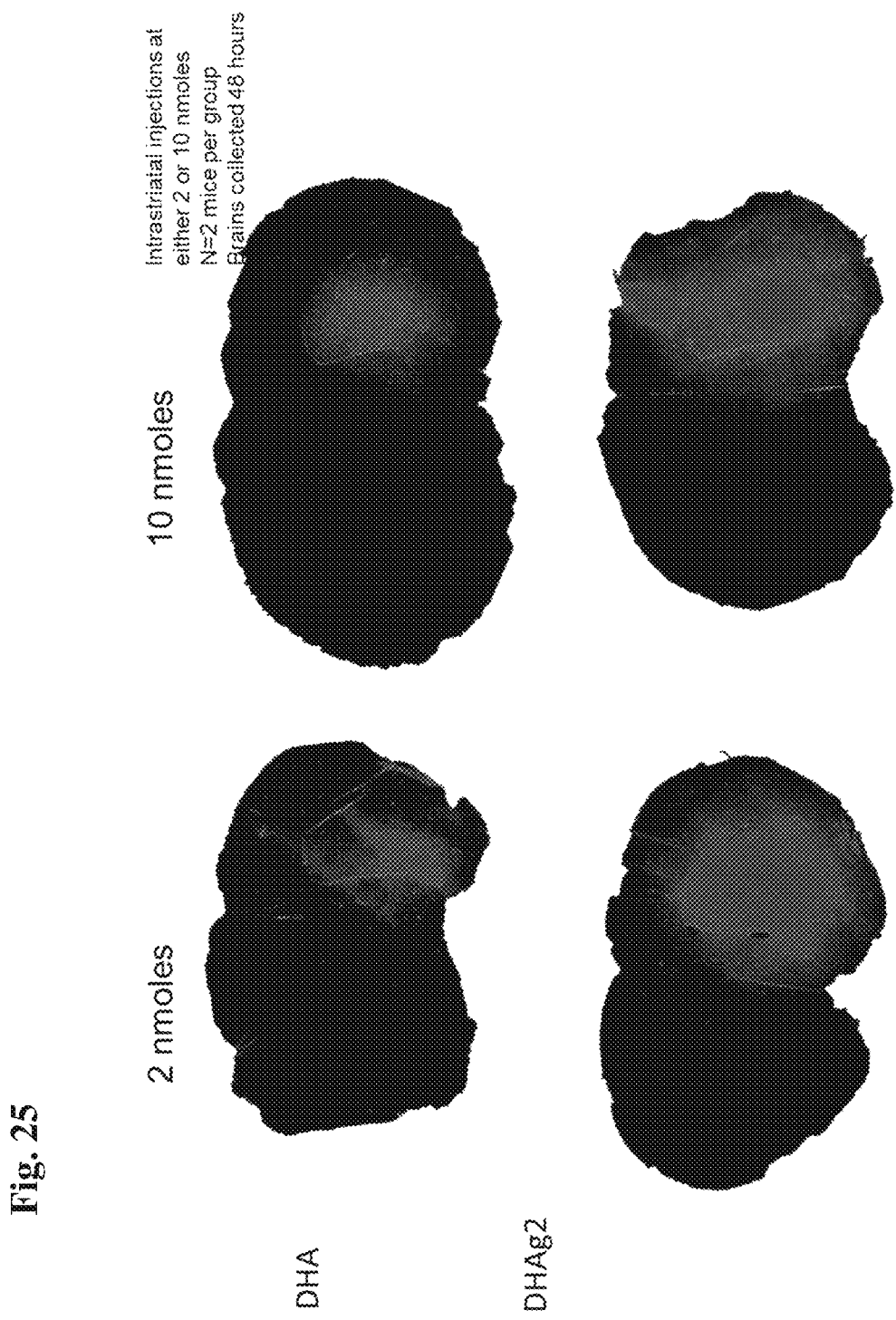
FIG. 25 shows brain retention and distribution of g2DHA-hsiRNA.
Figure 26A:
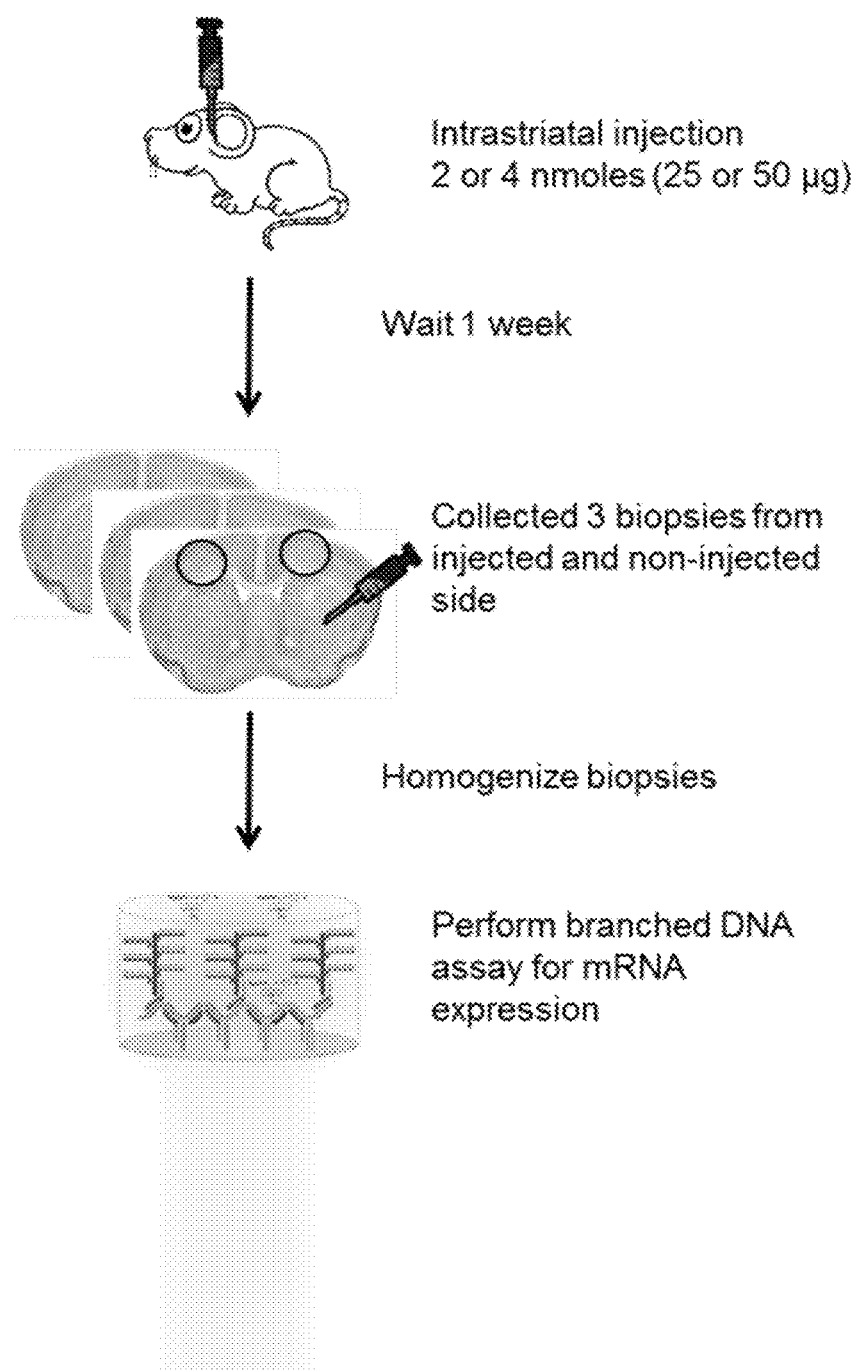
FIG. 26A-C shows the effects upon single IS injection of g2DHA-hsiRNA: (A) experimental procedure; (B) approximately 80% silencing in mouse striatum; (C) approximately 80% silencing in mouse cortex. There was no indication of toxicity and silencing was limited to injected side of the brain. hsiRNA-conjugate structures and modifications are shown in FIG. 9A-F and the hsiRNA sequence is shown in FIG. 14.
Figure 26B:
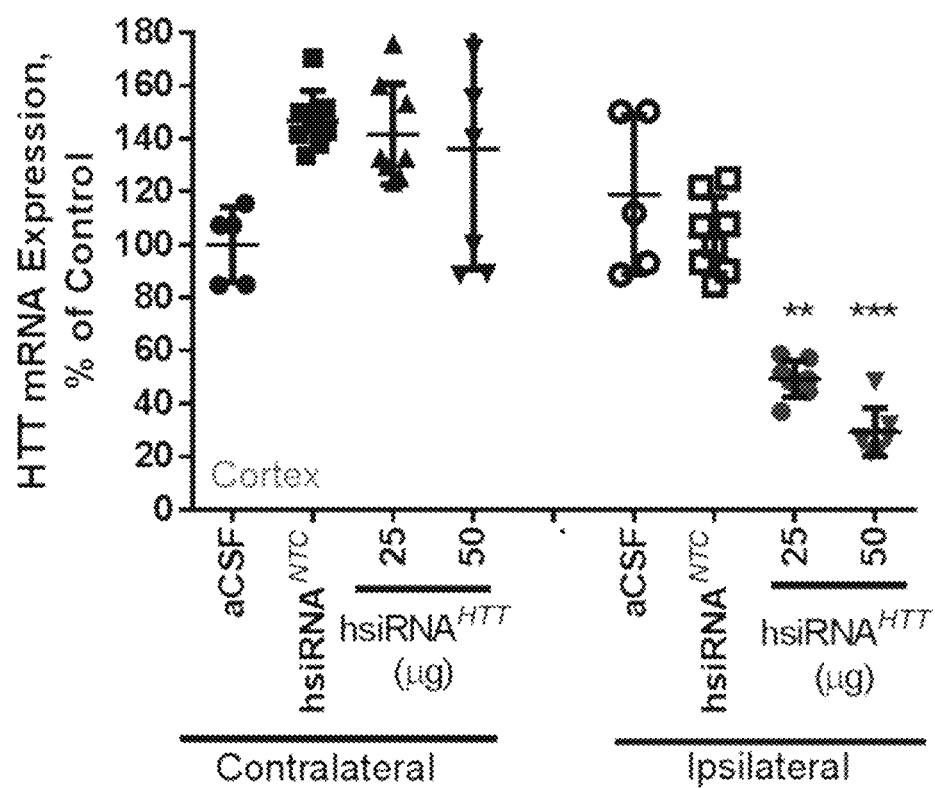
Figure 26C:
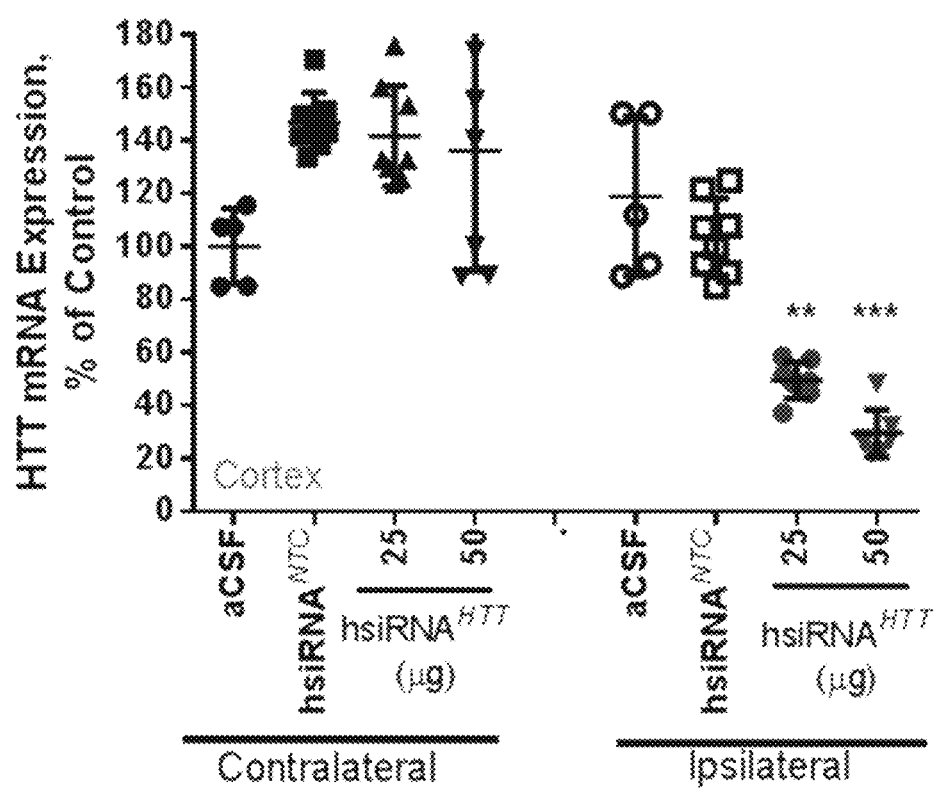
Figure 27:
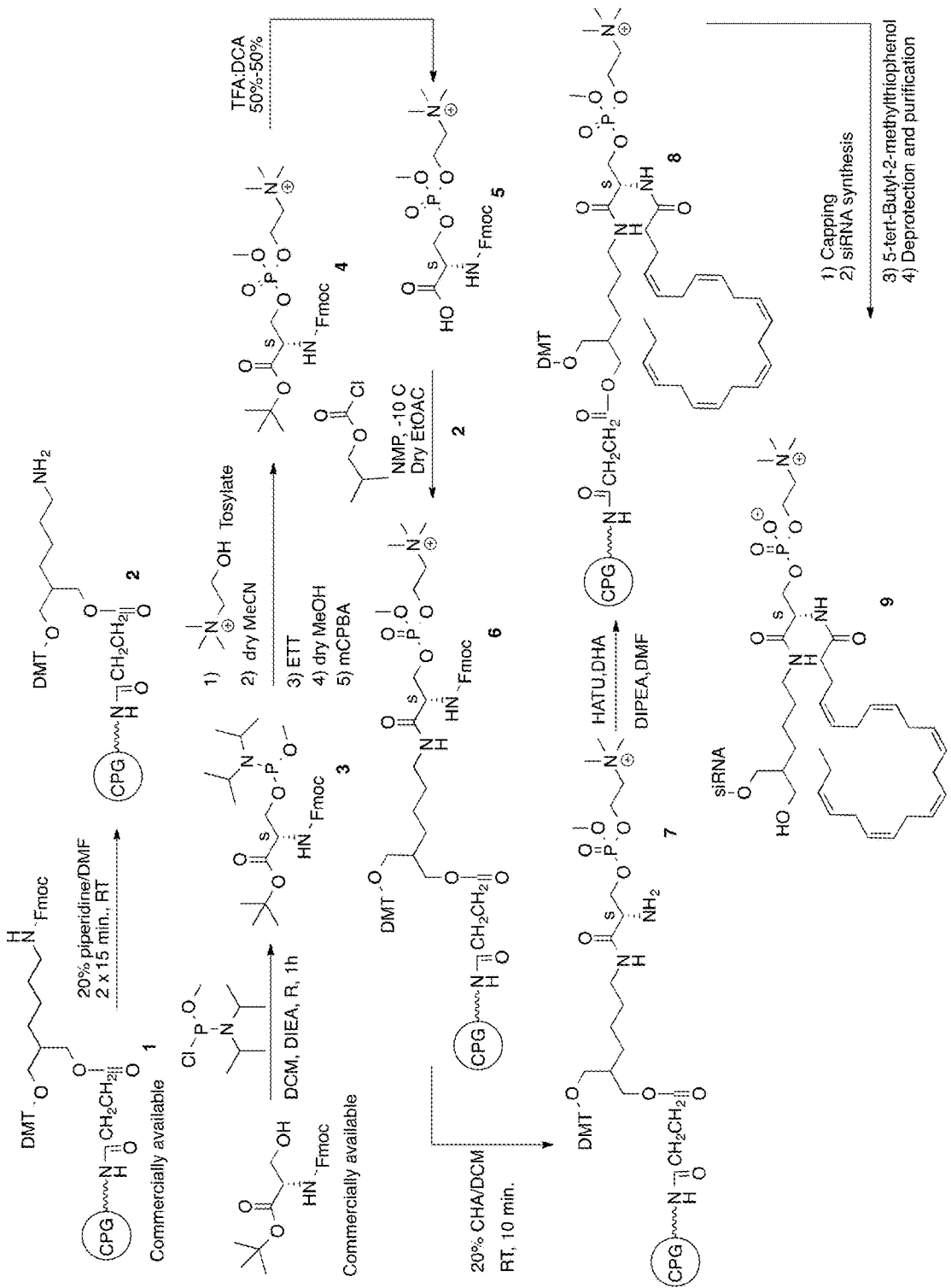
FIG. 27 shows g2DHA support synthesis I.

In another aspect, provided herein is a method for selectively delivering a nucleic acid as described herein to the kidneys of a patient, comprising administering said nucleic acid to the patient intravenously, wherein the hydrophobic moiety comprises DHA-G2 (also referred to as hsiRNA-DHAPCL (see FIG. 20).

In one embodiment, DHA-hsiRNA is delivered preferentially to proximal convoluted tubuoles.

DHA Conjugation

Direct conjugation of DHA to a fully chemically stabilized siRNA scaffold shows significant tissue retention with wide distribution and robust efficacy in mouse brain. Notably, DHA-hsiRNA conjugates do not elicit measurable microglial activation and have no adverse effect on neuronal viability at concentrations over 20-fold higher than the efficacious dose.

DHA-hsiRNA alleviates one of the major obstacles to neurological applications of siRNA, which is achieving widespread brain distribution. Following a direct intrastriatal injection, DHA-hsiRNA distributed broadly throughout the striatum and cortex of the injected hemisphere, with no dramatic compound accumulation around the site of injection (a typical feature of Chol-hsiRNA). DHA-hsiRNA co-localizes with both neuronal (NeuN) and astrocyte (GFAP) markers. DHA-hsiRNA clearly localized to the perinuclear space in both striatal and cortical neurons (the cytoplasmic site of active RNAi).

DHA-hsiRNA accumulates to a functional degree in both the striatum and cortex. Htt silencing is achieved at concentrations as low as 6 μg (~25% silencing) in the striatum and 12 μg (~30% silencing) in the cortex. In the study of Example 8, a maximal knockdown of 70% was seen following administration of 25 μg in the striatum. Duration of effect studies reveal persistent target silencing in mouse striatum up to four weeks after a single, 12 μg intrastriatal injection.

Comparing increasing concentrations of DHA-hsiRNA and Chol-hsiRNA, it was found that Chol-hsiRNA induced significant loss of brain matter and occasionally animal morbidity at doses above 25 μg. In contrast, animals injected with 200 μg of DHA-hsiRNA appeared healthy, with normal brain morphology. 200 μg is the maximal amount that can be delivered intrastriatally, given the solubility limit of DHA-hsiRNA.

The study described in Example 8 targeted Huntingtin, the causative gene of Huntington's disease (HD). Currently prescribed small molecule drugs for genetically defined neurodegenerative diseases, such as Huntington's disease, seek to treat disease symptoms without addressing the underlying genetic cause. A major advantage of RNAi-based therapeutics is that it permits specific targeting of the gene(s) underlining the clinical pathology. It has been shown that transient modulation of both wild-type and mutant Htt alleles was sufficient to support reversal of disease phenotype. DHA-hsiRNA$^{HTT}$ demonstrates robust and durable silencing in both striatum and cortex, the brain regions primarily affected in HD.

Design of siRNA Molecules

In some embodiments, an siRNA molecule of the invention is a duplex consisting of a sense strand and complementary antisense strand, the antisense strand having sufficient complementary to an htt mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, siRNAs can be designed by using any method known in the art, for instance, by using the following protocol:

1. The siRNA should be specific for a target sequence. In one embodiment, the target sequence is found in sFlt1. In another embodiment, a target sequence is found in a mutant huntingtin (htt) allele, but not a wild-type huntingtin allele. In another embodiment, a target sequence is found in both a mutant huntingtin (htt) allele, and a wild-type huntingtin allele. In another embodiment, a target sequence is found in a wild-type huntingtin allele. The first strand should be complementary to the target sequence, and the other strand is substantially complementary to the first strand. In one embodiment, the target sequence is outside the expanded CAG repeat of the mutant huntingin (htt) allele. In another embodiment, the target sequence is outside a coding region of the target gene. Exemplary target sequences are selected from the 5' untranslated region (5'-UTR) or an intronic region of a target gene. Cleavage of mRNA at these sites should eliminate translation of corresponding mutant protein. Target sequences from other regions of the htt gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. Preferably the RNA silencing agents of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., percent (%) homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant: wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)-(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant huntingtin mRNA), the siRNA may be incubated with target cDNA (e.g., huntingtin cDNA) in a *Drosophila*-based in vitro mRNA expression system. Radiolabeled with $^{32}$P, newly synthesized target mRNAs (e.g., huntingtin mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

In certain embodiments, the siRNA comprises a sense strand comprising a sequence set forth in FIG. 23, and an antisense strand comprising a sequence set forth in FIG. 23.

Sites of siRNA-mRNA complementation are selected which result in optimal mRNA specificity and maximal mRNA cleavage.

siRNA-Like Molecules siRNA-like molecules of the invention have a sequence (i.e., have a strand having a sequence) that is "sufficiently complementary" to a target sequence of an mRNA (e.g. htt mRNA) to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

Modified RNA Silencing Agents

In certain aspects of the invention, an RNA silencing agent (or any portion thereof) of the invention as described supra may be modified such that the activity of the agent is further improved. For example, the RNA silencing agents described in above may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyino sine, 2'-aza-2'-deoxyinosine, PNA-inosine, morpholine-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention, the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, $NHR$, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base. In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; 0- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, 03-(oleoyl)lithocholic acid, 03-(oleoyl) cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., 0-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralen, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, 03-(oleoyl)lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

EXAMPLES

Methods

All chemical reactions were performed under argon atmosphere using anhydrous freshly distilled solvents unless otherwise stated. Dichloromethane (DCM), acetonitrile (ACN) and dimethylformamide (DMF) were dried using a PureSolv MD 5× Channel Solvent Purification System, tested with Karl Fischer titration and stored on molecular sieves. Flash chromatography was performed using Teledyne Isco CombiFlash Rf system and prepacked (silica gel) columns purchased from Bonna-Agela Technologies (Tianjin, China). Analytical thin-layer chromatography (TLC) was performed using silica gel 60 F254 using UV light as visualizing agent. 1H, 13C and 31P NMR spectra were recorded on a Varian 400 MHz instruments using residual solvent or 85% phosphoric acid (for 31-P NMR) as reference. High-resolution mass spectra were obtained on an Agilent 6530 accurate-mass Q-TOF LC/MS (Agilent technologies, Santa Clara, Calif.).

Example 1: Synthetic Approaches Used for Conjugation of Hydrophobic Compounds to Oligonucleotides Using synthetic approaches outlined in FIGS. 1a-h, hsiRNAs covalently conjugated to cortisol, DHA, calciferol, cholesterol, and GM1 were synthesized. For cortisol (FIG. 1a) and calciferol (FIG. 1b), primary hydroxyls were converted to chloroformate and directly conjugated to the previously synthesized bi-functional, primary amine-containing, solid support. DHA was directly attached to the amino-modified linker using standard amide coupling conditions (FIG. 1c). GM1 was attached post-synthetically by click chemistry through the reaction of GM1-azide with alkyne modified siRNA (FIG. 1d and FIG. 1e). All compounds were HPLC-purified and characterized by mass spectrometry. The general synthesis strategies outlined in FIG. 1a-e are used to synthesize other related conjugates of FIG. 1f. Additional synthetic strategies are shown in FIG. 1g and FIG. 1h for the synthesis of calciferol conjugation, which may improve yields.

Figure 1L:
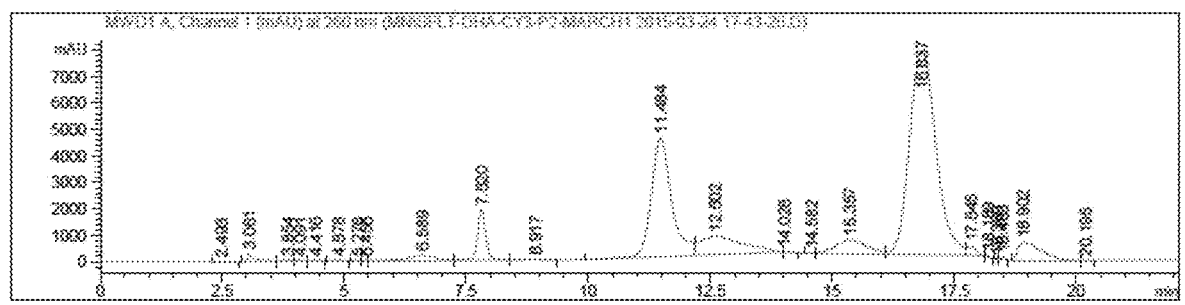
FIG. 1L shows a representative semi-prep reverse-phase-HPLC trace of a synthesized hsiRNA conjugate; Cy3-labeled sFLT-DHA conjugate (crude reaction mixture) shown.
Figure 1M:
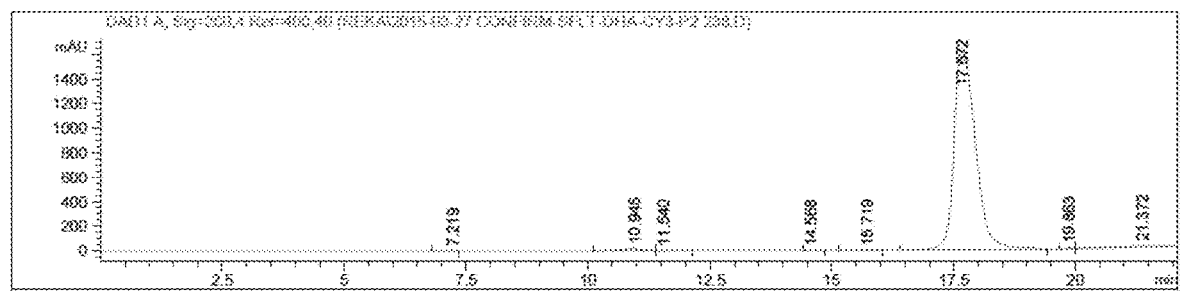
FIG. 1M shows a representative analytical reverse-phase-HPLC following purification of a synthesized hsiRNA conjugate as in FIG. 1L; Cy3-labeled sFLT-DHA conjugate (pure product) shown.

The oligonucleotide-conjugates were purified by reverse-phase HPLC, and the purity was assessed by liquid chromatography-mass spectrometry (LC-MS). Conditions: for analytical (FIG. 1i and FIG. 1j) (Anal HPLC: HTT-g2DHA-Cy3-P2, Pure product, Gradient: 10% MeCN, 90% TEAA to 90% MeCN, 10% TEAA in 30 minutes, Temp: room temperature, C8); for semi-preparative RP-HPLC (FIG. 1l) (Hamilton column, C18 HxSil 5 μm, 150×21.2 mm); for analytical RP-HPLC (FIG. 1m) (Agilent eclipse plus column, C18, 3.5 um, 4.6×100 mm): Cy3-labeled sFLT-DHA conjugate (pure product), gradient: 10% acetonitrile, 90% TEAA to 90% acetonitrile, 10% TEAA in 30 minutes, Temperature: 60° C. (Analytical) and 55° C. (Preparative), flow rate: 20 mL/min (Preparative) and 1 ml/min (Analytical); for LC-MS (FIG. 1n) (Buffer A: 15 mM Dibutylamine/25 mM HFIP, Buffer B: 20% A in MeOH, Column: xbidge OST C18, 2.5 μm).

Figure 2B:
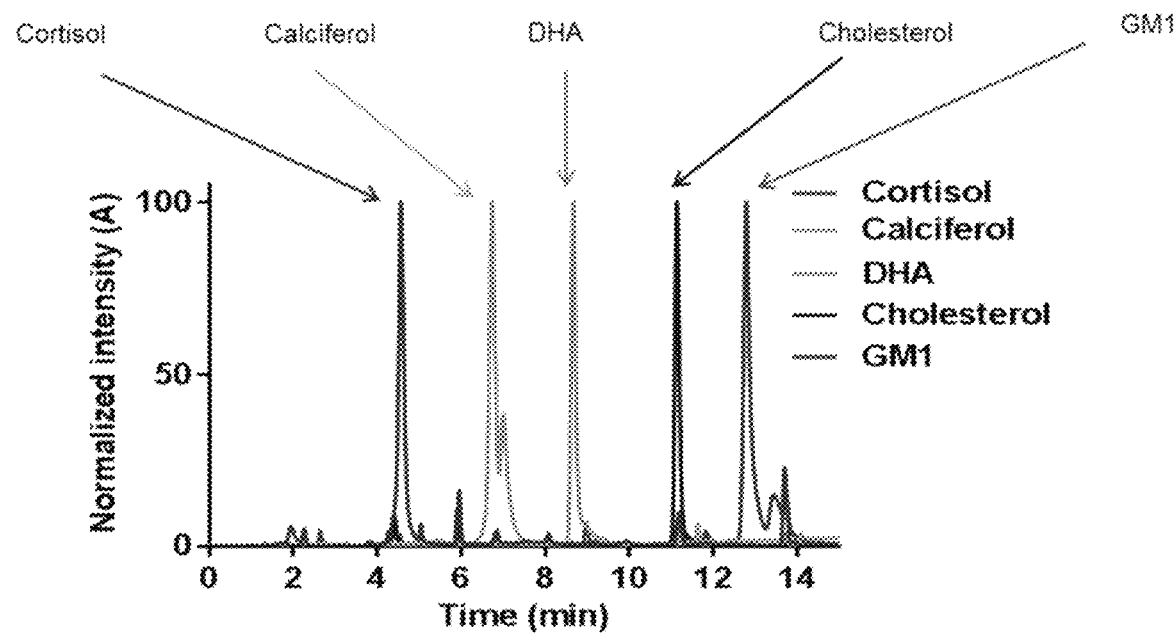
FIG. 2B shows the differences in hydrophobicity profiles of synthesized siRNA conjugates as observed by reverse-phase HPLC (C8).

Example 2: Structure and Hydrophobicity Profile of Selected Oligonucleotide Conjugates To determine the relative hydrophobicity of a panel of novel conjugates, the retention time on a C8 reversed-phase HPLC column was measured. A higher hydrophobicity is correlated with longer retention times. FIG. 2b shows that the synthesized panel of conjugates encompasses a range of hydrophobicities: from cortisol (elution time of 4.5 min) to GM1 (elution time of 14 min).

Figure 2C:
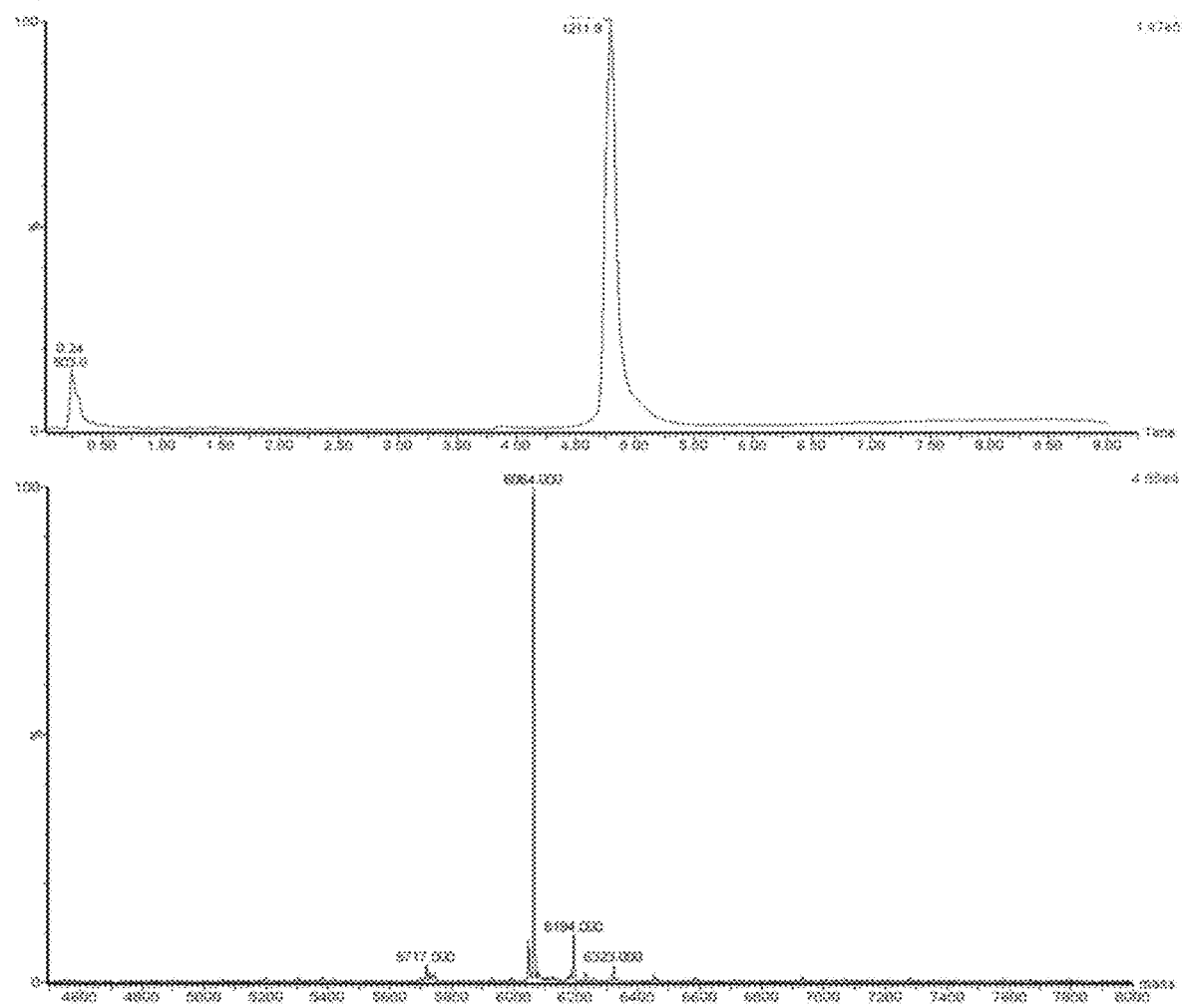
FIG. 2C shows an exemplary LC-MS analysis of a synthesized hsiRNA conjugate; DHA-hsiRNA shown.

All oligonucleotide conjugates were purified by reverse phase HPLC, and characterized by mass spectrometry (data for DHA-hsiRNA shown in FIG. 2c). The HPLC method was as follows: Reverse phase HPLC, C8; Buffer A: 100 mM NaAc and 5% acetonitrile, Buffer B: acetonitrile; Gradient: 5% B to 100% B over 15 minutes, 1.5 mL/min at 50° C.

Example 3: In Vivo Brain Distribution of FMS-hsiRNA is Directly Related to Hydrophobicity The present disclosure (FIG. 3a) shows that chemically modified and fully stabilized hydrophobic siRNA (hsiRNA) conjugates are successfully internalized by neurons and glia in the brain after intrastriatal administration (FIG. 3b). Furthermore, these data show a profound effect of conjugate chemistries on the pattern of in vivo brain distribution. The distribution of highly hydrophobic hsiRNA conjugates, including cholesterol- and GM1-, seem to be somewhat limited to the site of injection with very high intensity at this site. On the other hand, less hydrophobic hsiRNA conjugates, such as C7Linker- and TEGLinker-, show a more diffuse pattern with lower overall intensities. In addition, conjugates containing Calciferol- and DHA-show a distinct pattern of distribution characterized by a good spread throughout the section, which might be explained by potential receptor-mediated mechanism of uptake. Finally, it is also important to highlight that more hydrophobic hsiRNA conjugates, such as hsiRNA-GM1, hsiRNA-Calciferol, hsiRNA-DHA, and hsiRNA-cholesterol, enabled distribution to neuronal nerve bundles in the striatum. This may potentially result in retrograde axonal transport to the cortex.

To test the impact of hydrophobicity on tissue retention and brain distribution, 25 μg Cy3-labeled novel conjugates were injected unilaterally into striatum of wild-type mice and the fluorescence distribution was examined 48 hours later in both coronal and sagittal sections of the brain (FIG. 3b). Non-conjugated or linker-only hsiRNAs showed minimal but detectable retention in brain tissue. Importantly, it was found that the degree of tissue retention and distribution strongly correlates with hydrophobicity. Cortisol-hsiRNA (lowest degree of hydrophobicity) showed diffuse distribution, but the lowest tissue retention. The most hydrophobic compounds, cholesterol, and GM1, are effectively retained but do not distribute far from the site of injection. Tissue retention of FMS-hsiRNA was similar to that of LNA-gapmers, suggesting that the 13 phosphorothioate linkages in FMS-hsiRNA confer some level of tissue association. DHA and Calciferol hsiRNAs show optimal retention and spread throughout the injected side of the brain. The distribution of the calciferol-hsiRNA was so uniform, that it was impossible to map the site of injection, which is easily observed in animals injected with cholesterol or GM1 conjugates. In summary, it has been demonstrated that tuning the hydrophobicity of conjugates can be utilized to attain optimal retention and distribution in brain tissue.

Figure 3A:
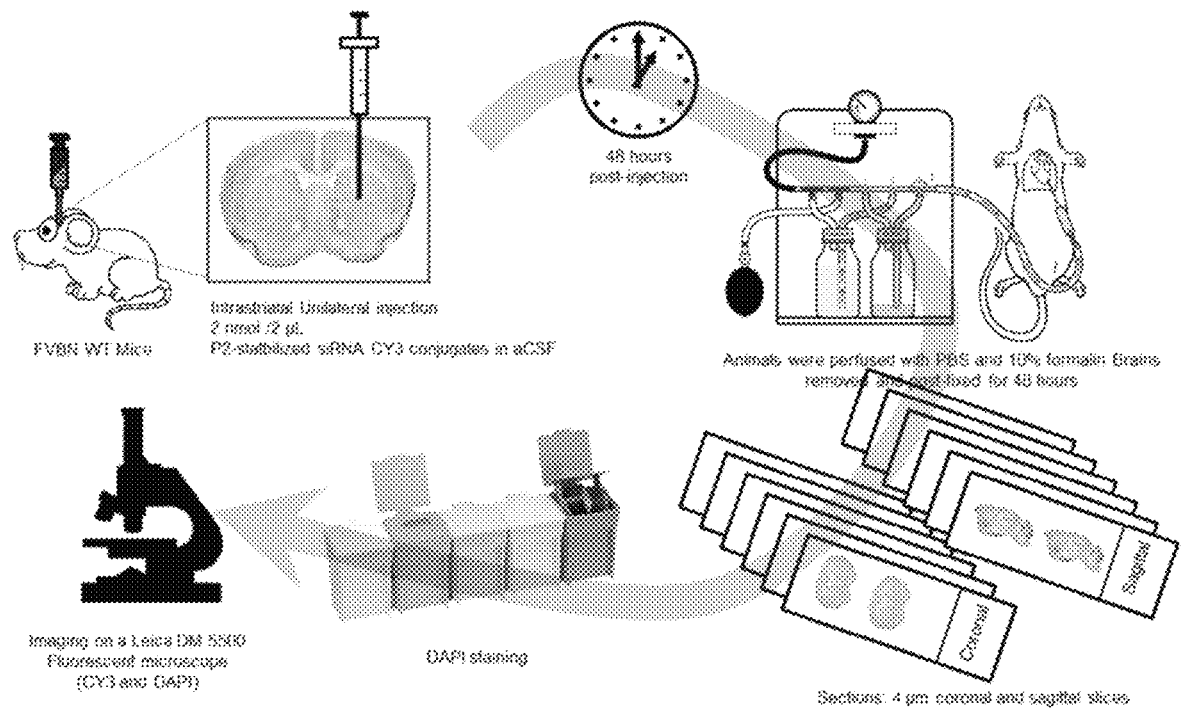
FIG. 3A shows a biodistribution study protocol.
Figure 3B:
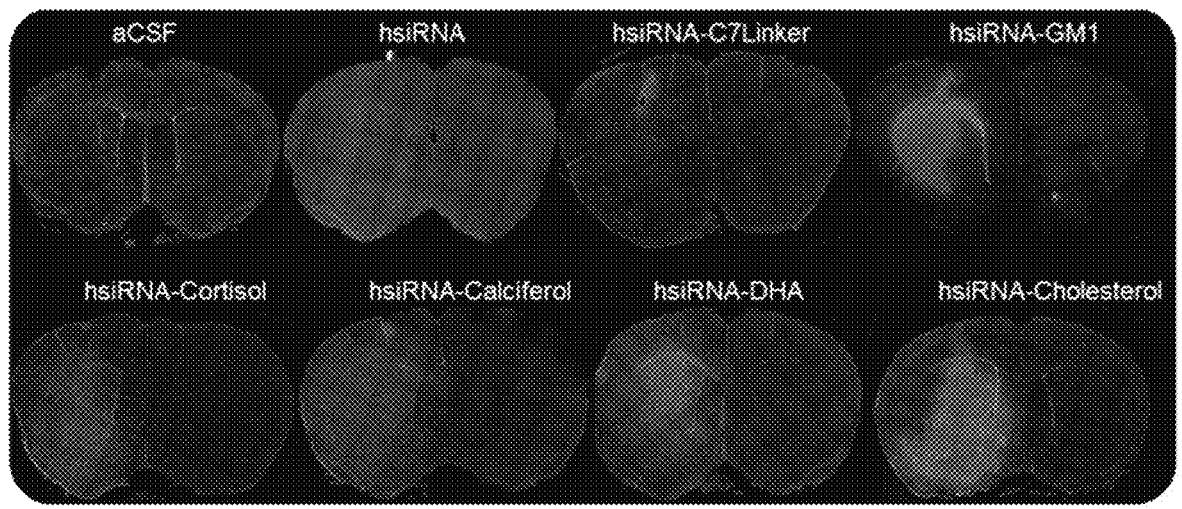
FIG. 3B shows that the in vivo brain distribution of FMS-hsiRNA is defined by conjugation modality.

As shown in the biodistribution study protocol of FIG. 3a, FVBN WT mice (n-3 per chemistry) were injected with 25 μg of Cy3-hsiRNA variants (P2-stabilized siRNA Cy3 conjugates in aCSF) via intrastitial unilateral injection (2 nmol/2 μL). After 48 hours, animals were perfused with PBS and 10% formalin. Brains were removed and post-fixed for 48 hours. 4 µm slices of coronal and sagittal sections were obtained, followed by DAPI staining. The samples were imaged (10×) on a Leica DM 5500 fluorescent microscope (Cy3 and DAPI); hsiRNA-FMS conjugates (Cy3—red), nuclei (DAPI—blue).

Figure 4:
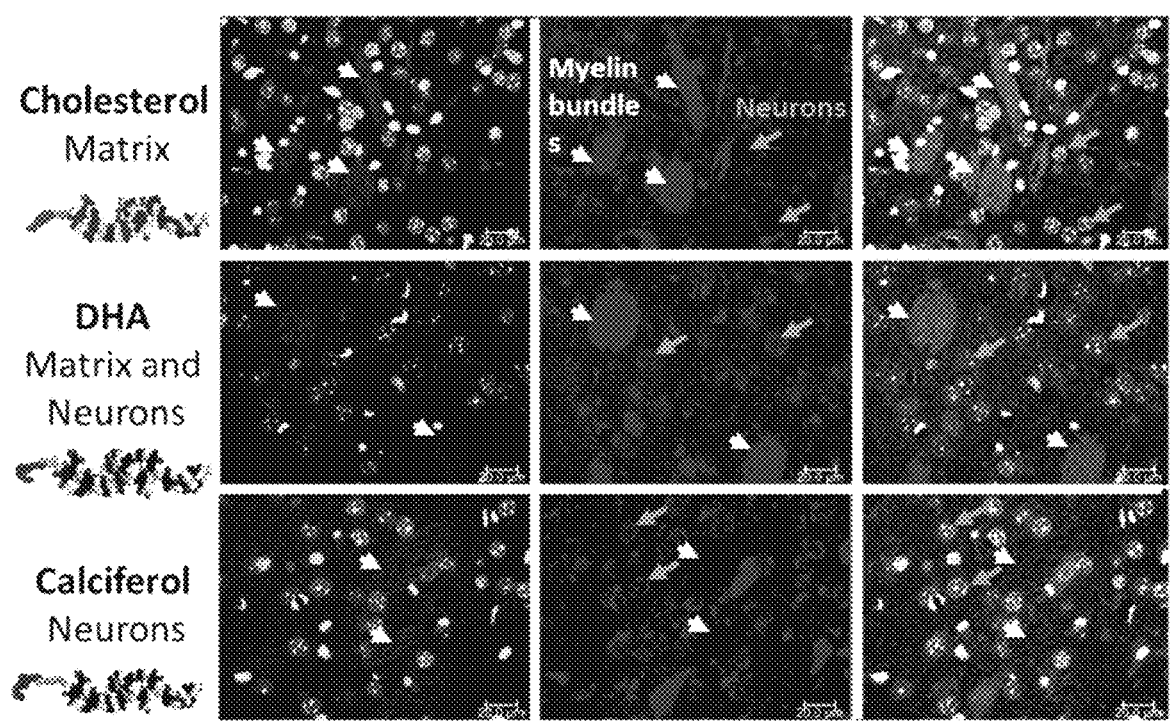
FIG. 4 shows that calciferol and DHA-hsiRNA conjugates display a dramatically improved spread through the brain as well as robust neuronal uptake.

Example 4: Nature of Hydrophobic Conjugate Significantly Affects hsiRNA Striatum Distribution—Calciferol Shows Preferential Neuronal Uptake It was observed that DHA- and calciferol-hsiRNAs show the best distribution in brain tissue. Interestingly, clear differences in both the extent of tissue penetration and cell types that internalize each conjugate were observed. After intrastriatal injection, for example, cholesterol conjugates were taken up by neurons but primarily associated with myelinated fibers in the matrix (FIG. 4), limiting diffusion from the site of administration. By contrast, calciferol-hsiRNAs are selectively internalized by NeuN-positive neurons (downward-left-pointed arrows, FIG. 4) and other cell types but do not associate with myelinated fibers in the tissue matrix (downward-right-pointed arrows, FIG. 4), resulting in efficient diffusion through the tissue. DHA conjugates show an intermediate distribution, with both neuronal uptake and some association with myelin fibers. Thus calciferol and DHA-hsiRNA conjugates show a dramatically improved spread through the brain and robust neuronal uptake.

Thus, 12 µg of Cholesterol, DHA and Calciferol CY3-FMS-hsiRNAs conjugates were injected intrastriatal and processed as described in Example 3. Images (63×) were acquired on a Leica DM 5500 fluorescent microscope. Cholesterol conjugates preferentially associated with the tissue matrix especially myelinated neuronal bundles (shown by downward-right-pointed arrows). Calciferol conjugates have no association with neuronal bundles but are preferentially internalized by neurons (downward-left-pointed arrows). DHA conjugates display intermediate behavior with both neuronal bundles and neurons association.

Figure 5:
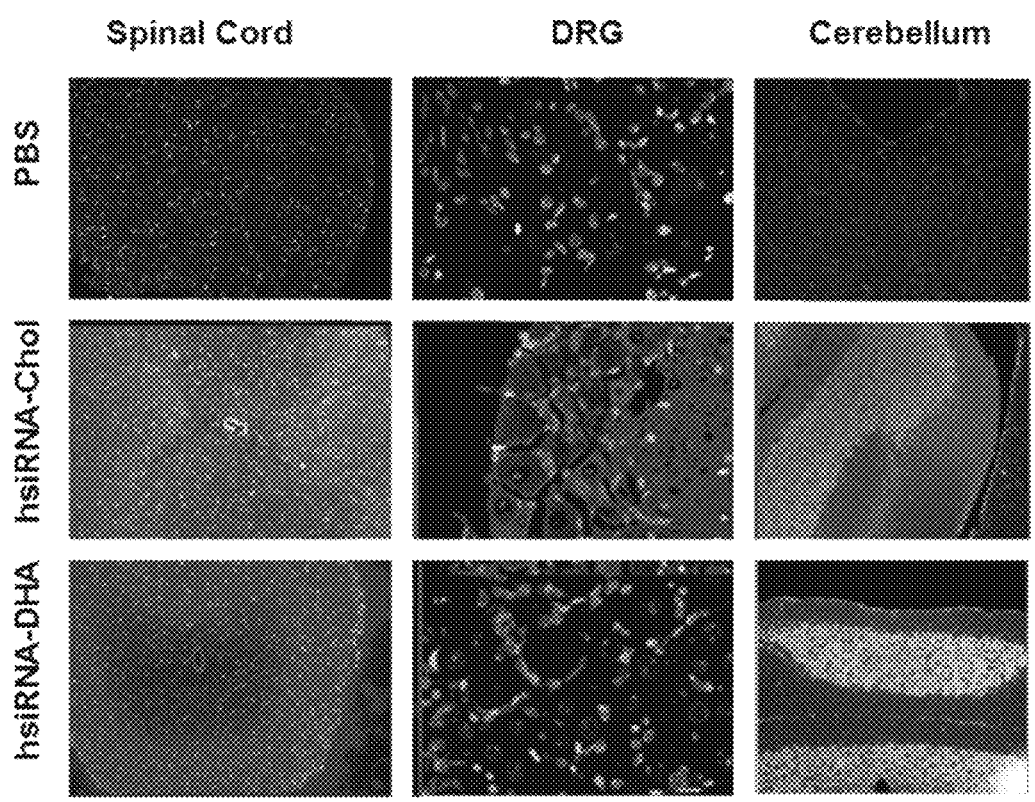
FIG. 5 shows dramatic differences in patterns of CNS tissue distribution upon intrathecal (IT) injection of Cholesterol and DHA-hsiRNA conjugates.

Example 5: Dramatic Differences in Patterns of CNS Tissue Distribution Upon Intrathecal (IT) Injection of Cholesterol and DHA hsiRNA Conjugates A surprising observation was made when the behavior of DHA and cholesterol conjugates upon single intrathecal (CSF) injection were compared. Both chemistries distribute throughout the spinal cord (from the surface all the way to the center) (FIG. 5), with distinct distribution in the dorsal root ganglia and cerebellum. Cholesterol-hsiRNA distribute throughout the DRG and cerebellum, while DHA preferentially delivers to distinct cell types, preliminarily identified as endothelial or purkinje cells, or both. These distinct cellular distribution patterns are indicative of selective receptor mediated internalization.

Figure 6A:
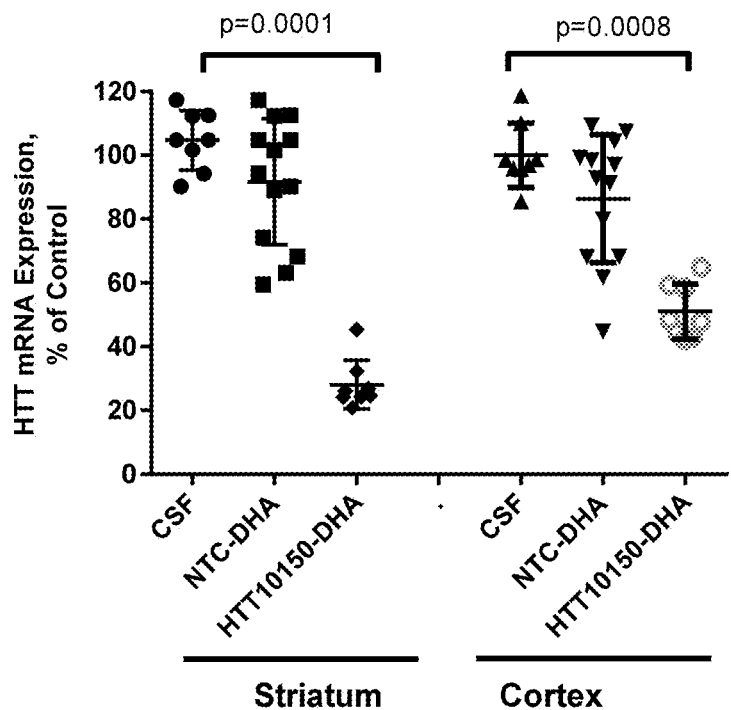
FIG. 6A shows that a single 25 μg injection of DHA-hsiRNA induced potent silencing not only in the striatum but also in the cortex.

Example 6: Single IS Injection of DHA-conjugated hsiRNA-FMS Induces Potent HTT Silencing in Both Striatum and Cortex Tissue Neuronal silencing by Cy3-labeled DHA-hsiRNA conjugates was undistinguishable from chol-hsiRNA in vitro in primary neurons. A single 25 µg injection of DHA-hsiRNA induced potent silencing not only in the striatum but also in the cortex (FIG. 6a), consistent with observed wide distribution. Surprisingly, there was a marked lack of toxicity with DHA-hsiRNA.

Figure 6B:
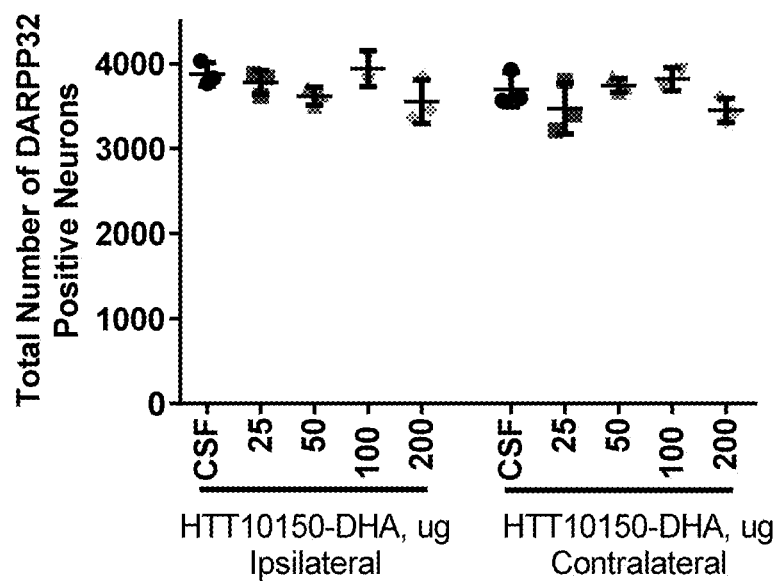
FIG. 6B shows that administration with as much as 200 μg DHA-hsiRNA conjugates induces no observable signs of neuronal damage.

Comparing increasing concentrations of DHA-hsiRNA and chol-hsiRNA conjugates, it was observed that chol-hsiRNA induced significant visual toxicity at doses above 25-50 µg, perhaps related to the excessive concentration of compound retained around the injection site, effectively solidifying the tissues. In contrast, animals injected with as much as 200 µg DHA-hsiRNA conjugates, 4×-8× that of chol-hsiRNA, appeared healthy, their brains looked normal, and DARP-32 (FIG. 6b) and IBA1 staining reveal no signs of neuronal damage or excessive immune activation.

Thus, DHA-HTT10150-FMS single unilateral injection were administered into the striatum of WT (FVB) mice (n=8 per group). Mice were sacrificed after five days. Brains were sliced into 300 µm sections and 2 mm punch biopsies (n=3 per mice) of the striatum or cortex were analyzed by QUANTIGENE (Affymetrix). Levels of htt mRNA expression were normalized to a housekeeping mRNA (PPIB). NTC—non-targeting control of the same chemical composition. For FIG. 6b, increasing doses of HTT10150 were injected unilaterally and the neuronal integrity was evaluated by counting DARP32 positive neurons.

Example 7: Systemic Delivery

Different hsiRNA variants were synthesized as described above and injected systemically (iv/sc) at 20 mg/kg. The level of accumulation of oligonucleotide in various tissues was determined by PNA Assay. The PNA (Peptide Nucleic Acid) hybridization assay directly measures an amount of intact guide strand in tissue lysates. This assay allows direct assessment of the rate of oligonucleotide clearance from CSF or blood as well as the degree of tissue distribution and accumulation (e.g., in different brain regions). This assay can detect both labeled and unlabeled compounds. Tissue accumulation of oligonucleotides above 10 ng/mg was sufficient to induce silencing.

Figure 7:
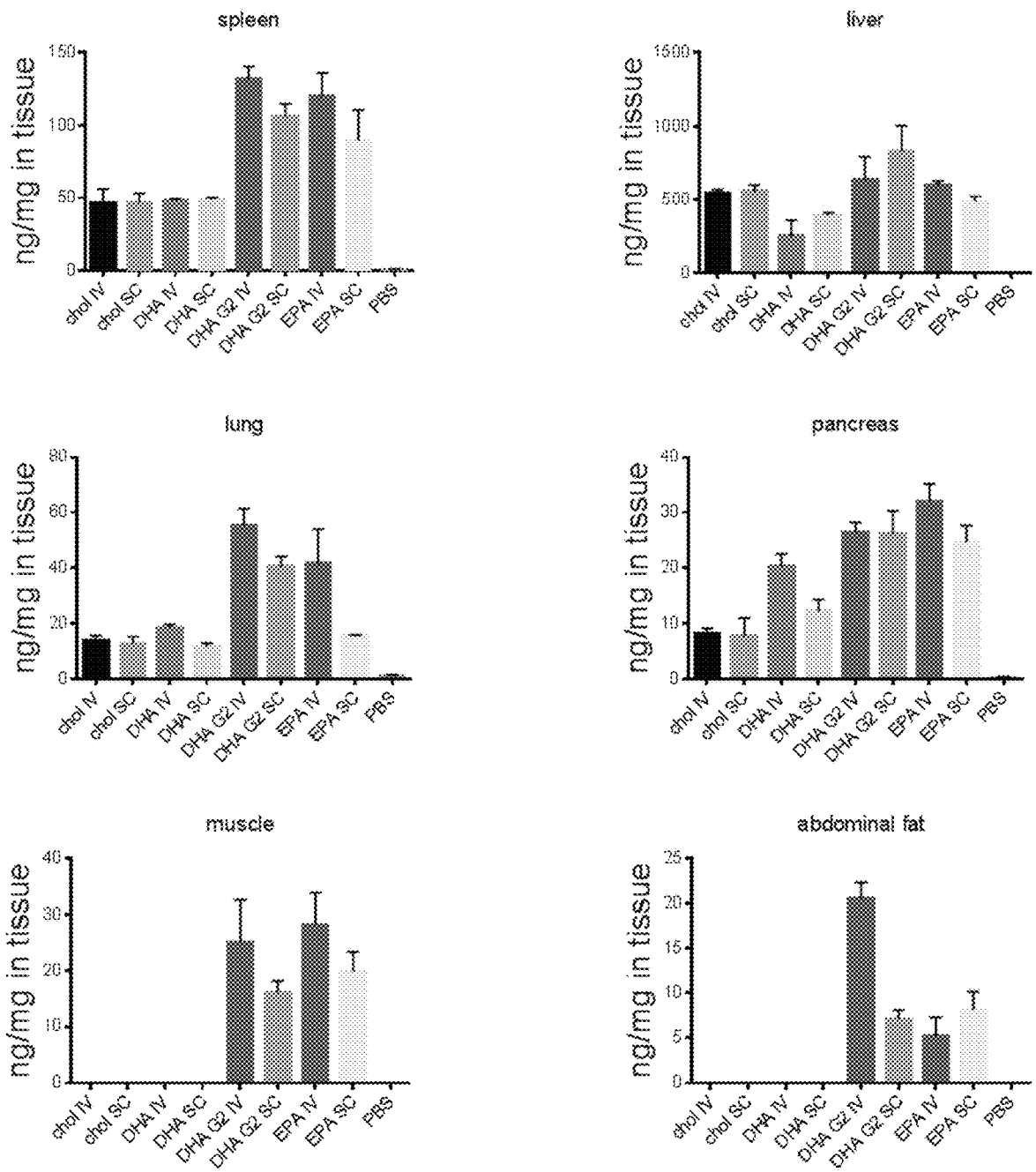
FIG. 7 shows accumulation in various tissues upon systemic administration of hsiRNA-conjugates. hsiRNA-conjugate structures and modifications are found in FIG. 9A-F. All compounds have the sequence of PPIB, as shown in FIG. 14.
Figure 7:
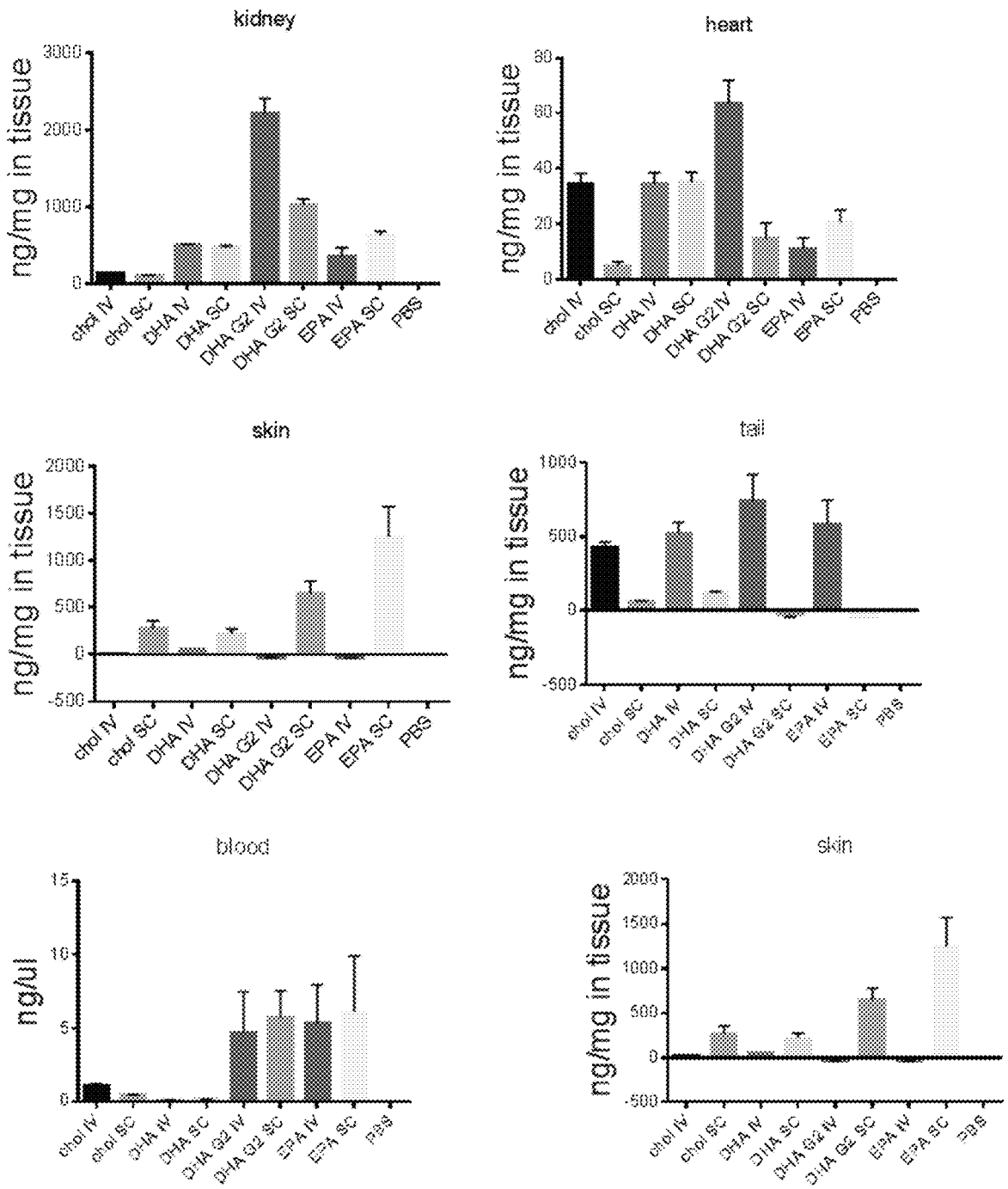
Figure 7:
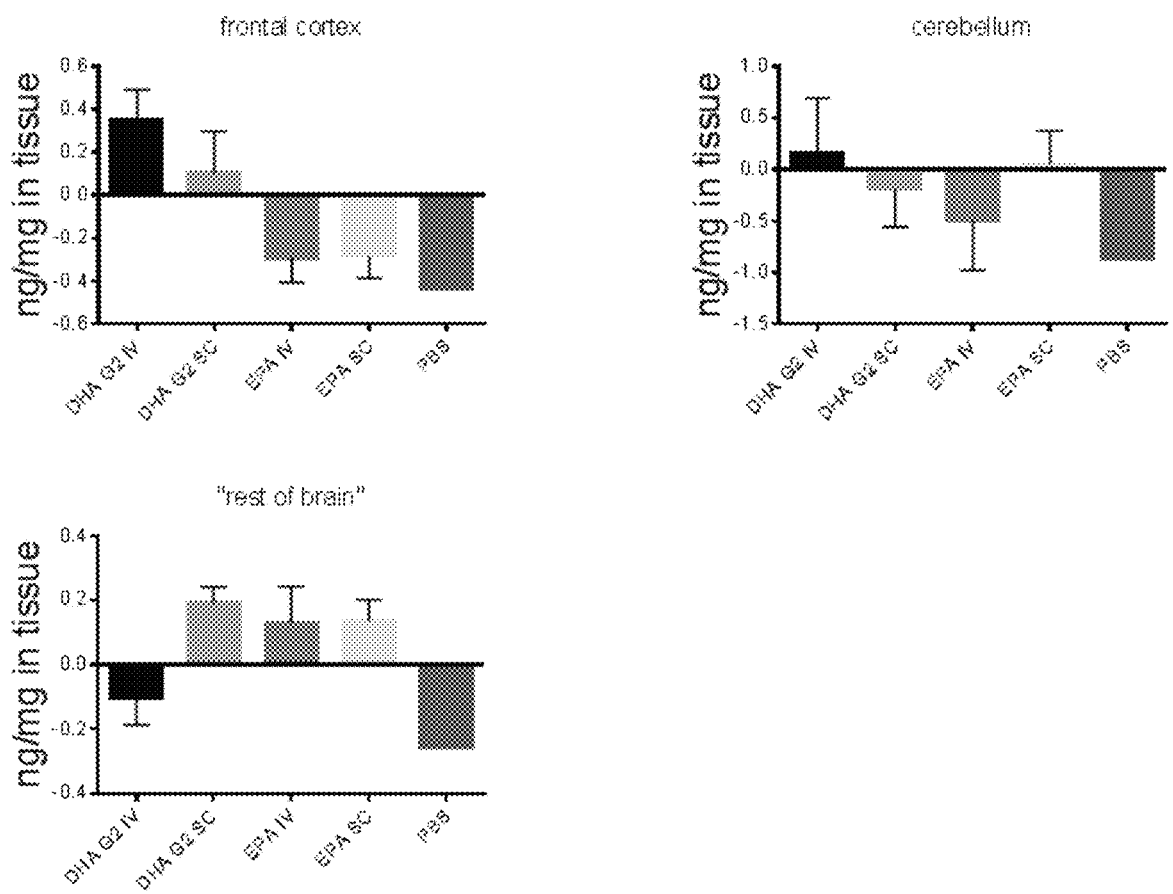
Figure 9A:
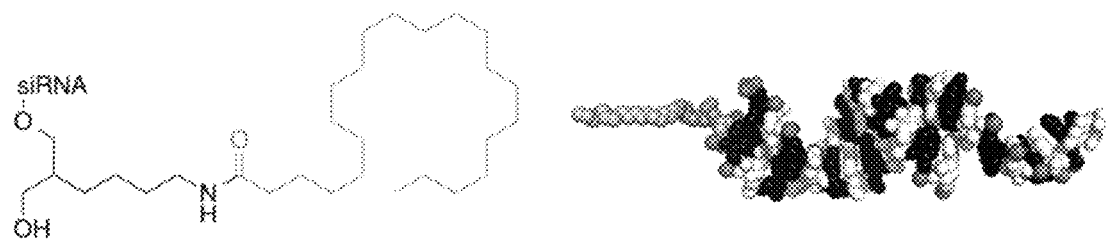
FIG. 9A-F show chemical structures of conjugated hsiRNAs. (A) Docosanoic (DCA)-conjugated hsiRNA. (B) Docosahexaenoic acid (DHA)-conjugated hsiRNA, 22:6 (n-3). (C) Phosphatidylcholine-DHA-conjugated hsiRNA (g2DHA-hsiRNA or DHAPCL-hsiRNA) (D) Eicosapentanoic acid (EPA)-conjugated hsiRNA, 20:5(n-3). (E) Cholesterol (Chol)-conjugated hsiRNA. (F) Cholesterol (Chol)-conjugated hsiRNA. hsiRNA conjugates represented to scale using PyMOL.
Figure 9B:
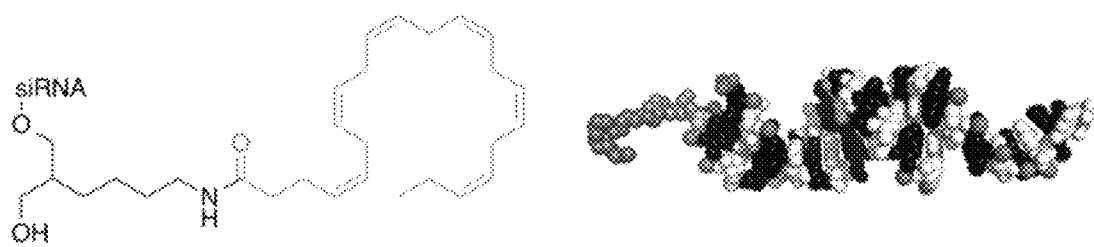
Figure 9C:
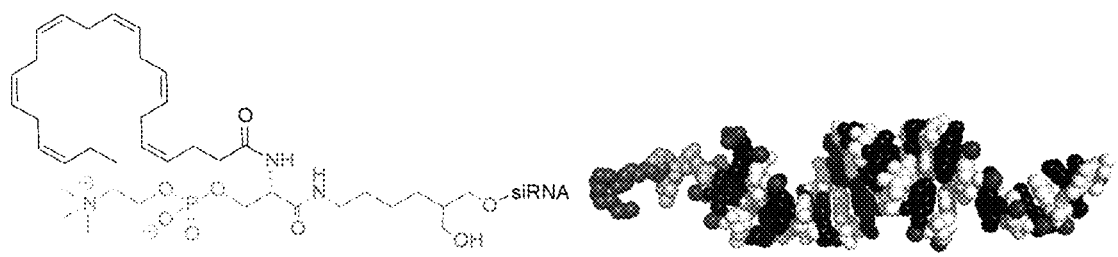
Figure 9D:
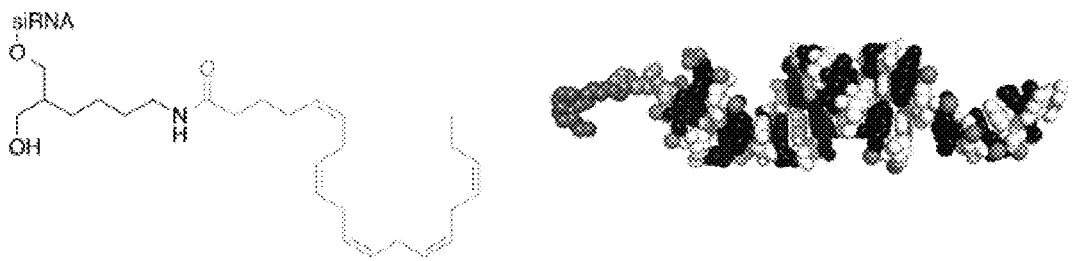
Figure 9E:
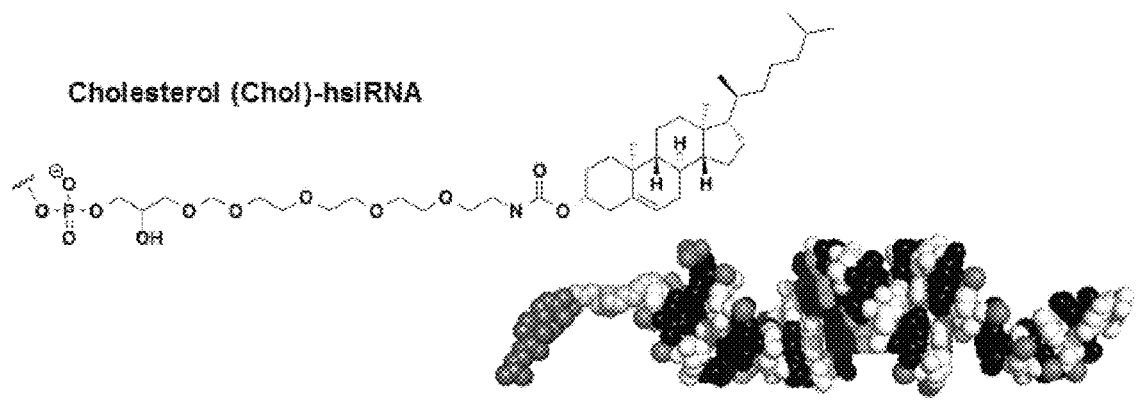
Figure 9F:
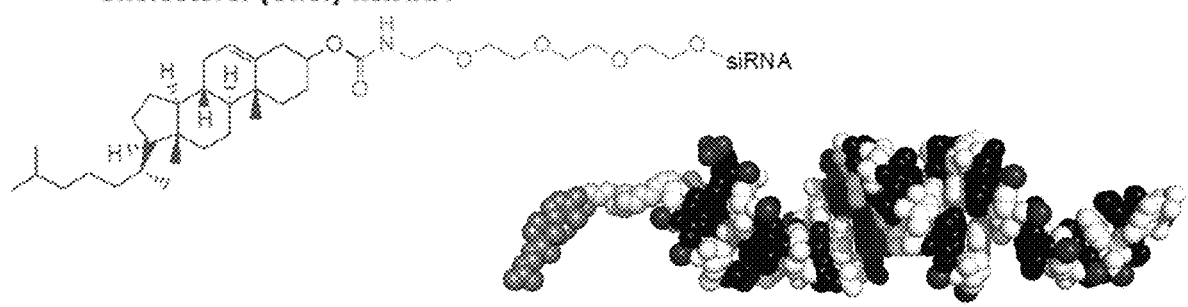
Figure 10:
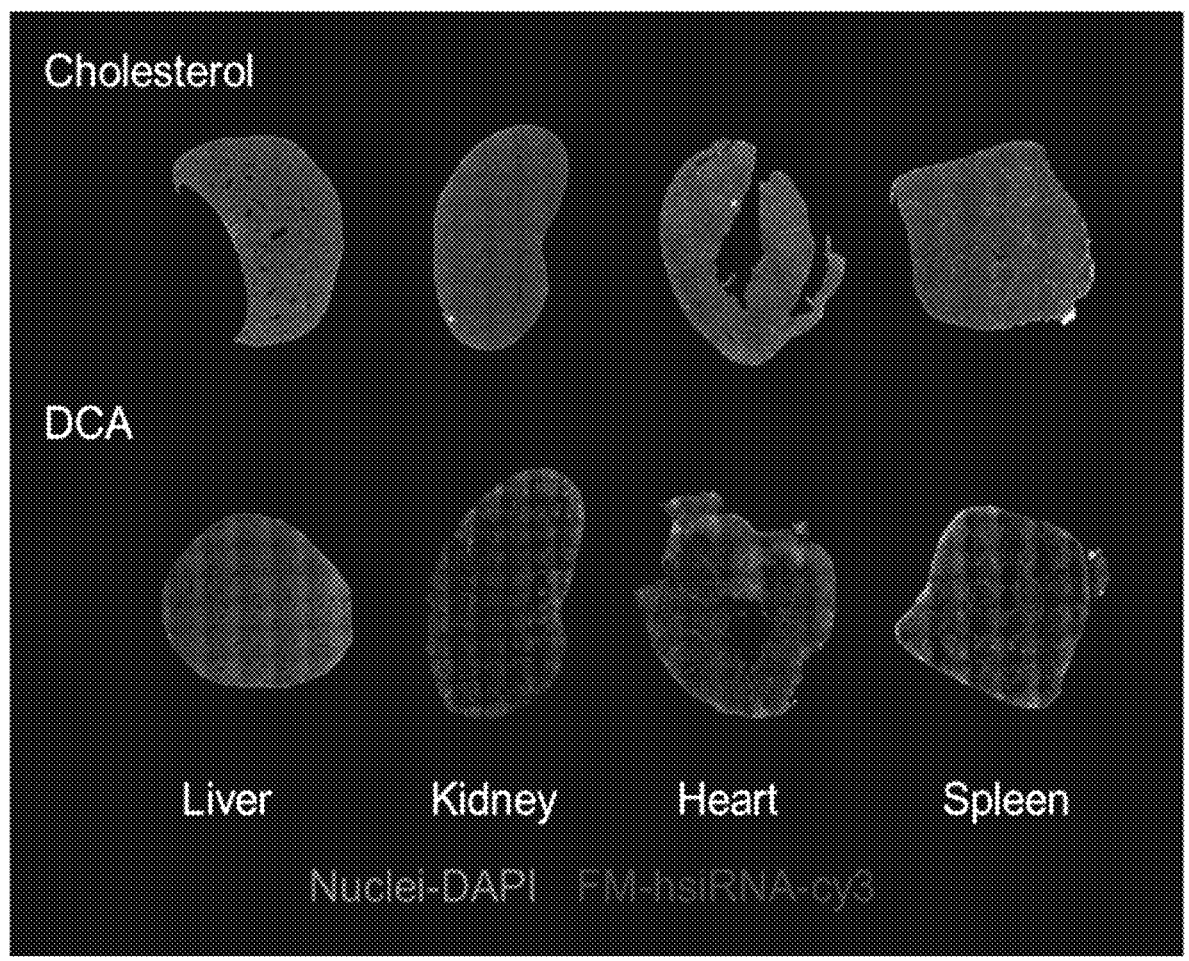
FIG. 10 shows distribution following intravenous administration of Cy3 labeled cholesterol- or DCA-conjugated hsiRNAs. Mice were injected intravenously (tail vein) with two doses of 20 mg/kg on two consecutive days with either cholesterol- or DCA-conjugated hsiRNAs. 24 hours after the last dose, mice were euthanized, perfused with PBS and organs harvested for either immunohistochemistry or the PNA assay. Predominate distribution to the liver and red pulp of the spleen was observed for both conjugates.
Figure 11:
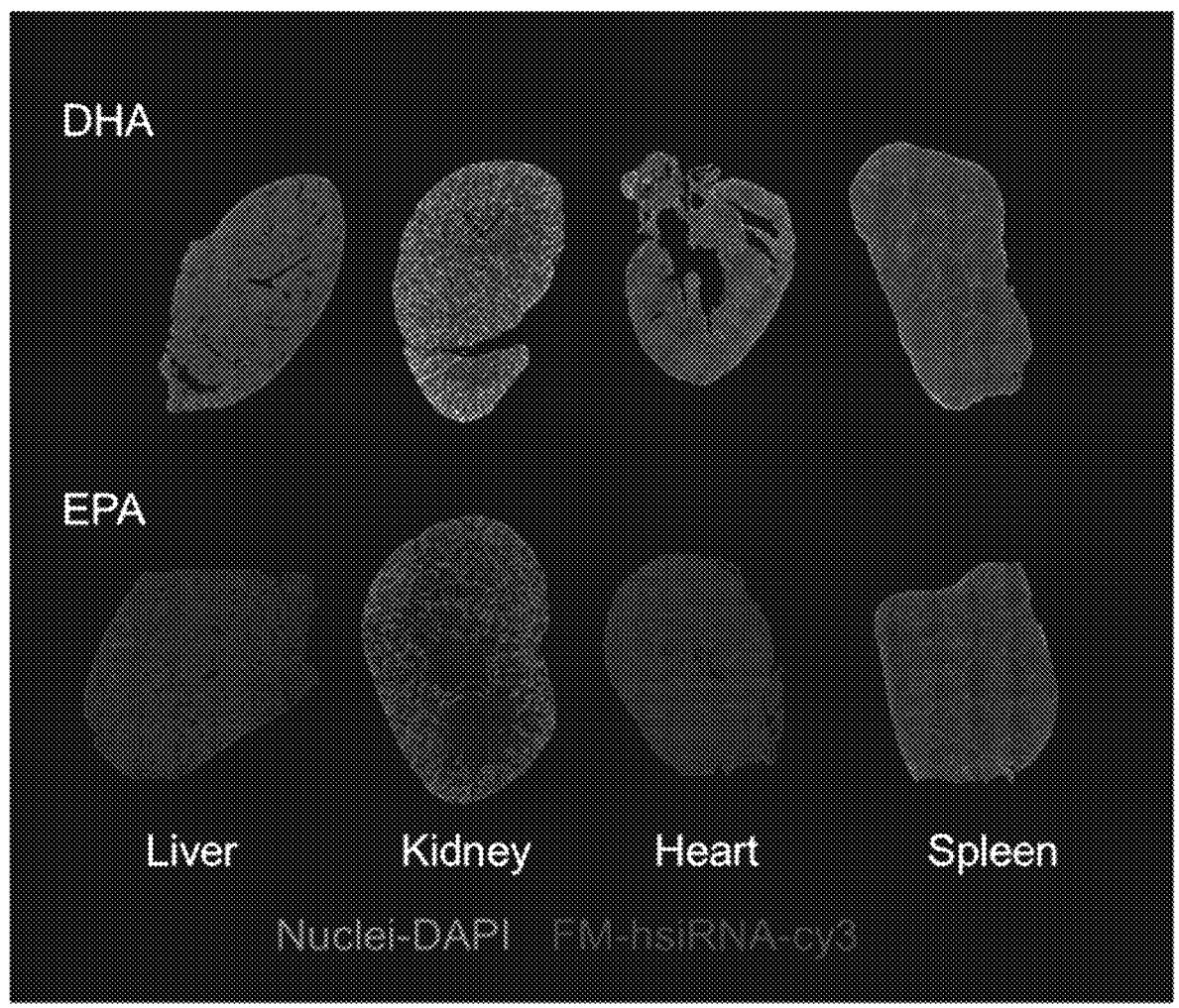
FIG. 11 shows distribution following intravenous administration of Cy3 labeled DHA- or EPA-conjugated hsiRNAs. Mice were injected intravenously (tail vein) with two doses of 20 mg/kg on two consecutive days with either DHA- or EPA-conjugated hsiRNAs. 24 hours after the last dose, mice were euthanized, perfused with PBS and organs harvested for either immunohistochemistry or the PNA assay. Significant distribution to the kidney, red pulp of the spleen, liver, and heart was observed.
Figure 12A:
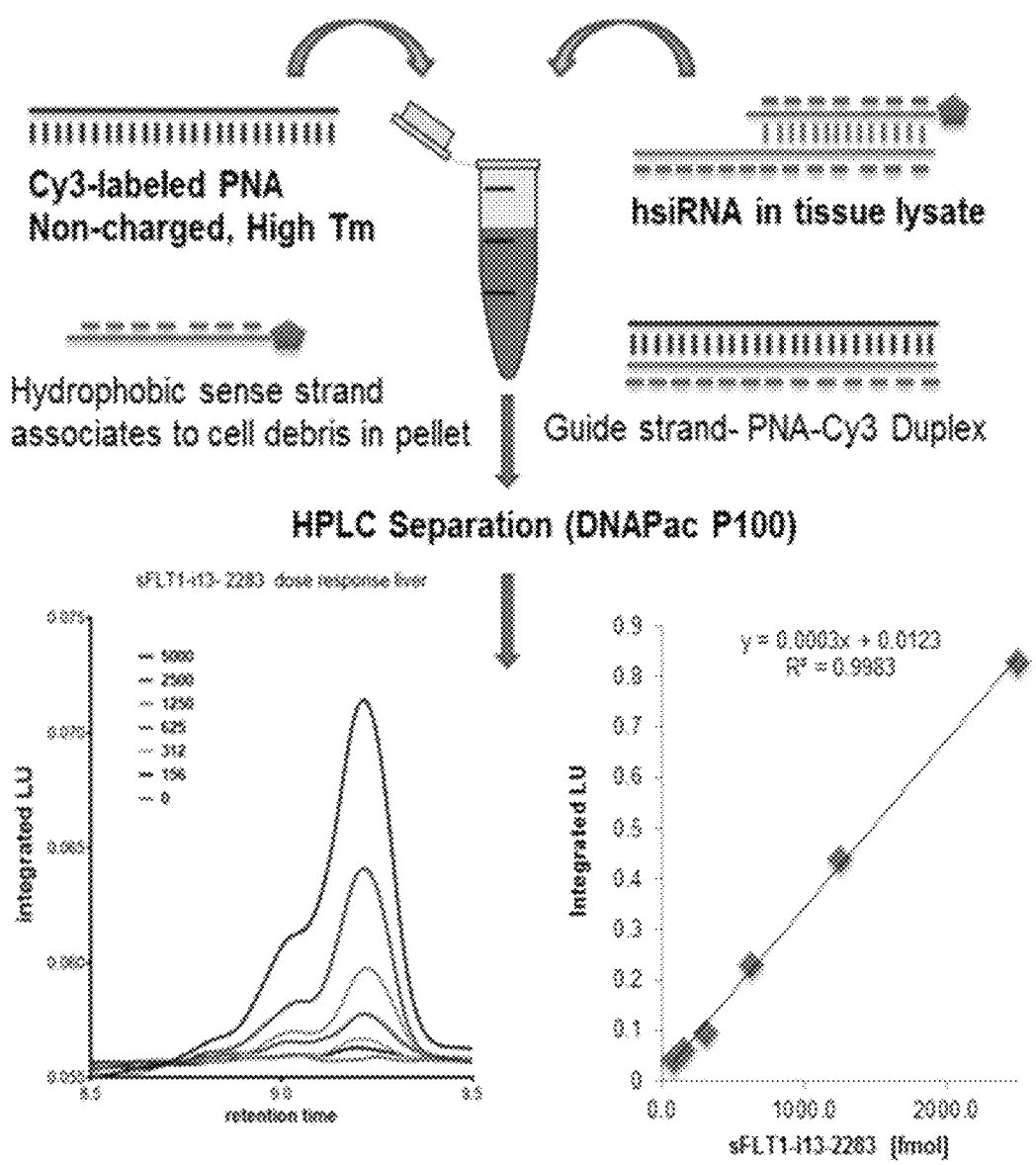
FIG. 12A-B shows PNA (Peptide Nucleic Acid) based assay for detection of hsiRNA guide strand in mouse tissues. (A) Tissues were lysed, debris separated by precipitation, PNA-guide strand duplex purified by HPLC (DNAPac P100, 50% water 50% acetonitrile, salt gradient 0-1M NaClO4). (B) Liver and kidney from mice injected with 40 mg/kg of either cholesterol, DCA, EPA, or DHA were used to quantify the guide strand after 48 hours, showing differential distribution of fatty acid conjugates.
Figure 12B:
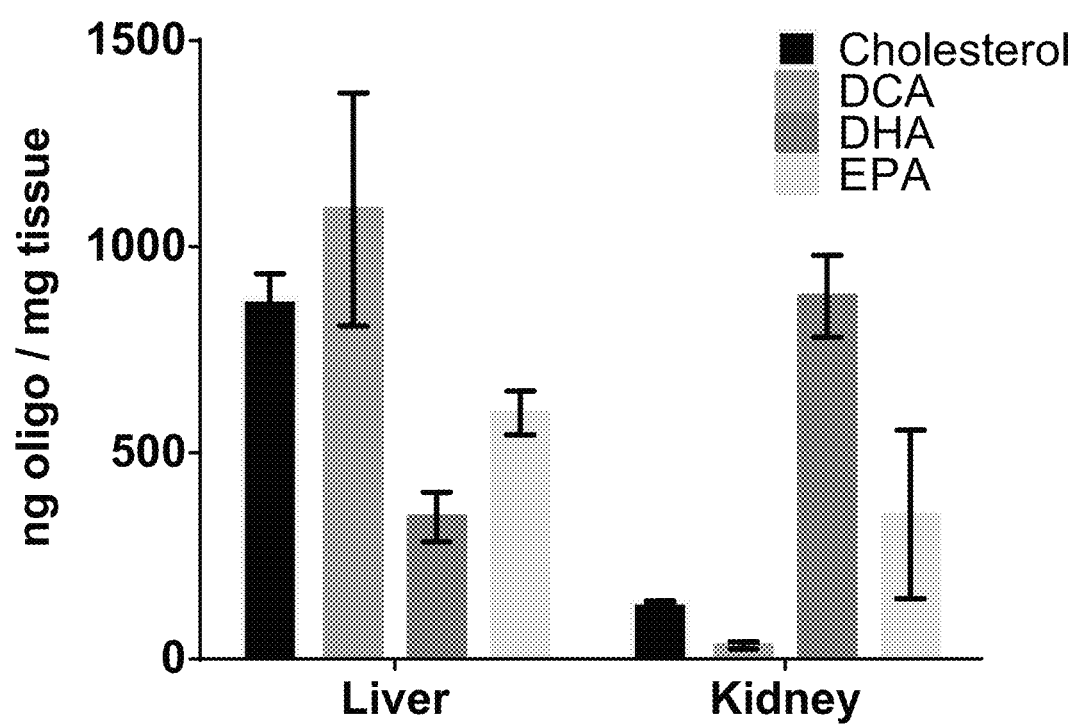
Figure 13A:
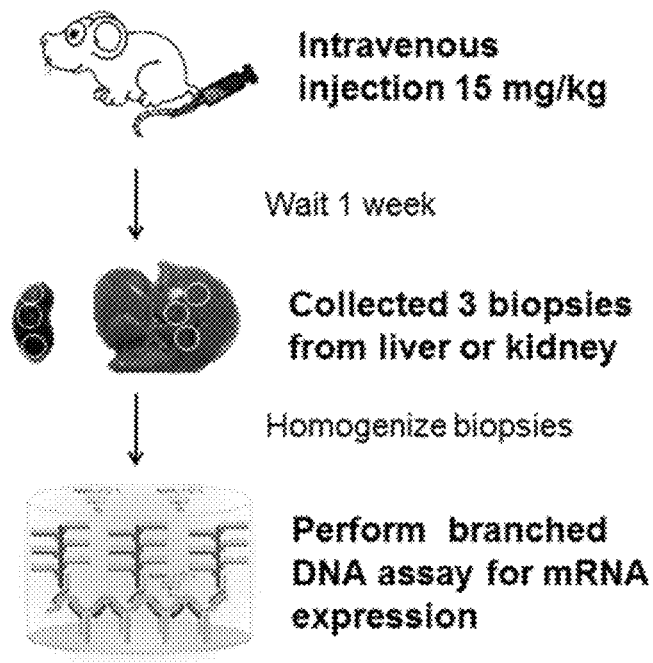
FIG. 13A-B shows efficacy of DHA-hsiRNA targeting sFLT1 after IV injection. (A) Schematic of experimental design. (B) Mice (n=8) were injected intravenously (tail vein) with 15 mg/kg DHA-conjugated hsiRNA targeting sFLT1 and livers and kidneys were harvested 5 days later. Three tissue biopsies were taken from each organ and used for mRNA quantification (Quantigene® assay)
Figure 13B:
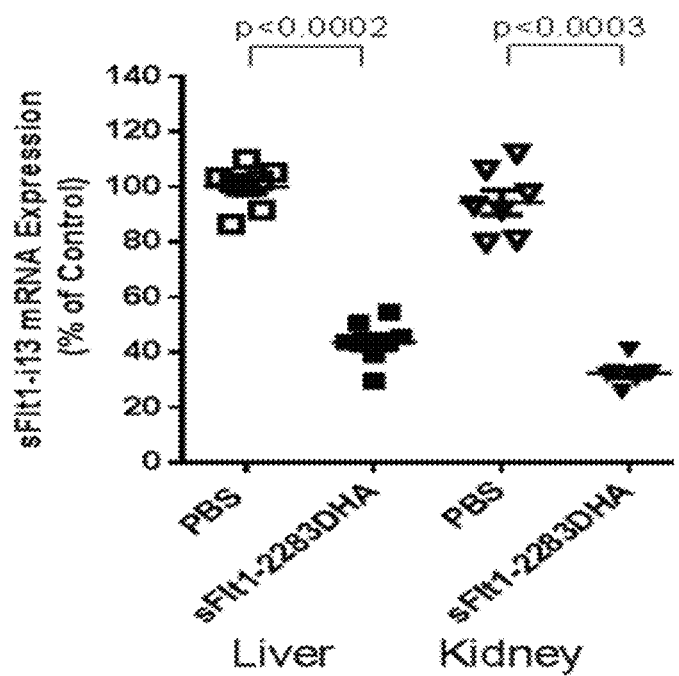

Surprisingly, different chemistries show preferential distribution to different tissues (FIG. 7). For example, PC-DHA shows accumulation in kidneys at above 2000 ng/mg levels and more compounds goes to kidney than to lung. Calciferol shows unprecedented distribution and preferential delivery to neurons in the brain. EPA shows the best skin distribution, relative to the compounds tested herein, where local injection delivers to a very wide area near the injection side.

Example 8: Docosahexaenoic Acid (DHA)-siRNA Conjugates Demonstrate Robust Efficacy, Broad Distribution, and Safety in Mouse Brain 1. Design and Synthesis of Docosahexaenoic Acid (DHA)-hsiRNA.

Figure 15:
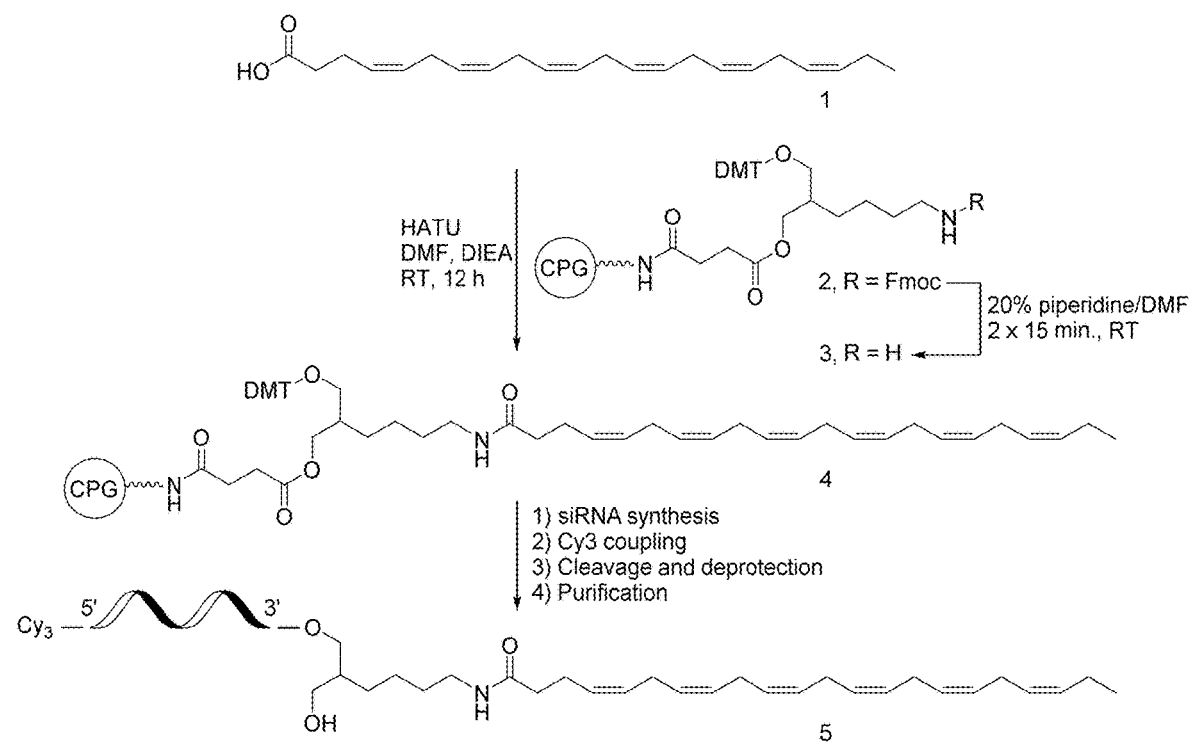
FIG. 15 shows the solid-phase synthesis of DHA-conjugated hsiRNA.

These experiments used (see FIG. 14) siRNA having a functional sequence targeting both human and mouse huntingtin mRNA (Htt). The asymmetric siRNA compounds were composed of a 20-nucleotide antisense (guide) strand and a 15-nucleotide sense (passenger) strand, stabilized with alternating 2'-O-methyl and 2'-fluoro sugar modifications. These modifications are essential for the evaluation of conjugate-mediated delivery in vivo, as partially modified or unmodified siRNAs are rapidly degraded and cleared from the circulation and brain, limiting the ability to evaluate the conjugate's RNAi activity (M. R. Hassler et al., 2015, manuscript submitted). The backbone of the terminal nucleotides is fully phosphorothioated to enhance stability against exonuclease-mediated degradation and to promote cellular internalization. The DHA moiety was conjugated through a commercially available C7 linker to the 3'-end of the sense strand via an amide bond (see FIG. 15). DHA-hsiRNA conjugates were synthesized on functionalized solid support bearing the DHA moiety (40 mol/gram) following standard solid-phase synthesis and deprotection protocols. Newly synthesized oligonucleotides were purified by high-performance liquid chromatography (HPLC) and characterized by liquid chromatography-mass spectrometry (LC-MS) (see FIG. 16).

2. DHA-hsiRNA$^{HTT}$ is Internalized in Primary Cortical Neurons and Shows Potent Huntingtin mRNA Silencing.

Figure 17A:
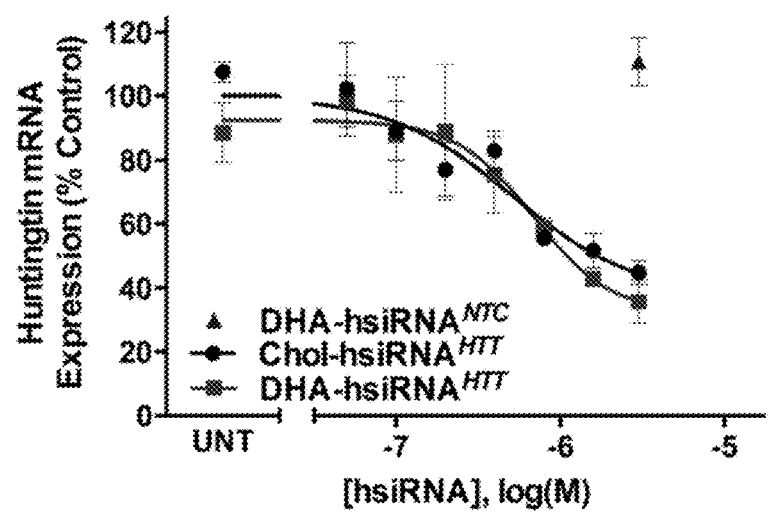
FIG. 17A-B shows neuronal uptake of DHA-hsiRNA, equivalent Huntingtin mRNA silencing, and reduced hydrophobicity compared to Chol-hsiRNA. (A) Primary cortical neurons were incubated with Cy3-DHA-hsiRNA$^{HTT}$ and Chol-hsiRNA$^{HTT}$ at concentrations shown for one week. Level of huntingtin mRNA was measured using Quanti-Gene® (Affymetrix) normalized to housekeeping gene, Ppib (cyclophillin B), and presented as percent of untreated control (n=3, mean+/−SD). UNT—untreated cells. (B) HPLC traces of DHA-hsiRNA$^{HTT}$ and Chol-hsiRNA$^{HTT}$ following C8 reverse phase chromatography. hsiRNA-conjugate structures, sequences, and modifications are shown in FIG. 9A-F and FIG. 14.
Figure 17B:
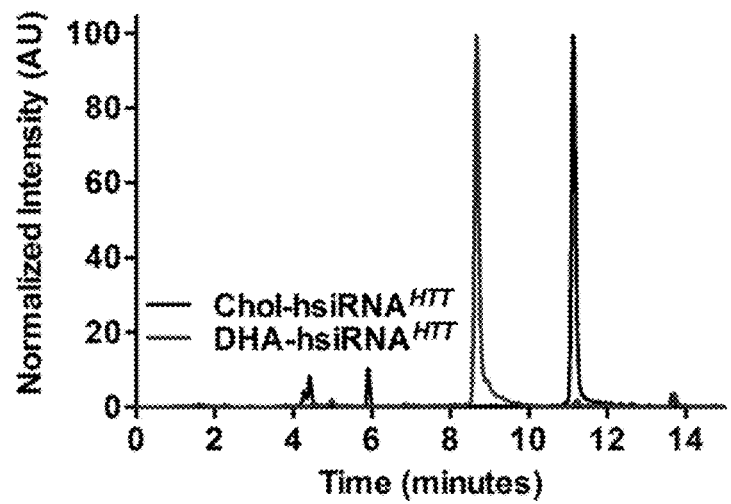

The live cell uptake kinetics of Chol-hsiRNA$^{HTT}$ and DHA-hsiRNAH$^{TT}$ in primary cortical neurons from wild-type (C57BL6) mice, were first analyzed and compared using confocal imaging. While hsiRNA$^{HTT}$ rapidly associated with the cellular membrane (within minutes) and exhibited diffuse cytoplasmic staining, DHA-hsiRNA$^{HTT}$ showed slower uptake kinetics to cytoplasmic foci with no detectable membrane binding. During early time points (of 4-6 hours) significant amounts of Chol-hsiRNA$^{HTT}$ were detected inside the cells, while levels of internalized DHA-hsiRNA$^{HTT}$ were minimal. Interestingly, the overall level of DHA-hsiRNA$^{HTT}$ neuronal accumulation at 72 hours was comparable with that of Chol-hsiRNA$^{HTT}$, resulting in similar levels of Htt silencing (see FIG. 17).

To evaluate the impact of the bioconjugate on overall hsiRNA hydrophobicity, the retention times of DHA-hsiRNA$^{HTT}$ and Chol-hsiRNA$^{HTT}$ were compared using reverse phase chromatography (using a C8 modified column and triethylammonium acetate/acetonitrile eluents). It was observed that DHA-hsiRNA$^{HTT}$ eluted at 8.5 minutes while Chol-hsiRNA$^{HTT}$ eluted at 11.8 minutes under these conditions, suggesting that DHA-hsiRNA$^{HTT}$ is significantly less hydrophobic than cholesterol. This finding indicates that overall hsiRNA hydrophobicity can be strongly affected by the linked conjugate. While DHA- and Chol-hsiRNA$^{HTT}$ conjugates have comparable activity in primary cortical neurons, the reductions in overall compound hydrophobicity may improve pharmacokinetic properties in vivo in mouse brain.

3. DHA-hsiRNA$^{HTT}$ Showed Widespread Distribution in the Mouse Brain Following Intrastriatal Injection.

The bio-distribution and neural cell uptake of Chol-hsiRNA$^{HTT}$ and DHA-hsiRNA$^{HTT}$ in mouse brain was evaluated. When administered directly via a single intrastriatal injection, Cy3-labeled Chol-hsiRNAHTT was primarily detected on the ipsilateral (injected) side of the brain. There is a steep gradient in distribution from the site of injection, however, with little detectable fluorescence present in the cortex or contralateral (non-injected) striatum. Chol-hsiRNA$^{HTT}$ retention in the striatum may result from strong hydrophobic interactions with lipid-rich substructures (e.g. myelin-coated nerve bundles) in this region. Indeed, by high-resolution fluorescent microscopy (63X), we observe that Chol-hsiRNA$^{HTT}$ mainly associates with hydrophobic myelin sheaths and appears to co-localize with striatal nerve bundles at the site of injection. Chol-hsiRNA$^{HTT}$ is effectively internalized by neurons, and also, but to a smaller extent, by astrocytes. In neurons, Chol-hsiRNA$^{HTT}$ is primarily observed in the neuronal processes, but also in the perinuclear area, the site of action of siRNAs.

DHA-hsiRNA$^{HTT}$ distributed more broadly than Chol-hsiRNA$^{HTT}$ to both the ipsilateral striatum and cortex. This effect was specific to the DHA conjugate, as hsiRNA attached to the carbon linker alone was rapidly cleared. Although DHA-hsiRNA$^{HTT}$ also co-localizes with striatal nerve bundles, the pattern of distribution and neuronal internalization significantly differs from Chol-hsiRNA$^{HTT}$. In both striatal and cortical neurons, DHA-hsiRNA$^{HTT}$ appears to primarily localize in the perinuclear area. Furthermore, the lower hydrophobicity of DHA-hsiRNA$^{HTT}$ compared to Chol-hsiRNA$^{HTT}$ appears to promote spread throughout the extracellular matrix and interstitial fluid, enabling an improved diffusion from the site of injection throughout the injected hemisphere.

4. DHA-hsiRNA$^{HTT}$ Demonstrates Significant, Durable Huntingtin mRNA Silencing in Both Striatum and Cortex Following an Intrastriatal Injection.

Figure 18A:
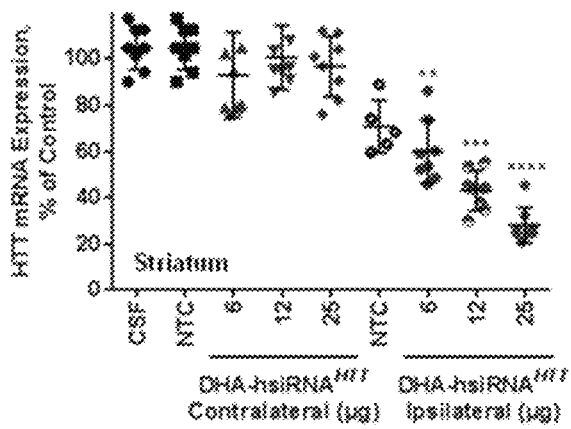
FIG. 18A-C shows the efficacy and duration of effect of DHA-hsiRNA$^{HTT}$ following intrastriatal injection. DHA-siRNA was unilaterally injected into the striatum of WT mice. Punch biopsies of the striatum (A) and cortex (B) were collected after 5 days. For duration of effect studies (C), punch biopsies of the striatum were collected at times shown. Level of Htt mRNA was measured using Quanti-Gene® (Affymetrix) normalized to housekeeping gene, Ppib (cyclophillin B), and presented as percent of untreated control (n=8 mice, mean±SD). NTC=non-targeting control; CSF=artificial cerebrospinal fluid (*=$p<0.05$, =$p<0.01$, *=$p<0.001$, ****=$p<0.0001$). hsiRNA-conjugate structures, sequences, and modifications are shown in FIG. 9A-F and FIG. 14.

Wild-type mice (FVB/NJ) were injected with artificial CSF, a non-targeting control NTC, hsiRNA (DHA-hsiRNA 25 μg), or DHA-hsiRNA$^{HTT}$ (6-25 μg), into the right striatum (n=8 per group). After five days, levels of Huntingtin mRNA expression were measured by QuantiGene® assay, normalized to the housekeeping gene (Ppib) and presented as percent of an untreated control. Robust, dose-dependent Htt silencing in both the striatum and cortex was observed (see FIG. 18a,b). This degree of silencing in both cortex and striatum is consistent with the observed wide distribution pattern. While Chol-hsiRNA$^{HTT}$ Htt silencing was equally as effective in the striatum, there was no statistically significant Htt knockdown observed in the cortex.

Figure 18B:
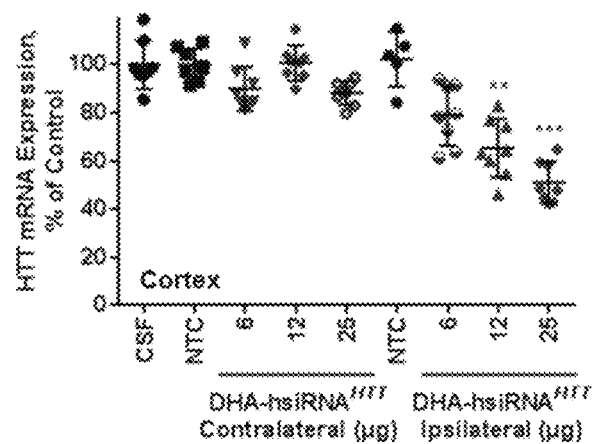
Figure 18C:
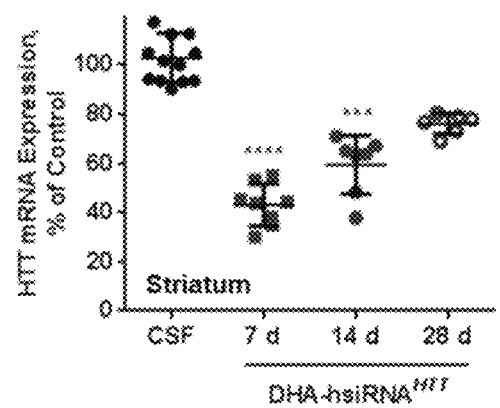

To evaluate the duration of effect, Htt silencing following a single, 12 μg DHA-hsiRNA$^{HTT}$ injection was measured at 7, 14 and 28-day timepoints. The level of Htt silencing reduced over time, from ~60% at 7 days to 24% after 28 days. The 7 and 14-day timepoints were significant assuming a nonparametric distribution using one-way ANOVA with Dunns multiplicity correction (see FIG. 18c).

5. DHA-hsiRNA$^{HTT}$ does not Induce Measurable Immune Stimulation or Adverse Impact on Neuronal Viability Over a Broad Dosage Range.

To evaluate the safety of DHA-hsiRNA conjugates, changes in the expression of IBA-1 and DARPP-32, markers for innate immune stimulation and neuronal integrity, respectively, were monitored. IBA-1 is a microglial-specific cell marker up-regulated following neuron injury, and IBA-1 staining is used to estimate levels of microglial activation following hsiRNA treatment by distinguishing between resting and activated microglia based on morphology. DARPP-32 is an established marker for striatal dopamine receptor activity and neuron viability.

Partially modified Chol-hsiRNAs have no impact on DARPP-32 levels (neuronal viability) at efficacious levels, but induce a slight increase in the level of activated microglia using an IBA-1 marker. When cholesterol was conjugated to fully modified scaffold utilized herein, severe toxicity was observed at doses higher than 25 μg, causing mortality in ~30% of injected animals. This pronounced increase in toxicity is attributed to poor distribution from the site of injection, with excess accumulation of the chemically stabilized hsiRNA causing neuronal loss, consistent with the hypothesis that a high local compound concentration is toxic within brain tissues.

Figure 19A:
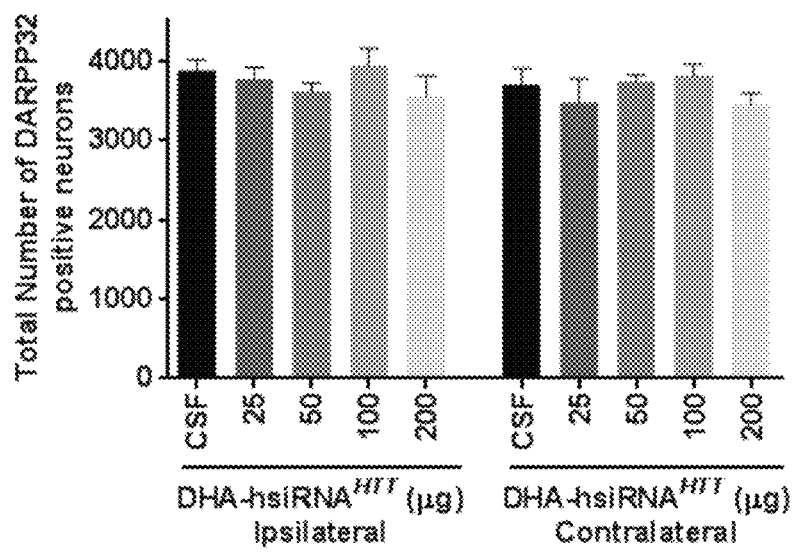
FIG. 19 shows that (A) DHA-hsiRNA$^{HTT}$ has no impact on neuronal integrity or measurable innate immune activation at ~20-fold higher concentrations than what is required for activity. DHA-hsiRNA$^{HTT}$ was administered by unilateral intrastriatal injection. Brains were collected after 5 days, fixed, sectioned, and stained with antibodies against DARPP-32, a marker for spiny medium neurons, or IBA-1, a marker for microglia. Data represented as total number of DARPP-32 positive neurons per tissue section (n=3 mice, mean±SD); (B) There was no detectable induction of innate immune response identified at dose levels 20 fold higher than efficacies (data shown for total microglia for DHA-hsiRNA). Data represented as total number of IBA-1 resting or activated microglia per tissue section, classified by morphology (n=3 mice, mean±SD). hsiRNA-conjugate structures, sequences, and modifications are shown in FIG. 9A-F and FIG. 14.
Figure 19B:
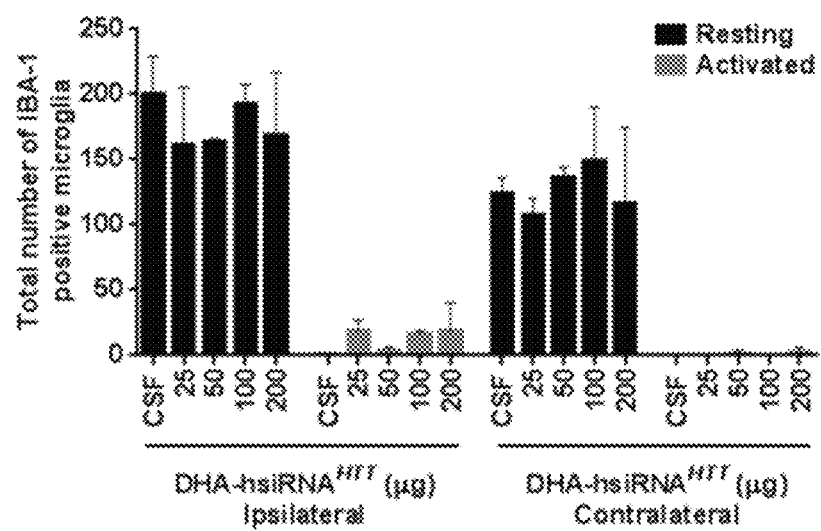

To evaluate the toxicity of DHA-hsiRNA in vivo, animals were injected with a broad range of DHA-hsiRNA concentrations (25-200 μg). Given the solubility limit of DHA-hsiRNA (10 mM in aCSF) and the injection volume (2 μL), 200 μg is the highest possible dose that can be administered intrastriatally, and 25 μg is four-fold higher than what is required for detectible silencing activity (see FIG. 18). No reduction in DARPP-32 levels (see FIG. 19a) or significant elevation of activated microglia was observed in coronal brain sections of mice treated at the highest dose level. Moreover, all injected animals appeared normal, with no signs of distress or toxicity. These results indicate that administration of DHA-hsiRNA has no measureable impact on neuronal integrity or innate immune system activation (see FIG. 19).

Materials and methods were obtained and handled as described by Nikan et al. ("Docosahexaenoic acid (DHA)-siRNA conjugates demonstrate robust efficacy, broad distribution, and safety in mouse brain," Molecular Therapy-Nucleic Acids, 2016).

Example 9: g2DHA Support Synthesis II

Figure 28:
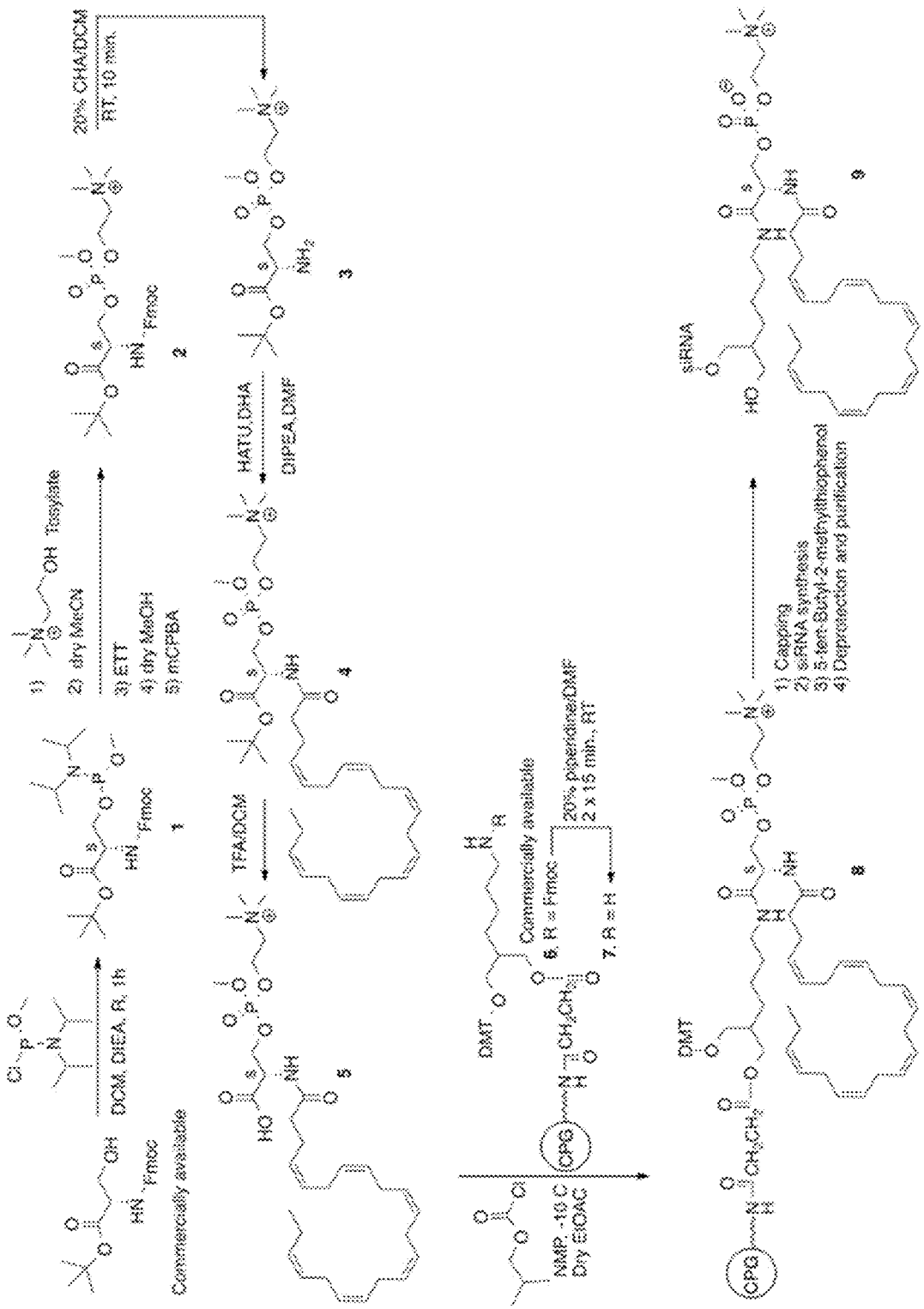
FIG. 28 shows g2DHA support synthesis II (see Example 9).

As shown in FIG. 28, commercially available Fmoc-Ser (tBu)-OH is reacted with N,N-diisopropylamino methoxy phosphonamidic chloride to afford (1). (1) is then reacted with choline tosylate followed by oxidation with mCPBA to afford (2). Next, the Fmoc group on (2) is removed with 20% cyclohexylamine in DCM and the free amine is coupled to docosahexaenoic acid to afford (3) and (4) respectively. Following this, the tBu ester group on (4) is deprotected under acidic condition to yield (5). In a parallel line, the Fmoc group on a commercially available 1-O-DMT-6-N-Fmoc-2-hydroxymethylhexane support (6) is removed using a solution of 20% piperidine in dimethylformamide to produce (7). Finally, (5) and (7) are coupled in the presence of isobutyl chloroformate to yield the functionalized support (8).

CPG 8 (6.00 g, 330 mol, 1 equiv.) was first treated with 20% piperidine in dry DMF for 15 minutes. This procedure was repeated twice to ensure complete deprotection of the Fmoc group. The amine-bearing CPG 9 was filtered off and washed successively with DCM, ACN and ether and dried under vacuum. Then the CPG 9 was mixed with a mixture of DHA (0.65 g, 1.98 mmol, 6 equiv.), HATU (0.25 g, 0.66 mmol, 2 equiv.) and DIEA (449 µL, 2.64 mmol, 8 equiv.) in dry DMF (42 mL). The suspension was mixed on a rotary mixer for 24 h. The CPG was then filtered off and washed with DCM, ACN and ether and dried under vacuum. The CPG was capped with 16% N-methylimidazole in THF (CAP A) and acetic anhydride:pyridine:THF (1:2:2, v/v/v) (CAP B) (1:1, v/v) during 15 min and was washed with DCM, ACN and ether and dried under vacuum.

Example 10: Synthesis of DHAg2-hsiRNA from Functionalized Solid Support

Preparation of amine-bearing CPG 3

Figure 34:
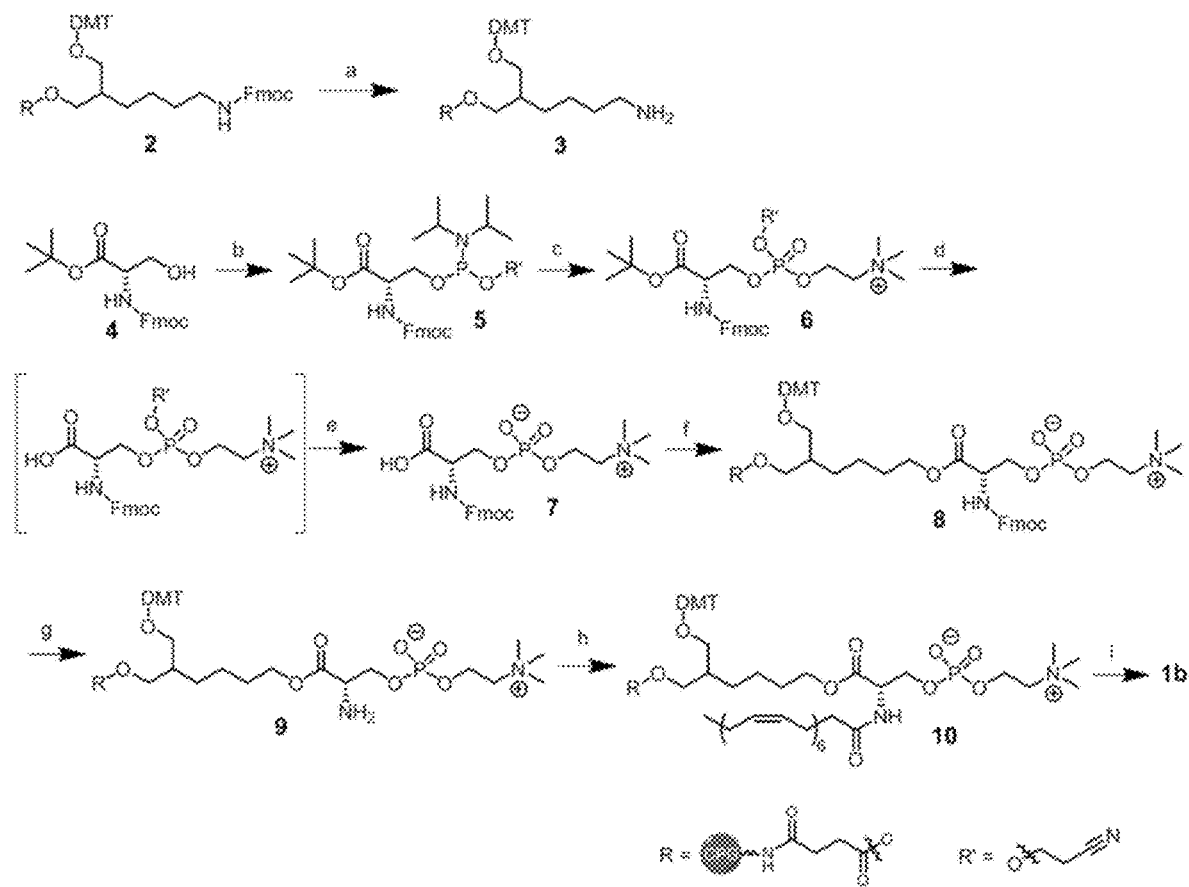
FIG. 34 shows the optimized solution phase synthetic route to g2DHA-hsiRNA (1b). Reagents and conditions: (a) 20% piperidine in DMF (2×15 min); (b) 2-cyanoethyl N,N-diisopropylchlorophosphoramidite, DIEA, DCM, 2 h, rt, 95%; (c) choline tosylate, ETT, MeCN, 2 h, rt, followed by mCPBA, 10 min, rt, 69%; (d) e) TFA in dry DCM (1:1), triisopropylsilane, 2 h, rt then 10% diisopropylethylamine in MeCN, 1.5 h, rt 74% (f) 3, BOP, HOBt, DMF, 2,4,6-collidine, rt, 12 h; (g) 20% piperidine in DMF (2×15 min), rt; (h) DHA, HATU, DMF, rt, 12 h; (i) RNA synthesis, cleaving, deprotection, purification and ion-exchange. See also Example 10.

As shown in FIG. 34, a functionalized CPG (3, Scheme 2) was prepared and used for the solid-phase conjugation of DHA. First, the LCAA-CPG support (particle size 125-177 µm, pore diameter 500 Å and primary amino loading 145 µmol/g) was activated and dried overnight according to published protocols.[1] Then, the commercially available 1-O-DMT-6-N-Fmoc-2-hydroxymethylhexane was converted to succinate and loaded on CPG following a reported procedure to afford 2.[2] The linker loading was determined by DMT assay to be around 55 µmol/g. Subsequently, the Fmoc goup was removed from 2 using a solution of 20% piperidine in DMF for 15 minutes. This procedure was repeated twice to ensure complete deprotection of the Fmoc group. The amine-bearing CPG 3 was filtered off and washed successively with DCM, ACN and ether and dried under vacuum.

Scheme S1: Synthesis route of compound 3

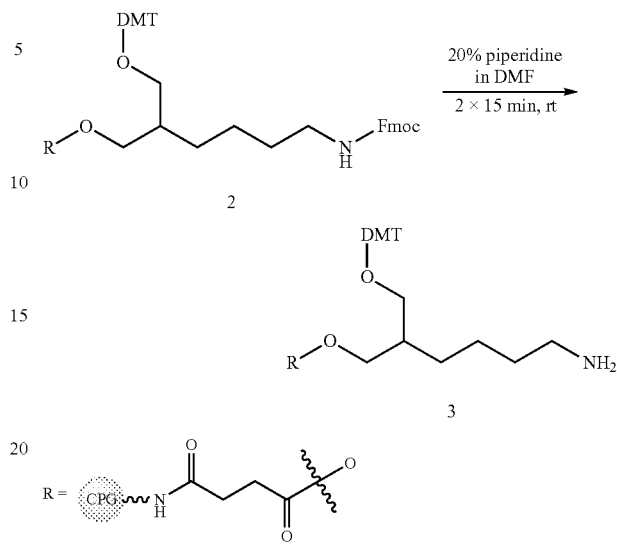

[1] M. J. Damha, P. A. Giannaris, S. V. Zabarylo, An improved procedure dor derivatization of controlled-pore glass beads for solid-phase oligonucleotide synthesis. *Nucleic acids research* 1990, 18, 3813-3821.

[2] P. S. Nelson, M. Kent, S. Muthini, Oligonucleotide labeling methods 3. Direct labeling of oligonucleotides employing a novel, non-nucleosidic, 2-aminobutyl-1,3-propanediol backbone. *Nucleic acids research* 1992, 20, 6253-6259.

Synthesis of 5

Compound 4 (2.0 g, 5.21 mmol, 1 equiv.) was first dried by co-evaporation with toluene. Dry DCM (15 mL) and DIPEA (1.54 mL, 8.86 mmol, 1.7 equiv.) were added under argon and 2'-cyanoethyl-N,N-diisopropylchlorophosphoramidite (1.6 g, 6.78 mmol, 1.3 equiv.) was added slowly via a syringe. The reaction mixture was stirred 2 h at room temperature. After reaching completion, the reaction mixture was quenched with methanol and was washed with a solution of sodium bicarbonate and brine. The aqueous phase was extracted with DCM. The organic phase was dried on magnesium sulfate, filtrated and evaporated under vacuum. The crude was then purified by column chromatography on silica gel using a mixture of EtOAc/Hexane (8/2) with 1% pyridine as eluent, to afford 5 as a white solid (2.9 g, 4.97 mmol, yield 95%).

Scheme S2: Synthesis route of compound 5

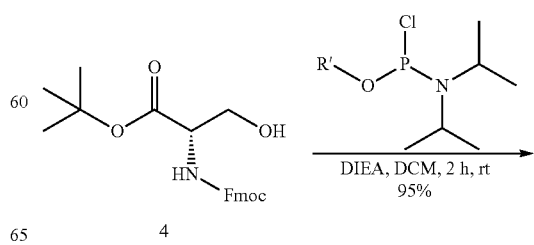

5

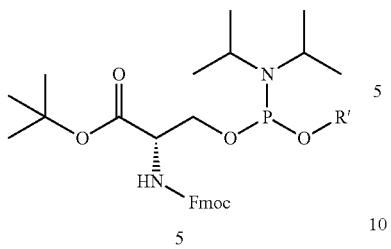

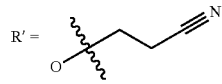

¹H NMR (400 MHz, CDCl₃) $\delta_H$ (ppm) 7.76 (d, J=7.6 Hz, 2H, Ar Fmoc); 7.62 (t, J=6.8 Hz, 2H, Ar Fmoc); 7.41 (t, J=7.6 Hz, 2H, Ar Fmoc); 7.32 (m, 2H, Ar Fmoc); 5.79-5.68 (dd, J=36.4 Hz, J=8.0 Hz, 1H, NH); 4.43-4.22 (m, 4H, CH₂ Fmoc+CH₂); 4.11-3.73 (m, 4H, 2*CH+CH₂ CE); 3.59 (m, 2H, 2*CH); 2.63-2.53 (m, 2H, CH₂ CE); 1.50, 1.49 (s, s, 9H, CH₃ tBu); 1.18 (m, 12H, CH₃). ¹³C NMR (100 MHz, CDCl₃) $\delta_C$ (ppm) 168.95 (C=O); 155.75 (C=O); 143.85, 143.70, 141.20, 141.18 (Cq Fmoc); 127.62, 126.99, 125.15, 125.09, 125.05, 125.03, 119.93, 119.80 (CH Ar Fmoc); 117.53 (Cq CE); 82.40 (Cq tBu); 67.08 (CH₂ Fmoc); 64.35 (CH₂); 63.93 (CH); 58.36 (CH₂ CE); 55.39 (CH); 47.07 (CH); 43.10 (CH Fmoc); 27.94 (CH₃ tBu); 24.56, 24.49 (CH₃); 20.30 (CH₂ CE). ³¹P NMR (161 MHz, CDCl₃) $\delta_P$ (ppm) 149.77, 149.74. HRMS (ESI⁻) m/z calculated for C₃₁H₄₂N₃O₆P (M+Na) 605.2708; Found 605.2306.

Synthesis of 6

Compound 5 (2.9 g, 5.39 mmol, 1 equiv.) was dried with dry toluene and dry ACN. Choline p-toluenesulfonate (1.63 g, 5.93 mmol, 1.1 equiv.) was dried with toluene and dissolved in dry ACN (46 mL). This mixture was added to compound 5 through a cannula. ETT (0.25 M in ACN) (21.6 mL, 5.39 mmol, 1 equiv.) was added slowly with a syringe. The mixture was stirred 2 h at room temperature. After reaching completion, the reaction mixture was quenched with methanol. Meta-chloroperoxybenzoic acid (mCPBA) (1.86 g, 10.78 mmol, 2 equiv.) was added by portion to the mixture. After 30 min of stirring, the mixture was reduced under vacuum. The crude was then purified by column chromatography on silica gel using a gradient of MeOH in DCM (0-30%) as eluent, to afford 6 as a mixture of tetrazolium (major counter anion) and tosylate (less than 5%) salts (2.7 g, 3.69 mmol, yield 69%).

Scheme S3: Synthesis route of compound 6

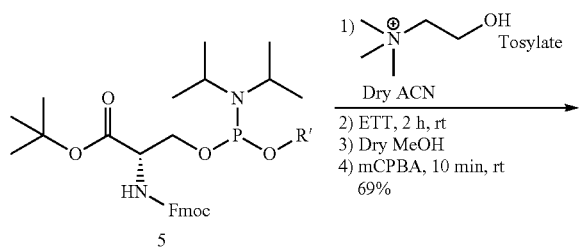

6

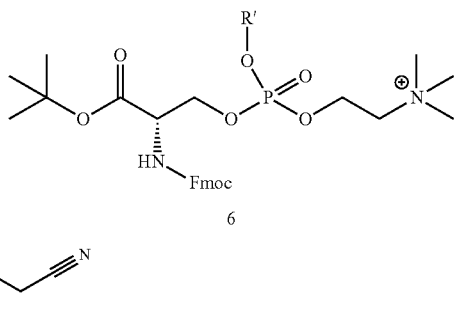

¹H NMR (400 MHz, CDCl₃) $\delta_H$ (ppm) 7.72 (d, J=7.6 Hz, 2H, Ar Fmoc); 7.66 (d, J=8.0 Hz, 2H, Ar tosylate); 7.59 (d, J=7.2 Hz, 2H, Ar Fmoc); 7.36 (t, J=7.2 Hz, 2H, Ar Fmoc); 7.27 (t, J=8.0 Hz, 2H, Ar Fmoc); 7.09 (d, J=8.0 Hz, 2H, Ar tosylate); 6.80-6.70 (dd, J=33.2 Hz, J=7.2 Hz, 1H, NH); 4.51-4.36 (m, 6H, CH₂ Fmoc+2*CH₂); 4.29-4.15 (m, 4H, CH₂ CE+2*CH); 3.83 (m, 2H, CH₂); 3.25 (q, J=7.2 Hz, 2H, CH₂ tetrazolium); 3.19 (s, 9H, CH₃); 2.72 (m, 2H, CH₂ CE); 2.27 (s, 3H, CH₃ tosylate); 1.44 (s, 9H, CH₃ tBu); 1.18 (t, J=7.2 Hz, 3H, CH₃ tetrazolium). ¹³C NMR (100 MHz, CDCl₃) $\delta_C$ (ppm) 167.77 (C=O); 163.89 (Cq tetrazolium); 156.16 (C=O); 143.69, 143.63, 141.11 (Cq Fmoc); 128.81, 125.63 (CH tosylate); 127.69, 127.07, 125.24, 125.17, 119.91, (CH Ar Fmoc); 143.15, 139.73 (Cq tosylate); 117.18 (Cq CE); 83.22 (Cq tBu); 67.96 (CH₂); 67.14 (CH₂ Fmoc); 65.25 (CH₂); 62.91 (CH₂ CE); 61.88 (CH); 54.85 (CH₂); 54.10 (CH₃); 46.88 (CH Fmoc); 27.86 (CH₃ tBu); 21.18 (CH₃ tosylate); 19.58 (CH₂ tetrazolium); 19.51 (CH₂ CE); 6.80 (CH₃ tetrazolium). ³¹P NMR (161 MHz, CDCl₃) $\delta_P$ (ppm) -2.60, -2.71. HRMS (ESI⁺) m/z for calculated C₃₀H₄₁N₃O₈P (M+H) 603.2799; Found 603.2853.

Note:

The order of addition of reactants during the synthesis of 6 is important. If compound 5 and ETT are mixed prior to the addition of choline p-toluenesulfonate a side reaction will occur according to the Scheme S4.

Scheme S4: Side reaction between 5 and ETT, which forms a cyclic byproduct

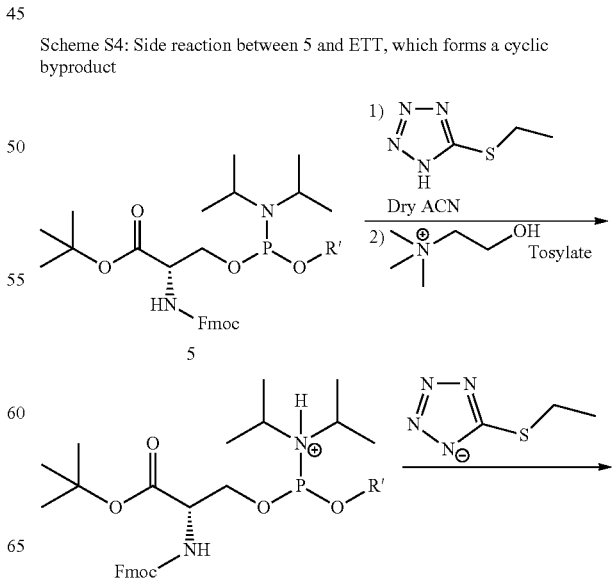

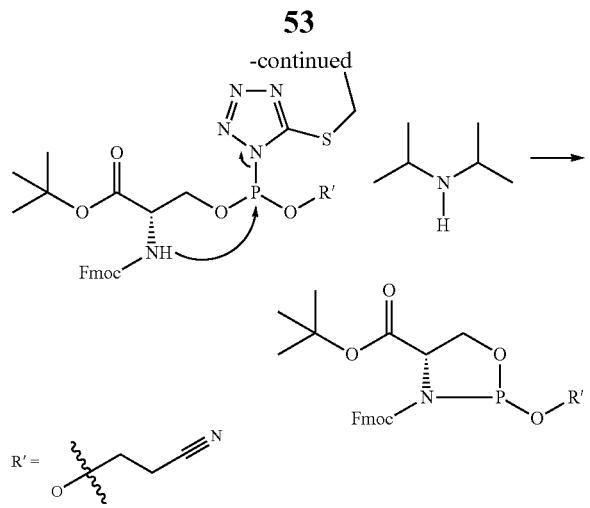

Synthesis of 7

Compound 6 (2.30 g, 3.15 mmol, 1 equiv.) was dissolved in 60 mL of (1:1) solution of TFA:dry DCM. Triisopropylsilane (2.39 mL, 11.66 mmol, 3.7 equiv.) was added and the mixture was stirred at room temperature for 2 h. The solvent and TFA were evaporated and the residue was purified by reverse phase HPLC ($C_{18}$, Buffer A=Water, Buffer B=ACN, Gradient=5-65% of B in 12 min, T=45° C.). The ACN was removed under vacuum and the aqueous solution was freeze-dried. The lyophilized powder was dissolved in 10% diisopropylethylamine (14 mL) in ACN (140 mL) and the mixture was stirred at room temperature for 2 h. The solvent was evaporated under vacuum and the crude was purified by reverse phase HPLC ($C_{18}$, Buffer A=Water, Buffer B=ACN, Gradient=5-65% of B in 12 min, T=45° C.). The ACN was removed under vacuum and the aqueous solution was freeze-dried to afford 7 as diisopropylammonium salt (1.38 g, 2.32 mmol, yield 74% over two steps).

Scheme S5: Synthesis route of compound 7

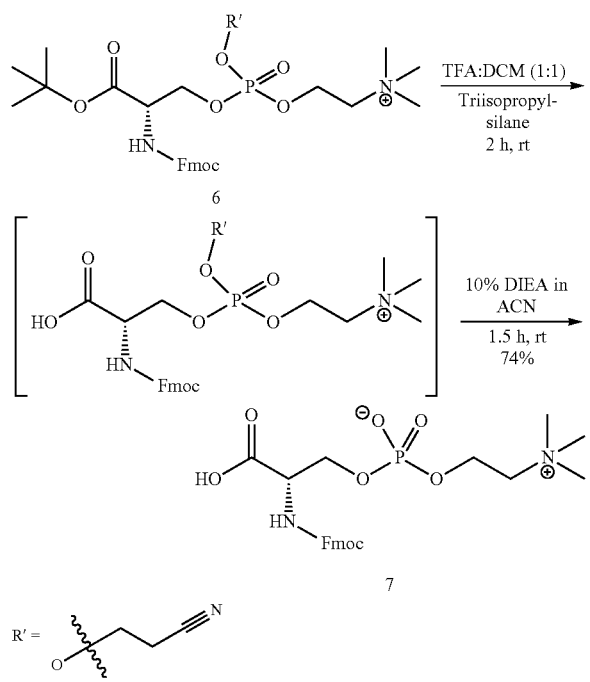

$^1$H NMR (400 MHz, DMSO-d6) $\delta_H$ (ppm) 7.88 (d, J=7.5 Hz, 2H, Ar Fmoc); 7.85-7.70 (m, 2H, Ar Fmoc); 7.41 (t, J=7.0 Hz, 2H, Ar Fmoc); 7.34 (t, J=7.0 Hz, 2H, Ar Fmoc); 6.75 (s, 1H NH); 7.28 (s, 1H NH); 4.26-4.04 (m, 5H, $CH_2$+CH Fmoc+$CH_2$ Fmoc); 3.92 (s, 2H, $CH_2$); 3.78-3.38 (m, 5H, CH+$CH_2$+2*CH DIPEA); 3.13 (s, 9H, $CH_3$); 1.14, 1.12 (s,s, 12H, $CH_3$ DIPEA). $^{13}$C NMR (100 MHz, DMSO-d6) $\delta_C$ (ppm) 170.94 (C=O); 155.13 (C=O); 143.90, 142.46, 140.57, 139.31 (Cq Fmoc); 137.32, 128.81, 127.48, 127.18, 125.11, 121.27, 119.92, 109.64 (CH Ar Fmoc); 65.39 ($CH_2$); 65.24 ($CH_2$Fmoc); 65.15 (CH); 58.21 ($CH_2$); 56.78 ($CH_2$); 52.89 ($CH_3$); 46.61 (CH Fmoc); 45.12 (CH DIPEA); 19.78 ($CH_3$ DIPEA). $^{31}$P NMR (161 MHz, $CDCl_3$) $\delta_P$ (ppm) −1.15 HRMS (ESI$^{\pm}$) m/z for calculated $C_{23}H_{29}N_2O_8P$ (M+H) 493.1788; Found 493.1783.

Solid-Phase Synthesis of 8

Compound 7 (1.00 g, 1.69 mmol, 4.75 equiv.) was dissolved in dry DMF (100 mL). (Benzotriazol-1-yloxy)tris(dimethylamino)phosphonium hexafluorophosphate (BOP) (0.59 g, 1.34 mmol, 3.76 equiv.) and hydroxybenzotriazol (HOBt) (0.21 g, 1.34 mmol, 3.76 equiv.) were added and stirred until the solution went clear. 2,4,6-collidine (560 µL, 4.32 mmol, 12.42 equiv.) was added followed by 3 (6.55 g, loading of 55 µmol/g, 360 mol, 1 equiv.) and the suspension was mixed overnight on a rotary mixer. The CPG was filtered off and washed with DCM, ACN and ether and dried under vacuum. The CPG was capped with 16% N-methylimidazole in THF (CAP A) and acetic anhydride:pyridine:THF (1:2:2, v/v/v) (CAP B) (1:1, v/v) for 1 h and was washed with DCM, ACN and ether and dried under vacuum.

Scheme S6: Synthesis route of compound 8

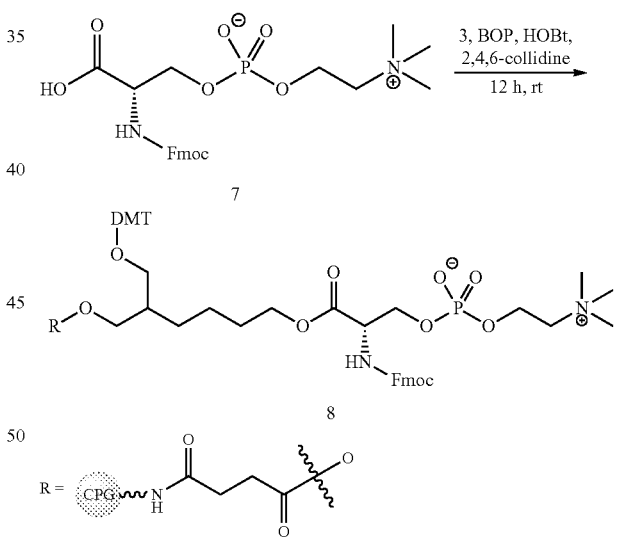

Solid-Phase Synthesis of 9 and 10

CPG 8 (6.00 g, 330 µmol, 1 equiv.) was first treated with 20% piperidine in dry DMF for 15 minutes. This procedure was repeated twice to ensure complete deprotection of the Fmoc group. The amine-bearing CPG 9 was filtered off and washed successively with DCM, ACN and ether and dried under vacuum. Then the CPG 9 was mixed with a mixture of DHA (0.65 g, 1.98 mmol, 6 equiv.), HATU (0.25 g, 0.66 mmol, 2 equiv.) and DIEA (449 µL, 2.64 mmol, 8 equiv.) in dry DMF (42 mL). The suspension was mixed on a rotary mixer for 24 h. The CPG was then filtered off and washed with DCM, ACN and ether and dried under vacuum. The CPG was capped with 16% N-methylimidazole in THF (CAP A) and acetic anhydride:pyridine:THF (1:2:2, v/v/v) (CAP B) (1:1, v/v) during 15 min and was washed with DCM, ACN and ether and dried under vacuum.

Scheme S7: Synthesis route of compounds 9 and 10

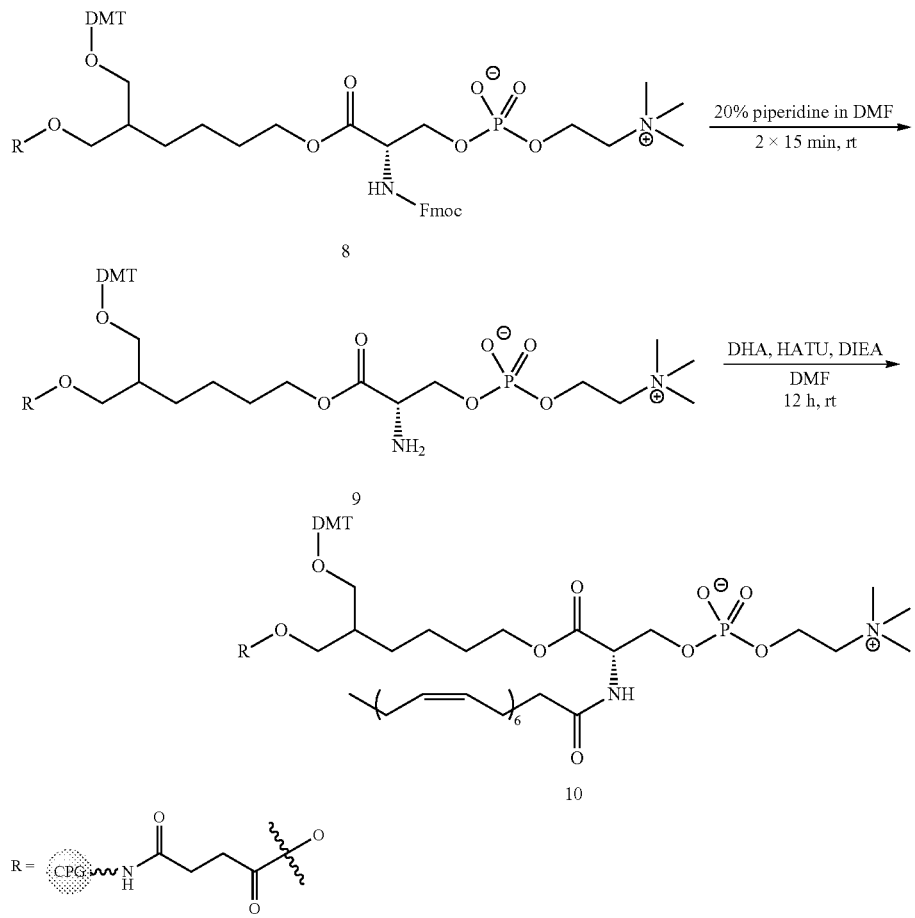

minutes. The oligonucleotide solutions were then cooled in a freezer for a few minutes and dried under vacuum in a Speedvac. The resulting pellets were suspended in 10 mL of triethylammonium acetate (TEAA) buffer (0.1 M, pH 7) and filtered through a 0.2 µm filter. The final purification of oligonucleotides was performed on an Agilent Prostar System (Agilent, Santa Clara, Calif.) equipped with a Hamilton HxSil C8 column (150×21.2) using the following conditions: buffer A: (0.1 M, TEAA, PH 7), B: (ACN), gradient: 90% A, 10% B to 10% A, 90% B in 30 minutes, temperature: 55° C., flow rate: 20 ml/min. The pure oligonucleotides were collected and cation-exchanged on a HiTrap 5 ml SP HP column (GE Healthcare Life Sciences, Marlborough, Mass.) and lyophilized.

Standard Solid-Phase Oligonucleotide Synthesis

Oligonucleotides were synthesized on an Expedite ABI DNA/RNA Synthesizer following standard protocols. Each synthesis was done at a 1-µmole scale using DHA-conjugated CPG 10 for the sense strand and a Unylinker® terminus (ChemGenes, Wilmington, Mass.) for the antisense strand. Phosphoramidites were prepared as 0.15 M solutions for 2'-O-methyl (ChemGenes, Wilmington, Mass.) and Cy3 (Gene Pharma, Shanghai, China) and 0.13 M for 2'-fluoro (BioAutomation, Irving, Tex.) in ACN. 5-(Benzylthio)-1H-tetrazole (BTT) 0.25 M in ACN was used as coupling activator. Detritylations were performed using 3% dichloroacetic acid (DCA) in DCM for 80 s and capping was done with a 16% N-methylimidazole in THF (CAP A) and THF: acetic anhydride:2,6-lutidine, (80:10:10, v/v/v) (CAP B) for 15 s. Sulfurizations were carried out with 0.1 M solution of DDTT in ACN for 3 minutes. Oxidation was performed using 0.02 M iodine in THF:pyridine:water (70:20:10, v/v/v) for 80 s. Phosphoramidite coupling times were 250 s for all amidites.

Deprotection and Purification of Oligonucleotides

Both sense and antisense strands were cleaved and deprotected using 1 mL of 40% aq. methylamine at 65° C. for 10

Example 11: Solid Phase Synthesis of DHAg2-hsiRNA

Figure 35:
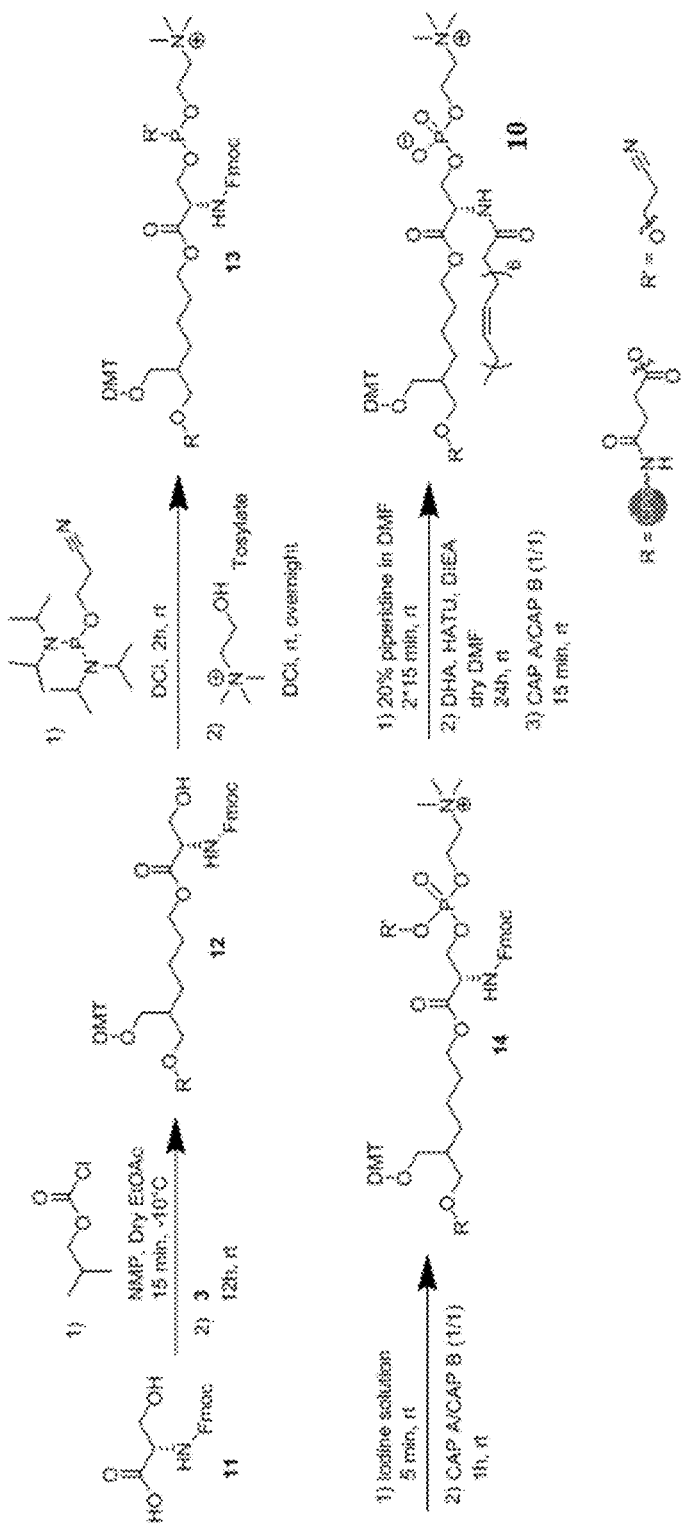
FIG. 35 shows the optimized solid-phase synthetic route to g2DHA-hsiRNA (1b). See also Example 11.

As shown in FIG. 35, the commercially available N-Fmoc-L-serine 11 (0.38 g, 1.14 mmol) was placed in a round bottom flask and dried by coevaporation with toluene. Anhydrous ethyl acetate (3 mL) was delivered to the flask and the solution was cooled down to −10° C. Isobutyl chloroformate (0.15 mL, 0.16 g, 1.16 mmol) and N-methyl-2-pyrrolidone (NMP) (0.26 mL, 2.65 mmol) were added to this solution and the mixture was stirred for 15 minutes. Linker 3 (0.08 mmol) was added under argon and the suspension was mixed on a rotary mixer for 12 h. The CPG was filtered off and washed with DCM, ACN and ether and dried under vacuum to afford 12. 12 was placed in a small peptide synthesis flask and rinsed twice with dry ACN and kept under argon. 2-cyanoethyl-N,N,N'N'-tetraisopropyl-phosphorodiamidite (0.61 mL, 1.91 mmol) and 4,5-dicya-noimmidazole (DCI) (7.65 mL of a 0.25 M solution in ACN, 1.91 mmol) were added and the suspension was mixed on a rotary mixer for 2 h. The solution was decanted and the CPG was kept under argon. Choline p-toluenesulfonate (0.53 g, 1.91 mmol) that was previously dried by coevaporation with toluene was mixed with 4,5-dicyanoimmidazole (DCI) (7.65 mL of a 0.25 M solution in ACN, 1.91 mmol) and delivered to the flask via a syringe. The suspension was mixed on a rotary mixer overnight. The solution was decanted and the CPG was washed with dry acetonitrile to afford CPG 13. Subsequently, the phosphotriester group was oxidized with iodine solution (7.6 mL of a 0.02 M iodine in THF:pyridine: water 70:20:10, v/v/v, 0.15 mmol) for 5 minutes and capped with a mixture (1/1, v/v) of 16% N-methylimidazole in THF (CAP A) and THF:acetic anhydride:2,6-lutidine, (80:10:10, v/v/v) (CAP B) for 1 h. The CPG was washed with DCM, ACN and ether and dried under vacuum to yield 14. The Fmoc group of 14 was then removed by treating the CPG with 20% piperidine in DMF (2×15 minutes). Piperidine simultaneously removes the β-cyanoethyl protecting group generating a phosphodiester specie. The CPG was washed and dried again as previously described. The amine-bearing CPG was then added to a mixture of DHA (0.19 g, 0.20 mL, 0.568 mmol), HATU (0.07 g, 0.18 mmol, and DIEA (0.39 mL, 2.24 mL) in dry DMF and stirred overnight. The solution was decanted and the CPG was capped with 16% N-methylimidazole in THF (CAP A) and acetic anhydride: pyridine:THF (1:2:2, v/v/v) (CAP B) (1:1, v/v) for 30 minutes. Finally, the CPG was washed with DCM, ACN and ether and dried under vacuum to afford 10.

The invention claimed is:

1. A compound of formula (I):

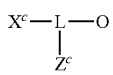

wherein:
O is a double-stranded nucleic acid comprising a first oligonucleotide and a second oligonucleotide, wherein:
(1) the first oligonucleotide comprises at least 16 contiguous nucleotides, a 5' end, a 3' end and has complementarity to a target;
(2) the second oligonucleotide comprises at least 15 contiguous nucleotides, a 5' end, a 3' end, and has homology with a target; and
(3) a portion of the first oligonucleotide is complementary to a portion of the second oligonucleotide;
L is a divalent or trivalent linker;
$X^c$ is a hydrophobic moiety; and
$Z^c$ is selected from the group consisting of:

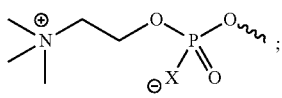

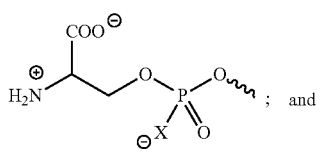

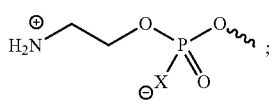

wherein X is O, S or $BH_3$.

2. The compound of claim 1, wherein L comprises an ethylene glycol chain, an alkyl chain, a peptide, RNA, DNA, a phosphodiester, a phosphorothioate, a phosphoramidate, an amide, a carbamate, or a combination thereof; and wherein L is attached to O via the second oligonucleotide.

3. The compound of claim 1, wherein $X^c$ is selected from the group consisting of fatty acids, steroids, secosteroids, lipids, gangliosides and nucleoside analogs, and endocannabinoids.

4. The compound of claim 1, wherein $X^c$ is a saturated or unsaturated moiety having fewer than three double bonds, or wherein $X^c$ is a polyunsaturated moiety having three or more double bonds.

5. The compound of claim 1, wherein:
(1) the first oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the first oligonucleotide are not 2'-methoxy-ribonucleotides;
(2) the second oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the second oligonucleotide are 2'-methoxy-ribonucleotides;
(3) the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages; and
(4) the nucleotides of the second oligonucleotide are connected to adjacent nucleotides via phosphodiester or phosphorothioate linkages, wherein the nucleotides at positions 1 and 2 from the 3' end are connected to adjacent nucleotides via phosphorothioate linkages.

6. The compound of claim 1, wherein the first oligonucleotide comprises a moiety X at the 5' end, wherein X is selected from the group consisting of:

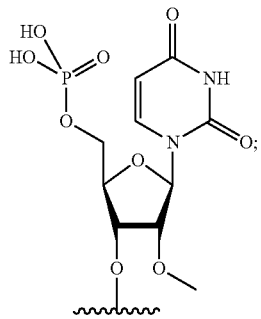

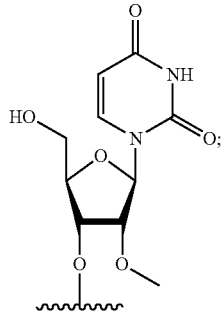

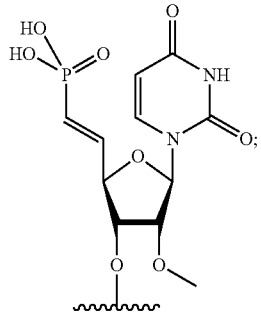

X4
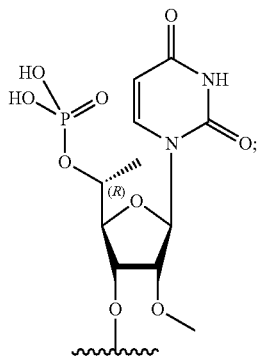
X5
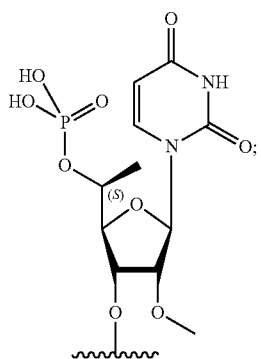
X6
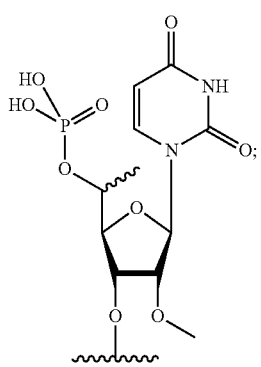
X7
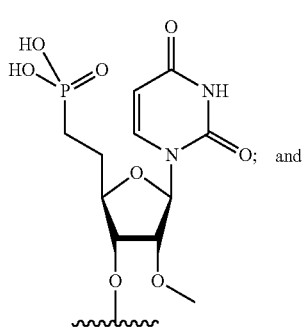; and
X8
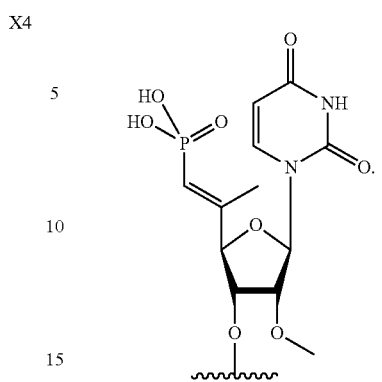
7. The compound of claim 1, wherein the first oligonucleotide has the structure of formula (Ia):
$$X(-K-B-K-A)_j(-S-B-S-A)_r(-S-B)_t-OR \qquad (Ia)$$
wherein:
X is selected from the group consisting of:
X1
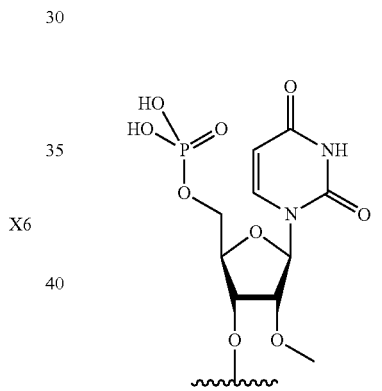
X2
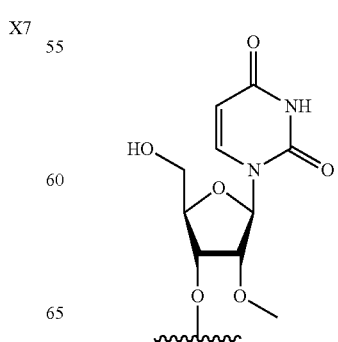

X3

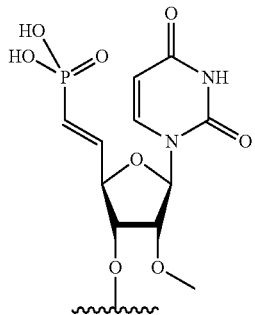

X4

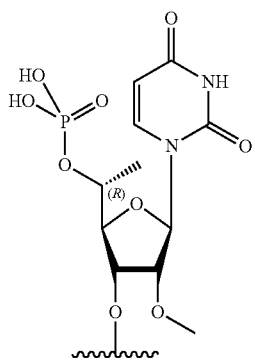

X5

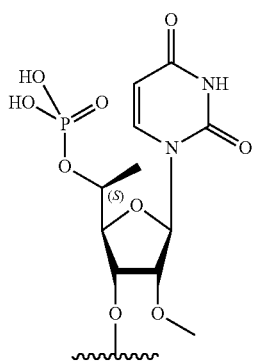

X6

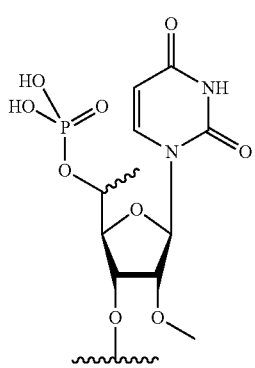

X7

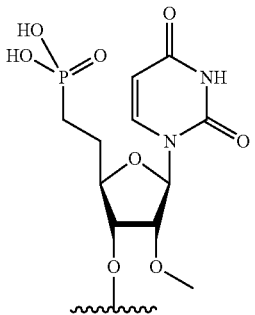

X8

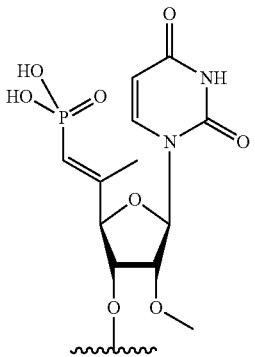

A, for each occurrence, independently is a 2'-methoxy-ribonucleotide;

B, for each occurrence, independently is a 2'-fluoro-ribonucleotide;

K, for each occurrence independently is a phosphodiester or phosphorothioate linker;

S is a phosphorothioate linker;

R is hydrogen, phosphate, vinylphosphonate, or a capping group;

j is 4, 5, 6 or 7;

r is 2 or 3; and t is 0 or 1.

8. The compound of claim 1, wherein the first oligonucleotide has the structure of formula (IIa):

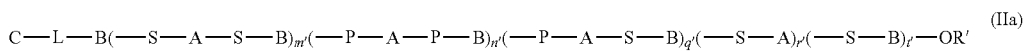

wherein:
C-L is:

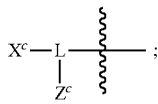

A, for each occurrence, independently is a 2'-methoxy-ribonucleotide;
B, for each occurrence, independently is a 2'-fluoro-ribonucleotide;
S is a phosphorothioate linker;
P is a phosphodiester linker;
R' is hydrogen, phosphate, vinylphosphonate, or a capping group;
m' is 0 or 1;
n' is 4, 5 or 6;
q' is 0 or 1;
r' is 0 or 1; and
t' is 0 or 1.

9. The compound of claim 1, wherein the first oligonucleotide has the structure:

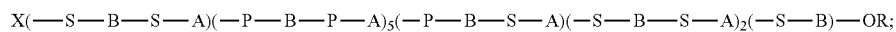

the second oligonucleotide has the structure:

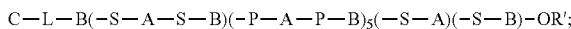

and
the compound has the structure of formula (IIIa):

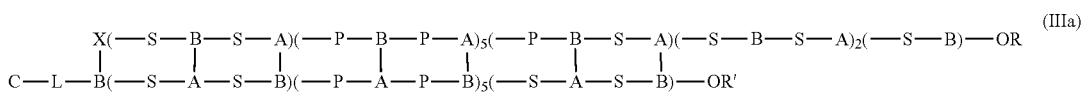

wherein each | represents a hydrogen bonding interaction
wherein:

X is selected from the group consisting of:

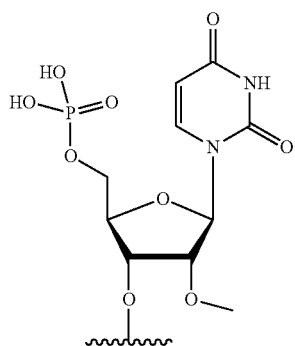

X1

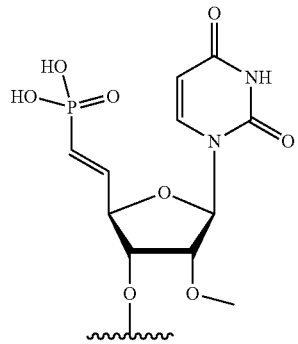

X3

X2

-continued

-continued

X4 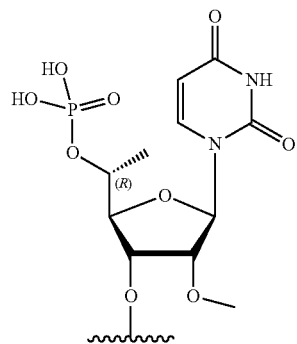

X5 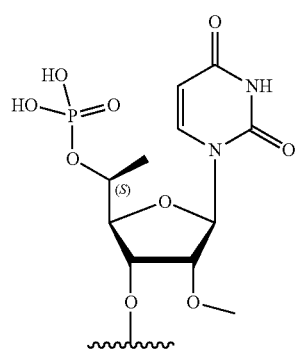

X6 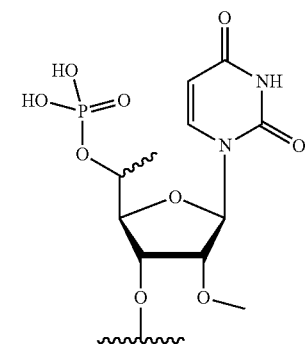

X7 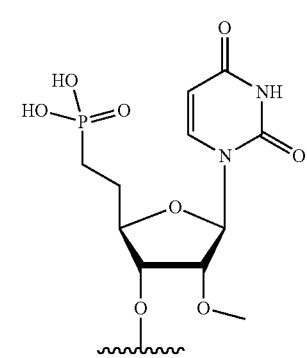

X8 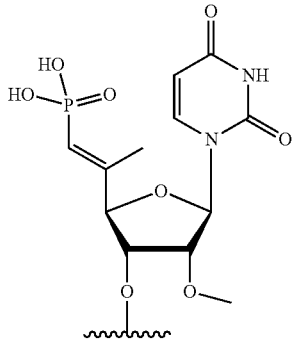

C-L is:

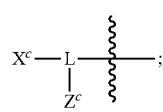

A, for each occurrence, independently is a 2'-methoxy-ribonucleotide;
B, for each occurrence, independently is a 2'-fluoro-ribonucleotide;
S is a phosphorothioate linker;
P is a phosphodiester linker; R is hydrogen, phosphate, vinylphosphonate, or a capping group;
R' is hydrogen, phosphate, vinylphosphonate, or a capping group.

10. The compound of claim 9, wherein:
X is (X3)

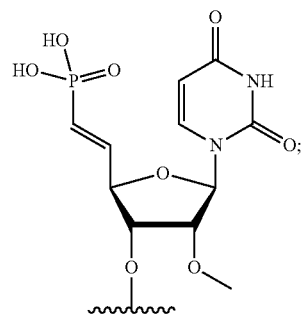

L is (L1)

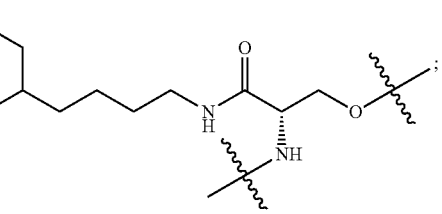

$X^c$ is docosahexaenoic acid (DHA);
$Z^c$ is $Z^{c1}$;

R is hydrogen or phosphate; and
R' is hydrogen or phosphate.

11. The compound of claim 1, wherein the first oligonucleotide has structure:

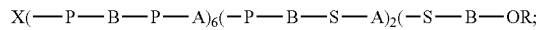

X(—P—B—P—A)₆(—P—B—S—A)₂(—S—B—OR;

the second oligonucleotide has the structure:

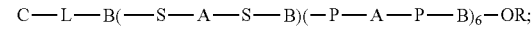

C—L—B(—S—A—S—B)(—P—A—P—B)₆—OR;

and
the compound has the structure of compound (IIIb):

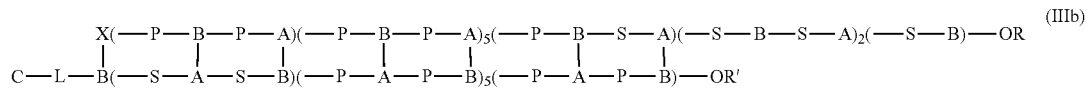

(IIIb)
X(—P—B—P—A)(—P—B—P—A)₅(—P—B—S—A)(—S—B—S—A)₂(—S—B)—OR
    |           |                |             |
C—L—B(—S—A—S—B)(—P—A—P—B)₅(—P—A—P—B)—OR' wherein each | represents a hydrogen bonding interaction
wherein:
C-L is:

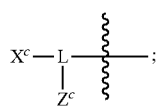

X is selected from the group consisting of:

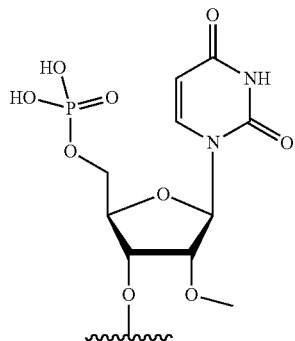
X1

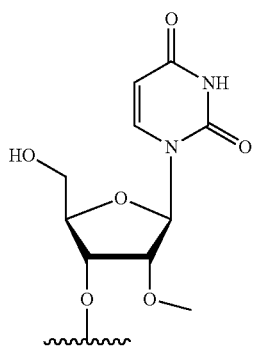
X2

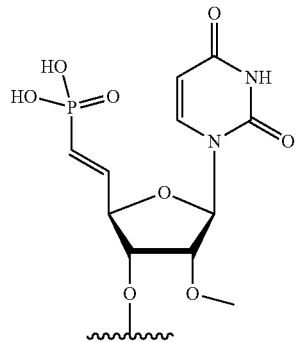
X3

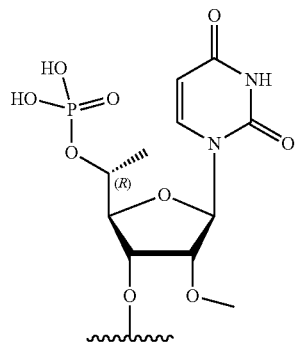
X4

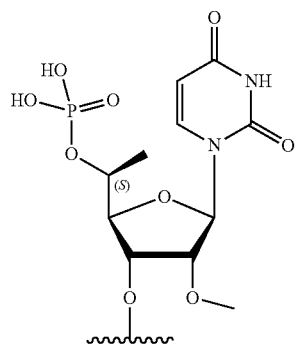
X5

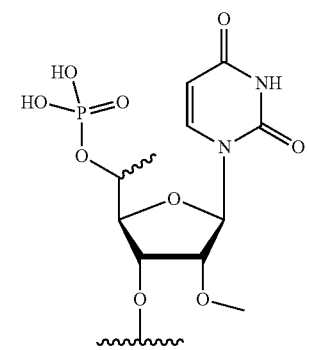
X6

X7
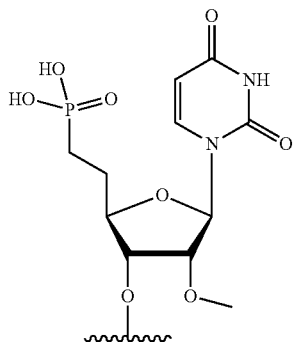

X8
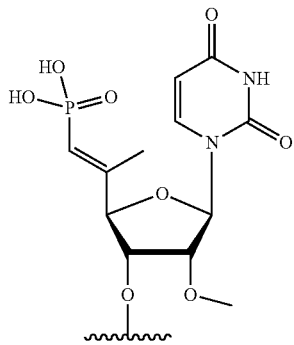

A, for each occurrence, independently is a 2'-methoxy-ribonucleotide;

B, for each occurrence, independently is a 2'-fluoro-ribonucleotide;

S is a phosphorothioate linker;

P is a phosphodiester linker;

R is hydrogen, phosphate, vinylphosphonate, or a capping group; and

R' is hydrogen, phosphate, vinylphosphonate, or a capping group.

12. The compound of claim 11, wherein:

X is (X3)
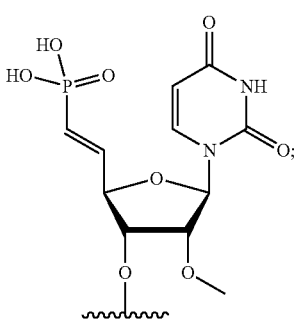

L is

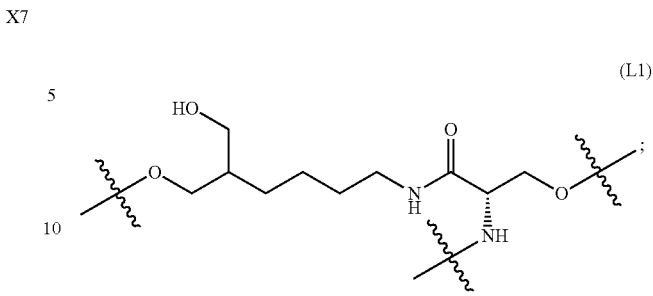

$X^c$ is DHA;

$Z^c$ is $Z^{c1}$;

R is hydrogen or phosphate; and

R' is hydrogen or phosphate.

13. The compound of claim 1, wherein when $X^c$ is DHA, $Z^c$ is not $Z^{c1}$.

14. The compound of claim 1, wherein when $Z^c$ is $Z^{c1}$, $X^c$ is not DHA.

15. A compound of formula (I):

$$X^c\!-\!L\!-\!O \atop | \atop Z^c \qquad (I)$$

wherein:

O is a double-stranded nucleic acid comprising a first oligonucleotide and a second oligonucleotide, wherein:

(1) the first oligonucleotide comprises at least 16 contiguous nucleotides, a 5' end, a 3' end and has complementarity to a target;

(2) the second oligonucleotide comprises at least 15 contiguous nucleotides, a 5' end, a 3' end, and has homology with a target; and (3) a portion of the first oligonucleotide is complementary to a portion of the second oligonucleotide;

wherein the first oligonucleotide has structure:

X(—P—B—P—A)₆(—P—B—S—A)(—S—B—S—A)₂(—S—B)-OR;

the second oligonucleotide has the structure:

C—L—B(—S—A—S—B)(—P—A—P—B)₆—OR;

and the compound has the structure of compound (IIIb):

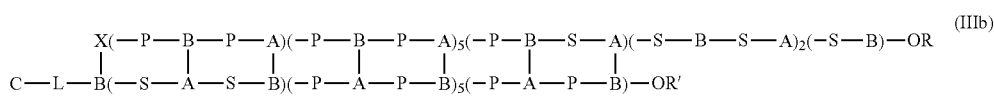

wherein each | represents a hydrogen bonding interaction wherein:

C-L is:

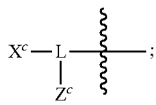

$X^c$ is DHA;
$Z^c$ is $Z^{c1}$;
A, for each occurrence, independently is a 2'-methoxyribonucleotide;
B, for each occurrence, independently is a 2'-fluororibonucleotide;
S is a phosphorothioate linker;
P is a phosphodiester linker;
X is (X3)

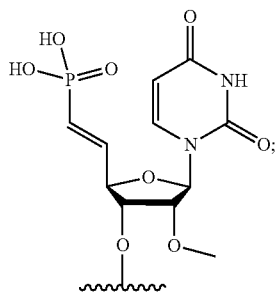

L is (L1)

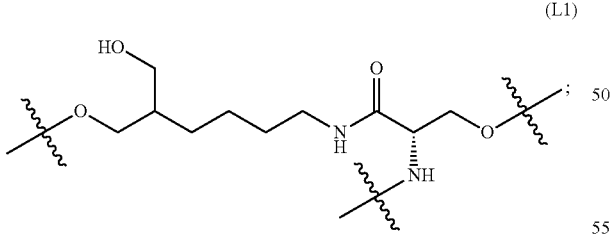

R is hydrogen or phosphate; and
R' is hydrogen or phosphate.

16. A compound of formula (I):

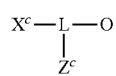
(I)

wherein:
O is a double-stranded nucleic acid comprising a first oligonucleotide and a second oligonucleotide, wherein:

(1) the first oligonucleotide comprises at least 16 contiguous nucleotides, a 5' end, a 3' end and has complementarity to a target;

(2) the second oligonucleotide comprises at least 15 contiguous nucleotides, a 5' end, a 3' end, and has homology with a target; and (3) a portion of the first oligonucleotide is complementary to a portion of the second oligonucleotide;

wherein the first oligonucleotide has structure:

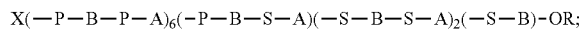

the second oligonucleotide has the structure:

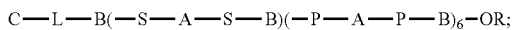

and the compound has the structure of compound (IIIb):

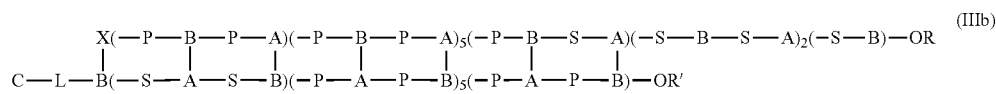
(IIIb)

wherein each | represents a hydrogen bonding interaction wherein:

C-L is:

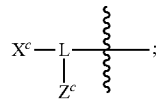

$X^c$ is eicosapentanoic acid (EPA);
$Z^c$ a phosphodiester or phosphodiester derivative, or is absent;
A, for each occurrence, independently is a 2'-methoxyribonucleotide;
B, for each occurrence, independently is a 2'-fluororibonucleotide;
S is a phosphorothioate linker;
P is a phosphodiester linker;

X is

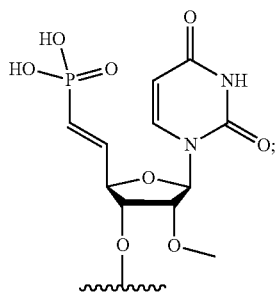
(X3)

L is

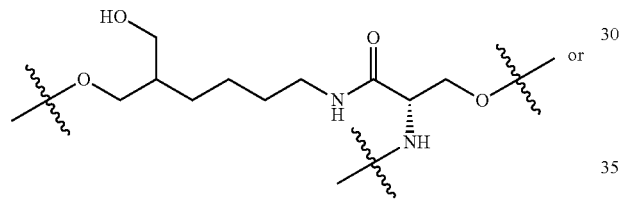

R is hydrogen or phosphate; and
R' is hydrogen or phosphate.

17. A compound of formula (I):

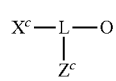
(I)

wherein:
O is a double-stranded nucleic acid comprising a first oligonucleotide and a second oligonucleotide, wherein:
(1) the first oligonucleotide comprises at least 16 contiguous nucleotides, a 5' end, a 3' end and has complementarity to a target;
(2) the second oligonucleotide comprises at least 15 contiguous nucleotides, a 5' end, a 3' end, and has homology with a target; and
(3) a portion of the first oligonucleotide is complementary to a portion of the second oligonucleotide;

wherein the first oligonucleotide has structure:

X(—P—B—P—A)$_6$(—P—B—S—A)(—S—B—S—A)$_2$(—S—B)-OR;

the second oligonucleotide has the structure:

C—L—B(—S—A—S—B)(—P—A—P—B)$_6$—OR;

and
the compound has the structure of compound (IIIb):

$$X(-P-B-P-A)(-P-B-P-A)_5(-P-B-S-A)(-S-B-S-A)_2(-S-B)-OR$$
$$C-L-B(-S-A-S-B)(-P-A-P-B)_5(-P-A-P-B)-OR'$$
(IIIb)

wherein each | represents a hydrogen bonding interaction wherein:
C-L is:

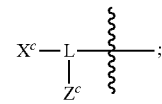

$X^c$ is Docosanoic Acid (DCA);
$Z^c$ a phosphodiester or phosphodiester derivative, or is absent;
A, for each occurrence, independently is a 2'-methoxy-ribonucleotide;
B, for each occurrence, independently is a 2'-fluoro-ribonucleotide;
S is a phosphorothioate linker;
P is a phosphodiester linker;
X is

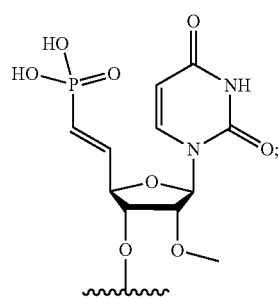
(X3)

L is
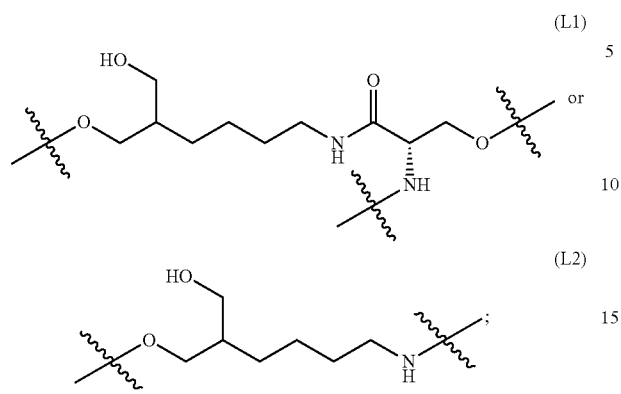
R is hydrogen or phosphate; and
R' is hydrogen or phosphate.
18. The compound of claim 1, wherein $X^c$ is selected from the group consisting of DHA, EPA, DCA, and calciferol.
* * * * *